US012655408B2

(12) United States Patent
Palese et al.

(10) Patent No.: US 12,655,408 B2
(45) Date of Patent: Jun. 16, 2026

(54) RECOMBINANT NEURAMINIDASE AND USES THEREOF

(71) Applicant: ICAHN SCHOOL OF MEDICINE AT MOUNT SINAI, New York, NY (US)

(72) Inventors: Peter Palese, New York, NY (US); Adolfo Garcia-Sastre, New York, NY (US); Florian Krammer, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 811 days.

(21) Appl. No.: 17/770,591

(22) PCT Filed: Oct. 21, 2020

(86) PCT No.: PCT/US2020/056703
§ 371 (c)(1),
(2) Date: Apr. 20, 2022

(87) PCT Pub. No.: WO2021/081120
PCT Pub. Date: Apr. 29, 2021

(65) Prior Publication Data
US 2022/0403358 A1 Dec. 22, 2022

Related U.S. Application Data

(60) Provisional application No. 62/924,511, filed on Oct. 22, 2019.

(51) Int. Cl.
*C12N 9/24* (2006.01)
*C07K 14/005* (2006.01)

(52) U.S. Cl.
CPC .......... *C12N 9/2402* (2013.01); *C07K 14/005* (2013.01); *C12Y 302/01018* (2013.01); *C07K 2319/02* (2013.01); *C07K 2319/03* (2013.01); *C07K 2319/21* (2013.01); *C07K 2319/43* (2013.01); *C12N 2760/16122* (2013.01)

(58) Field of Classification Search
CPC ........ C12N 9/2402; C12N 2760/16122; C07K 14/005; C07K 2319/02; C07K 2319/03; C07K 2319/43; C12Y 302/01018
See application file for complete search history.

(56) References Cited

U.S. PATENT DOCUMENTS

| | | | |
|---|---|---|---|
| 4,444,887 A | 4/1984 | Hoffmann | |
| 4,522,811 A | 6/1985 | Eppstein et al. | |
| 4,603,112 A | 7/1986 | Paoletti et al. | |
| 4,693,981 A | 9/1987 | Wiesehahn et al. | |
| 4,716,111 A | 12/1987 | Osband et al. | |
| 4,722,848 A | 2/1988 | Paoletti et al. | |
| 4,769,330 A | 9/1988 | Paoletti et al. | |
| 5,057,540 A | 10/1991 | Kensil et al. | |
| 5,106,619 A | 4/1992 | Wiesehahn et al. | |
| 5,110,587 A | 5/1992 | Paoletti et al. | |
| 5,166,057 A | 11/1992 | Palese et al. | |
| 5,174,993 A | 12/1992 | Paoletti | |
| 5,182,192 A | 1/1993 | Steplewski et al. | |
| 5,413,923 A | 5/1995 | Kucherlapati et al. | |
| 5,484,719 A | 1/1996 | Lam et al. | |
| 5,545,806 A | 8/1996 | Lonberg et al. | |
| 5,569,825 A | 10/1996 | Lonberg et al. | |
| 5,571,709 A | 11/1996 | Devauchelle et al. | |
| 5,573,916 A | 11/1996 | Cheronis et al. | |
| 5,589,174 A | 12/1996 | Okuno et al. | |
| 5,612,487 A | 3/1997 | Lam et al. | |
| 5,625,126 A | 4/1997 | Lonberg et al. | |
| 5,631,350 A | 5/1997 | Okuno et al. | |
| 5,633,425 A | 5/1997 | Lonberg et al. | |

(Continued)

FOREIGN PATENT DOCUMENTS

| | | |
|---|---|---|
| CA | 2121559 A1 | 10/1994 |
| CA | 2718923 A1 | 9/2009 |

(Continued)

OTHER PUBLICATIONS

UniProt ID A0A076FF09_9MONO, integrated into UniProt Oct. 29, 2014 (https://www.uniprot.org/uniprotkb/A0A076FF09/entry) (Year: 2014).*

(Continued)

*Primary Examiner* — Louise W Humphrey
*Assistant Examiner* — Rachel Emily Martin
(74) *Attorney, Agent, or Firm* — JONES DAY

(57) ABSTRACT

In one aspect, provided herein are recombinant neuraminidases comprising an ectodomain of influenza virus neuraminidase with amino acid substitutions or insertions of cysteines in the stalk domain to generate a more stable, tetrameric influenza virus neuraminidase. In specific embodiments, the influenza virus neuraminidase further comprises influenza virus neuraminidase transmembrane and cytoplasmic domains. In another aspect, provided herein are recombinant neuraminidase comprising a globular head domain of influenza virus neuraminidase and a tetramerization domain, wherein the recombinant neuraminidase lacks influenza virus neuraminidase stalk, transmembrane and cytoplasmic domains. In another aspect, provided herein are methods of immunizing against influenza virus using such recombinant neuraminidases or compositions thereof.

18 Claims, 28 Drawing Sheets

Specification includes a Sequence Listing.

(56) References Cited

U.S. PATENT DOCUMENTS

| | | | |
|---|---|---|---|
| 5,643,576 A | 7/1997 | Johnston et al. | |
| 5,661,016 A | 8/1997 | Lonberg et al. | |
| 5,820,871 A | 10/1998 | Palese et al. | |
| 5,854,037 A | 12/1998 | Palese et al. | |
| 5,885,793 A | 3/1999 | Griffiths et al. | |
| 5,891,705 A | 4/1999 | Budowsky et al. | |
| 5,916,771 A | 6/1999 | Hori et al. | |
| 5,929,304 A | 7/1999 | Radin et al. | |
| 6,001,634 A | 12/1999 | Palese et al. | |
| 6,022,726 A | 2/2000 | Palese et al. | |
| 6,034,298 A | 3/2000 | Lam et al. | |
| 6,136,320 A | 10/2000 | Arntzen et al. | |
| 6,146,642 A | 11/2000 | Garcia-Sastre et al. | |
| 6,165,476 A | 12/2000 | Strom et al. | |
| 6,265,189 B1 | 7/2001 | Paoletti et al. | |
| 6,337,070 B1 | 1/2002 | Okuno et al. | |
| 6,468,544 B1 | 10/2002 | Egorov et al. | |
| 6,544,785 B1 | 4/2003 | Palese et al. | |
| 6,551,820 B1 | 4/2003 | Mason et al. | |
| 6,573,079 B1 | 6/2003 | Palese et al. | |
| 6,589,940 B1 | 7/2003 | Raz et al. | |
| 6,635,246 B1 | 10/2003 | Barrett et al. | |
| 6,649,372 B1 | 11/2003 | Palese et al. | |
| 6,669,943 B1 | 12/2003 | Palese et al. | |
| 6,720,409 B2 | 4/2004 | Okuno et al. | |
| 6,770,799 B2 | 8/2004 | Mor et al. | |
| 6,852,522 B1 | 2/2005 | Palese et al. | |
| 6,867,293 B2 | 3/2005 | Andrews et al. | |
| 6,887,699 B1 | 5/2005 | Palese et al. | |
| 6,942,861 B2 | 9/2005 | McKee et al. | |
| 6,951,754 B2 | 10/2005 | Hoffmann | |
| 7,312,064 B2 | 12/2007 | Hoffmann | |
| 7,384,774 B2 | 6/2008 | Palese et al. | |
| 7,442,379 B2 | 10/2008 | Garcia-Sastre et al. | |
| 7,494,808 B2 | 2/2009 | Palese et al. | |
| 7,504,560 B2 | 3/2009 | Arntzen et al. | |
| 7,566,458 B2 | 7/2009 | Yang et al. | |
| 7,585,943 B2 * | 9/2009 | Kim .................... C07K 7/08 | |
| | | | 530/397 |
| 7,968,101 B2 | 6/2011 | Kawaoka et al. | |
| 8,367,077 B2 | 2/2013 | Zurbriggen et al. | |
| 8,603,467 B2 | 12/2013 | Chen et al. | |
| 8,673,314 B2 | 3/2014 | Garcia Sastre et al. | |
| 8,828,406 B2 | 9/2014 | Garcia-Sastre et al. | |
| 9,051,359 B2 | 6/2015 | Garcia-Sastre et al. | |
| 9,175,069 B2 | 11/2015 | Garcia-Sastre et al. | |
| 9,371,366 B2 | 6/2016 | Garcia-Sastre et al. | |
| 9,452,211 B2 | 9/2016 | Meijberg et al. | |
| 9,688,965 B2 | 6/2017 | Wu et al. | |
| 9,701,723 B2 | 7/2017 | Garcia-Sastre et al. | |
| 9,707,288 B2 | 7/2017 | Schrader | |
| 9,708,373 B2 | 7/2017 | Garcia-Sastre et al. | |
| 9,849,172 B2 | 12/2017 | Garcia-Sastre et al. | |
| 9,908,930 B2 | 3/2018 | Palese et al. | |
| 9,968,670 B2 | 5/2018 | Garcia-Sastre et al. | |
| 10,131,695 B2 | 11/2018 | Garcia-Sastre et al. | |
| 10,137,189 B2 | 11/2018 | Garcia-Sastre et al. | |
| 10,179,806 B2 | 1/2019 | Garcia-Sastre et al. | |
| 10,544,207 B2 | 1/2020 | Palese et al. | |
| 10,583,188 B2 | 3/2020 | Garcia-Sastre et al. | |
| 10,736,956 B2 | 8/2020 | Palese et al. | |
| 11,254,733 B2 | 2/2022 | Palese et al. | |
| 11,266,734 B2 | 3/2022 | Palese et al. | |
| 12,030,928 B2 | 7/2024 | Palese et al. | |
| 2002/0054882 A1 | 5/2002 | Okuno et al. | |
| 2002/0164770 A1 | 11/2002 | Hoffman | |
| 2003/0134338 A1 | 7/2003 | Makarocskiy | |
| 2004/0002061 A1 | 1/2004 | Kawaoka | |
| 2004/0073011 A1 | 4/2004 | Hagay et al. | |
| 2005/0009008 A1 | 1/2005 | Robinson et al. | |
| 2005/0042229 A1 | 2/2005 | Yang et al. | |
| 2005/0048074 A1 | 3/2005 | Cardineau et al. | |
| 2005/0064391 A1 | 3/2005 | Segal et al. | |
| 2005/0106178 A1 | 5/2005 | O'hagan et al. | |
| 2005/0201946 A1 | 9/2005 | Friede et al. | |
| 2006/0008473 A1 | 1/2006 | Yana et al. | |
| 2006/0019350 A1 | 1/2006 | Palese et al. | |
| 2006/0204487 A1 | 9/2006 | Shaaltiel et al. | |
| 2006/0217338 A1 | 9/2006 | Lu et al. | |
| 2006/0280754 A1 | 12/2006 | Garry et al. | |
| 2007/0020238 A1 | 1/2007 | Baltimore et al. | |
| 2007/0036809 A1 | 2/2007 | Michl et al. | |
| 2007/0207171 A1 | 9/2007 | Dubensky et al. | |
| 2007/0275014 A1 | 11/2007 | Yusibov et al. | |
| 2008/0019998 A1 | 1/2008 | Wang et al. | |
| 2008/0032921 A1 | 2/2008 | Alexander et al. | |
| 2008/0038232 A1 | 2/2008 | Shaaltiel et al. | |
| 2008/0152657 A1 | 6/2008 | Horowitz et al. | |
| 2008/0176247 A1 | 7/2008 | Chou et al. | |
| 2008/0193455 A1 | 8/2008 | Stassen et al. | |
| 2008/0207550 A1 | 8/2008 | Fearon et al. | |
| 2008/0248066 A1 | 10/2008 | Dubensky et al. | |
| 2008/0254060 A1 | 10/2008 | Palese et al. | |
| 2009/0053762 A1 | 2/2009 | Shaaltiel | |
| 2009/0068221 A1 | 3/2009 | Morrison | |
| 2009/0081255 A1 | 3/2009 | Bublot et al. | |
| 2009/0082548 A1 | 3/2009 | Shaaltiel et al. | |
| 2009/0169547 A1 | 7/2009 | Sahin et al. | |
| 2009/0208477 A1 | 8/2009 | Shaaltiel et al. | |
| 2009/0246830 A1 | 10/2009 | Kawaoka et al. | |
| 2009/0291472 A1 | 11/2009 | Lu et al. | |
| 2009/0304730 A1 | 12/2009 | Amon et al. | |
| 2009/0304739 A1 | 12/2009 | Rappouli et al. | |
| 2009/0311265 A1 | 12/2009 | Van Den Brink et al. | |
| 2009/0311669 A1 | 12/2009 | Kawaoka | |
| 2010/0184192 A1 | 7/2010 | Smith et al. | |
| 2010/0247571 A1 | 9/2010 | Wong et al. | |
| 2010/0297165 A1 | 11/2010 | Berzofsky et al. | |
| 2010/0297174 A1 | 11/2010 | Garcia-Sastre et al. | |
| 2011/0027270 A1 | 2/2011 | Garcia-Sastre et al. | |
| 2011/0111494 A1 | 5/2011 | Hill et al. | |
| 2011/0182938 A1 | 7/2011 | Weiner et al. | |
| 2011/0300604 A1 | 12/2011 | Kawaoka et al. | |
| 2012/0039898 A1 | 2/2012 | Throsby et al. | |
| 2012/0058538 A1 | 3/2012 | Palese et al. | |
| 2012/0122185 A1 | 5/2012 | Palese et al. | |
| 2012/0189658 A1 | 7/2012 | Couture et al. | |
| 2012/0244183 A1 | 9/2012 | Garcia-Sastre et al. | |
| 2012/0294796 A1 | 11/2012 | Johnson et al. | |
| 2013/0022623 A1 | 1/2013 | Karsunky et al. | |
| 2013/0129747 A1 | 5/2013 | Schrader | |
| 2013/0129761 A1 | 5/2013 | Garcia-Sastre et al. | |
| 2013/0209499 A1 | 8/2013 | Garcia-Sastre et al. | |
| 2013/0224187 A1 | 8/2013 | Rother et al. | |
| 2013/0315929 A1 | 11/2013 | Bock | |
| 2014/0004149 A1 | 1/2014 | Tobin et al. | |
| 2014/0170163 A1 | 6/2014 | Garcia Sastre et al. | |
| 2014/0193484 A1 | 7/2014 | Bertholet Girardin et al. | |
| 2014/0328875 A1 | 11/2014 | Garcia Sastre et al. | |
| 2015/0132253 A1 | 5/2015 | Sahin et al. | |
| 2015/0132330 A1 | 5/2015 | Garcia-Sastre et al. | |
| 2015/0239960 A1 | 8/2015 | Garcia-Sastre et al. | |
| 2015/0252103 A1 | 9/2015 | Sahin et al. | |
| 2015/0266951 A1 | 9/2015 | Song | |
| 2015/0297712 A1 | 10/2015 | Garcia-Sastre et al. | |
| 2015/0299270 A1 | 10/2015 | Galarza et al. | |
| 2015/0335729 A1 | 11/2015 | Garcia-Sastre et al. | |
| 2015/0352202 A1 | 12/2015 | Osorio et al. | |
| 2016/0015828 A1 | 1/2016 | Torgov et al. | |
| 2016/0017025 A1 | 1/2016 | Samira et al. | |
| 2016/0022806 A1 | 1/2016 | Weiner et al. | |
| 2016/0024196 A1 | 1/2016 | Majeti et al. | |
| 2016/0038585 A1 | 2/2016 | Dormitzer et al. | |
| 2016/0067328 A1 | 3/2016 | Wu et al. | |
| 2016/0137721 A1 | 5/2016 | Palese et al. | |
| 2016/0185860 A1 | 6/2016 | Sahin et al. | |
| 2016/0311918 A1 | 10/2016 | Wang et al. | |
| 2016/0355553 A1 | 12/2016 | Meijberg et al. | |
| 2016/0355590 A1 | 12/2016 | Epstein | |
| 2016/0361408 A1 | 12/2016 | Garcia-Sastre et al. | |
| 2016/0362455 A1 | 12/2016 | Meijberg et al. | |
| 2016/0376347 A1 | 12/2016 | Saelens et al. | |
| 2017/0204177 A1 | 7/2017 | Wang et al. | |
| 2017/0327565 A1 | 11/2017 | Schrader | |

(56) References Cited

U.S. PATENT DOCUMENTS

| | | |
|---|---|---|
| 2018/0002385 A1 | 1/2018 | Garcia-Sastre et al. |
| 2018/0008696 A1 | 1/2018 | Palese et al. |
| 2018/0022804 A1 | 1/2018 | Peters et al. |
| 2018/0265573 A1 | 9/2018 | Palese et al. |
| 2018/0312592 A1 | 11/2018 | Junutula et al. |
| 2018/0333479 A1 | 11/2018 | Garcia-Sastre et al. |
| 2019/0048324 A1 | 2/2019 | Kawaoka et al. |
| 2019/0099484 A1 | 4/2019 | Garcia-Sastre et al. |
| 2019/0106461 A1 | 4/2019 | Garcia-Sastre et al. |
| 2019/0125859 A1 | 5/2019 | Palese et al. |
| 2019/0292229 A1 | 9/2019 | Blackledge et al. |
| 2019/0314485 A1 | 10/2019 | Palese et al. |
| 2020/0223905 A1 | 7/2020 | Palese et al. |
| 2021/0246432 A1 | 8/2021 | Kawaoka et al. |
| 2021/0260179 A1 | 8/2021 | Palese et al. |
| 2022/0153873 A1 | 5/2022 | Krammer et al. |
| 2022/0168368 A1 | 6/2022 | Wu |
| 2022/0249652 A1 | 8/2022 | Palese et al. |
| 2022/0257749 A1 | 8/2022 | Palese et al. |
| 2022/0363736 A1 | 11/2022 | Palese et al. |

FOREIGN PATENT DOCUMENTS

| | | | |
|---|---|---|---|
| CN | 1196788 C | 4/2005 | |
| CN | 103665155 A | 3/2014 | |
| CN | 104185476 A | 12/2014 | |
| CN | 105263516 A | 1/2016 | |
| CN | 105400753 A | 3/2016 | |
| CN | 110283794 A | 9/2019 | |
| EP | 0621339 A2 | 10/1994 | |
| EP | 0702085 A1 | 3/1996 | |
| EP | 0780475 A1 | 6/1997 | |
| EP | 2540312 A1 | 1/2013 | |
| JP | H 789992 A | 4/1995 | |
| JP | H 10-502168 A | 2/1998 | |
| JP | 2004258814 A | 9/2004 | |
| JP | 2006347922 A | 12/2006 | |
| JP | 2008249712 A | 10/2008 | |
| JP | 2009022186 A | 2/2009 | |
| JP | 2009131237 A | 6/2009 | |
| JP | 2012521786 A | 10/2010 | |
| JP | 2011057653 A | 3/2011 | |
| JP | 2012530499 A | 12/2012 | |
| JP | 2014530003 A | 11/2014 | |
| JP | 2016508133 A | 3/2016 | |
| WO | WO 1984000687 A1 | 3/1984 | |
| WO | WO 1991010741 A1 | 7/1991 | |
| WO | WO 1992001047 A1 | 1/1992 | |
| WO | WO 1994009136 A1 | 4/1994 | |
| WO | WO 1994012629 A1 | 6/1994 | |
| WO | WO 1994016109 A1 | 7/1994 | |
| WO | WO 1994017826 A1 | 8/1994 | |
| WO | WO 1995034324 A1 | 12/1995 | |
| WO | WO 1996011279 A2 | 4/1996 | |
| WO | WO 1996033735 A1 | 10/1996 | |
| WO | WO 1996034096 A1 | 10/1996 | |
| WO | WO 1996034625 A1 | 11/1996 | |
| WO | WO 1997006270 A1 | 2/1997 | |
| WO | WO 1997012032 A1 | 4/1997 | |
| WO | WO 1997040161 A1 | 10/1997 | |
| WO | WO 1997040177 A1 | 10/1997 | |
| WO | WO 1998002530 A1 | 1/1998 | |
| WO | WO 1998013501 A2 | 4/1998 | |
| WO | WO 1998016654 A1 | 4/1998 | |
| WO | WO 1998024893 A2 | 6/1998 | |
| WO | WO 1998046645 A2 | 10/1998 | |
| WO | WO 1998050433 A2 | 11/1998 | |
| WO | WO 1998053078 A1 | 11/1998 | |
| WO | WO 1999002657 A1 | 1/1999 | |
| WO | WO 1999015672 A1 | 4/1999 | |
| WO | WO 2001004333 A1 | 1/2001 | |
| WO | WO 2002000885 A2 | 1/2002 | |
| WO | WO 2003068923 A2 | 8/2003 | |
| WO | WO 2003068923 A3 | 8/2003 | |
| WO | WO 2005000901 A2 | 1/2005 | |
| WO | WO 2007045674 A1 | 4/2007 | |
| WO | WO 2007064802 A1 | 6/2007 | |
| WO | WO 2007103322 A2 | 9/2007 | |
| WO | WO 2007109812 A2 | 9/2007 | |
| WO | WO 2007109813 A1 | 9/2007 | |
| WO | WO 2007110776 A1 | 10/2007 | |
| WO | WO 2007134237 A2 | 11/2007 | |
| WO | WO 2007134327 A2 | 11/2007 | |
| WO | WO 2008005777 A2 | 1/2008 | |
| WO | WO 2008028946 A2 | 3/2008 | |
| WO | WO 2008032219 A2 | 3/2008 | |
| WO | WO 2009001217 A2 | 12/2008 | |
| WO | WO 2009009876 A1 | 1/2009 | |
| WO | WO 2009012489 A1 | 1/2009 | |
| WO | WO 2009025770 A2 | 2/2009 | |
| WO | WO 2009036157 A1 | 3/2009 | |
| WO | WO 2009068992 A1 | 6/2009 | |
| WO | WO 2009076778 A1 | 6/2009 | |
| WO | WO 2009079259 A2 | 6/2009 | |
| WO | WO 2009092038 A1 | 7/2009 | |
| WO | WO 2009121004 A2 | 10/2009 | |
| WO | WO 2009150532 A1 | 12/2009 | |
| WO | WO 2009156405 A1 | 12/2009 | |
| WO | WO 2010003235 A1 | 1/2010 | |
| WO | WO 2010036170 A1 | 4/2010 | |
| WO | WO 2010036948 A2 | 4/2010 | |
| WO | WO 2010117786 A1 | 10/2010 | |
| WO | WO 2010130636 A1 | 11/2010 | |
| WO | WO 2010138564 A1 | 12/2010 | |
| WO | WO 2010148511 A1 | 12/2010 | |
| WO | WO 2011014645 A1 | 2/2011 | |
| WO | WO 2011044152 A1 | 4/2011 | |
| WO | WO 2011087092 A1 | 7/2011 | |
| WO | WO 2011103453 A2 | 8/2011 | |
| WO | WO 2011111966 A2 | 9/2011 | |
| WO | WO 2011123495 A1 | 10/2011 | |
| WO | WO 2011126370 A1 | 10/2011 | |
| WO | WO 2012009790 A1 | 1/2012 | |
| WO | WO 2013043729 A1 | 3/2013 | |
| WO | WO 2013079473 A1 | 6/2013 | |
| WO | WO 2014159960 A1 | 1/2014 | |
| WO | WO 2014099931 A1 | 6/2014 | |
| WO | WO 2014152841 A1 | 9/2014 | |
| WO | WO 2015199564 A1 | 12/2015 | |
| WO | WO 2016005480 A1 | 1/2016 | |
| WO | WO 2016005482 A1 | 1/2016 | |
| WO | WO 2016118937 A1 | 7/2016 | |
| WO | WO 2016205347 A1 | 12/2016 | |
| WO | WO 2017021893 A1 | 2/2017 | |
| WO | WO 2017035479 A1 | 3/2017 | |
| WO | WO 2017053413 A1 | 3/2017 | |
| WO | WO 2017136575 A1 | 8/2017 | |
| WO | WO 2017136575 A8 | 8/2017 | |
| WO | WO 2017148889 A1 | 9/2017 | |
| WO | WO 2017210445 A1 | 12/2017 | |
| WO | WO 2017218624 A1 | 12/2017 | |
| WO | WO 2018089407 A1 | 5/2018 | |
| WO | WO 2018148383 A1 | 8/2018 | |
| WO | WO 2018187706 A2 | 10/2018 | |
| WO | WO 2019032463 A1 | 2/2019 | |
| WO | WO 2019246363 A1 | 12/2019 | |
| WO | WO 2020219719 A1 | 10/2020 | |
| WO | WO 2020264141 A1 | 12/2020 | |
| WO | WO 2023167868 A2 | 9/2023 | |
| WO | WO 2023167868 A3 | 9/2023 | |

OTHER PUBLICATIONS

Basler CF, García-Sastre A, Palese P. Mutation of neuraminidase cysteine residues yields temperature-sensitive influenza viruses. J Virol. Oct. 1999;73(10):8095-103. doi: 10.1128/JVI.73.10.8095-8103.1999. PMID: 10482558; PMCID: PMC112825. (Year: 1999).*

Abe et al., 2004, "Effect of the addition of oligosaccharides on the biological activities and antigenicity of influenza A/H3N2 virus hemagglutinin," J Virol., 78(18):9605-9611.

Abed et al., 2002, "Divergent evolution of hemagglutinin and neuraminidase genes in recent influenza A:H3N2 viruses isolated in Canada," J. Med. Virol., 67(4):589-595.

(56)                    References Cited

OTHER PUBLICATIONS

Air et al., 1985, "Location of antigenic sites on the three-dimensional structure of the influenza N2 virus neuraminidase," Virology, 145(2):237-248.

Air et al., 1990, "Antigenic, sequence, and crystal variation in influenza B neuraminidase," Virology, 177(2):578-587.

Air et al., 2012, "Influenza neuraminidase," Influenza Other Respir Viruses, 6(4):245-256 (Epub 2011).

Air, 2015, "Influenza virus antigenicity and broadly neutralizing epitopes," Curr. Opin. Virol. 11:113-121.

Altman et al., 2018, "Antibody Immunodominance: The Key to Understanding Influenza Virus Antigenic Drift," Viral. Immunol., 31(2):142-149.

Altschul et al., 1997, "Gapped BLAST and PSI-BLAST: a new generation of protein database search programs," Nucleic Acids Res., 25(17):3389-3402.

Amanat et al., 2019, "Cross-reactive antibodies binding to H4 hemagglutinin protect against a lethal H4N6 influenza virus challenge in the mouse model," Emerg. Microbes. Infect., 8(1):155-168.

Angeletti et al., 2017, "Defining B cell immunodominance to viruses," Nat Immunol., 18(4):456-463.

Angeletti et al., 2018, "Is It Possible to Develop a "Universal" Influenza Virus Vaccine? Outflanking Antibody Immunodominance on the Road to Universal Influenza Vaccination," Cold Spring Harb Perspect Biol., 10(7):a028852 (9 pages).

Anonymous, "alignment" IBIS—Integrated Biotechnological Information, European Patent Office, retrieved from ibis.internal.epo.org/exam/jobResult?id=285344, on Sep. 26, 2014 (1 page).

Anonymous, "Amino Acids Reference Chart—Sigma-Aldrich" retrieved from www.sigmaaldrich.com/life-science/metabolomics/learning-center/amino-acid-reference-chart.html, on Jul. 17, 2015 (3 pages).

Anthony et al., 2012, "Emergence of fatal avian influenza in New England harbor seals," MBio., 3(4):e00166-12.

Antoine et al., 1998, "The complete genomic sequence of the modified vaccinia Ankara strain: comparison with other orthopoxviruses," Virology, 244(2):365-396.

Arzey et al., 2012, "Influenza virus A (H10N7) in chickens and poultry abattoir workers, Australia," Emerg Infect Dis., 18(5):814-816.

Babai et al., 2001, "A novel liposomal influenza vaccine (INFLUSOME-VAC) containing hemagglutinin-neuraminidase and IL-2 or GM-CSF induces protective anti-neuraminidase antibodies cross-reacting with a wide spectrum of influenza A viral strains," Vaccine 20(3-4):505-515.

Babu et al., 2014, "Live attenuated H7N7 influenza vaccine primes for a vigorous antibody response to inactivated H7N7 influenza vaccine," Vaccine 32:6798-6804.

Bailey et al., 2018, "A Method to Assess Fc-mediated Effector Functions Induced by Influenza Hemagglutinin Specific Antibodies," J. Vis. Exp., (132):e56256 (5 pages).

Baker et al., 1976, "Effect of Ca++ on the stability of influenza virus neuraminidase," Arch Virol., 52(1-2):7-18.

Baker et al., 2013, "Protection against lethal influenza with a viral mimic," J Virol., 87(15):8591-8605.

Basler et al., 1999, "Mutation of neuraminidase cysteine residues yields temperature-sensitive influenza viruses," J Virol., 73(10):8095-8103.

Baz et al., 2013, "Replication and immunogenicity of swine, equine, and avian h3 subtype influenza viruses in mice and ferrets," J Virol., 87(12):6901-6910.

Beare et al., 1975, "Trials in man with live recombinants made from A/PR/8/34 (H0 N1) and wild H3 N2 influenza viruses," Lancet, 2(7938):729-732.

Belongia et al., 2016, "Variable influenza vaccine effectiveness by subtype: a systematic review and meta-analysis of test-negative design studies," Lancet Infect. Dis., 16(8):942-951.

Belshe, 2007, "Translational research on vaccines: influenza as an example," Clin Pharmacol Ther., 82(6):745-749.

Benjamin et al., 2014, "A broadly neutralizing human monoclonal antibody directed against a novel conserved epitope on the influenza virus H3 hemagglutinin globular head," J. Virol., 88(12):6743-6750.

Benne et al., 1998, "Comparison of neutralizing and hemagglutination-inhibiting antibody responses to influenza A virus vaccination of human immunodeficiency virus-infected individuals," Clin. Diagn. Lab Immunol., 5(1):114-117.

Benoit et al., 2015, "Hemagglutination Inhibition Antibody Titers as a Correlate of Protection Against Seasonal A/H3N2 Influenza Disease," Open Forum Infect. Dis., 2(2):ofv067 (8 pages).

Berry, 2007, "Cross-reactive MAb to the binding domain of botulinum neurotoxin A, B, and E developed using a sequential immunization strategy: anti-botulinum neurotoxin," Hybridoma 26(6):435-436.

Bett et al., 1993, "Packaging capacity and stability of human adenovirus type 5 vectors," J Virol., 67(10):5911-5921.

Beyer et al., 2013, "Cochrane re-arranged: support for policies to vaccinate elderly people against influenza," Vaccine, 31(50):6030-6033.

Bhatt et al., 2011, "The genomic rate of molecular adaptation of the human influenza A virus," Mol. Biol. Evol., 28(9):2443-2451.

Bianchi et al., 2005, "Universal influenza B vaccine based on the maturational cleavage site of the hemagglutinin precursor," J. Virol. 79(12):7380-7388.

Bommakanti et al., 2010, "Design of an HA2-based Escherichia coli expressed influenza immunogen that protects mice from pathogenic challenge," Proc. Natl. Acad. Sci. USA 107:13701-13706.

Bommakanti et al., 2012, "Design of Eschericia coli-Expressed Stalk Domain Immunogens of H1N1 Hemagglutinin That Protect Mice from Lethal Challenge," J. Virol. 86(24):13434-13444.

Boni et al., 2010, "Guidelines for identifying homologous recombination events in influenza A virus," PLoS One 5(5):e10434.

Boni et al., 2012, "No evidence for intra-segment recombination of 2009 H1N1 influenza virus in swine," Gene 494(2):242-245.

Bouvier et al., 2008, "Oseltamivir-resistant influenza A viruses are transmitted efficiently among guinea pigs by direct contact but not by aerosol," J Virol., 82(20):10052-10058.

Bouvier et al., 2010, "Animal Models for Influenza Virus Pathogenesis and Transmission," Viruses, 2(8):1530-1563.

Bowie et al., 1990, "Deciphering the Message in Protein Sequences: Tolerance to Amino Acid Substitutions," Science 247:1306-1310.

Bright et al., 2007, "Influenza virus-like particles elicit broader immune responses than whole virion inactivated influenza virus or recombinant hemagglutinin," Vaccine, 25(19):3871-3878.

Broecker et al., 2018, "Immunodominance of Antigenic Site B in the Hemagglutinin of the Current H3N2 Influenza Virus in Humans and Mice," J Virol., 92(20):e01100-18.

Broecker et al., 2019, "A Mosaic Hemagglutinin-Based Influenza Virus Vaccine Candidate Protects Mice From Challenge With Divergent H3N2 Strains," NPJ Vaccines, 4:31 (9 pages).

Broecker et al., 2019, "Extending the Stalk Enhances Immunogenicity of the Influenza Virus Neuraminidase," J. Virol., 93(18):e00840-19 (12 pages).

Brottet et al., 2014, "Influenza season in Réunion dominated by influenza B virus circulation associated with numerous cases of severe disease, France, 2014," Eurosurveillance (4 pages).

Bruhn et al., 2014, "Crystal structure of the nipah virus phosphoprotein tetramerization domain," J Virol., 88(1):758-762 (Epub 2013).

Budd et al., 2018, "Update: Influenza Activity—United States, Oct. 1, 2017-Feb. 3, 2018," MMWR Morb Mortal Wkly Rep., 67(6):169-179.

Bullough et al., 1994, "Structure of influenza haemagglutinin at the pH of membrane fusion," Nature 371:37-43.

Carter et al., 2016, "Design and Characterization of a Computationally Optimized Broadly Reactive Hemagglutinin Vaccine for H1N1 Influenza Viruses," J Virol., 90(9):4720-4734.

Casali et al., 2008, "Site-directed mutagenesis of the hinge peptide from the hemagglutinin protein: enhancement of the pH-responsive conformational change," Protein Eng. Des. Sel. 21(6):395-404.

Castrucci et al., 1993, "Biologic importance of neuraminidase stalk length in influenza A virus," J. Virol., 67(2):759-764.

(56)                References Cited

OTHER PUBLICATIONS

Caton et al., 1982, "The antigenic structure of the influenza virus A/PR/8/34 hemagglutinin (H1 subtype)," Cell, 31(2 Pt 1):417-427.
Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf, pp. A32-A108 (2007).
Centers for Disease Control and Prevention (CDC), 2009, "Swine influenza A (H1N1) infection in two children—Southern California, Mar.-Apr. 2009," MMWR Morb Mortal Wkly Rep., 58(15):400-402.
Centers for Disease Control and Prevention (CDC), 2009, "Update on influenza A (H1N1) 2009 monovalent vaccines," MMWR Morb Mortal Wkly Rep., 58(39):1100-1101.
Centers for Disease Control and Prevention (CDC), 2010, "Estimates of deaths associated with seasonal influenza—United States, 1976-2007," MMWR Morb Mortal Wkly Rep., 59(33):1057-1062.
Centers for Disease Control and Prevention (CDC), 2011, "Influenza-Associated Pediatric Deaths—United States, Sep. 2010—Aug. 2011," MMWR Morb Mortal Wkly Rep., 60(36):1233-1267.
Centers for Disease Control and Prevention (CDC), 2012, "Notes from the field: Highly pathogenic avian influenza A (H7N3) virus infection in two poultry workers—Jalisco, Mexico, Jul. 2012," MMWR Morb Mortal Wkly Rep., 61(36):726-727.
Centers for Disease Control and Prevention (CDC), 2012, "Notes from the field: Outbreak of influenza A (H3N2) virus among persons and swine at a county fair—Indiana, Jul. 2012," MMWR Morb Mortal Wkly Rep., 61(29):561.
Centers for Disease Control and Prevention (CDC), 2018, "Interim Estimates of 2017-18 Seasonal Influenza Vaccine Effectiveness—United States, Feb. 2018," MMWR Morb Mortal Wkly Rep., 67(6);180-185.
Chen et al., 1999, "N- and C-terminal residues combine in the fusion-pH influenza hemagglutinin HA$_2$ subunit to form an N cap that terminates the triple-stranded coiled coil," Proc. Natl. Acad. Sci. 96(16):8967-8972.
Chen et al., 2000, "Cross-protection against a lethal influenza virus infection by DNA vaccine to neuraminidase," Vaccine, 18(28):3214-3222.
Chen et al., 2007, "Exploration of the emergence of the Victoria lineage of influenza B virus," Arch Virol., 152(2):415-422 (Epub 2006).
Chen et al., 2007, "Influenza Virus Hemagglutinin and Neuraminidase, but Not the Matrix Protein, Are Required for Assembly and Budding of Plasmid-Derived Virus-Like Particles," J. Virol. 81(13):7111-7123.
Chen et al., 2009, "Evaluation of live attenuated influenza a virus h6 vaccines in mice and ferrets," J Virol., 83(1):65-72.
Chen et al., 2010, "Generation of Live Attenuated Novel Influenza Virus A/California/7/09 (H1N1) Vaccines with High Yield in Embryonated Chicken Eggs," J. Virol. 84(1):44-51.
Chen et al., 2011, "Vaccine design of hemagglutinin glycoprotein against influenza," Trends Biotechnol. 29(9):426-434.
Chen et al., 2012, "The 2009 pandemic H1N1 virus induces anti-neuraminidase (NA) antibodies that cross-react with the NA of H5N1 viruses in ferrets," Vaccine, 30(15):2516-2522.
Chen et al., 2014, "Clinical and epidemiological characteristics of a fatal case of avian influenza A H10N8 virus infection: a descriptive study," Lancet, 383(9918):714-721.
Chen et al., 2016, "Influenza A viruses expressing intra- or intergroup chimeric hemagglutinins," 90:3789-3793, doi:10.1128/JVI.03060-15.
Chen et al., 2018, "Influenza Infection in Humans Induces Broadly Cross-Reactive and Protective Neuraminidase-Reactive Antibodies," Cell, 173(2):417-429.
Chromikova et al., 2017, "Generation of a serum free CHO DG44 cell line stably producing a broadly protective anti-influenza virus monoclonal antibody," PLoS One, 12(9):e0183315 (11 pages).
Claas et al., 1998, "Human influenza A H5N1 virus related to a highly pathogenic avian influenza virus," Lancet, 351(9101):472-477.
Clementi et al., 2011, "A Human Monoclonal Antibody with Neutralizing Activity against Highly Divergent Influenza Subtypes," PLoS ONE 6(12):e28001.
Clements et al., 1986, "Serum and nasal wash antibodies associated with resistance to experimental challenge with influenza A wild-type virus," J. Clin. Microbiol., 24(1):157-160.
Cobey et al., 2017, "Immune history and influenza virus susceptibility," Curr. Opin. Virol., 22:105-111.
Cohen et al., 2013, "Influenza A penetrates host mucus by cleaving sialic acids with neuraminidase," Virol J., 10:321 (13 pages).
Communie et al., 2013, "Structure of the tetramerization domain of measles virus phosphoprotein," J Virol., 87(12):7166-7169.
Copeland et al., 2005, "Functional chimeras of human immunodeficiency virus type 1 Gp120 and influenza A virus (H3) hemagglutinin," J. Virol. 79:6459-6471.
Corti et al., 2010, "Heterosubtypic neutralizing antibodies are produced by individuals immunized with a seasonal influenza vaccine," J Clin Invest., 120(5):1663-1673.
Corti et al., 2011, "A neutralizing antibody selected from plasma cells that binds to group 1 and group 2 influenza A hemagglutinins," Science 333(6044):850-856.
Cotter et al., 2014, "A Single Amino Acid in the Stalk Region of the H1N1pdm Influenza Virus HA Protein Affects Viral Fusion, Stability and Infectivity," PLoS Pathogens 10(1):e1003831.
Couch et al., 1974, "Induction of partial immunity to influenza by a neuraminidase-specific vaccine," J Infect Dis., 129(4):411-420.
Couch et al., 2012, "A randomized clinical trial of an inactivated avian influenza A (H7N7) vaccine," PLoS One, 7(12):e49704 (6 pages).
Couch et al., 2012, "Randomized comparative study of the serum antihemagglutinin and antineuraminidase antibody responses to six licensed trivalent influenza vaccines," Vaccine, 31(1):190-195.
Couch et al., 2013, "Antibody correlates and predictors of immunity to naturally occurring influenza in humans and the importance of antibody to the neuraminidase," J Infect Dis., 207(6):974-981.
Coudeville et al., 2010, "Relationship between haemagglutination-inhibiting antibody titres and clinical protection against influenza: development and application of a bayesian random-effects model," BMC Med. Res. Methodol., 10:18 (11 pages).
Cox et al., 1998, "Influenza," Infect. Dis. Clin. North Am. 12(1):27-38.
Cox, 2013, "Correlates of protection to influenza virus, where do we go from here?," Hum. Vaccin. Immunother., 9(2):405-408.
Crotty et al., 2004, "Tracking human antigen-specific memory B cells: a sensitive and generalized ELISPOT system," J. Immunol. Methods 286 (1-2):111-122.
D'Aoust et al., 2008, "Influenza virus-like particles produced by transient expression in Nicotiana benthaminana induce a protective immune response against a lethal viral challenge in mice," J. Plant Biotechnol. 6(9):930-940.
D'Aoust et al., 2010, "The production of hemagglutinin-based virus-like particles in plants: a rapid, efficient and safe response to pandemic influenza," Plant Biotechnol. 8(5):607-619.
Da Silva et al., 2013, "Assembly of subtype 1 influenza neuraminidase is driven by both the transmembrane and head domains," J Biol Chem., 288(1):644-653 (Epub 2012).
Dai et al., 2016, "Identification of Residues That Affect Oligomerization and/or Enzymatic Activity of Influenza Virus H5N1 Neuraminidase Proteins," J. Virol., 90(20): 9457-9470.
Dalakouras et al., 2006, "Development of recombinant protein-based influenza vaccine. Expression and affinity purification of H1N1 influenza virus neuraminidase," J Chromatogr A., 1136(1):48-56.
Das et al., 2010, "Glycosylation Focuses Sequence Variation in the Influenza A Virus H1 Hemagglutinin Globular Domain," PLoS Pathogens 6(11):e1001211.
Das et al., 2013, "Defining influenza A virus hemagglutinin antigenic drift by sequential monoclonal antibody selection," Cell Host Microbe, 13(3):314-323.

(56)                    References Cited

OTHER PUBLICATIONS

Database Geneseq "Influenza A virus hemagglutinin protein, H1PR8", Accession No. AJG95109, dated Nov. 15, 2007.

Database GenPept "Hemagglutinin precursor [Contains: Hemagglutinin HA1 chain; Hemagglutinin HA2 chain]", Accession No. P03437, dated Jul. 21, 1986.

De Jong et al., 2000, "Mismatch between the 1997/1998 influenza vaccine and the major epidemic A(H3N2) virus strain as the cause of an inadequate vaccine-induced antibody response to this strain in the elderly," J Med Virol., 61(1):94-99.

Deroo et al., 1996, "Recombinant neuraminidase vaccine protects against lethal influenza," Vaccine, 14(6):561-569.

Desselberger et al., 1978, "Biochemical evidence that "new" influenza virus strains in nature may arise by recombination (reassortment)," Proc Natl Acad Sci USA, 75(7):3341-3345.

Dijkstra et al., 2009, "Long time trends in influenza-like illness and associated determinants in The Netherlands," Epidemiol Infect., 137(4):473-479.

Dilillo et al., 2014, "Broadly neutralizing hemagglutinin stalk-specific antibodies require FcγR interactions for protection against influenza virus in vivo," Nat Med., 20(2):143-151.

Dilillo et al., 2016, "Broadly neutralizing anti-influenza antibodies require Fc receptor engagement for in vivo protection," J Clin Invest., 126(2):605-610.

Dillon et al., 1992, "Induction of protective class I MHC-restricted CTL in mice by a recombinant influenza vaccine in aluminum hydroxide adjuvant," Vaccine 10(5):309-318.

Domnich et al., 2017, "Effectiveness of MF59-adjuvanted seasonal influenza vaccine in the elderly: A systematic review and meta-analysis," Vaccine, 35(4):513-520.

Doms et al., 2000, "HIV-1 Membrane Fusion: Targets of Opportunity," JCB, 151(2): F9-F13.

Dowdle et al., 1973, "Inactivated influenza vaccines. 2. Laboratory indices of protection," Postgrad Med J., 49(569):159-163.

Doyle et al., 1986, "Analysis of Progressive Deletions of the Transmembrane and Cytoplasmic Domains of Influenza Hemagglutinin," JCB 103:1193-1204.

Doyle et al., 2013, "A monoclonal antibody targeting a highly conserved epitope in influenza B neuraminidase provides protection against drug resistant strains," Biochem. Biophys. Res. Commun. 441(1):226-229.

Doyle et al., 2013, "Universal anti-neuraminidase antibody inhibiting all influenza A subtypes," Antiviral Res., 100(2):567-574.

Dreyfus et al., 2012, "Highly conserved protective epitopes on influenza B viruses," Science, 337(6100):1343-1348.

Dubensky et al., 1996, "Sindbis virus DNA-based expression vectors: utility for in vitro and in vivo gene transfer," J Virol., 70(1):508-519.

Dunand et al., 2016, "Both Neutralizing and Non-Neutralizing Human H7N9 Influenza Vaccine-Induced Monoclonal Antibodies Confer Protection," Cell Host Microbe., 19(6):800-813.

Durrant et al., 2016, "Microsecond Molecular Dynamics Simulations of Influenza Neuraminidase Suggest a Mechanism for the Increased Virulence of Stalk-Deletion Mutants," J. Phys. Chem. B., 120(33):8590-8599.

Easterbrook et al., 2012, "Protection against a lethal H5N1 influenza challenge by intranasal immunization with virus-like particles containing 2009 pandemic H1N1 neuraminidase in mice," Virology, 432(1):39-44.

Eda et al., 2006, "Sequential immunization with V3 peptides from primary human immunodeficiency virus type 1 produces cross-neutralizing antibodies against primary isolates with a matching narrow-neutralization sequence motif," J. Virol. 80(11):5552-5562.

Edwards et al., 2003, "The remarkable flexibility of the human antibody repertoire; isolation of over one thousand different antibodies to a single protein, BLyS," J. Mol. Biol., 334(1):103-118.

Ekiert et al., 2009, "Antibody recognition of a highly conserved influenza virus epitope", Science;324(5924):246-251.

Ekiert et al., 2011, "A highly conserved neutralizing epitope on group 2 influenza A viruses", Science 333:843-850.

Ekiert et al., 2012, "Broadly neutralizing antibodies against influenza virus and prospects for universal therapies," Curr Opin Virol., 2(2):134-141.

Ekiert et al., 2012, "Cross-neutralization of influenza A viruses mediated by a single antibody loop," Nature 489:526-532.

Ellebedy et al., 2014, "Induction of broadly cross-reactive antibody responses to the influenza HA stem region following H5N1 vaccination in humans," Proc Natl Acad Sci USA, 111(36):13133-13138.

EMA Guideline on the exposure to medicinal products during pregnancy: need for post-authorization data (Doc. Ref. EMEA/CHMP/313666/2005), adopted at Community level in May 2006; http://www.ema.europa.eu/docs/en_GB/document_library/Regulatory_and_procedural_guideline/2009/11/WC500011303.pdf (21 pages).

Eriksson et al., 2007, "Local and systemic cytokine and chemokine responses after parenteral influenza vaccination," Influenza Other Respir Viruses, 1(4):139-146.

Ermler et al., 2017, "Chimeric Hemagglutinin Constructs Induce Broad Protection against Influenza B Virus Challenge in the Mouse Model," J. Virol. 91(12): e00286-17.

Extended European Search Report for European Application No. 11763347.9, dated Feb. 2, 2015.

Fields et al., 1981, "Structure of the neuraminidase gene in human influenza virus A/PR/8/34," Nature, 290(5803):213-217.

Fiore et al., 2010, "Prevention and control of influenza with vaccines: recommendations of the Advisory Committee on Immunization Practices (ACIP), 2010," MMWR Recomm. Rep., 59(RR-8):1-62.

Fiore et al., 2011, "Antiviral agents for the treatment and chemoprophylaxis of influenza—recommendations of the Advisory Committee on Immunization Practices (ACIP)," MMWR Recomm Rep., 60(1):1-24.

Fitch et al., 1997, "Long term trends in the evolution of H(3) HA1 human influenza type A," Proc. Natl. Acad. Sci. USA, 94(15):7712-7718.

Flandorfer et al., 2003, "Chimeric Influenza A Viruses with a Functional Influenza B Virus Neuraminidase or Hemagglutinin," J. Virol. 77(17):9116-9123.

Fleury, et al., 2007, GenBank Acc. No. P03437, Updated Apr. 3, 2007.

Fluzone®, 2009-2010 Fluzone Seasonal influenza vaccine package insert, 2009.

Fodor et al., 1999, "Rescue of influenza A virus from recombinant DNA," J. Virol. 73:9679-9682 (1999).

Fouchier et al., 2004, "Avian influenza A virus (H7N7) associated with human conjunctivitis and a fatal case of acute respiratory distress syndrome," Proc Natl Acad Sci USA, 101(5):1356-1361.

Fox et al., 1982, "Influenzavirus infections in Seattle families, 1975-1979. II. Pattern of infection in invaded households and relation of age and prior antibody to occurrence of infection and related illness," Am J Epidemiol., 116(2):228-242.

Friesen et al., 2014, "A common solution to group 2 influenza virus neutralization," Proc. Natl. Acad. Sci. USA, 111(1):445-450 (Epub 2013).

Fujii et al., 2002, "Selective incorporation of influenza virus RNA segments into virions," Proc. Natl. Acad. Sci. USA 100:2002-2007.

Fulton et al., 2018, "The Influenza B Virus Hemagglutinin Head Domain Is Less Tolerant to Transposon Mutagenesis than That of the Influenza A Virus," J Virol., 92(16):e00754-18 (13 pages).

Gamblin et al., 2004, "The structure and receptor binding properties of the 1918 influenza hemagglutinin," Science, 303(5665):1838-1842.

Gao et al., 2009, "Rewiring the RNAs of influenza virus to prevent reassortment," Proc. Natl. Acad. Sci. USA 106:15891-15896.

Gao et al., 2013, "Human infection with a novel avian-origin influenza A(H7N9) virus," N. Engl. J. Med. 368:1888-1897.

Gao et al., 2016, "Measuring Influenza Neuraminidase Inhibition Antibody Titers by Enzyme-linked Lectin Assay," J. Vis. Exp., (115):e54573 (9 pages).

Gao et al., 2019, "Antigenic Drift of the Influenza A(H1N1)pdm09 Virus Neuraminidase Results in Reduced Effectiveness of A/California/7/2009 (H1N1pdm09)-Specific Antibodies," mBio, 10(2):e00307-19 (17 pages).

(56) References Cited

OTHER PUBLICATIONS

García-Sastre et al., 1994, "Introduction of foreign sequences into the genome of influenza A virus," Dev. Biol. Stand 82:237-246.

García-Sastre et al., 1994, "Use of a mammalian internal ribosomal entry site element for expression of a foreign protein by a transfectant influenza virus," J. Virol. 68:6254-6261.

Garcon et al., 2012, "Development and evaluation of AS03, an Adjuvant System containing α-tocopherol and squalene in an oil-in-water emulsion," Expert Rev Vaccines, 11(3):349-366.

Gauger et al., 2011, "Enhanced pneumonia and disease in pigs vaccinated with an inactivated human-like (δ-cluster) HIN2 vaccine and challenged with pandemic 2009 H1N1 influenza virus," Vaccine 29(15):2712-2719.

Gavigan et al., 2019, "Influenza: annual seasonal severity," Curr. Opin. Pediatr., 31(1):112-118.

Gaymard et al., 2016, "Functional balance between neuraminidase and haemagglutinin in influenza viruses," Clin. Microbiol. Infect., 22(12):975-983.

GenBank Accession No. AAA43397.1, neuraminidase [Influenza A virus (A/WSN/1933(H1N1))], 1982.

GenBank Accession No. AAA43412.1, neuraminidase [Influenza A virus (A/Puerto Rico/Aug. 1934(H1N1))], 1981.

GenBank Accession No. AAQ90293.1, neuraminidase [Influenza A virus (A/equine/Santiago/77(H7N7))], 2003.

GenBank Accession No. AAS89005.1, neuraminidase [Influenza A virus (A/Thailand/3(SP-83)/2004(H5N1))], 2005.

GenBank Accession No. ABE97718.1, neuraminidase [Influenza A virus (A/Vietnam/CL100/2004(H5N1))], 2006.

GenBank Accession No. ABE97719.1, neuraminidase [Influenza A virus (A/Vietnam/CL105/2005(H5N1))], 2006.

GenBank Accession No. ABE97720.1, neuraminidase [Influenza A virus (A/Vietnam/CL115/2005(H5N1))], 2006.

GenBank Accession No. ABG23658.1, neuraminidase, partial [Influenza A virus (A/Zhejiang/16/2006(H5N1))], 2007.

GenBank Accession No. ACQ76318, hemagglutinin [Influenza A virus (A/California/04/2009(H1N1))], 2009.

GenBank Accession No. ACS71642, haemagglutinin [Influenza A virus (A/Perth/16/2009(H3N2))], 2009.

GenBank Accession No. AEX30531.1, neuraminidase [Influenza A virus (A/chicken/N101/Iran/2011(H9N2))], 2011.

GenBank Accession No. AEX30532.1, neuraminidase [Influenza A virus (A/chicken/N102/Iran/2011(H9N2))], 2011.

GenBank Accession No. AG018161.1, *Homo sapiens* genomic DNA, 21q region, clone: B396A17A4a015, genomic survey sequence, 1999.

GenBank Accession No. AIA62041.1, neuraminidase [Influenza A virus (A/goose/Guangxi/020G/2009(H3N8))], 2014.

GenBank Accession No. AII30325.1, neuraminidase [Influenza A virus (A/pigeon/Guangxi/020P/2009(H3N6))], 2015.

GenBank Accession No. BAF48478-2007, haemagglutinin [Influenza A virus (A/duck/Czech/1956(H4N6))], 2007.

GenBank Accession No. CRI06477.1, neuraminidase [Influenza A virus (A/England/10740685/2010(H1N1))], 2015.

GenBank Accession No. CY209719.1, Influenza B virus (B/Arizona/36/2016) NB protein (NB) and neuraminidase (NA) genes, complete cds, last modified Dec. 21, 2016.

GenBank Accession No. DQ017504.1, Influenza A virus (A/mallard/Alberta/24/01(H7N3)) from Canada segment 4, complete sequence, 2005.

GenBank Accession No. KY090574.1, Influenza B virus (B/Pennsylvania/34/2015) segment 6 NB protein (NB) and neuraminidase (NA) genes, complete cds, last modified Aug. 24, 2017.

GenBank Accession No. NP_040981.1, neuraminidase [Influenza A virus (A/Puerto Rico/8/1934(H1N1))], 1981.

GenBank NCBI Reference Sequence: YP_163736.1, HA2 [Influenza A virus (A/Puerto Rico/8/1934(H1N1))].

Georgiev et al., 2018, "Two-Component Ferritin Nanoparticles for Multimerization of Diverse Trimeric Antigens," ACS Infect Dis., 4(5):788-796.

Gerdil, 2003, "The annual production cycle for influenza vaccine," Vaccine, 21(16):1776-1779.

Gerhard et al., 1981, "Antigenic structure of influenza virus haemagglutinin defined by hybridoma antibodies," Nature, 290(5808):713-717.

Gerhard et al., 2006, "Prospects for universal influenza virus vaccine," Emerging Infectious Diseases; 12(4):569-574.

Gibbs et al., 2001, "Recombination in the hemagglutinin gene of the 1918 Spanish Flu," Science 293(5536):1842-1845.

Giddings et al., 2000, "Transgenic plants as factories for biopharmaceuticals," Nat. Biotechnol. 18:1151-1155.

Giles et al., 2012, "Computationally optimized antigens to overcome influenza viral diversity," Expert Rev Vaccines, 11(3):267-269.

Glezen et al., 1978, "Interpandemic influenza in the Houston area, 1974-76," N Engl J Med., 298(11):587-592.

Gocnik et al., 2008, "Antibodies Induced by the HA2 Glycopolypeptide of Influenza Virus Haemagglutinin Improve Recovery from Influenza A Virus Infection," J Gen Virol., 89:958-967.

Goel et al., 2004, "Plasticity within the antigen-combining site may manifest as molecular mimicry in the humoral immune response," J. Immunol., 173(12):7358-7367.

Goff et al., 2013, "Induction of cross-reactive antibodies to novel H7N9 influenza virus by recombinant Newcastle disease virus expressing a North American lineage H7 subtype hemagglutinin," J. Virol., 87(14): 8235-8240.

Goff et al., 2013, "Adjuvants and immunization strategies to induce influenza virus hemagglutinin stalk antibodies", PLoS One 8:e79194.

Gomord et al., 2005, "Biopharmaceutical production in plants: problems, solutions and opportunities." TRENDS in Biotechnology, 23(11):559-565.

Goto et al., 2013, "The genome-packaging signal of the influenza A virus genome comprises a genome incorporation signal and a genome-bundling signal," J. Virol., 87(21):11316-11322.

Gould et al., 1987, "Mouse H-2k-Restricted Cytotoxic T Cells Recognize Antigenic Determinants in Both The HAI and HA2 Subunits of the Influenza A/PR/8/34 Hemagglutinin," J. Exp. Med., 166:693-701.

Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.

Gravel et al., 2010, "Qualitative and quantitative analyses of virtually all subtypes of influenza A and B viral neuraminidases using antibodies targeting the universally conserved sequences," Vaccine 28(36):5774-5784.

Graves et al., 1983, "Preparation of influenza virus subviral particles lacking the HAI subunit of hemagglutinin: unmasking of cross-reactive HA2 determinants," Virology 126(1):106-116.

Grohskopf et al., 2017, "Prevention and Control of Seasonal Influenza with Vaccines: Recommendations of the Advisory Committee on Immunization Practices—United States, 2017-18 Influenza Season," MMWR Recomm. Rep., 66(2): 1-20.

Gross et al., 1995, "The efficacy of influenza vaccine in elderly persons. A meta-analysis and review of the literature," Ann Intern Med., 123(7):518-527.

Gubareva et al., 2000, "Influenza virus neuraminidase inhibitors," Lancet, 355(9206):827-835.

Gulati et al., 2002, "Antibody epitopes on the neuraminidase of a recent H3N2 influenza virus (A/Memphis/31/98)," J Virol., 76(23):12274-12280.

Haffer et al., 1990, "Human immunodeficiency virus-like, nonreplicating, gag-env particles assemble in a recombinant vaccinia virus expression system," J Virol., 64(6):2653-2659.

Hagnesee et al., 1991, "Self-assembly of human papillomavirus type 1 capsids by expression of the L1 protein alone or by coexpression of the L1 and L2 capsid proteins," J Virol., 67(1):315-322.

Hai et al., 2008, "Influenza B virus NS1-truncated mutants: live-attenuated vaccine approach", J Virol 82:10580-10590.

Hai et al., 2011, "A reassortment-incompetent live attenuated influenza virus vaccine for protection against pandemic virus strains", Journal of virology 85:6832-6843.

(56)        References Cited

OTHER PUBLICATIONS

Hai et al., 2012, "Influenza viruses expressing chimeric hemag-glutinins: globular head and stalk domains derived from different subtypes", J. Virol. 86:5774-5781.

Hai et al., 2013, "Influenza A(H7N9) virus gains neuraminidase inhibitor resistance without loss of in vivo virulence or transmis-sibility," Nat Commun., 4:2854 (9 pages).

Halbherr et al., 2015, "Biological and protective properties of immune sera directed to the influenza virus neuraminidase," J Virol., 89(3):1550-1563 (Epub Nov. 12, 2014).

Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.

Hamilton et al., 2016, "Club cells surviving influenza A virus infection induce temporary nonspecific antiviral immunity," Proc Natl Acad Sci USA, 113(14):3861-3866.

Hanks et al., 2005, "Re-engineered CD40 receptor enables potent pharmacological activation of dendritic-cell cancer vaccines in vivo," Nat Med., 11(2):130-137 and supplemental materials.

Harris et al., 2006, "Influenza virus pleiomorphy characterized by cryoelectron tomography," Proc Natl Acad Sci USA, 103(50):19123-19127.

Harvey et al., 2011, "Improved antigen yield in pandemic H1N1 (2009) candidate vaccine viruses with chimeric hemagglutinin molecules," J Virol., 85(12):6086-6090.

Haynes, 2009, "Influenza virus-like particle vaccines", Expert Rev. Vaccines, 8(4): 435-445.

He et al., 2014, "Infection of influenza virus neuraminidase-vaccinated mice with homologous influenza virus leads to strong protection against heterologous influenza viruses," J Gen Virol., 95(Pt 12):2627-2637.

He et al., 2017, "Alveolar macrophages are critical for broadly-reactive antibody-mediated protection against influenza A virus in mice," Nat. Commun., 8(1):846 (14 pages).

Heaton et al., 2013, "Genome-wide mutagenesis of influenza virus reveals unique plasticity of the hemagglutinin and NS1 proteins," Proc Natl Acad Sci USA, 110(50):20248-20253.

Heaton et al., 2013, "In Vivo Bioluminescent Imaging of Influenza A Virus Infection and Characterization of Novel Cross-Protective Monoclonal Antibodies," J. Virol. 87(15):8272-8281.

Heikkinen et al., 2014, ",Impact of influenza B lineage-level mis-match between trivalent seasonal influenza vaccines and circulating viruses, 1999-2012" Clin Infect Dis., 59(11):1519-1524.

Heinonen et al., 2010, "Early oseltamivir treatment of influenza in children 1-3 years of age: a randomized controlled trial," Clin Infect Dis., 51(8):887-894.

Hobson et al., 1972, "The role of serum haemagglutination-inhibiting antibody in protection against challenge infection with influenza A2 and B viruses," J Hyg (Lond), 70(4):767-777.

Hoffmann et al., 2000, "A DNA transfection system for generation of influenza A virus from eight plasmids," Proc Natl Acad Sci USA, 97(11):6108-6113.

Hong et al., 2013, "Antibody recognition of the pandemic H1N1 Influenza virus hemagglutinin receptor binding site," J. Virol. 87(22):12471-12480.

Horimoto et al., 2003, "Generation of influenza A viruses with chimeric (type A/B) hemagglutinins." J Virol. 77(14):8031-8038.

Horimoto et al., 2004, "Influenza A viruses possessing type B hemagglutinin and neuraminidase: potential as vaccine compo-nents," Microbes and Infection, 6(6):579-583.

Horvath et al., 1998, "Hemagglutinin-based multipeptide construct elicits enhanced protective immune response in mice against influ-enza A virus infection", Immunology Letters; 60(2/03):127-136.

Hu et al., 2013, "Fully human broadly neutralizing monoclonal antibodies against influenza A viruses generated from the memory B cells of a 2009 pandemic H1N1 influenza vaccine recipient," Virology 435(2):320-328.

Huang et al., 2004, "The Reverse Genetics Systems for Human and Animal RNA Viruses," Chinese Journal of Biotechnology, vol. 20, Issue 3, which is also published in Lian Yu, "Molecular Biology of Infectious Bursal Disease Virus and Research on New Vaccines," Zhejiang University Press, pp. 254-266, published on Dec. 31, 2007 (in Chinese with English abstract).

Hutchinson et al., 2010, "Genome packaging in influenza A virus," J. Gen. Virol., 91(Pt 2):313-328 (Epub 2009).

Iba et al., 2014, "Conserved neutralizing epitope at globular head of hemagglutinin in H3N2 influenza viruses" J. Virol., 88(13):7130-7144.

Igarashi et al.: 2008, "Genetically destined potentials for N-linked glycosylation of influenza virus hemagglutinin" Virology, 376:323-329.

Impagliazzo et al., 2015, "A stable trimeric influenza hemagglutinin stem as a broadly protective immunogen." Science, 349(6254):1301-1306 and supplemental materials.

Influenza Research Database, strain name: A/Anhui/1/2005, Col-lection Date: 2005 (2 pages).

Influenza Research Database, strain name: A/Bar-headed Goose/Qinghai/59/05, Collection Date: 2005 (2 pages).

Influenza Research Database, strain name: A/California/07/2009, Collection Date: Apr. 9, 2009 (3 pages).

Influenza Research Database, strain name: A/Indonesia/5/2005, Collection Date: 2005 (3 pages).

Influenza Research Database, strain name: A/turkey/Turkey/1/2005, Collection Date: 2005 (2 pages).

Influenza Research Database, strain name: A/Viet Nam/1203/2004, Collection Date: 2004 (3 pages).

Influenza Research Database, strain name: A/whooper swan/Mongolia/244/2005, Collection Date: 2005 (2 pages).

Influenza Research Database, strain name: B/Brisbane/60/2008, Collection Date: 2008 (2 pages).

Influenza Research Database, strain name: B/Florida/04/2006, Col-lection Date: Nov. 1, 2006 (1 page).

Influenza Research Database, strain name: B/lee/40, Collection Date: 1940 (1 page).

Influenza Research Database, strain name: B/Malaysia/2506/2004, Collection Date: May 12, 2004 (2 pages).

Influenza Research Database, strain name: B/Massachusetts/02/2012, Collection Date: Mar. 13, 2012 (1 page).

Influenza Research Database, strain name: B/New Jersey/01/2012, Collection Date: Apr. 26, 2012 (1 page).

Influenza Research Database, strain name: B/Texas/02/2013, Col-lection Date: Jan. 9, 2013 (1 page).

Influenza Research Database, strain name: B/Victoria/2/87, Collec-tion Date: 1987 (1 page).

Influenza Research Database, strain name: B/Wisconsin/01/2010, Collection Date: 2010 (1 page).

Influenza Research Database, strain name: B/Yamagata/16/88, Col-lection Date: 1988 (2 pages).

International Preliminary Report on Patentability for International Patent Application No. PCT/US2010/043697 (Pub No. WO 2011014645) issued Jan. 31, 2012 (10 pages).

International Preliminary Report on Patentability of International application No. PCT/US2011/030441, dated Oct. 2, 2012.

International Search Report and Corrected Written Opinion for International Patent Application No. PCT/US2020/029582 (Pub No. WO 2020219719) mailed Sep. 28, 2020 (30 pages).

International Search Report and Written Opinion for International Patent Application No. PCT/US2010/043697 (Pub No. WO 2011014645) mailed Nov. 17, 2010 (16 pages).

International Search Report and Written Opinion for International Patent Application No. PCT/US2020/039588 (Pub No. WO 2020264141) mailed Nov. 9, 2020 (18 pages).

International Search Report and Written Opinion for International Patent Application No. PCT/US2020/056703 (Pub No. WO 2021081120) mailed Feb. 9, 2021 (13 pages).

International Search Report and Written Opinion mailed Oct. 29, 2019 of International Patent Application No. PCT/US2019/038178 (16 pages).

International Search Report issued on Feb. 19, 2013 or PCT Application No. PCT/US2012/056122, Published as WO 2013/043729.

(56) References Cited

OTHER PUBLICATIONS

International Search Report issued on Apr. 28, 2014 of PCT Application No. PCT/US2013/075697, Published as WO 2014/099931.
International Search Report issued on Jun. 26, 2014 for PCT Application No. PCT/US2014/025526, Published as WO 2014/159960.
International Search Report issued on Jul. 13, 2011 of PCT Application No. PCT/US2011/030441, Published as WO 2011/123495.
International Search Report issued on Aug. 24, 2010 or PCT Application No. PCT/US2010/029202, Published as WO 2010/117786.
International Search Report of International Application No. PCT/US2010/036170, dated Aug. 17, 2010.
International Search Report of International Application No. PCT/US2011/025467, dated Oct. 19, 2011.
International Search Report of International Application No. PCT/US2016/014640, mailed Jun. 3, 2016.
International Search Report of International Application No. PCT/US2016/037595, mailed Sep. 15, 2016.
International Search Report of International Application No. PCT/US2017/035479, mailed Oct. 25, 2017.
International Search Report of International Application No. PCT/US2017/037384, mailed Nov. 3, 2017.
International Search Report of International Application No. PCT/US2018/026489, mailed Aug. 27, 2018.
International Search Report of International Application No. PCT/US2018/045399, mailed Nov. 29, 2018.
Isakova-Sivak et al., 2011, "Genetic bases of the temperature-sensitive phenotype of a master donor virus used in live attenuated influenza vaccines: A/Leningrad/134/17/57 (H2N2)," Virology, 412(2):297-305.
Isakova-Sivak et al., 2015, "Safety, immunogenicity and infectivity of new live attenuated influenza vaccines," Expert Rev Vaccines, 14(10):1313-1329.
Izurieta et al., 2000, "Influenza and the rates of hospitalization for respiratory disease among infants and young children," NEJM 342(4):232-239.
Jacobsen et al., 2017, "Influenza Virus Hemagglutinin Stalk-Specific Antibodies in Human Serum are a Surrogate Marker for In Vivo Protection in a Serum Transfer Mouse Challenge Model," mBio, 8(5):e01463-17 (13 pages).
Jayasundara et al., 2014, "Natural attack rate of influenza in unvaccinated children and adults: a meta-regression analysis," BMC Infect Dis., 14:670 (9 pages).
Jefferson et al., 2005, "Assessment of the efficacy and effectiveness of influenza vaccines in healthy children: systematic review," Lancet, 365(9461):773-780.
Jefferson et al., 2005, "Efficacy and effectiveness of influenza vaccines in elderly people: a systematic review," Lancet, 366(9492):1165-1174.
Jeoung et al., 1995, "Effects of tumor necrosis factor-alpha on antimitogenicity and cell cycle-related proteins in MCF-7 cells." J Biol Chem., 270(31):18367-18373.
Jerne et al., 1982, "Recurrent idiotopes and internal images," EMBO J., 1(2):243-247.
Jin et al., 2003, "Multiple amino acid residues confer temperature sensitivity to human influenza virus vaccine strains (FluMist) derived from cold-adapted A/Ann Arbor/6/60," Virology, 306(1):18-24.
Job et al., 2018, "Broadened immunity against influenza by vaccination with computationally designed influenza virus N1 neuraminidase constructs," NPJ Vaccines, 3:55 (11 pages).
Joh Hira et al., 2004, "Production of monoclonal antibodies against a conserved region of Hemagglutinin of Influenza A virus and enzymatic activity of the light chain," Lectures in the Chemical Society of Japan, 84(2):1156, 2 J6-15 in Japanese with English translation of Abstract (4 pages).

Johansson et al., 1987, "Antigen-presenting B cells and helper T cells cooperatively mediate intravirionic antigenic competition between influenza A virus surface glycoproteins," Proc Natl Acad Sci USA, 84(19):6869-6873.
Johansson et al., 1987, "Immunologic response to influenza virus neuraminidase is influenced by prior experience with the associated viral hemagglutinin. II. Sequential infection of mice simulates human experience," J. Immunol., 139(6):2010-2014.
Johansson et al., 1989, "Purified influenza virus hemagglutinin and neuraminidase are equivalent in stimulation of antibody response but induce contrasting types of immunity to infection," J. Virol., 63(3):1239-1246.
Johansson et al., 1993, "Dissociation of influenza virus hemagglutinin and neuraminidase eliminates their intravirionic antigenic competition," J Virol., 67(10):5721-5723.
Johansson et al., 1994, "Immunization with purified N1 and N2 influenza virus neuraminidases demonstrates cross-reactivity without antigenic competition," Proc Natl Acad Sci USA, 91(6):2358-2361.
Johansson et al., 1998, "Supplementation of conventional influenza A vaccine with purified viral neuraminidase results in a balanced and broadened immune response," Vaccine, 16(9-10):1009-1015.
Johansson et al., 2011, "Influenza viral neuraminidase: the forgotten antigen," Expert Rev. Vaccines, 10(12):1683-1695.
Johnson et al., 2002, "Updating the accounts: global mortality of the 1918-1920 "Spanish" influenza pandemic," Bull Hist Med., 76(1):105-115.
Joseph et al., 2007, "Evaluation of replication and pathogenicity of avian influenza a H7 subtype viruses in a mouse model," J Virol., 81(19):10558-10566.
Kabat et al., 1971, "Attempts to locate complementarity-determining residues in the variable positions of light and heavy chains," Ann N Y Acad Sci., 190:382-393.
Kamlangdee et al., 2016, "Mosaic H5 Hemagglutinin Provides Broad Humoral and Cellular Immune Responses Against Influenza Viruses," J Virol., 90(15):6771-6783.
Kanekiyo et al., 2013, "Self-assembling influenza nanoparticle vaccines elicit broadly neutralizing H1N1 antibodies." Nature, 499(7456):102-106.
Karlin et al., 1990, "Methods for assessing the statistical significance of molecular sequence features by using general scoring schemes," Proc Natl Acad Sci USA, 87(6):2264-2268.
Karlin et al., 1993, "Applications and statistics for multiple high-scoring segments in molecular sequences," Proc Natl Acad Sci USA, 90(12):5873-5877.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Kawai et al., 2006, "A comparison of the effectiveness of oseltamivir for the treatment of influenza A and influenza B: a Japanese multicenter study of the 2003-2004 and 2004-2005 influenza seasons," Clin Infect Dis., 43(4):439-444.
Kawai et al., 2007, "Longer virus shedding in influenza B than in influenza A among outpatients treated with oseltamivir," J Infect., 55(3):267-272.
Kayali et al., 2011, "Evidence of infection with H4 and H11 avian influenza viruses among Lebanese chicken growers," PLoS One, 6(10):e26818.
Khanna et al., 2014, "Protective Immunity Based on the Conserved Hemagglutinin Stalk Domain and Its Prospects for Universal Influenza Vaccine Development," Biomed Res Int., 2014:546274 (7 pages).
Khiabanian et al., 2009, "Differences in patient age distribution between influenza A subtypes," PLoS One, 4(8):e6832 (5 pages).
Khurana et al., 2011, "MF59 adjuvant enhances diversity and affinity of antibody-mediated immune response to pandemic influenza vaccines," Sci. Transl. Med., 3(85):85ra48 (10 pages).

(56)                    References Cited

OTHER PUBLICATIONS

Khurana et al., 2013, "Vaccine-induced anti-HA2 antibodies pro-
mote virus fusion and enhance influenza virus respiratory disease,"
Sci Transl Med., 5(200):200ra114.
Khurana et al., 2013, "DNA Priming Prior to Inactivated Influenza
A(H5N1) Vaccination Expands the Antibody Epitope Repertoire
and Increases Affinity Maturation in a Boost-Interval-Dependent
Manner in Adults," Journal of Infectious Disease, 208:413-417.
Kilbourne et al., 1976, "Comparative efficacy of neuraminidase-
specific and conventional influenza virus vaccines in induction of
antibody to neuraminidase in humans," J Infect Dis., 134(4):384-
394.
Kilbourne et al., 1987, "Immunologic response to the influenza
virus neuraminidase is influenced by prior experience with the
associated viral hemagglutinin. I. Studies in human vaccinees," J
Immunol., 138(9):3010-3013.
Kilbourne et al., 1990, "Independent and disparate evolution in
nature of influenza A virus hemagglutinin and neuraminidase
glycoproteins," Proc Natl Acad Sci USA, 87(2):786-790.
Kilbourne et al., 1995, "Purified influenza A virus N2 neuraminidase
vaccine is immunogenic and non-toxic in humans," Vaccine,
13(18):1799-1803.
Kirnbauer et al., 1992, "Papillomavirus L1 major capsid protein
self-assembles into virus-like particles that are highly immuno-
genic," Proc Natl Acad Sci USA, 89(24):12180-12184.
Kistner et al., 2007, "Cell culture (Vero) derived whole virus
(H5N1) vaccine based on wild-type virus strain induces cross-
protective immune responses," Vaccine 25(32):6028-6036.
Klausberger et al., 2014, "One-shot vaccination with an insect
cell-derived low-dose influenza A H7 virus-like particle preparation
protects mice against H7N9 challenge," Vaccine, 32(3):355-362
(Epub 2013).
Koel et al., 2013, "Substitutions near the receptor binding site
determine major antigenic change during influenza virus evolution,"
Science, 342(6161):976-979.
Kon et al., 2016, "Influenza Vaccine Manufacturing: Effect of
Inactivation, Splitting and Site of Manufacturing. Comparison of
Influenza Vaccine Production Processes," PLoS One, 11(3):e0150700
(19 pages).
Kosik et al., 2019, "Neuraminidase inhibition contributes to influ-
enza A virus neutralization by anti-hemagglutinin stem antibodies,"
J. Exp. Med., 216(2):304-316.
Krammer et al., 2010. "Trichoplusia ni cells (High Five) are highly
efficient for the production of influenza A virus-like particles: a
comparison of two insect cell lines as production platforms for
influenza vaccines," Mol Biotechnol., 45(3):226-234.
Krammer et al., 2012, "A carboxy-terminal trimerization domain
stabilizes conformational epitopes on the stalk domain of soluble
recombinant hemagglutinin substrates," PLoS One. 7:e43603.
Krammer et al., 2012, "Hemagglutinin stalk-reactive antibodies are
boosted following sequential infection with seasonal and pandemic
H1N1 influenza virus in mice", J Virol, 86:10302-10307.
Krammer et al., 2013, "Influenza virus hemagglutinin stalk-based
antibodies and vaccines," Curr. Opin. Virol., 3(5):521-530.
Krammer et al., 2013, "Chimeric hemagglutinin influenza virus
vaccine constructs elicit broadly protective stalk-specific antibod-
ies", J Virol. 87:6542-6550.
Krammer et al., 2014, "An H7N1 influenza virus vaccine induces
broadly reactive antibody responses against H7N9 in humans," Clin
Vaccine Immunol., 21(8):1153-1163.
Krammer et al., 2014, "Divergent H7 immunogens offer protection
from H7N9 virus challenge," J Virol., 88(8):3976-3985.
Krammer et al., 2014, "Assessment of influenza virus hemag-
glutinin stalk-based immunity in ferrets," J. Virol., 88:3432-3442.
Krammer et al., 2014, "H3 stalk-based chimeric hemagglutinin
influenza virus constructs protect mice from H7N9 challenge", J
Virol, 88:2340-2343.
Krammer et al., 2015, "Advances in the development of influenza
virus vaccines," Nat Rev Drug Discov., 14(3):167-182.

Krammer et al., 2018, "Influenza," Nat. Rev. Dis. Primers, 4(1):3
(21 pages).
Krammer et al., 2018, "NAction! How Can Neuraminidase-Based
Immunity Contribute to Better Influenza Virus Vaccines?," mBio,
9(2):e02332-17 (12 pages).
Krammer et al., 2019, "Emerging from the Shadow of Hemag-
glutinin: Neuraminidase Is an Important Target for Influenza Vac-
cination," Cell Host Microbe., 26(6):712-713.
Krammer et al., 2019, "Universal Influenza Virus Vaccines That
Target the Conserved Hemagglutinin Stalk and Conserved Sites in
the Head Domain, " J. Infect. Dis., 219(Suppl_1):S62-S67.
Krammer, 2015, "Emerging influenza viruses and the prospect of a
universal influenza virus vaccine," Biotechnol. J., 10(5):690-701.
Krammer, 2015, "The quest for a universal flu vaccine: headless HA
2.0", Cell Host Microbe, 18:395-397.
Krammer, 2016, "Novel universal influenza virus vaccine approaches",
Current Opinion in Virology, 17:95-103.
Krammer, 2017, "Annex I: Sequence comparison of the J&J, VRC
and MSSM headless HA constructs (tentative H3 numbering included)"
(3 pages).
Krammer, 2017, "Strategies to induce broadly protective antibody
responses to viral glycoproteins," Expert Rev. Vaccines, 16(5):503-
513.
Krammer, 2019, "The human antibody response to influenza A virus
infection and vaccination, " Nat. Rev. Immunol., 19(6):383-397.
Krause et al., 2011, "A broadly neutralizing human monoclonal
antibody that recognizes a conserved, novel epitope on the globular
head of the influenza H1N1 virus hemagglutinin", J. Virol.,
85(20):10905-10908.
Krause et al., 2012, "Human monoclonal antibodies to pandemic
1957 H2N2 and pandemic 1968 H3N2 influenza viruses", J. Virol.
86:6334-6340.
Laguio-Vila et al., 2015, "Comparison of serum hemagglutinin and
neuraminidase inhibition antibodies after 2010-2011 trivalent inac-
tivated influenza vaccination in healthcare personnel," Open Forum
Infect. Dis., 2(1):ofu115 (9 pages).
Lambe et al., 2013, "Immunity against heterosubtypic influenza
virus induced by adenovirus and MVA expressing nucleoprotein and
matrix protein-1," Sci Rep., 3:1443 (8 pages).
Landry et al., 2008, "Three-dimensional structure determines the
pattern of CD4+ T-cell epitope dominance in influenza virus hemag-
glutinin", Journal of Virology; 82(3):1238-1248.
Landry et al., 2010, "Preclinical and Clinical Development of
Plant-Made Virus-Like Particle Vaccine against Avian H5N1 Influ-
enza", PLoS One, 5(12): e15559. (12 pages).
Larkin et al., 2007, "Clustal W and Clustal X version 2.0," Bioin-
formatics, 23(21):2947-2948.
Laver et al., 1981, "Mechanism of antigenic drift in influenza virus.
Amino acid sequence changes in an antigenically active region of
Hong Kong (H3N2) influenza virus hemagglutinin," J Mol Biol.,
145(2):339-361.
Laver et al., 1988, "Crystallization and preliminary X-ray analysis
of type B influenza virus neuraminidase complexed with antibody
Fab fragments," Virology, 167(2):621-624.
Lebendiker, 2006, "Purification Protocols." The Wolfson Centre for
Applied Structural Biology, http://wolfson.huji.ac.il/purification/
Purification_Protocols.html. Apr. 5, 2006 (30 pages).
Ledgerwood et al., 2011, "DNA priming and influenza vaccine
immunogenicity: two phase 1 open label randomised clinical trials,"
Lancet Infect Dis., 11(12):916-924.
Ledgerwood, et al., 2013, "Prime-Boost Interval Matters: A Ran-
domized Phase 1 Study to Identify the Minimum Interval Necessary
to Observe the H5 DNA Influenza Vaccine Priming Effect," Journal
of Infectious Diseases, 208:418-422.
Lee et al., 2012, "Heterosubtypic antibody recognition of the
influenza virus hemagglutinin receptor binding site enhanced by
avidity", Proc. Natl. Acad. Sci. USA 109:17040-17045.
Lee et al., 2014, "Receptor mimicry by antibody F045-092 facili-
tates universal binding to the H3 subtype of influenza virus," Nat.
Commun., 5:3614 (9 pages).
Lehninger et al., 1993, "Chapter 7: The Three-Dimensional Struc-
ture of Proteins," Principles of Biochemistry with an Extended

(56)        References Cited

OTHER PUBLICATIONS

Desicussion of Oxygen-Binding Proteins, Second Edition, Worth Publishers, pp. 160, 161 and 175-185.

Leon et al., 2016, "Optimal activation of Fc-mediated effector functions by influenza virus hemagglutinin antibodies requires two points of contact," Proc. Natl. Acad. Sci. USA, 113(40):E5944-E5951.

Leroux-Roels, et al. 2008. "Broad Glade 2 cross-reactive immunity induced by an adjuvanted Glade 1 rH5N1 pandemic influenza vaccine", PLOS One; 3(2):e1665 (5 pages).

Li et al., 1992, "Influenza A virus transfectants with chimaeric haemagglutinins containing epitopes from different subtpes", Journal of Virology, 67:399-404.

Li et al., 1999, "Recombinant influenza A virus vaccines for the pathogenic human A/Hong Kong/97 (H5N1) viruses," J Infect Dis., 179(5):1132-1138.

Li et al., 2011, "A novel tetrameric PilZ domain structure from xanthomonads," PLoS One, 6(7):e22036 (13 pages).

Li et al., 2011, "Emergence and genetic variation of neuraminidase stalk deletions in avian influenza viruses," PLoS One, 6(2):e14722 (11 pages).

Li et al., 2012, "Pandemic H1N1 influenza vaccine induces a recall response in humans that favors broadly cross-reactive memory B cells," Proc Natl Acad Sci USA, 109(23):9047-9052.

Liang et al., 1994, "Heterosubtypic immunity to influenza type A virus in mice. Effector mechanisms and their longevity," J Immunol., 152(4):1653-1661.

Liang et al., 2005, "cis-Acting packaging signals in the influenza virus PB1, PB2, and PA genomic RNA segments," J. Virol., 79(16):10348-10355.

Liu et al., 2015, "Cross-Reactive Neuraminidase-Inhibiting Antibodies Elicited by Immunization with Recombinant Neuraminidase Proteins of H5N1 and Pandemic H1N1 Influenza A Viruses," J. Virol., 89(14):7224-7234.

Liu et al., 2019, "Sequential Immunization With Live-Attenuated Chimeric Hemagglutinin-Based Vaccines Confers Heterosubtypic Immunity Against Influenza A Viruses in a Preclinical Ferret Model," Front. Immunol., 10:756 and Supplemental Figs. S1 to S7 (25 pages).

Lloyd et al., 2009, "Modelling the human immune response: performance of a 1011 human antibody repertoire against a broad panel of therapeutically relevant antigens," Protein Eng. Des. Sel., 22(3):159-168 (Epub 2008).

Lorieau et al., 2010, "The complete influenza hemagglutinin fusion domain adopts a tight helical hairpin arrangement at the lipid:water interface," PNAS, 107(25):11341-11346.

Lowen et al., 2006, "The guinea pig as a transmission model for human influenza viruses," Proc Natl Acad Sci USA, 103(26):9988-9992.

Lowen et al., 2009, "Blocking interhost transmission of influenza virus by vaccination in the guinea pig model," J. Virol. 83(7):2803-2818.

Lu et al., 2013, "Production and stabilization of the trimeric influenza hemagglutinin stem domain for potentially broadly protective influenza vaccines." PNAS, 111(1):125-130.

Luke et al., 2014, "Improving pandemic H5N1 influenza vaccines by combining different vaccine platforms," Expert Review of Vaccines 13(7):873-883.

Luo et al., 1993, "Alterations of the stalk of the influenza virus neuraminidase: deletions and insertions," Virus Res., 29(2):141-153.

Madsen et al., 2020, "Human Antibodies Targeting Influenza B Virus Neuraminidase Active Site Are Broadly Protective," Immunity, 53(4):852-863.e7 (20 pages).

Maier et al., 2020, "Pre-existing Antineuraminidase Antibodies Are Associated With Shortened Duration of Influenza A(H1N1)pdm Virus Shedding and Illness in Naturally Infected Adults," Clin Infect Dis., 70(11):2290-2297.

Mallajosyula et al., 2014, "Influenza hemagglutinin stem-fragment immunogen elicits broadly neutralizing antibodies and confers heterologous protection." PNAS, 111(25):E2514-23.

Manini et al., 2015, "Flucelvax (Optaflu) for seasonal influenza," Expert Rev. Vaccines, 14(6):789-804.

Marasco et al.. 2007, "The growth and potential of human antiviral monoclonal antibody therapeutics", Nat. Biotechnol: 25(12):1421-1434.

Marathe et al., 2016, "Combinations of Oseltamivir and T-705 Extend the Treatment Window for Highly Pathogenic Influenza A(H5N1) Virus Infection in Mice," Sci Rep., 6:26742 (14 pages).

Marcelin et al., 2012, "Contribution of antibody production against neuraminidase to the protection afforded by influenza vaccines," Rev Med Virol., 22(4):267-279.

Margine et al., 2013, "Expression of functional recombinant hemagglutinin and neuraminidase proteins from the novel H7N9 influenza virus using the baculovirus expression system," J Vis Exp., (81):e51112 (10 pages).

Margine et al., 2013, "H3N2 influenza virus infection induces broadly reactive hemagglutinin stalk antibodies in humans and mice", J. Virol. 87(8):4728-4737.

Margine et al., 2013, "Hemagglutinin stalk-based universal vaccine constructs protect against group 2 influenza A viruses", J Virol, 10435-10446.

Marsh et al., 2007, "Specific residues of the influenza A virus hemagglutinin viral RNA are important for efficient packaging into budding virions," J. Virol., 81(18):9727-9736.

Martinez-Romero et al., 2013, "Substitutions T200A and E227A in the hemagglutinin of pandemic 2009 influenza A virus increase lethality but decrease transmission," J Virol., 87(11):6507-6511.

Martinez-Sobrido et al., 2010, "Generation of recombinant influenza virus from plasmid DNA," J Vis Exp., 3(42):e2057 (5 pages).

Matias et al., 2016, "Model estimates of the burden of outpatient visits attributable to influenza in the United States," BMC Infect. Dis., 16(1):641 (11 pages).

Matrosovich et al., 2004, "Neuraminidase is important for the initiation of influenza virus infection in human airway epithelium," J Virol., 78(22):12665-12667.

Matsuzaki et al., 2014, "Epitope mapping of the hemagglutinin molecule of A/(H1N1)pdm09 influenza virus by using monoclonal antibody escape mutants," J. Virol., 88(21):12364-12373.

Matthews et al., 2006, "A tryptophan amphiphilic tetramerization domain-containing acetylcholinesterase from the bovine lungworm, Dictyocaulus viviparus," Parasitology, 133(Pt 3):381-387.

Mbawuike et al., 1994, "Influenza A subtype cross-protection after immunization of outbred mice with purified chimeric NS1/HA2 influenza virus protein", Vaccine, 1994: 12(14):1340-1348.

McAuley et al., 2019, "Influenza Virus Neuraminidase Structure and Functions," Front Microbiol., 10:39 (13 pages).

McMahon et al., 2019, "Mucosal Immunity against Neuraminidase Prevents Influenza B Virus Transmission in Guinea Pigs," mBio, 10(3):e00560-19 (12 pages).

Memoli et al., 2016, "Evaluation of Antihemagglutinin and Antineuraminidase Antibodies as Correlates of Protection in an Influenza A/H1N1 Virus Healthy Human Challenge Model," mBio, 7(2):e00417-16 (12 pages).

Mendez-Legaza et al., 2019, "Heterotypic Neuraminidase Antibodies Against Different A(H1N1) Strains are Elicited after Seasonal Influenza Vaccination," Vaccines (Basel), 7(1):30 (15 pages).

Meseda et al., 2018, "Immunogenicity and Protection Against Influenza H7N3 in Mice by Modified Vaccinia Virus Ankara Vectors Expressing Influenza Virus Hemagglutinin or Neuraminidase," Sci. Rep., 8(1):5364 (14 pages).

Mett et al., 2008, "A plant-produced influenza subunit vaccine protects ferrets against virus challenge", Influenza and Other Respiratory Viruses, 2(1):33-40.

Miller et al., 2013, "1976 and 2009 H1N1 influenza virus vaccines boost anti-hemagglutinin stalk antibodies in humans", J. Infect. Dis. 207:98-105.

Mo et al., 2003. "Coexpression of complementary fragments of CIC-5 and restoration of chloride channel function in a Dent's disease mutation", Am J Physiol Cell Physiol; 286:C79-C89.

(56)                    References Cited

OTHER PUBLICATIONS

Mok et al., 2008, "Enhancement of the CD8<+> T cell response to a subdominant epitope respiratory syncytial virus by deletion of an immunodominant epitope", Vaccine: 26(37):4775-4782.

Molinari et al., 2007, "The annual impact of seasonal influenza in the US: measuring disease burden and costs," Vaccine, 25(27):5086-5096.

Montgomery et al., 1993, "Heterologous and homologous protection against influenza A by DNA vaccination: optimization of DNA vectors," DNA Cell Biol. 12(9):777-783.

Monto et al., 2015, "Antibody to Influenza Virus Neuraminidase: An Independent Correlate of Protection," J Infect Dis., 212(8):1191-1199.

Montplaisir et al., 2009, "Risk of narcolepsy associated with inactivated adjuvanted (AS03) A/H1N1 (2009) pandemic influenza vaccine in Quebec," PLoS One 9 (9): e108489 (9 pages).

Moody et al., 2011, "H3N2 influenza infection elicits more cross-reactive and less clonally expanded anti-hemagglutinin antibodies than influenza vaccination," PLoS One, 6(10):e25797 (14 pages).

Morel et al., 2011, "Adjuvant System AS03 containing α-tocopherol modulates innate immune response and leads to improved adaptive immunity," Vaccine, 29(13):2461-2473.

Moscona, 2005, "Neuraminidase inhibitors for influenza," N Engl J Med., 353(13):1363-1373.

Mullarkey et al., 2016, "Broadly Neutralizing Hemagglutinin Stalk-Specific Antibodies Induce Potent Phagocytosis of Immune Complexes by Neutrophils in an Fc-Dependent Manner," mBio, 7(5):e01624-16 (12 pages).

Muramoto et al., 2006, "Hierarchy among viral RNA (vRNA) segments in their role in vRNA incorporation into influenza A virions," J. Virol., 80(5):2318-2325.

Murphy et al., 1972, "Association of serum anti-neuraminidase antibody with resistance to influenza in man," N. Engl. J. Med., 286(25):1329-1332.

Myers et al., 2013, "Compensatory hemagglutinin mutations alter antigenic properties of influenza viruses," J. Virol., 87(20):11168-11172.

Nachbagauer et al., 2014, "Induction of broadly reactive anti-hemagglutinin stalk antibodies by an H5N1 vaccine in humans," J. Virol. 88 (22): 13260-13268.

Nachbagauer et al., 2015, "Hemagglutinin stalk immunity reduces influenza virus replication and transmission in ferrets," J Virol., 90(6):3268-3273.

Nachbagauer et al., 2016, "A chimeric haemagglutinin-based influenza split virion vaccine adjuvanted with AS03 induces protective stalk-reactive antibodies in mice," Npj Vaccines 1:16015 (10 pages).

Nachbagauer et al., 2016, "Age Dependence and Isotype Specificity of Influenza Virus Hemagglutinin Stalk-Reactive Antibodies in Humans," MBio., 7(1):e01996-15 (10 pages).

Nachbagauer et al., 2017, "A universal influenza virus vaccine candidate confers protection against pandemic H1N1 infection in preclinical ferret studies," NPJ Vaccines, 2:26 (13 pages).

Nakajima et al., 2000, "Variation in response among individuals to antigenic sites on the HA protein of human influenza virus may be responsible for the emergence of drift strains in the human population," Virology, 274(1):220-231.

Nakaya et al., 2001, "Recombinant Newcastle disease virus as a vaccine vector," J Virol., 75(23):11868-11873.

National Insitutes of Health Pubchem, "Zanamivir," found at https://pubchem.ncbi.nim.nih.gov/zompound/Zanamivir (Year: 2021).

NCT01676402, Clinical Trial, "Seasonal Influenza HA DNA With Trivalent Inactivated Vaccine (TIV) Administered ID or IM in Healthy Adults 18-70 Years," last updated Jul. 17, 2014 (6 pages).

Nelson et al., 2008, "Lehninger Principles of Biochemistry—Fifth Edition," Chapter 4.3, p. 123, W.H. Freeman and Company.

Neumann et al., 1999, "Generation of influenza A viruses entirely from cloned cDNAs", PNAS 96:9345-9350.

Ni et al., 2013, "Structural basis for the divergent evolution of influenza B virus hemagglutinin," Virology 446(1-2):112-122.

Nichol et al., 1995, "The effectiveness of vaccination against influenza in healthy, working adults," N Engl J Med., 333(14):889-893.

Nicholson et al., 2000, "Efficacy and safety of oseltamivir in treatment of acute influenza: a randomised controlled trial," Lancet, 355(9218):1845-1850.

O'Brien et al. 2004, "Incidence of outpatient visits and hospitalizations related to influenza in infants and young children," Pediatrics, 113:585-593.

Ogburn et al., 2007, "Impact of clinic interventions on the rate of influenza vaccination in pregnant women," J Reprod Med., 52(9):753-756.

Ohkura et al., 2012, "Epitope mapping of neutralizing monoclonal antibody in avian influenza A H5N1 virus hemagglutinin," Biochem. Biophys. Res. Commun. 418(1):38-43 (Epub 2011).

Ohmit et al., 2011, "Influenza hemagglutination-inhibition antibody titer as a correlate of vaccine-induced protection," J Infect Dis., 204(12):1879-1885.

Okuno et al., 1993, "A common neutralizing epitope conserved between the hemagglutinins of influenza A virus H1 and H2 strains," J. Virol., 67(5):2552-2558.

Okuno et al., 1994, "Protection against the mouse-adapted A/FM/1/47 strain of influenza A virus in mice by a monoclonal antibody with cross-neutralizing activity among E11 and H2 strains," J. Virol., 68(1):517-520.

Olson et al., 2007, "Monitoring the impact of influenza by age: emergency department fever and respiratory complaint surveillance in New York City," PLoS Med., 4(8):e247 (13 pages).

Oshima et al., 2011, "Naturally Occurring Antibodies in Humans Can Neutralize a Variety of Influenza Virus Strains, Including H3, H1, H2, and H5". Journal of Virology, 85(21):11048-11057.

Ott et al., 2000. The Adjuvant MF59: A 10-Year Perspective, p. 211-228. In O'Hagan DT (ed.), Vaccine Adjuvants, vol. 42. Springer.

Oxford, 2013, "Towards a universal influenza vaccine: volunteer virus challenge studies in quarantine to speed the development and subsequent licensing," Br J Clin Pharmacol., 76(2):210-216.

Ozawa et al., 2007, "Contributions of two nuclear localization signals of influenza A virus nucleoprotein to viral replication," J. Virol., 81(1):30-41 (Epub 2006).

Ozawa et al., 2009, "Nucleotide sequence requirements at the 5' end of the influenza A virus M RNA segment for efficient virus replication," J. Virol., 83(7):3384-3388.

Palese et al., 1974, "Characterization of temperature sensitive influenza virus mutants defective in neuraminidase," Virology, 61(2):397-410.

Palese et al., 2007, "Orthomyxoviridae: The Viruses and Their Replication," in Fields Virology, D.M. Knipe, & P.M. Howley (Eds.), Philadelphia, PA: Wolters Kluwer Lippincott Williams & Wilkins, pp. 1647-1689.

Palese, 2004, "Influenza: old and new threats," Nat Med., 10(12 Suppl):S82-87.

Pan et al., 2011, "Selective pressure to increase charge in immunodominant epitopes of the H3 hemagglutinin influenza protein," J Mol Evol., 72(1):90-103.

Pantua et al., 2006, "Requirements for the assembly and release of Newcastle disease virus-like particles," J Virol, 80(22):11062-11073.

Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.

Park et al., 2006, "Engineered viral vaccine constructs with dual specificity: avian influenza and Newcastle disease," Proc Natl Acad Sci USA, 103(21):8203-8208.

Pearson et al., 1988, "Improved tools for biological sequence comparison," Proc Natl Acad Sci USA, 85(8):2444-2448.

Perricone et al., 2013, "Autoimmune/inflammatory syndrome induced by adjuvants (ASIA) 2013: Unveiling the pathogenic, clinical and diagnostic aspects," J Autoimmun., 47:1-16.

Pettersen et al., 2004, "UCSF Chimera—a visualization system for exploratory research and analysis," J Comput Chem., 25(13):1605-1612.

(56) References Cited

OTHER PUBLICATIONS

Pica et al., 2012, "Hemagglutinin stalk antibodies elicited by the 2009 pandemic influenza virus as a mechanism for the extinction or seasonal H1N1 viruses." Proc Nat Acad Sci USA, 109(7):2573-2578.

Piepenbrink et al., 2019, "Broad and Protective Influenza B Virus Neuraminidase Antibodies in Humans after Vaccination and their Clonal Persistence as Plasma Cells," mBio, 10(2):e00066-19 (17 pages).

Ping et al., 2015, "Development of high-yield influenza A virus vaccine viruses," Nat. Commun., 6:8148 (15 pages).

Pleschka et al., 1996, "A plasmid-based reverse genetics system for influenza A virus", J Virol 70:4188-4192.

Ponomarenko et al., 2009, "B-Cell Epitope Prediction" Ch. 35 in Structural Bioinformatics, 2nd Edition, Gu and Bourne Editors, John Wiley & Sons. Inc., pp. 849-879.

Popova et al., 2012, "Immunodominance of antigenic site B over site A of hemagglutinin of recent H3N2 influenza viruses," PLoS One, 7(7):e41895 (11 pages).

Potter et al., 1979, "Determinants of immunity to influenza infection in man," Br. Med. Bull, 35(1):69-75.

Powers et al., 1996, "Neuraminidase-specific antibody responses to inactivated influenza virus vaccine in young and elderly adults," Clin. Diagn. Lab. Immunol., 3(5):511-516.

Q0pzr5, UniProtKB Accession No. Q0PZR5, Oct. 29, 2014 [online]. [Retrieved on Sep. 2, 2016]. Retrieved from the internet <URL:http://www.uniprot.org/uniprot/Q0PZR5.txt?version=53> (2 pages).

Quinlivan et al., 2005, "Attenuation of equine influenza viruses through truncations of the NS1 protein," J Virol., 79(13):8431-8439.

Rajendran et al., 2017, "Analysis of Anti-Influenza Virus Neuraminidase Antibodies in Children, Adults, and the Elderly by ELISA and Enzyme Inhibition: Evidence for Original Antigenic Sin" mBio, 8(2):e02281-16 (12 pages).

Rambaut et al., 2008, "The genomic and epidemiological dynamics of human influenza A virus," Nature, 453(7195):615-619.

Rasala et al., 2010, "Production of therapeutic proteins in algae, analysis of expression of seven human proteins in the chloroplast of Chlamydomonas reinhardtii," Plant Biotechnol J., 8(6):719-733.

Reid et al., Hemagglutinin [Influenza A virus (A/South Carolina/1/1918(H1N1))]. GenBank Acc. No. AAD17229.1. Dep. Oct. 11, 2000.

Retamal et al., 2014, "Epitope mapping of the 2009 pandemic and the A/Brisbane/59/2007 seasonal (H1N1) influenza virus haemagglutinins using mAbs and escape mutants," J. Gen. Virol., 95(Pt 11):2377-2389.

Ridenour et al., 2015, "Development of influenza A(H7N9) candidate vaccine viruses with improved hemagglutinin antigen yield in eggs," Influenza Other Respir Viruses, 9(5):263-270.

Rivera et al., 1995, "Probing the structure of influenza B hemagglutinin using site-directed mutagenesis," Virology 206(2):787-795.

Roberts el al., 1993, "Role of conserved glycosylation sites in maturation and transport of influenza A virus hemagglutinin." J Virol, 67(6):3048-3060.

Robertson, 1987, "Sequence Analysis of the Haemagglutinin of A/Taiwan/1/86, a New Variant of Human Influenza A(H1/N1) Virus," J. Gen. Virol., 68(4):1205-1208.

Rockman et al., 2013, "Neuraminidase-inhibiting antibody is a correlate of cross-protection against lethal H5N1 influenza virus in ferrets immunized with seasonal influenza vaccine," J Virol., 87(6):3053-3061.

Rolfes et al., 2014, "Update: influenza activity—United States, Sep. 28-Dec. 6, 2014," MMWR Morb Mortal Wkly Rep., 63(50):1189-1194.

Rolfes et al., 2018, "Annual estimates of the burden of seasonal influenza in the United States: A tool for strengthening influenza surveillance and preparedness," Influenza Other Respir Viruses, 12(1):132-137.

Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.

Rudikoff et al., 1982, "Single amino acid substitution altering antigen-binding specificity." Proc Nat Acad Sci U S A., 79(6):1979-1983.

Rumpler et al., 2018, "A conserved leucine zipper-like motif accounts for strong tetramerization capabilities of SEPALLATA-like MADS-domain transcription factors," J Exp Bot., 69(8):1943-1954.

Runstadler et al., 2013, "Connecting the study of wild influenza with the potential for pandemic disease," Infect Genet Evol., 17:162-187.

Ryder et al., 2016, "Vaccination with VSV-vectored chimeric hemagglutinins protects mice against divergent influenza virus challenge strains", J. Virol., 90(5):2544-2550.

Sagawa et al., 1996, "The immunological activity of a deletion mutant of influenza virus haemagglutinin lacking the globular region", J Gen Virol; 77:1483-1487.

Salem, 2000, "In vivo acute depletion of CD8(+) T cells before murine cytomegalovirus infection upregulated innate antiviral activity of natural killer cells", Int. J. Immunopharmacol. 22:707-718.

Sandbulte et al., 2007, "Cross-reactive neuraminidase antibodies afford partial protection against H5N1 in mice and are present in unexposed humans," PLoS Med., 4(2):e59 (8 pages).

Sandbulte et al., 2011, "Discordant antigenic drift of neuraminidase and hemagglutinin in H1N1 and H3N2 influenza viruses," Proc. Natl. Acad. Sci. USA, 108(51):20748-20753.

Santak, 2012, "Old and new ways to combat human influenza virus." Periodicus Biologorum, 114(2):221-234.

Sautto et al., 2018, "Towards a Universal Influenza Vaccine: Different Approaches for One Goal," Virol J., 15(1):17 (12 pages).

Scheiffele et al., 1997, "Interaction of influenza virus haemagglutinin with sphingolipid-cholesterol membrane domains via its transmembrane domain, " EMBO J., 16(18):5501-5508.

Scheres, 2012, "RELION: implementation of a Bayesian approach to cryo-EM structure determination," J Struct Biol., 180(3):519-530.

Schneeman et al., 2012, "A Virus-Like Particle That Elicits Cross-Reactive Antibodies to the Conserved Stem of Influenza Virus Hemagglutinin," J. Virol., 86(21): 11686-22697.

Schuind et al., 2015, "Immunogenicity and Safety of an EB66 Cell-Culture-Derived Influenza A/Indonesia/5/2005(H5N1) AS03-Adjuvanted Vaccine: A Phase 1 Randomized Trial," J Infect Dis., 212(4):531-541.

Schulman et al., 1968, "Protective effects of specific immunity to viral neuraminidase on influenza virus infection of mice," J Virol., 2(8):778-786.

Schulman, 1969, "The role of antineuraminidase antibody in immunity to influenza virus infection," Bull World Health Organ., 41(3):647-650.

Schulze, 1997, "Effects of Glycosylation on the Properites and Functions of Influenza Virus Hemagglutinin", The Journal of Infectious Diseases, 176(S1):S24-S28.

Seibert et al., 2010, "Oseltamivir-resistant variants of the 2009 pandemic H1N1 influenza A virus are not attenuated in the guinea pig and ferret transmission models," J Virol., 84(21):11219-11226.

Seibert et al., 2013, "Recombinant IgA is sufficient to prevent influenza virus transmission in guinea pigs," J Virol., 87(14):7793-7804.

Shaw et al., 2013, "Chapter 40: Orthomyxoviridae," in Fields Virology, 6th Ed., Lippincott Williams & Wilkins, a Wolters Kluwer, Philadelphia, PA, pp. 1151-1181 and references (107 pages).

Shoji et al., 2008, "Plant-expressed HA as a seasonal influenza vaccine candidate", Vaccine, 26(23):2930-2934.

Shoji et al., 2011, "An influenza N1 neuraminidase-specific monoclonal antibody with broad neuraminidase inhibition activity against H5N1 HPAI viruses," Hum Vaccin., 7 Suppl:199-204.

Simmons et al., 2007. "Prophylactic and therapeutic efficacy of human monoclonal antibodies against H5N1 Influenza", PLOS Medicine; 4(5):928-936.

Singleton et al., 1995, "Dictionary of Microbiology and Molecular Biology—Second Edition." A Wiley-Interscience Publication (3 pages).

(56) References Cited

OTHER PUBLICATIONS

Skehel et al., 1984, "A carbohydrate side chain on hemagglutinins of Hong Kong influenza viruses inhibits recognition by a monoclonal antibody," Proc. Natl. Acad. Sci. USA, 81(6):1779-1783.

Skowronski et al., 2013, "Virus-host interactions and the unusual age and sex distribution of human cases of influenza A(H7N9) in China, Apr. 2013," Euro Surveill., 18(17):20465 (4 pages).

Smith et al., 1981, "Comparison of biosequences," Advances in Applied Mathematics, 2(4):482-489.

Smith et al., 2004, "Mapping the antigenic and genetic evolution of influenza virus," Science, 305(5682):371-376.

Smith et al., 2017, "Neuraminidase-based recombinant virus-like particles protect against lethal avian influenza A(H5N1) virus infection in ferrets," Virology, 509:90-97.

Song et al., 2007, "Influenza A Virus Hemagglutinin Protein, H1PR8," GENESEQ, XP002595511.

Sparrow et al., 2016, "Passive immunization for influenza through antibody therapies, a review of the pipeline, challenges, and potential applications." Vaccine, 34: 5442-5448.

Stadlbauer et al., 2018, "Cross-reactive mouse monoclonal antibodies raised against the hemagglutinin of A/Shanghai/1/2013 (H7N9) protect against novel H7 virus isolates in the mouse model," Emerg. Microbes. Infect., 7(1):110 (12 pages).

Stadlbauer et al., 2019, "Broadly Protective Human Antibodies That Target the Active Site of Influenza Virus Neuraminidase," Science, 366(6464):499-504.

Stech et al., 2005, "A new approach to an influenza live vaccine: modification of the cleavage site of hemagglutinin", Nat. Med. 11(6):683-689.

Steel et al., 2009, "Live attenuated influenza viruses containing NS1 truncations as vaccine candidates against H5N1 highly pathogenic avian influenza," J Virol., 83(4):1742-1753.

Steel et al., 2010, "Influenza Virus Vaccine Based on the Conserved Hemagglutinin Stalk Domain," mBIO 1(1). pii: e00018-10 (9 pages).

Stephenson et al., 2005, "Cross-reactivity to highly pathogenic avian influenza H5N1 viruses alter vaccination with nonadjuvanted and MF59-adjuvanted influenza A/Duck/Singapore/97 (H5N3) vaccine: a potential priming strategy." J Infect Dis., 191(8):1210-1215.

Steuler et al., 1984, "Sequence of the neuraminidase gene of an avian influenza A virus (A/parrot/ulster/73, H7N1)," Virology, 135(1):118-124.

Stevens et al., 2006, "Structure and Receptor Specificity of the Hemagglutinin from an H5N1 Influenza Virus" Science, 312:404-409.

Stoute et al., 1997, "A preliminary evaluation of a recombinant circumsporozoite protein vaccine against Plasmodium falciparum malaria. RTS,S Malaria Vaccine Evaluation Group," N Engl J Med., 336(2):86-91.

Strobel et al., 2000, "Efficient Expression of the Tumor-Associated Antigen MAGE-3 in Human Dendritic Cells, Using an Avian Influenza Virus Vector", Human Gene Therapy 11:2207-2218.

Strohmeier et al., 2021, "A Novel Recombinant Influenza Virus Neuraminidase Vaccine Candidate Stabilized by a Measles Virus Phosphoprotein Tetramerization Domain Provides Robust Protection from Virus Challenge in the Mouse Model," mBio., 12(6):e02241-21 (17 pages).

Su et al., 2014, "Comparing clinical characteristics between hospitalized adults with laboratory-confirmed influenza A and B virus infection," Clin Infect Dis., 59(2):252-255.

Subbarao et al., 2013, "The prospects and challenges of universal vaccines for influenza," Trends Microbiol., 21(7):350-358.

Sugaya et al., 2007, "Lower clinical effectiveness of oseltamivir against influenza B contrasted with influenza A infection in children," Clin Infect Dis., 44(2):197-202 (Epub 2006).

Sui et al., 2011, "Wide prevalence of heterosubtypic broadly neutralizing human anti-influenza A antibodies," Clin Infect Dis., 52(8):1003-1009.

Sui et al.. 2009, "Structural and functional bases for broad-spectrum neutralization of avian and human influenza A viruses", Nat Struct Mol Biol; 16(3):265-273 with Supplementary Information (31 pages).

Sultana et al., 2014, "Stability of neuraminidase in inactivated influenza vaccines," Vaccine, 32(19):2225-2230.

Sun et al., 2011, "Glycosylation Site Alteration in the Evolution of Influenza A (H1N1) Viruses." PLoS Pathogens, 6(7):e22844 (9 pages).

Sun et al., 2019, "Development of Influenza B Universal Vaccine Candidates Using the "Mosaic" Hemagglutinin Approach," J Virol., 93(12):e00333-19 (17 pages).

Sutter et al., 1992, "Nonreplicating vaccinia vector efficiently expresses recombinant genes," Proc Natl Acad Sci USA, 89(22):10847-10851.

Swayne et al., 2003, "Recombinant paramyxovirus type 1-avian influenza-H7 virus as a vaccine for protection of chickens against influenza and Newcastle disease," Avian Dis., 47(3 Suppl):1047-1050.

Sylte et al., 2007, "Influenza neuraminidase antibodies provide partial protection for chickens against high pathogenic avian influenza infection," Vaccine, 25(19):3763-3772.

Talaat et al., 2014, "A Live Attenuated Influenza A(H5N1) Vaccine Induces Long-Term Immunity in the Absence of a Primary Antibody Response," Journal of Infectious Disease; 208:1860-1869.

Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.

Tan et al., 2012, "A pan-H1 anti-hemagglutinin monoclonal antibody with potent broad-spectrum efficacy in vivo", J. Virol. 86:6179-6188.

Tan et al., 2014, "Characterization of a broadly neutralizing monoclonal antibody that targets the fusion domain of group 2 influenza A virus hemagglutinin," J. Virol., 88(23):13580-13592.

Tan et al., 2018, "Universal influenza virus vaccines and therapeutics: where do we stand with influenza B virus?," Curr Opin Immunol., 53:45-50.

Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.

Tarbouriech et al., 2000, "Tetrameric coiled coil domain of Sendai virus phosphoprotein," Nat Struct Biol., 7(9):777-781.

Tate et al., 2011, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.

Tete et al., 2016, "Dissecting the hemagglutinin head and stalk-specific IgG antibody response in healthcare workers following pandemic H1N1 vaccination," Nature Partner Journals (NPJ) Vaccine, Article No. 16001 doi:10.1038/npjvaccines.2016.1 (9 pages).

Thoennes et al., 2008, "Analysis of residues near the fusion peptide in the influenza hemagglutinin structure for roles in triggering membrane fusion", Virology; 370(2):403-414.

Thompson et al., 2003, "Mortality associated with influenza and respiratory syncytial virus in the United States," JAMA, 289(2):179-186.

Thomson et al., 2012, "Pandemic H1N1 Influenza Infection and Vaccination in Humans Induces Cross-Protective Antibodies that Target the Hemagglutinin Stem", Front. Immunol. 3:87 (19 pages).

Throsby et al., 2008, "Heterosubtypic neutralizing monoclonal antibodies cross-protective against H5N1 and H1N1 recovered from human IgM+ memory B cells", PLoS ONE; 3(12):e3942 (15 pages).

Tong et al., 2013. "New world bats harbor diverse influenza A viruses," PLoS Pathog. 9: e1003657 (12 pages).

Tran et al., 2016, "Cryo-electron microscopy structures of chimeric hemagglutinin displayed on a universal influenza vaccine candidate", MBio, 7(2): e00257-16 (9 pages).

Treanor et al., 2007, "Safety and immunogenicity of a baculovirus-expressed hemagglutinin influenza vaccine: a randomized controlled trial," JAMA, 297(14):1577-1582.

(56) References Cited

OTHER PUBLICATIONS

Tricco et al., 2013, "Comparing influenza vaccine efficacy against mismatched and matched strains: a systematic review and meta-analysis," BMC Med., 11:153 (19 pages).

Truelove et al., 2016, "A comparison of hemagglutination inhibition and neutralization assays for characterizing immunity to seasonal influenza A," Influenza Other Respir Viruses, 10(6):518-524.

Tscherne et al., 2010, "An enzymatic virus-like particle assay for sensitive detection of virus entry," J Virol Methods, 163(2):336-343.

Tsibane et al., 2012, "Influenza human monoclonal antibody 1F1 interacts with three major antigenic sites and residues mediating human receptor specificity in H1N1 viruses," PLoS Pathog., 8(12):e1003067 (9 pages).

Turbelin et al., 2013, "Age distribution of influenza like illness cases during post-pandemic A(H3N2): comparison with the twelve previous seasons, in France," PLoS One, 8(6):e65919 (9 pages).

Tweed et al., 2004, "Human illness from avian influenza H7N3, British Columbia," Emerg Infect Dis., 10(12):2196-2199.

UniProtKB: P16199.1, Influenza B virus (B/Memphis/3/89), last modified Dec. 11, 2019.

UniProtKB: P16203.1, Influenza B virus (B/Singapore/222/79), last modified Apr. 22, 2020.

UniProtKB: P16205.1, Influenza B virus (B/USSR/100/83), last modified Dec. 11, 2019.

UniProtKB: P16207.1, Influenza B virus (Strain B/VICTORIA/3/85), last modified Dec. 11, 2019.

UniProtKB: P27907.1, Influenza B virus (strain B/Beijing/1/1987), last modified Dec. 11, 2019.

UniProtKB: Q90021.1, Influenza B virus (B/Yamagata/16/1988), last modified Dec. 11, 2019.

Vahey et al., 2019, "Low-Fidelity Assembly of Influenza A Virus Promotes Escape from Host Cells," Cell, 176(1-2):281-294.e19 (Epub 2018).

Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.

Van Den Brand et al., 2011, "Efficacy of vaccination with different combinations of MF59-adjuvanted and nonadjuvanted seasonal and pandemic influenza vaccines against pandemic H1N1 (2009) influenza virus infection in ferrets," J Virol., 85(6):2851-2858.

Van Der Lubbe, 2018, "Mini-HA Is Superior to Full Length Hemagglutinin Immunization in Inducing Stem-Specific Antibodies and Protection Against Group 1 Influenza Virus Challenges in Mice," Front Immunol., 9:2350 (13 pages).

Van Der Most et al., 2014, "Seeking help: B cells adapting to flu variability," Sci Transl Med., 6(246):246ps8 (7 pages).

Van Reeth et al., 2009, "Prior infection with an H1N1 swine influenza virus partially protects pigs against a low pathogenic H5N1 avian influenza virus," Vaccine, 27(45):6330-6339.

Vanlandschoot et al., 1995. "A fairly conserved epitope on the hemagglutinin of influenza A (H3N2) virus with variable accessibility to neutralizing antibody." Virology, 212(2)526-534.

Vanlandschoot et al., 1998. "An antibody which binds to the membrane-proximal end of influenza virus haemagglutinin (1-13 subtype) inhibits the low-pH-induced conformational change and cell-cell fusion but does not neutralize virus", Journal of General Virology; 79:1781-1791.

Vareckova et al., 2008, "HA2-specific monoclonal antibodies as tools for differential recognition of influenza A virus antigenic subtypes," Virus Research, 132:181-186.

Vaughn et al., 2014, "Safety of AS03-adjuvanted inactivated split virion A(H1N1)pdm09 and H5N1 influenza virus vaccines administered to adults: pooled analysis of 28 clinical trials," Hum Vaccin Immunother, 10(10):2942-2957.

Vavricka et al., 2011, "Structural and functional analysis of laninamivir and its octanoate prodrug reveals group specific mechanisms for influenza NA inhibition," PLoS Pathog., 7(10):e1002249 (10 pages).

Vigerust et al., 2007, "N-Linked Glycosylation Attenuates H3N2 Influenza Viruses", Journal of Virology, 81(16): 8593-8600.

Vincent et al., 2008, "Failure of protection and enhanced pneumonia with a US H1N2 swine influenza virus in pigs vaccinated with an inactivated classical swine H1N1 vaccine," Vet Microbiol., 126(4):310-323.

Wagner et al., 2002, "Functional balance between haemagglutinin and neuraminidase in influenza virus infections," Rev. Med. Virol., 12(3):159-166.

Walz et al., 2018, "Neuraminidase-Inhibiting Antibody Titers Correlate with Protection from Heterologous Influenza Virus Strains of the Same Neuraminidase Subtype," J Virol., 92(17):e01006-18 (15 pages).

Wan et al., 2013, "Molecular basis for broad neuraminidase immunity: conserved epitopes in seasonal and pandemic H1N1 as well as H5N1 influenza viruses," J Virol., 87(16):9290-9300.

Wan et al., 2015, "Structural characterization of a protective epitope spanning A(H1N1)pdm09 influenza virus neuraminidase monomers," Nat Commun., 6:6114 (10 pages).

Wang et al., 1992, "High-affinity laminin receptor is a receptor for Sindbis virus in mammalian cells," J Virol., 66(8):4992-5001.

Wang et al., 2006, "Hemagglutinin (HA) proteins from H1 and H3 serotypes of influenza A viruses require different antigen designs for the induction of optimal protective antibody responses as studied by codon-optimized HA DNA vaccines," J Virol., 80(23):11628-11637.

Wang et al., 2007, "Incorporation of High Levels of Chimeric Human Immunodeficiency Virus Envelope Glycoproteins into Virus-Like Particles", J. Virol., 81(20):10869-10878.

Wang et al., 2008, "Crystal structure of unliganded influenza B virus hemagglutinin," J. Virol. 82(6):3011-3020.

Wang et al., 2008, "Simplified recombinational approach for influenza A virus reverse genetics", J. Virol. Methods 151:74-78.

Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.

Wang et al., 2009, "Glycans on influenza hemagglutinin affect receptor binding and immune response." PNAS, 106(43): 18137-18142.

Wang et al., 2009, "Universal epitopes of influenza virus hemagglutinins?", Nature Structural and Molecular Biology; 16(3):233-234.

Wang et al., 2010, "Broadly protective monoclonal antibodies against H3 influenza viruses following sequential immunization with different hemagglutinins", PLOS Pathogens; 6(2):e1000796 (9 pages).

Wang et al., 2010, "Vaccination with a synthetic peptide from the influenza virus hemagglutinin provides protection against distinct viral subtypes". PNAS. 107(44):18979-18984.

Wang et al., 2011, "Biochemistry. Catching a moving target," Science, 333(6044):834-835.

Wang et al., 2012, "Generation of recombinant pandemic H1N1 influenza virus with the HA cleavable by bromelain and identification of the residues influencing HA bromelain cleavage." Vaccine, 30(4):872-878.

Ward et al., 1982, "Amino acid sequence of the Pronase-released heads of neuraminidase subtype N2 from the Asian strain A/Tokyo/3/67 of influenza virus," Biochem J., 207(1):91-95.

Webby et al., 2010, Hemagglutinin [Influenza A virus (A/Brisbane/59/2007(H1N1))]. GenBank Acc. No. ADE28750.1. Dep. Mar. 29, 2010.

Webster et al., 1968, "Reactions of antibodies with surface antigens of influenza virus," J Gen Virol., 3(3):315-326.

Webster et al., 1980, "Determination of the number of nonoverlapping antigenic areas on Hong Kong (H3N2) influenza virus hemagglutinin with monoclonal antibodies and the selection of variants with potential epidemiological significance," Virology, 104(1):139-148.

Webster et al., 1984, "Antigenic and biological characterization of influenza virus neuraminidase (N2) with monoclonal antibodies," Virology, 135(1):30-42.

Wei et al., 2010, "Induction of Broadly Neutralizing H1N1 Influenza Antibodies by Vaccination," Science; 329:1060-1064.

Wei et al., 2020, "Next-generation influenza vaccines: opportunities and challenges," Nat. Rev. Drug Discov., 19(4):239-252.

(56)　　　　　　References Cited

OTHER PUBLICATIONS

Weir et al., 2016, "An overview of the regulation of influenza vaccines in the United States," Influenza Other Respir Viruses, 10(5):354-360.

Weis et al., 1988, "Structure of the influenza virus haemagglutinin complexed with its receptor, sialic acid." Nature, 333:426-431.

Weis et al., 1990, "Refinement of the Influenza Virus Hemagglutinin by Simulated Annealing." J. Mol. Biol. 212:737-761.

Weldon et al., 2010, "Enhanced immunogenicity of stabilized trimeric soluble influenza hemagglutinin", PLoSONE 5(9):e12466 (8 pages).

Whittle et al., 2011, "Broadly neutralizing human antibody that recognizes the receptor-binding pocket of influenza virus hemagglutinin," Proc. Natl. Acad. Sci. USA, 108(34):14216-14221.

WHO World Health Organization Factsheet No. 211. Influenza Nov. 2016. https://www.who.int/mediacentre/factsheets/fs211/en.

Wiley et al., 1981, "Structural identification of the antibody-binding sites of Hong Kong influenza haemagglutinin and their involvement in antigenic variation," Nature, 289(5796):373-378.

Wiley et al., 1983, "The three-dimensional structure and antigenic variation of the influenza virus haemagglutinin." Division of Virology, 107-111.

Wiley, 1987, "The Structure And Function Of The Hemagglutinin Membrane Glycoprotein Of Influenza Virus." Ann. Rev. Biochem., 56:365-394.

Wilson et al., 1981, "Structure of the haemagglutinin membrane glycoprotein of influenza virus at 3 A resolution." Nature, 289:366-373.

Wilson et al., 1990, "Structural basis of immune recognition of influenza virus hemagglutinin," Annu. Rev. Immunol., 8:737-771.

Winokur et al., 1991, "The hepatitis A virus polyprotein expressed by a recombinant vaccinia virus undergoes proteolytic processing and assembly into viruslike particles," J Virol., 65(9):5029-5036.

Winter et al., 1981, "Nucleotide Sequence Of The Haemagglutinin Gene Of A Human Influenza Virus H1 Subtype" Nature, 292:72-75.

Wohlbold et al., 2014, "In the Shadow of Hemagglutinin: A Growing Interest in Influenza Viral Neuraminidase and Its Role as a Vaccine Antigen," Viruses 6(6):2465-2494.

Wohlbold et al., 2015, "An H10N8 influenza virus vaccine strain and mouse challenge model based on the human isolate A/Jiangxi-Donghu/346/13," Vaccine, 33(9):1102-1106.

Wohlbold et al., 2015, "Vaccination with soluble headless hemagglutinin protects mice from challenge with divergent influenza viruses." Vaccine, 33(29):3314-3321.

Wohlbold et al., 2015, "Vaccination with adjuvanted recombinant neuraminidase induces broad heterologous, but not heterosubtypic, cross-protection against influenza virus infection in mice." MBio, 6(2):e02556.

Wohlbold et al., 2016, "Hemagglutinin Stalk- and Neuraminidase-Specific Monoclonal Antibodies Protect against Lethal H10N8 Influenza Virus Infection in Mice," J Virol., 90(2):851-861.

Wohlbold et al., 2017, "Broadly protective murine monoclonal antibodies against influenza B virus target highly conserved neuraminidase epitopes," Nat. Microbiol. 2(10):1415-1424 with supplemental materials.

Wohlbold, 2019, "The influenza virus neuraminidase as a vaccine antigen and the potential of neuraminidase antibodies to protect against infection," dissertation submitted to the Graduate Faculty of the Graduate School of Biomedical Sciences, Biomedical Sciences Doctoral Program, in partial fulfillment of the requirements for the degree of Doctor of Philosophy, Icahn School of Medicine at Mount Sinai (236 pages).

Worobey et al., 2002, "Questioning the Evidence for Genetic Recombination in the 1918 "Spanish Flu" Virus", Science, 296(5566):211a (3 pages).

Wrammert et al., 2008, "Rapid cloning of high-affinity human monoclonal antibodies against influenza virus," Nature, 453(7195):667-671.

Wrammert et al., 2011, "Broadly cross-reactive antibodies dominate the human B cell response against 2009 pandemic H1N1 influenza virus infection", J. Exp. Med. 208:181-193.

Written Opinion dated Feb. 19, 2013 for PCT Application No. PCT/US2012/056122, Published as WO 2013/043729.

Written Opinion dated Apr. 28, 2014 for PCT Application No. PCT/US2013/075697, Published as WO 2014/099931.

Written Opinion dated Jun. 26, 2014 for PCT Application No. PCT/US2014/025526, Published as WO 2014/159960.

Written Opinion dated Jul. 13, 2011 for PCT Application No. PCT/US2011/030441, Published as WO 2011/123495.

Written Opinion dated Sep. 30, 2011 for PCT Application No. PCT/US2010/029202, Published as WO 2010/117786.

Written Opinion of International application No. PCT/US2010/036170, dated Aug. 17, 2010.

Written Opinion of International application No. PCT/US2011/025467, dated Oct. 19, 2011.

Written Opinion of the International Searching Authority for International Application No. PCT/US2016/014640, mailed Jun. 3, 2016.

Written Opinion of the International Searching Authority for International Application No. PCT/US2016/037595, mailed Sep. 15, 2016.

Written Opinion of the International Searching Authority for International Application No. PCT/US2017/035479, mailed Oct. 25, 2017.

Written Opinion of the International Searching Authority for International Application No. PCT/US2017/037384, mailed Nov. 3, 2017.

Written Opinion of the International Searching Authority for International Application No. PCT/US2018/026489, mailed Aug. 27, 2018.

Written Opinion of the International Searching Authority for International Application No. PCT/US2018/045399, mailed Nov. 29, 2018.

Wu et al., 2010, "A live bivalent influenza vaccine based on a H9N2 virus strain," Vaccine, 28(3):673-680 (Epub 2009).

Wu et al., 2018, "Structural insights into the design of novel anti-influenza therapies," Nat. Struct. Mol. Biol., 25(2):115-121.

Xiao et al., 1996, "High efficiency, long-term clinical expression of cottontail rabbit papillomavirus (CRPV) DNA in rabbit skin following particle-mediated DNA transfer," Nucleic Acids Res., 24(13):2620-2622.

Xie et al., 2011, "Revisiting the 1976 "swine flu" vaccine clinical trials: cross-reactive hemagglutinin and neuraminidase antibodies and their role in protection against the 2009 H1N1 pandemic virus in mice," Clin. Infect. Dis., 53(12):1179-1187.

Xu et al., 2008, "Structural characterization of the 1918 influenza virus H1N1 neuraminidase," J Virol., 82(21):10493-10501.

Xu et al., 2012, "Structural characterization of the hemagglutinin receptor specificity from the 2009 H1N1 influenza pandemic," J. Virol., 86(2):982-990 (Epub 2011).

Yan et al., 2012, "Microbial Resources and Utilization," Harbin Engineering University Press, pp. 100-101, in Chinese with machine English translation of Section 4 (11 pages).

Yang et al., 2006, "Targeting lentiviral vectors to specific cell types in vivo", PNAS 103: 11479-11484.

Yang et al., 2007, "Immunization by Avian H5 Influenza Hemagglutinin Mutants with Altered Receptor Binding Specificity", Science, 317(5839):825-828.

Yang et al., 2014, "A beneficiary role for neuraminidase in influenza virus penetration through the respiratory mucus," PLoS One, 9(10):e110026 (11 pages).

Yang et al., 2014, "Structural stability of influenza A(H1N1)pdm09 virus hemagglutinins." J. Virol., 88(9):4828-4838.

Yang, 2013, "Recombinant trivalent influenza vaccine (flublok®)): a review of its use in the prevention of seasonal influenza in adults," Drugs, 73(12):1357-1366.

Yassine et al., 2015, "Hemagglutinin-stem nanoparticles generate heterosubtypic influenza protection." Nat. Med. 21(9):1065-1070.

Yasugi et al., 2013, "Human monoclonal antibodies broadly neutralizing against influenza B virus", PLoS Pathog. 9(2):e1003150 (12 pages).

(56)          References Cited

OTHER PUBLICATIONS

Yasuhara et al., 2019, "Antigenic drift originating from changes to the lateral surface of the neuraminidase head of influenza A virus" Nat. Microbiol., 4(6):1024-1034.

Yen et al., 2011, "Hemagglutinin-neuraminidase balance confers respiratory-droplet transmissibility of the pandemic H1N1 influenza virus in ferrets," Proc. Natl. Acad. Sci. USA, 108(34):14264-14269.

Yewdell., 2013, "To dream the impossible dream: universal influenza vaccination," Curr Opin Virol., 3(3):316-321.

Yoshida et al., 2007, "Preparation of monoclonal antibodies against common region of influenza A virus hemagglutinin (HA)," Lectures in the Chemical Society of Japan, 87(2):1307, 2 J3-02 in Japanese with English translation of Abstract (4 pages).

Yoshida et al., 2009, "Cross-protective potential of a novel monoclonal antibody directed against antigenic site B of the hemagglutinin of influenza A viruses." PLoS Pathog., 5(3):e1000350 (9 pages).

Zamarin et al., 2006, "Influenza A virus PB1-F2 protein contributes to viral pathogenesis in mice," J Virol. 80(16):7976-7983.

Zerangue et al., 2000, "An artificial tetramerization domain restores efficient assembly of functional Shaker channels lacking T1," Proc Natl Acad Sci USA, 97(7):3591-3595.

Zhang et al., 2010, "Crystal structure of the swine-origin A (H1N1)-2009 influenza A virus hemagglutinin (HA) reveals similar antigenicity to that of the 1918 pandemic virus," Protein Cell 1(5):459-467.

Zhang et al., 2011, "Determination of serum neutralization antibodies against seasonal influenza A strain H3N2 and the emerging strains 2009 H1N1 and avian H5N1," Scand. J. Infect. Dis. 43(3):216-220.

Zhang et al., 2015, "A human-infecting H10N8 influenza virus retains a strong preference for avian-type receptors," Cell Host Microbe, 17(3):377-384.

Zhao et al., 2011, "Identification of a highly conserved H1 subtype-specific epitope with diagnostic potential in the hemagglutinin protein of influenza A virus," PLoS One, 6(8):e23374 (10 pages).

Zheng, et al. 1996, "Nonconserved nucleotides at the 3' and 5' ends of an influenza A virus RNA play an important role in viral RNA replication", Virology 217:242-251.

Zheng et al., 2020, "Enhancing Neuraminidase Immunogenicity of Influenza A Viruses by Rewiring RNA Packaging Signals," J. Virol., 94(16):e00742-20 (12 pages).

Zhou et al., 1994, "Adeno-associated virus 2-mediated high efficiency gene transfer into immature and mature subsets of hematopoietic progenitor cells in human umbilical cord blood," J Exp Med., 179(6):1867-1875.

Ziegler et al., 1995, "Type- and subtype-specific detection of influenza viruses in clinical specimens by rapid culture assay," J Clin Microbiol., 33(2):318-321.

Zost et al., 2017, "Contemporary H3N2 influenza viruses have a glycosylation site that alters binding of antibodies elicited by egg-adapted vaccine strains," Proc. Natl. Acad. Sci. USA, 114(47):12578-12583.

Strohmeier et al., 2022, "A CpG 1018 adjuvanted neuraminidase vaccine provides robust protection from influenza virus challenge in mice," NPJ Vaccines, 7(1):81 (13 pages).

Gao et al., 2021, "Balancing the influenza neuraminidase and hemagglutinin responses by exchanging the vaccine virus backbone," PLoS Pathog., 17(4):e1009171 (22 pages).

International Searching Authority, International Search Report and Written Opinion for International Patent Application No. PCT/US2023/014150 (Pub No. WO 2023167868) mailed Aug. 11, 2023 (14 pages).

Job et al., 2018, "Antibodies Directed toward Neuraminidase N1 Control Disease in a Mouse Model of Influenza," J. Virol., 92(4):e01584-17 (17 pages).

Johansson et al., 1990, "Comparative long-term effects in a mouse model system of influenza whole virus and purified neuraminidase vaccines followed by sequential infections," J. Infect. Dis., 162(4):800-809.

Johansson et al., 1991, "Programmed antigenic stimulation: kinetics of the immune response to challenge infections of mice primed with influenza inactivated whole virus or neuraminidase vaccine," Vaccine, 9(5):330-333.

Martinet et al., 1997, "Protection of mice against a lethal influenza challenge by immunization with yeast-derived recombinant influenza neuraminidase," Eur. J. Biochem., 247(1):332-338.

Nachbagauer et al., 2020, "Is a Universal Influenza Virus Vaccine Possible?" Annu. Rev. Med., 71:315-327.

Roubidoux et al., 2022, "Novel Epitopes of the Influenza Virus N1 Neuraminidase Targeted by Human Monoclonal Antibodies," J. Virol., 96(9):e0033222 (14 pages).

Schotsaert et al., 2016, "Long-Lasting Cross-Protection Against Influenza A by Neuraminidase and M2e-based immunization strategies," Sci. Rep., 6:24402 (22 pages).

Strohmeier et al., 2021, Introduction of Cysteines in the Stalk Domain of Recombinant Influenza Virus N1 Neuraminidase Enhances Protein Stability and Immunogenicity in Mice, Vaccines (Basel), 9(4):404 (13 pages).

Tan et al., 2022, "Murine Broadly Reactive Antineuraminidase Monoclonal Antibodies Protect Mice from Recent Influenza B Virus Isolates and Partially Inhibit Virus Transmission in the Guinea Pig Model," mSphere, 7(5):e0092721 (13 pages).

Braun et al., 1988, "Immunogenic duplex nucleic acids are nuclease resistant," J. Immunol., 141(6):2084-2089.

Campbell, 2017, "Development of the CpG Adjuvant 1018: A Case Study," Methods Mol. Biol., 1494:15-27.

Chambers et al., 2015, "Identification of Hemagglutinin Residues Responsible for H3N2 Antigenic Drift during the 2014-2015 Influenza Season," Cell Rep., 12(1):1-6.

Coffman et al., 2010, "Vaccine adjuvants: putting innate immunity to work," Immunity, 33(4):492-503.

Hoxie et al., 2024, "A recombinant N2 neuraminidase-based CpG 1018® adjuvanted vaccine provides protection against challenge with heterologous influenza viruses in mice and hamsters," Vaccine, 42(24):126269 (16 pages).

Jackson et al., 2018, "Immunogenicity of a two-dose investigational hepatitis B vaccine, HBsAg-1018, using a toll-like receptor 9 agonist adjuvant compared with a licensed hepatitis B vaccine in adults," Vaccine, 36(5):668-674 (Epub 2017).

Kanekiyo et al., 2021, "Next-Generation Influenza Vaccines," Cold Spring Harb. Perspect Med., 11(8):a038448 (17 pages).

Kilbourne et al., 2004, "Protection of mice with recombinant influenza virus neuraminidase," J. Infect. Dis., 189(3):459-461.

Kirkpatrick Roubidoux et al., 2021, "Identification and Characterization of Novel Antibody Epitopes on the N2 Neuraminidase," mSphere, 6(1):e00958-20 (11 pages).

Lai et al., 2019, "Neuraminidase activity and specificity of influenza A virus are influenced by haemagglutinin-receptor binding," Emerg Microbes Infect., 8(1):327-338.

Latimer et al., 1995, "Specificity of monoclonal antibodies produced against phosphorothioate and ribo modified DNAs," Mol. Immunol., 32(14-15):1057-1064.

Marcelin et al., 2011, "A contributing role for anti-neuraminidase antibodies on immunity to pandemic H1N1 2009 influenza A virus," PLoS One, 6(10):e26335 (10 pages).

McMahon et al., 2020, "Correctly folded—but not necessarily functional—influenza virus neuraminidase is required to induce protective antibody responses in mice," Vaccine, 38(45):7129-7137.

McMahon et al., 2023, "Immunity induced by vaccination with recombinant influenza B virus neuraminidase protein breaks viral transmission chains in guinea pigs in an exposure intensity-dependent manner," J. Virol., 97(10):e0105723.

Protein Data Bank, Sequence and structure of the GCN4-pLI tetramerization, ">1GCL_1|Chains A, B, C, D|GCN4|*Saccharomyces cerevisiae* (4932)" [online]. [Retrieved on Jul. 7, 2025]. Retrieved from the internet <URL: https://www.rcsb.org/fasta/entry/1GCL/display> (1 page).

Puente-Massaguer et al., 2025, "Combination of recombinant neuraminidase with cHA-based inactivated split vaccines improves the breadth of cross-reactivity and protection against influenza viruses in mice," Vaccine, 61:127388 (5 pages).

(56) References Cited

OTHER PUBLICATIONS

Skowronski et al., 2019, "Paradoxical clade- and age-specific vaccine effectiveness during the 2018/19 influenza A(H3N2) epidemic in Canada: potential imprint-regulated effect of vaccine (I-REV)," Euro. Surveill., 24(46):1900585 (12 pages).

Sliepen et al., 2015, "Immunosilencing a highly immunogenic protein trimerization domain," J. Biol. Chem., 290(12):7436-7442.

Xie et al., 2015, "H3N2 Mismatch of 2014-15 Northern Hemisphere Influenza Vaccines and Head-to-head Comparison between Human and Ferret Antisera derived Antigenic Maps," Sci. Rep., 5:15279 (10 pages).

* cited by examiner

PR8 N1    MNPNQKITTIGSICLVVGLISLILQIGNIISIWISHSIQ------TGSQNHTGIQNQNIITY    56
          MNPNQKI TIGS+ L + I        +QI  +I+        H Q        + N        II
HK14 N2   MNPNQKITIGSVSLTISTICFFMQIAILITTVTLHFKQYEFNSPPMNQVMLEPTIIER    60

PR8 N1    KNSTWVKDTTSVILTGNSSLCP------------IRGWAIYSKDNSIRIGSKGDVFVI    102
          + V   T + I        +CP              I G+A +SKDNSIR+ + GD++V
HK14 N2   NITEIVYLTNTTI------EKEICPKPAEYRNWSKPQCGIITGFAPFSKDNSIRLSAGGDIWVT    117

```
B_Mal       MLPS------------TIQTLTLFLTSGGVLLSLYVSASLSYLPYSDILLKFPSTEITAPT   49
N5_aw       MNPNQKIITIGSVSLALVVFNILLHIASIVIGII----SV---TKEISVSS---------   44
N5_md       MNPNQKIITIGSISLGLVVFNILLHVASIVLGII----SV---TKDHG-AY---------   43
N8_cN       MNPNQKIVTIGSISLGLVVFNVLLHAVSIILTVL----AL---GKSEN-NG---------   43
N8_cL       MNPNQKIITIGSVSLGLVVLNILLHIVSITVTVL----VL---PRNGN-NG---------   43
N4_duck     MNPNQKIITIGSVSIVLTTIGLLLQITSLCSIWF----SHYNQVTQT-SEQ---------   46
N4_rt       MNPNQKIITIGSVSIILTTIGLLLQITSLCSIWF----SHYNQVTQT-HEQ---------   46
N1-Mich15   MNPNQKIITIGSICMTIGMANLILQIGNIISIWV----SHSIQIGNQSQIE---------   47
N1_PR8      MNPNQKITTIGSICLVVGLISLILQIGNIISIWI----SHSIQTGSQNHTG---------   47
N1_WSN      MNPNQKIITIGSICMVVGIISLILQIGNIISIWI----SHSIQTGNQNHTG---------   47
N7_cN       MNPNQKLFALSGVAIALSVLNLLIGISNVGLNVS----LHLKEKGPKQEENLTC--TTI-   53
N7_cG       MNPNQKLFALSGVAIALSVLNLLIGISNVGLNVS----LHLKEKGPKQEENLTC--TTI-   53
N9_AH13     MNPNQKILCTSATAIIIGAIAVLIGIANLGLNIG----LHLKPGCNCSHSQPET--T---   51
N9_ck       MNPNQKILCTSATAIIIGAIAVLIGIANLGLNIG----LHLKPGCNCSHSQPET--T---   51
N6_Sz       MNPNQKITCISATGVTLSVVSLLIGIANLGLNIG----LHYKVSDSTTINIPNM--NET-   53
N6_cs       MNPNQKIICISATGMTLSVVSLLIGIANLGLNIG----LHYKVGDTPDVNIPSM--NET-   53
N3_duck     MNPNQKIITIGVVNTTLSTIALLIGIGNLIFNTV----IHEKIGVHQTVVYPTI--TPPV   54
N3_sw       MNPNQKIITIGVVNTTLSTIALLIGVGNLIFNTV----IHEKIGDHQIVTYPTI--TTPA   54
N3_bwt      MNPNQKIITIGVVNTTLSTIALLIGVGNLVFNTV----IHEKIGDHQTVTHPTI--TTPA   54
N2_HK14     MNPNQKIITIGSVSLTISTICFFMQIAILITTVT----LHFKQY-----EFNSP--PNNQ   49
N2_ck       MNPNQKIIALGSASLTIAIVCLLIQIAILATTMT----LHFTQS-----EYTNS--STNK   49
            * *.          :        .::       :

B_Mal       MPLDCANASNVQAVN-----RSAT--KGVTLLLPEPE------WTYPRLSCPGSTFQKAL   96
N5_aw       ---TCNT---TEVYNETVRLETITIPINNTVYIERESHQEPEFLNNTEPLCNVSGFAIVS   98
N5_md       ---TCNT---TEVYNETVRVETVTIPVNNTIYIERELTHEPEFLNNTEPLCEVSGFAIVS   97
N8_cN       ----ICNGTV-VREYNETVRIEKVTQWYNTSVVEYVPHWNEGTYINNTEPICDVKGFAPFS   99
N8_cL       ---SCNETV-IREYNETVRVEKVTQWHNTNVIEYIERPENDHFMNNTEALCDAKGFAPFS   99
N4_duck     ----SCSNNT-TNYYNETFVNVTNVQNNYTTI-T-EPSSPQVIHYSSGRDLCPVKGWAPLS  100
N4_rt       ----PCSNNT-TNYYNETFVNVTNVQNNYTTV-T-EPSTPDVVHYSSGRDLCPIRGWAPLS  100
N1-Mich15   ---TCNQSV-ITYENNTWVNQTYVNISNTNF-A-AGQSVVSVKLAGNSSLCPVSGWAIYS  101
N1_PR8      ----ICNQNI-ITYKNSTWVKDT--------------------TSVILTGNSSLCPIRGWAIYS   86
N1_WSN      ---ICNQGS-ITYKVVA-GQDS---------------TSVILTGNSSLCPIRGWAIHS   85
N7_cN       ----NQNNTT-V-V-E-----NTYVNNTTIITK--GTDLKTPSYLLLNKSLCNVEGWVVIA  100
N7_cG       ----NQNNTT-V-V-E-----NTYVNNTTIITK--GTDLKTPSYLLLNKSLCNVEGWVVIA  100
N9_AH13     ---NTSQTI-I-N-N--------YYNETNITNI-QMEERTSRNFNNLTKGLCTINSWHIYG   97
N9_ck       ---NTSQTI-I-N-N--------YYNETNITNI-QMEERTSKNFNNLTKGLCTINSWHIYG   97
N6_Sz       ----NSTT---------------TNITNI-IVNKNEERTFLNLTKPLCEVNSWHILS   90
N6_cs       ----NSTTTI-I-N-N-----NTQNNFTNITNI-IVNKEEGRTFLNLTKPLCEVNSWHILS  101
N3_duck     I-PNCSDTT-ITY-N------NTVVNNITATIINKAEKQ------FKPSLPLCPFRGFFPFH  101
N3_sw       V-PNCSDTI-ITY-N------NTVINNITTTIITEEERP------FKSPLPLCPFRGFFPFH  101
N3_bwt      I-PNCSDTI-ITY-N------NTVINNITTTIITEAERP------FKSPLPLCPFRGFFPFH  101
N2_HK14     V-MLCEPTI-IER-N------ITEIVYLTNTTIEKEICPKPAEYRNWSKPQCGITGFAPFS  101
N2_ck       V-VSCESTI-IER-N------ITEIVHLNGTIIERESCPKSAEYKNWSKPQCQITGFAPFS  101
                                                    *       :
```

FIG. 9A

```
B_Mal       LISPHRFGETKGNSAPLIIREPFIACGPKECKHFALTHYAAQPGGYYNGTRGDRNKLRHL  156
N5_aw       KDNGIRIGS---RGHVFVIREPFVACGPTECRTFFLTQGALLNDKHSNNTVKDRSPYRAL  155
N5_md       KDNGIRIGS---RGHVFVIREPFVACGPSECRTFFLTQGALLNDKHSNNTVKDRSPYRAL  154
N8_cN       KDNGIRVGS---RGHIFVIREPFVSCSPVECRTFFLTQGSLLNDKHSNGTVKDRSPFRTL  156
N8_cL       KDNGIRIGS---RGHVFVIREPFVSCSPTECRTFFLTQGSLLNDKHSNGTVKDRSPYRTL  156
N4_duck     KDNGIRIGS---RGEVFVIREPFISCSINECRTFFLTQGALLNDKHSNGTVKDRSPFRTL  157
N4_rt       KDNGIRIGS---RGEVFVIREPFISCSISECRTFFLTQGALLNDKHSNGTVKDRSPFRTL  157
N1-Mich15   KDNSVRIGS---KGDVFVIREPFISCSPLECRTFFLTQGALLNDKHSNGTIKDRSPYRTL  158
N1_PR8      KDNSIRIGS---KGDVFVIREPFISCSHLECRTFFLTQGALLNDKHSNGTVKDRSPYRAL  143
N1_WSN      KDNGIRIGS---KGDVFVIREPFISCSHLECRTFFLTQGALLNDKHSRGTFKDRSPYRAL  142
N7_cN       KDNAVRFGE----SEQIIVTREPYVSCDPTGCKMYALHQGTTIRNKHSNGTIHDRTAFRGL  157
N7_cG       KDNAVRFGE----SEQIIVTREPYVSCDPTGCKMYALHQGTTIRNKHSNGTIHDRTAFRGL  157
N9_AH13     KDNAVRIGE----SSDVLVTREPYVSCDPDECRFYALSQGTTIRGKHSNGTIHDRSQYRAL  154
N9_ck       KDNAVRIGE----SSDVLVTREPYVSCDPDECRFYALSQGTTIRGKHSNGTIHDRSQYRAL  154
N6_Sz       KDNAIRIGE----DAHILVTREPYLSCDPQGCRMFALSQGTTLRGRHANGTIHDRGPFRAL  147
```

FIG. 9A (cont.)

```
N6_cs         KDNAIRIGE----DAHILVTREPYLSCDPQGCRMFALSQGTTLRGRHANGTIHDRSPFRAL    158
N3_duck       KDNAIRLGE----NKDVIVTREPYVSCDNDDCWSFALAQGALLGTKHSNGTIKDRTPYRSL    158
N3_sw         KDNAIRLGE----NKDVIVTREPYVSCDNDNCWSFALTQGALLGTKHSNGTIKDRTPYRSL    158
N3_bwt        KDNAIRLGE----NKGVIVTREPYISCDNDNCWSFALAQGALLGTKHSNGTIKDRTPYRSL    158
N2_HK14       KDNSIRLSA----GGDIWVTREPYVSCDPDKCYQFALGQGTTLNNVHSNNXVRDRTPYRTL    158
N2_ck         KDNSIRLSA----GGDIWVTREPYVSCSLNKCYQFALGQGTTLNNRHSNGTTHDRSPYRTL    158
                   .  *..         :  ***::*.      *   :  *  : :        :  ..    **     *  *

B_Mal         ISVKLGKIPTVENSIFHMAAWSGSACHDGKEWTYIGVDGPDNNALLKIKYGEAYTDTYHS    216
N5_aw         MSVPLGSSPNAYQAKFESVAWSATACHDGKGWLAVGISGADDDAYAVIHYGGMPTDVVRS    215
N5_md         MSVPLGSSPNAYQAKFESVGWSATACHDGKEWMAIGVSGADDDAYAVIHYGGIPTDVVRS    214
N8_cN         MSVEVGQSPNVYQARFEAVAWSATACHDGKKWMTIGVTGPDSKAVAVVHYGGVPTDVVNS    216
N8_cL         MSVEIGQSPNVYQARFEAVAWSATACHDGKKWMTIGVTGPDAKAVAVVHYGGIPTDVINS    216
N4_duck       MSCPIGVAPSPSNSRFESVAWSATACSDGPGWLTLGITGPDSTAVAVIKYNGIITDTLKS    217
N4_rt         MSCPIGVAPSPSNSRFESVAWSATACSDGPGWLTLGITGPDTTAVAVLKYNGIITDTFKS    217
N1-Mich15     MSCPIGEVPSPYNSRFESVAWSASACHDGINWLTIGISGPDSGAVAVLKYNGIITDTIKS    218
N1_PR8        MSCPVGEAPSPYNSRFESVAWSASACHDGMGWLTIGISGPDNGAVAVLKYNGIITETIKS    203
N1_WSN        MSCPVGEAPSPYNSRFESVAWSASACHDGMGWLTIGISGPDDGAVAVLKYNRIITETIKS    202
N7_cN         ISTPLGTPPTVSNSDFMCVGWSSTTCHDGIARMTICIQGNNDNATATVYYNRRLTTTIKT    217
N7_cG         ISTPLGTPPTVSNSDFMCVGWSSTTCHDGIARMTICIQGNNDNATATVYYNRRLTTTIKT    217
N9_AH13       ISWPLSSPPTVYNSRVECIGWSSTSCHDGKSRMSICISGPNNNASAVVWYNRRPVAEINT    214
N9_ck         ISWPLSSPPTVYNSRVECIGWSSTSCHDGKSRMSICISGPNNNASAVVWYNRRPVAEINT    214
N6_Sz         ISWEMGQAPSPYNTRVECIGWSSTSCHDGISRMSICISGPNDNASAVVWYRGRPVTEIPS    207
N6_cs         VSWEMGQAPSPYNVRVECIGWSSTSCHDGISRMSICMSGPNNNASAVVWYGGRPVTEIPS    218
N3_duck       IRFPIGTAPVLGNYKEICVAWSSSSCFDGKEWMHVCMTGNDNDASGQIIYAGKMTDSIKS    218
N3_sw         IRFPIGTAPVLGNYKEICIAWSSSSCFDGKEWMHVCMTGNDNDASAQIIYGGRMTDSIKS    218
N3_bwt        IRFPIGTAPVLGNYKEICIAWSSSSCFDGKEWMHVCMTGNDNDASAQIIYAGRMTDSIKS    218
N2_HK14       LMNELGVPFHLG-TKQVCIAWSSSSCHDGKAWLHVCITGDDKNATASFIYNGRLVDSVVS    217
N2_ck         LMSELGVPFHLG-TKQVCIAWSSSSCHDGRAWLHVCVTGDDKNATASVIYDGMLTDSIVS    217
                   :   :.           .**.::* **     :  : *  :   *   .  *     .      :
```

FIG. 9B

```
B_Mal        YANNILRTQESACNCIGGNCYLMITDGSASGVSECRFLKIREGRIIKEIFPT-GRIKHTE    275
N5_aw        WRKQILRTQESSCVCMTGNCYWVMTDGPANSQASYKIFKSHRGMVTNEREVS-FQGGHIE    274
N5_md        WRKQILRTQESSCVCMKGECYWVMTDGPANNQASYKIFKSQKGLVVDEKEIS-FQGGHIE    273
N8_cN        WAGDILRTQESSCTCIQGNCYWVMTDGPANRQAQYRIYKANQGKIIGRTDVS-FSGGHIE    275
N8_cL        WAGDILRTQESSCTCIQGECFWVMTDGPANRQAQYRAFKAKQGKIVGQAEIS-FNGGHIE    275
N4_duck      WKGNIMRTQESECVCQDEFCYTLITDGPSDAQAFYKILKIRKGKIMSVKDVD-ATGFHFE    276
N4_rt        WKGNIMRTQESECVCQDEFCYTLITDGPSDAQAFYKILKIRKGKIVSMKDVD-ATGFHFE    276
N1-Mich15    WRNNILRTQESECACVNGSCFTIMTDGPSDGQASYKIFRIEKGKIIKSVEMK-APNYHYE    277
N1_PR8       WRKKILRTQESECACVNGSCFTIMTDGPSDGLASYKIFKIEKGKVTKSIELN-APNSHYE    262
N1_WSN       WRKNILRTQESECTCVNGSCFTIMTDGPSDGLASYKIFKIEKGKVTKSIELN-APNSHYE    261
N7_cN        WARNILRTQESECVCHNGTCAVVMTDGSASSQAYTKVMYFHKGLVVKEEELR-GSARHIE    276
N7_cG        WARNILRTQESECVCHNGTCAVVMTDGSASSQAYTKVMYFHKGLVVKEEELR-GSARHIE    276
N9_AH13      WARNILRTQESECVCHNGVCPVVFTDGSATGPADTRIYYFKEGKILKWESLT-GTAKHIE    273
N9_ck        WARNILRTQESECVCHNGVCPVVFTDGSATGPADTRIYYFKEGKILKWESLT-GTAKHIE    273
N6_Sz        WVGNILRTQESECVCHKGICPVVMTDGPANNKAATKIIYFKEGKIQKIEELQ-GNAQHIE    266
N6_cs        WAGNILRTQESECVCHKGICPVVMTDGPANNRAATKIIYFKEGKIQKIEELE-GNAQHIE    277
N3_duck      WRRDILRTQESECQCIDGTCIVAVTDGPAASSADHRIYWIRKGKIIKYEDIPKTKIQHLE    278
N3_sw        WRKDILRTQESECQCIDGTCVVAVTDGPAANSADYRVYWIREGKIIKYENVPKTKIQHLE    278
N3_bwt       WRKDILRTQESECQCIDGTCVVAVTDGPAANSADHRVYWIREGKIIKYEDVPKTKIQHLE    278
N2_HK14      WSKDILRTQESECICINGTCTVVMTDGSASGKADTKILFIEEGKIVHTSTLS-GSAQHVE    276
N2_ck        WSKNILRTQESECVCINGTCTVVMTDGSASGMADTRILFIREGKIVHISPLS-GSAQHVE    276
             : .*:***** * *     *   .*** :    :  :    ..* :         * *

B_Mal        ECTCGFASNKTIECACRDNSYTAKRPFVKLNVETDTAEIRLMCTETYLDTPRPDDGSITG    335
N5_aw        ECSC-YPNLGKVECVCRDNWNGMNRPVLTFDED-LNYEVGYLCAGIPTDTPRVQDNSFTG    332
N5_md        ECSC-YPNMGKVECVCRDNWNGMNRPILTFDEN-LEYEVGYLCAGIPTDTPRVQDSSFTG    331
N8_cN        ECSC-YPNDGKVECVCRDNWTGTNRPVLIISPD-LSYRVGYLCAGLPSDTPRGEDTQFAG    333
N8_cL        ECSC-YPNEGKVECVCRDNWTGTNRPVLVISPD-LSYRVGYLCAGIPSDTPRGEDSQFTG    333
N4_duck      ECSC-YPSGENVECVCRDNWRGSNRPWIRFNSD-LDYQIGYVCSGVFGDNPRPVDG--TG    332
```

FIG. 9B (cont.)

```
N4_rt       ECSC-YPSRTDIECVCRDNWRGSNRPWIRFNSD-LDYQIGYVCSGIFGDNPRPVDG---TG   332
N1-Mich15   ECSC-YPDSSEITCVCRDNWHGSNRPWVSFNQN-LEYQMGYICSGVFGDNPRPNDK--TG    333
N1_PR8      ECSC-YPDTGKVMCVCRDNWHGSNRPWVSFDQN-LDYQIGYICSGVFGDNPRPEDG---TG   318
N1_WSN      ECSC-YPDTGKVMCVCRDNWHGSNRPWVSFDQN-LDYKIGYICSGVFGDNPRPKDG---TG   317
N7_cN       ECSC-YGHNQKVTCVCRDNWQGANRPIIEIDMNTLEHTSRYVCTGILTDTSRPGDKS-SG   334
N7_cG       ECSC-YGHNQKVTCVCRDNWQGANRPIIEIDMNTLEHTSRYVCTGILTDTSRPGDKS-SG   334
N9_AH13     ECSC-YGERTGITCTCRDNWQGSNRPVIQIDPVAMTHTSQYICSPVLTDNPRPNDPN-IG   331
N9_ck       ECSC-YGERTGITCTCRDNWQGSNRPVIQIDPVAMTHTSQYICSPVLTDNPRPNDPN-IG   331
N6_Sz       ECSC-YGAAGMIKCVCRDNWKGANRPIITIDPEMMTHTSKYLCSKILTDTSRPNDPT-NG   324
N6_cs       ECSC-YGAAGVIKCICRDNWKGANRPVIIIDPEMMTHTSKYLCSRVLTDTSRPNDPT-SG   335
N3_duck     ECSC-YVDT-DVYCICRDNWKGSNRPWMRINNE-TILETGYVCSKFHSDTPRPADPS-TV   334
N3_sw       ECSC-YVDI-DVYCICRDNWKGSNRPWMRINNE-TILETGYVCSKFHSDTPRPADPS-TM   334
N3_bwt      ECSC-YVDI-DVYCICRDNWKGSNRPWMRINNE-TILETGYVCSKFHSDTPRPADPS-TM   334
N2_HK14     ECSC-YPRYPGVRCVCRDNWKGSNRPIVDINIKDHSIVSSYVCSGLVGDTPRKNDSSSSS   335
N2_ck       ECSC-YPRYPEVRCVCRDNWKGSNRPVLYINMADYNIDSNYVCSGLVGDTPRSDDSSSSS   335
            **:* :       : * ****     :** : .            :*:    *. *   *

B_Mal       PCESNG---DKGSGGIKGGFVHQRMASKIGRWYSRTMSKTKRMGMGLYVKYDGDPWADSD   392
N5_aw       SCTNAVGGSGTNNYGVKGFG----FRQGNSVWAGRTVSISSRSGFEILLIE--DGWIKTS   386
N5_md       SCTNAVGGSGTNNYGVKGFG----FRQGTSVWAGRTISISSRSGFEVLLIK--DGWIRPS   385
N8_cN       SCTSPMGN---QGYGVKGFG----FRQGTDVWVGRTISRTSRSGFEIIRIK--NGWTQTS   384
N8_cL       SCTSPMGN---QGYGVKGFG----FRQGSDVWMGRTISRTSRSGFEILKVR--NGWVQNS   384
N4_duck     SCSGPI-NNGKGRYGVKGFS----FRYGDGVWIGRTKSLESRSGFEMVWDA--NGWVSTD   385
N4_rt       SCNSPV-NNGKGRYGVKGFS----FRYGDGVWIGRTKSLEFRSGFEMVWDA--NGWVSTD   385
N1-Mich15   SCGPVS-S--NGANGVKGFS----FKYGNGVWIGRTKSISSRKGFEMIWDP--NGWTGTD   384
N1_PR8      SCGPVY-V--DGANGVKGFS----YRYGNGVWIGRTKSHSSRHGFEMIWDP--NGWTETD   369
N1_WSN      SCGPVS-A--DGANGVKGFS----YKYGNGVWIGRTKSDSSRHGFEMIWDP--NGWTETD   368
N7_cN       DCSNPI-TGSPGAPGVKGFG----FLNGDNTWLGRTISPRSRSGFEMLKIP---NAGTDPN  387
N7_cG       DCSNPI-TGSPGAPGVKGFG----FLNGDNTWLGRTISPRSRSGFEMLKIP---NAGTDPN  387
N9_AH13     KCNDPY-PGN-NNNGVKGFS----YLDGANTWLGRTISTASRSGYEMLKVP---NALTDDR  383
N9_ck       KCNDPY-PGN-NNNGVKGFS----YLDGANTWLGRTISTASRSGYEMLKVP---NALTDDR  383
N6_Sz       NCDAPI-TGGSPDPGVKGFA----FLDGENSWLGRTISKDSRSGYEMLKVP---NAETDTQ  377
N6_cs       NCDAPI-TGGSPDPGVKGFA----FLDGENSWLGRTISKDSRSGYEMLKVP---NAETDTQ  388
N3_duck     SCDSPS-NIN-GGPGVKGFG----FRAGNDVWLGRTVSTTGRSGFEVIKVT---EGWINSL  386
N3_sw       SCDSPS-NVN-GGPGVKGFG----FKAGDDVWLGRTVSTSGRSGFEIIKVT---EGWINSP  386
N3_bwt      SCDSPS-NVN-GGPGVKGFG----FKAGDDVWLGRTVSTSGRSGFEIIKVT---EGWINSP  386
N2_HK14     HCLDPN-NEE-GGHGVKGWA----FDDGNDVWMGRTINETSRLGYETFKVI---EGWSNPK  387
N2_ck       NCRDPN-NER-GGPGVKGWA----FDXGDDVWMGRTIKKDSRAGYETFRVV---DGWTVAN  387
            *        *:**          . * ,** . * *           :
```

FIG. 9C

```
B_Mal       ALAFSGVMVSMEEPGW---YSFGF----EIKDKKCDVPCIGIEMVHDGGKE----TWHSAA   442
N5_aw       KN-VVKKVEVLNNKNWSGYSGAFTIPITMTSKQCLVPCFWLEMIRGKPEERT-SIWTSSS   444
N5_md       KT-ISKKVEVLDNKNWSGYSGSFTIPTAMTSKSCLVPCFWLEMIRGKPEERT-SIWTSSS   443
N8_cN       KE-QIRRQVVVDNSNWSGYSGSFTLPVELSGRECLVPCFWVEMIRGRPEER--TIWTSSS   441
N8_cL       KE-QIKRQVVVDNLNWSGYSGSFTLPVELTKRNCLVPCFWVEMIRGKPEEK--TIWTSSS   441
N4_duck     KD-SNGVQDIIDNDNWSGYSGSFSIRGETTGKNCTVPCFWVEMIRGQPKEK--TIWTSGS   442
N4_rt       KD-SNGVQDIIDNDNWSGYSGSFSIRGEKTGRNCTVPCFWVEMIRGQPKEK--TIWTSGS   442
N1-Mich15   NK-FSIKQDIVGINEWSGYSGSFVQHPELTGLDCIRPCFWVELIRGRPEEN--TIWTSGS   441
N1_PR8      SK-FSVRQDVVAMTDWSGYSGSFVQHPELTGLDCMRPCFWVELIRGRPKEK--TIWTSAS   426
N1_WSN      SR-FSMRQDVVAITNRSGYSGSFVQHPELTGLDCMRPCFWVELIRGLPEED--AIWTSGS   425
N7_cN       SR-IAERQEIVDNNNWSGYSGSFIDYW-NDNSECYNPCFYVELIRGRPEEAKYVWWTSNS   445
N7_cG       SR-IAERQEIVDNNNWSGYSGSFIDYW-NDNSECYNPCFYVELIRGRPEEAKYVWWASNS   445
N9_AH13     SK-PIQGQTIVLNADWSGYSGSFMDYW-AE-GDCYRACFYVELIRGRPKEDK-VWWTSNS   439
N9_ck       SK-PIQGQTIVLNADWSGYSGSFMDYW-AK-GDCYRACFYVELIRGRPKEDK-VWWTSNS   439
N6_Sz       SG-PTSYQLIVNNQNWSGYSGAFIDYW-AN-KGCFNPCFYVELIRGRPKEID-VLWTSSS   433
N6_cs       SG-PTSHQVIVNNQNWSGYSGAFIDYW-AN-KECFNPCFYVELIRGRPKESS-VLWTSNS   444
N3_duck     NHAKSITQTLVSNNDWSGYSGSFIV----ENNGCFQPCFYIELIRGRPNRNDDVSWTSNS   442
N3_sw       NHVKSITQTLVSNNDWSGYSGSFIV----KAKDCFQPCFYVELIRGRPNKNDDVSWTSNS   442
N3_bwt      NHAKSITQTLVSNNDWSGYSGSFIV----KTKDCFQPCFYVELIRGRPNKNDDVSWTSNS   442
```

FIG. 9C (cont.)

```
N2_HK14    SKLQTNRQVIVDRGDRSGYSGIFSV----EGKSCINRCFYVELIRGRKEE-TEVLWTSNS  442
N2_ck      SKSQTNRQVIVESDNRSGYSGIFSV----EGKTCINRCFYVELIRGRPQE-TRVWWTSNS  442
                  :        **  *         *   *: :*:::.  :.     *  * :

B_Mal      TAIYCLMGSGQLLWDTVTGVNMAL------  466
N5_aw      STVFCGVSSEVPGWSWDDGAILPFDIDKM-  473
N5_md      STVFCGVSSEVPGWSWDDGAILPFDIDKM-  472
N8_cN      SIVMCGVDYEIADWSWHDGAILPFDIDKT*  470
N8_cL      SIVMCGVDHEIADWSWHDGAILPFDIDKM-  470
N4_duck    SIAFCGVDSDTTGWSWPDGALLPFDIDK--  470
N4_rt      SIAFCGVNSDTTGWSWPDGALLPFDIDK--  470
N1-Mich15  SISFCGVNSDTVGWSWPDGAELPFTIDK*-  469
N1_PR8     SISFCGVNSDTVDWSWPDGAELPFSIDK*-  454
N1_WSN     IISFCGVNSDTVDWSWPDGAELPFTIDK*-  453
N7_cN      LIALCGSPFPVGPGSFPDGAQIQYFS----  471
N7_cG      LIALCGSPFPVGSGSFPDGAQIQYFS----  471
N9_AH13    IVSMCSSTEFLGQWNWPDGAKIEYFL----  465
N9_ck      IVSMCSSTEFLGQWNWPDGAKIEYFL----  465
N6_Sz      MVALCGSRERLGSWSWHDGAEIIYFK*---  459
N6_cs      IVALCGSKERLGSWSWHDGAEIIYFK----  470
N3_duck    IVTFCGLDNEPGSGNWPDGSNIGFMPK---  469
N3_sw      IVTFCGLDNEPGSGNWPDGSNIGFMPK*--  469
N3_bwt     IVTFCGLDNEPGSGNWPDGSNIGFMPK---  469
N2_HK14    IVVFCGTSGTYGTGSWPDGADLNLMPI*--  469
N2_ck      IIVFCGTSGTYGTGSWPDGANINFMSI---  469
                  *          .   *   :
```

FIG. 9D

| Prime | Boost | Challenge |
|---|---|---|
| 3ug N1-MPP | 3ug N1-MPP | A/Singapore/GP1908/2015 (H1N1) |
| 3ug N1-MPP + AddaVax | 3ug N1-MPP + AddaVax | |
| Neg. Ctrl. | Neg. Ctrl. | |

| Prime | Boost | Challenge |
|---|---|---|
| 3ug N2-MPP | 3ug N2-MPP | A/Switzerland/9715293/2013 (H3N2) |
| 3ug N2-MPP + AddaVax | 3ug N2-MPP + AddaVax | |
| Neg. Ctrl. | Neg. Ctrl. | |

| Prime | Boost | Challenge |
|---|---|---|
| 3ug B-NA-MPP | 3ug B-NA-MPP | B/New York/PV01181/2018 |
| 3ug B-NA-MPP + AddaVax | 3ug B-NA-MPP + AddaVax | |
| Neg. Ctrl. | Neg. Ctrl. | |

FIG. 15

ELISA N1-VASP

Neuraminidase inhibition

Serum dilution

```
                         SEQUENCE LISTING

<160> NUMBER OF SEQ ID NOS: 66

<210> SEQ ID NO 1
<211> LENGTH: 85
<212> TYPE: PRT
<213> ORGANISM: Artificial Sequence
<220> FEATURE:
<223> OTHER INFORMATION: Tetramerization domain from SEPPALLATA-like
      MADS domain transcription factor from Arabidopsis thaliana (SMDTF)

<400> SEQUENCE: 1

Val Glu Leu Ser Ser Gln Gln Glu Tyr Leu Lys Leu Lys Glu Arg Tyr
1               5                   10                  15

Asp Ala Leu Gln Arg Thr Gln Arg Asn Leu Leu Gly Glu Asp Leu Gly
            20                  25                  30

Pro Leu Ser Thr Lys Glu Leu Glu Ser Leu Glu Arg Gln Leu Asp Ser
        35                  40                  45

Ser Leu Lys Gln Ile Arg Ala Leu Arg Thr Gln Phe Met Leu Asp Gln
    50                  55                  60

Ser Lys Glu Arg Met Leu Thr Glu Thr Asn Lys Thr Leu Arg Leu Arg
65                  70                  75                  80

Leu Ala Asp Gly Tyr
                85

<210> SEQ ID NO 2
<211> LENGTH: 113
<212> TYPE: PRT
<213> ORGANISM: Artificial Sequence
<220> FEATURE:
<223> OTHER INFORMATION: Sendai virus phosphoprotein tetramerization
      domain (SPP)

<400> SEQUENCE: 2

Glu Asn Thr Ser Ser Met Lys Glu Met Ala Thr Leu Leu Thr Ser Leu
1               5                   10                  15

Gly Val Ile Gln Ser Ala Gln Glu Phe Glu Ser Ser Arg Asp Ala Ser
            20                  25                  30

Tyr Val Phe Ala Arg Arg Ala Leu Lys Ser Ala Asn Tyr Ala Glu Met
        35                  40                  45

Thr Phe Asn Val Cys Gly Leu Ile Leu Ser Ala Glu Lys Ser Ser Ala
    50                  55                  60

Arg Lys Val Asp Glu Asn Lys Gln Leu Leu Lys Ile Gln Glu Ser Val
65                  70                  75                  80
```

Glu Ser Phe Arg Asp Ile Tyr Lys Arg Phe Ser Glu Tyr Gln Lys Glu
                85                  90                  95

Gln Asn Ser Leu Leu Met Ser Asn Leu Ser Thr Leu His Ile Ile Thr
            100                 105                 110

Asp

<210> SEQ ID NO 3
<211> LENGTH: 24
<212> TYPE: PRT
<213> ORGANISM: Artificial Sequence
<220> FEATURE:
<223> OTHER INFORMATION: PiLZ structure from Xhantomonas campestris

<400> SEQUENCE: 3

Leu Leu Val Gln Arg Met Asp Ala Lys Leu Asp Leu Ile Leu Ala Leu
1               5                   10                  15

Ile Gly Arg Leu Val Arg Gln Ser
            20

<210> SEQ ID NO 4
<211> LENGTH: 74
<212> TYPE: PRT
<213> ORGANISM: Artificial Sequence
<220> FEATURE:
<223> OTHER INFORMATION: Measles virus phosphoprotein tetramerization
      domain (MPP)

<400> SEQUENCE: 4

Gly Asp His Tyr Asp Asp Glu Leu Phe Ser Asp Val Gln Asp Ile Lys
1               5                   10                  15

Thr Ala Leu Ala Lys Ile His Glu Asp Asn Gln Lys Ile Ile Ser Lys
                20                  25                  30

Leu Glu Ser Leu Leu Leu Leu Lys Gly Glu Val Glu Ser Ile Lys Lys
            35                  40                  45

Gln Ile Asn Arg Gln Asn Ile Ser Ile Ser Thr Leu Glu Gly His Leu
        50                  55                  60

Ser Ser Ile Met Ile Ala Ile Pro Gly Leu
65                  70

<210> SEQ ID NO 5
<211> LENGTH: 51
<212> TYPE: PRT
<213> ORGANISM: Artificial Sequence
<220> FEATURE:
<223> OTHER INFORMATION: Dictyocaulus viviparus ACE tetramerization
      domain

<400> SEQUENCE: 5

Ala Val Ala Asp Val Gly Asp Pro Phe Leu Leu Trp Lys Gln Gln Met
1               5                   10                  15

Asp Lys Trp Gln Asn Glu Tyr Ile Thr Asp Trp Gln Tyr His Phe Glu
                20                  25                  30

Gln Tyr Lys Lys Tyr Gln Thr Tyr Arg His Leu Asp Ser Asp Ser Cys
            35                  40                  45

Ser Gly Ser
        50

<210> SEQ ID NO 6
<211> LENGTH: 454
<212> TYPE: PRT
<213> ORGANISM: Artificial Sequence
<220> FEATURE:

-continued

<223> OTHER INFORMATION: PR8 N1 Wild-type

<400> SEQUENCE: 6

```
Met Asn Pro Asn Gln Lys Ile Thr Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Ile
        35                  40                  45

Cys Asn Gln Asn Ile Ile Thr Tyr Lys Asn Ser Thr Trp Val Lys Asp
    50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
            100                 105                 110

Glu Cys Arg Thr Phe Phe Leu Thr Gln Gly Ala Leu Leu Asn Asp Lys
        115                 120                 125

His Ser Asn Gly Thr Val Lys Asp Arg Ser Pro Tyr Arg Ala Leu Met
    130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
            180                 185                 190

Tyr Asn Gly Ile Ile Thr Glu Thr Ile Lys Ser Trp Arg Lys Lys Ile
            195                 200                 205

Leu Arg Thr Gln Glu Ser Glu Cys Ala Cys Val Asn Gly Ser Cys Phe
    210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Gly Lys
            260                 265                 270

Val Met Cys Val Cys Arg Asp Asn Trp His Gly Ser Asn Arg Pro Trp
        275                 280                 285

Val Ser Phe Asp Gln Asn Leu Asp Tyr Gln Ile Gly Tyr Ile Cys Ser
    290                 295                 300

Gly Val Phe Gly Asp Asn Pro Arg Pro Glu Asp Gly Thr Gly Ser Cys
305                 310                 315                 320

Gly Pro Val Tyr Val Asp Gly Ala Asn Gly Val Lys Gly Phe Ser Tyr
            325                 330                 335

Arg Tyr Gly Asn Gly Val Trp Ile Gly Arg Thr Lys Ser His Ser Ser
            340                 345                 350

Arg His Gly Phe Glu Met Ile Trp Asp Pro Asn Gly Trp Thr Glu Thr
        355                 360                 365

Asp Ser Lys Phe Ser Val Arg Gln Asp Val Val Ala Met Thr Asp Trp
    370                 375                 380

Ser Gly Tyr Ser Gly Ser Phe Val Gln His Pro Glu Leu Thr Gly Leu
385                 390                 395                 400
```

```
Asp Cys Met Arg Pro Cys Phe Trp Val Glu Leu Ile Arg Gly Arg Pro
            405             410             415

Lys Glu Lys Thr Ile Trp Thr Ser Ala Ser Ser Ile Ser Phe Cys Gly
            420             425             430

Val Asn Ser Asp Thr Val Asp Trp Ser Trp Pro Asp Gly Ala Glu Leu
            435             440             445

Pro Phe Ser Ile Asp Lys
    450

<210> SEQ ID NO 7
<211> LENGTH: 454
<212> TYPE: PRT
<213> ORGANISM: Artificial Sequence
<220> FEATURE:
<223> OTHER INFORMATION: PR8 N1 I48C

<400> SEQUENCE: 7

Met Asn Pro Asn Gln Lys Ile Thr Thr Ile Gly Ser Ile Cys Leu Val
1               5               10              15

Val Gly Leu Ile Ser Leu Ile Leu Gln Ile Gly Asn Ile Ile Ser Ile
            20              25              30

Trp Ile Ser His Ser Ile Gln Thr Gly Ser Gln Asn His Thr Gly Cys
            35              40              45

Cys Asn Gln Asn Ile Ile Thr Tyr Lys Asn Ser Thr Trp Val Lys Asp
    50              55              60

Thr Thr Ser Val Ile Leu Thr Gly Asn Ser Ser Leu Cys Pro Ile Arg
65              70              75              80

Gly Trp Ala Ile Tyr Ser Lys Asp Asn Ser Ile Arg Ile Gly Ser Lys
            85              90              95

Gly Asp Val Phe Val Ile Arg Glu Pro Phe Ile Ser Cys Ser His Leu
            100             105             110

Glu Cys Arg Thr Phe Phe Leu Thr Gln Gly Ala Leu Leu Asn Asp Lys
            115             120             125

His Ser Asn Gly Thr Val Lys Asp Arg Ser Pro Tyr Arg Ala Leu Met
    130             135             140

Ser Cys Pro Val Gly Glu Ala Pro Ser Pro Tyr Asn Ser Arg Phe Glu
145             150             155             160

Ser Val Ala Trp Ser Ala Ser Ala Cys His Asp Gly Met Gly Trp Leu
            165             170             175

Thr Ile Gly Ile Ser Gly Pro Asp Asn Gly Ala Val Ala Val Leu Lys
            180             185             190

Tyr Asn Gly Ile Ile Thr Glu Thr Ile Lys Ser Trp Arg Lys Lys Ile
            195             200             205

Leu Arg Thr Gln Glu Ser Glu Cys Ala Cys Val Asn Gly Ser Cys Phe
    210             215             220

Thr Ile Met Thr Asp Gly Pro Ser Asp Gly Leu Ala Ser Tyr Lys Ile
225             230             235             240

Phe Lys Ile Glu Lys Gly Lys Val Thr Lys Ser Ile Glu Leu Asn Ala
            245             250             255

Pro Asn Ser His Tyr Glu Glu Cys Ser Cys Tyr Pro Asp Thr Gly Lys
            260             265             270

Val Met Cys Val Cys Arg Asp Asn Trp His Gly Ser Asn Arg Pro Trp
            275             280             285

Val Ser Phe Asp Gln Asn Leu Asp Tyr Gln Ile Gly Tyr Ile Cys Ser
    290             295             300
```

-continued

Gly Val Phe Gly Asp Asn Pro Arg Pro Glu Asp Gly Thr Gly Ser Cys
305                 310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
                340                 345                 350

Arg His Gly Phe Glu Met Ile Trp Asp Pro Asn Gly Trp Thr Glu Thr
                355                 360                 365

Asp Ser Lys Phe Ser Val Arg Gln Asp Val Val Ala Met Thr Asp Trp
        370                 375                 380

Ser Gly Tyr Ser Gly Ser Phe Val Gln His Pro Glu Leu Thr Gly Leu
385                 390                 395                 400

Asp Cys Met Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
                420                 425                 430

Val Asn Ser Asp Thr Val Asp Trp Ser Trp Pro Asp Gly Ala Glu Leu
        435                 440                 445

Pro Phe Ser Ile Asp Lys
        450

<210> SEQ ID NO 8
<211> LENGTH: 454
<212> TYPE: PRT
<213> ORGANISM: Artificial Sequence
<220> FEATURE:
<223> OTHER INFORMATION: PR8 N1 N50C

<400> SEQUENCE: 8

Met Asn Pro Asn Gln Lys Ile Thr Thr Ile Gly Ser Ile Cys Leu Val
1                   5                   10                  15

Val Gly Leu Ile Ser Leu Ile Leu Gln Ile Gly Asn Ile Ile Ser Ile
                20                  25                  30

Trp Ile Ser His Ser Ile Gln Thr Gly Ser Gln Asn His Thr Gly Ile
                35                  40                  45

Cys Cys Gln Asn Ile Ile Thr Tyr Lys Asn Ser Thr Trp Val Lys Asp
        50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
                100                 105                 110

Glu Cys Arg Thr Phe Phe Leu Thr Gln Gly Ala Leu Leu Asn Asp Lys
                115                 120                 125

His Ser Asn Gly Thr Val Lys Asp Arg Ser Pro Tyr Arg Ala Leu Met
        130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
                180                 185                 190

Tyr Asn Gly Ile Ile Thr Glu Thr Ile Lys Ser Trp Arg Lys Lys Ile
                195                 200                 205

-continued

```
Leu Arg Thr Gln Glu Ser Glu Cys Ala Cys Val Asn Gly Ser Cys Phe
    210             215                 220

Thr Ile Met Thr Asp Gly Pro Ser Asp Gly Leu Ala Ser Tyr Lys Ile
225             230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Gly Lys
                260                 265                 270

Val Met Cys Val Cys Arg Asp Asn Trp His Gly Ser Asn Arg Pro Trp
                275                 280                 285

Val Ser Phe Asp Gln Asn Leu Asp Tyr Gln Ile Gly Tyr Ile Cys Ser
    290                 295                 300

Gly Val Phe Gly Asp Asn Pro Arg Pro Glu Asp Gly Thr Gly Ser Cys
305             310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
                340                 345                 350

Arg His Gly Phe Glu Met Ile Trp Asp Pro Asn Gly Trp Thr Glu Thr
                355                 360                 365

Asp Ser Lys Phe Ser Val Arg Gln Asp Val Val Ala Met Thr Asp Trp
    370                 375                 380

Ser Gly Tyr Ser Gly Ser Phe Val Gln His Pro Glu Leu Thr Gly Leu
385             390                 395                 400

Asp Cys Met Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
                420                 425                 430

Val Asn Ser Asp Thr Val Asp Trp Ser Trp Pro Asp Gly Ala Glu Leu
                435                 440                 445

Pro Phe Ser Ile Asp Lys
    450
```

```
<210> SEQ ID NO 9
<211> LENGTH: 455
<212> TYPE: PRT
<213> ORGANISM: Artificial Sequence
<220> FEATURE:
<223> OTHER INFORMATION: PR8 N1 61insertC

<400> SEQUENCE: 9
```

```
Met Asn Pro Asn Gln Lys Ile Thr Thr Ile Gly Ser Ile Cys Leu Val
1               5                   10                  15

Val Gly Leu Ile Ser Leu Ile Leu Gln Ile Gly Asn Ile Ile Ser Ile
                20                  25                  30

Trp Ile Ser His Ser Ile Gln Thr Gly Ser Gln Asn His Thr Gly Ile
            35                  40                  45

Cys Asn Gln Asn Ile Ile Thr Tyr Lys Asn Ser Thr Trp Cys Val Lys
        50                  55                  60

Asp Thr Thr Ser Val Ile Leu Thr Gly Asn Ser Ser Leu Cys Pro Ile
65                  70                  75                  80

Arg Gly Trp Ala Ile Tyr Ser Lys Asp Asn Ser Ile Arg Ile Gly Ser
                85                  90                  95

Lys Gly Asp Val Phe Val Ile Arg Glu Pro Phe Ile Ser Cys Ser His
                100                 105                 110
```

-continued

```
Leu Glu Cys Arg Thr Phe Phe Leu Thr Gln Gly Ala Leu Leu Asn Asp
        115                 120                 125

Lys His Ser Asn Gly Thr Val Lys Asp Arg Ser Pro Tyr Arg Ala Leu
    130                 135                 140

Met Ser Cys Pro Val Gly Glu Ala Pro Ser Pro Tyr Asn Ser Arg Phe
145                 150                 155                 160

Glu Ser Val Ala Trp Ser Ala Ser Ala Cys His Asp Gly Met Gly Trp
                165                 170                 175

Leu Thr Ile Gly Ile Ser Gly Pro Asp Asn Gly Ala Val Ala Val Leu
                180                 185                 190

Lys Tyr Asn Gly Ile Ile Thr Glu Thr Ile Lys Ser Trp Arg Lys Lys
                195                 200                 205

Ile Leu Arg Thr Gln Glu Ser Glu Cys Ala Cys Val Asn Gly Ser Cys
    210                 215                 220

Phe Thr Ile Met Thr Asp Gly Pro Ser Asp Gly Leu Ala Ser Tyr Lys
225                 230                 235                 240

Ile Phe Lys Ile Glu Lys Gly Lys Val Thr Lys Ser Ile Glu Leu Asn
                245                 250                 255

Ala Pro Asn Ser His Tyr Glu Glu Cys Ser Cys Tyr Pro Asp Thr Gly
                260                 265                 270

Lys Val Met Cys Val Cys Arg Asp Asn Trp His Gly Ser Asn Arg Pro
                275                 280                 285

Trp Val Ser Phe Asp Gln Asn Leu Asp Tyr Gln Ile Gly Tyr Ile Cys
    290                 295                 300

Ser Gly Val Phe Gly Asp Asn Pro Arg Pro Glu Asp Gly Thr Gly Ser
305                 310                 315                 320

Cys Gly Pro Val Tyr Val Asp Gly Ala Asn Gly Val Lys Gly Phe Ser
                325                 330                 335

Tyr Arg Tyr Gly Asn Gly Val Trp Ile Gly Arg Thr Lys Ser His Ser
                340                 345                 350

Ser Arg His Gly Phe Glu Met Ile Trp Asp Pro Asn Gly Trp Thr Glu
        355                 360                 365

Thr Asp Ser Lys Phe Ser Val Arg Gln Asp Val Val Ala Met Thr Asp
    370                 375                 380

Trp Ser Gly Tyr Ser Gly Ser Phe Val Gln His Pro Glu Leu Thr Gly
385                 390                 395                 400

Leu Asp Cys Met Arg Pro Cys Phe Trp Val Glu Leu Ile Arg Gly Arg
                405                 410                 415

Pro Lys Glu Lys Thr Ile Trp Thr Ser Ala Ser Ser Ile Ser Phe Cys
                420                 425                 430

Gly Val Asn Ser Asp Thr Val Asp Trp Ser Trp Pro Asp Gly Ala Glu
                435                 440                 445

Leu Pro Phe Ser Ile Asp Lys
        450                 455
```

```
<210> SEQ ID NO 10
<211> LENGTH: 454
<212> TYPE: PRT
<213> ORGANISM: Artificial Sequence
<220> FEATURE:
<223> OTHER INFORMATION: PR8 N1 I48C_N50C

<400> SEQUENCE: 10

Met Asn Pro Asn Gln Lys Ile Thr Thr Ile Gly Ser Ile Cys Leu Val
1               5                   10                  15
```

-continued

```
Val Gly Leu Ile Ser Leu Ile Leu Gln Ile Gly Asn Ile Ile Ser Ile
              20                  25                  30

Trp Ile Ser His Ser Ile Gln Thr Gly Ser Gln Asn His Thr Gly Cys
              35                  40                  45

Cys Cys Gln Asn Ile Ile Thr Tyr Lys Asn Ser Thr Trp Val Lys Asp
              50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                   85                  90                  95

Gly Asp Val Phe Val Ile Arg Glu Pro Phe Ile Ser Cys Ser His Leu
              100                 105                 110

Glu Cys Arg Thr Phe Phe Leu Thr Gln Gly Ala Leu Leu Asn Asp Lys
              115                 120                 125

His Ser Asn Gly Thr Val Lys Asp Arg Ser Pro Tyr Arg Ala Leu Met
     130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                   165                 170                 175

Thr Ile Gly Ile Ser Gly Pro Asp Asn Gly Ala Val Ala Val Leu Lys
              180                 185                 190

Tyr Asn Gly Ile Ile Thr Glu Thr Ile Lys Ser Trp Arg Lys Lys Ile
              195                 200                 205

Leu Arg Thr Gln Glu Ser Glu Cys Ala Cys Val Asn Gly Ser Cys Phe
     210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                   245                 250                 255

Pro Asn Ser His Tyr Glu Glu Cys Ser Cys Tyr Pro Asp Thr Gly Lys
              260                 265                 270

Val Met Cys Val Cys Arg Asp Asn Trp His Gly Ser Asn Arg Pro Trp
              275                 280                 285

Val Ser Phe Asp Gln Asn Leu Asp Tyr Gln Ile Gly Tyr Ile Cys Ser
     290                 295                 300

Gly Val Phe Gly Asp Asn Pro Arg Pro Glu Asp Gly Thr Gly Ser Cys
305                 310                 315                 320

Gly Pro Val Tyr Val Asp Gly Ala Asn Gly Val Lys Gly Phe Ser Tyr
                   325                 330                 335

Arg Tyr Gly Asn Gly Val Trp Ile Gly Arg Thr Lys Ser His Ser Ser
              340                 345                 350

Arg His Gly Phe Glu Met Ile Trp Asp Pro Asn Gly Trp Thr Glu Thr
     355                 360                 365

Asp Ser Lys Phe Ser Val Arg Gln Asp Val Val Ala Met Thr Asp Trp
     370                 375                 380

Ser Gly Tyr Ser Gly Ser Phe Val Gln His Pro Glu Leu Thr Gly Leu
385                 390                 395                 400

Asp Cys Met Arg Pro Cys Phe Trp Val Glu Leu Ile Arg Gly Arg Pro
              405                 410                 415

Lys Glu Lys Thr Ile Trp Thr Ser Ala Ser Ser Ile Ser Phe Cys Gly
              420                 425                 430

Val Asn Ser Asp Thr Val Asp Trp Ser Trp Pro Asp Gly Ala Glu Leu
```

-continued

```
            435              440              445
Pro Phe Ser Ile Asp Lys
    450

<210> SEQ ID NO 11
<211> LENGTH: 455
<212> TYPE: PRT
<213> ORGANISM: Artificial Sequence
<220> FEATURE:
<223> OTHER INFORMATION: PR8 N1 I48C_61insertC

<400> SEQUENCE: 11

Met Asn Pro Asn Gln Lys Ile Thr Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Cys
        35                  40                  45

Cys Asn Gln Asn Ile Ile Thr Tyr Lys Asn Ser Thr Trp Cys Val Lys
    50                  55                  60

Asp Thr Thr Ser Val Ile Leu Thr Gly Asn Ser Ser Leu Cys Pro Ile
65                  70                  75                  80

Arg Gly Trp Ala Ile Tyr Ser Lys Asp Asn Ser Ile Arg Ile Gly Ser
                85                  90                  95

Lys Gly Asp Val Phe Val Ile Arg Glu Pro Phe Ile Ser Cys Ser His
            100                 105                 110

Leu Glu Cys Arg Thr Phe Phe Leu Thr Gln Gly Ala Leu Leu Asn Asp
            115                 120                 125

Lys His Ser Asn Gly Thr Val Lys Asp Arg Ser Pro Tyr Arg Ala Leu
    130                 135                 140

Met Ser Cys Pro Val Gly Glu Ala Pro Ser Pro Tyr Asn Ser Arg Phe
145                 150                 155                 160

Glu Ser Val Ala Trp Ser Ala Ser Ala Cys His Asp Gly Met Gly Trp
                165                 170                 175

Leu Thr Ile Gly Ile Ser Gly Pro Asp Asn Gly Ala Val Ala Val Leu
            180                 185                 190

Lys Tyr Asn Gly Ile Ile Thr Glu Thr Ile Lys Ser Trp Arg Lys Lys
            195                 200                 205

Ile Leu Arg Thr Gln Glu Ser Glu Cys Ala Cys Val Asn Gly Ser Cys
    210                 215                 220

Phe Thr Ile Met Thr Asp Gly Pro Ser Asp Gly Leu Ala Ser Tyr Lys
225                 230                 235                 240

Ile Phe Lys Ile Glu Lys Gly Lys Val Thr Lys Ser Ile Glu Leu Asn
                245                 250                 255

Ala Pro Asn Ser His Tyr Glu Glu Cys Ser Cys Tyr Pro Asp Thr Gly
            260                 265                 270

Lys Val Met Cys Val Cys Arg Asp Asn Trp His Gly Ser Asn Arg Pro
            275                 280                 285

Trp Val Ser Phe Asp Gln Asn Leu Asp Tyr Gln Ile Gly Tyr Ile Cys
        290                 295                 300

Ser Gly Val Phe Gly Asp Asn Pro Arg Pro Glu Asp Gly Thr Gly Ser
305                 310                 315                 320

Cys Gly Pro Val Tyr Val Asp Gly Ala Asn Gly Val Lys Gly Phe Ser
                325                 330                 335

Tyr Arg Tyr Gly Asn Gly Val Trp Ile Gly Arg Thr Lys Ser His Ser
```

-continued

```
                   340                 345                 350

Ser Arg His Gly Phe Glu Met Ile Trp Asp Pro Asn Gly Trp Thr Glu
        355                 360                 365

Thr Asp Ser Lys Phe Ser Val Arg Gln Asp Val Val Ala Met Thr Asp
        370                 375                 380

Trp Ser Gly Tyr Ser Gly Ser Phe Val Gln His Pro Glu Leu Thr Gly
385                 390                 395                 400

Leu Asp Cys Met Arg Pro Cys Phe Trp Val Glu Leu Ile Arg Gly Arg
                405                 410                 415

Pro Lys Glu Lys Thr Ile Trp Thr Ser Ala Ser Ser Ile Ser Phe Cys
                420                 425                 430

Gly Val Asn Ser Asp Thr Val Asp Trp Ser Trp Pro Asp Gly Ala Glu
                435                 440                 445

Leu Pro Phe Ser Ile Asp Lys
        450                 455
```

<210> SEQ ID NO 12
<211> LENGTH: 469
<212> TYPE: PRT
<213> ORGANISM: Artificial Sequence
<220> FEATURE:
<223> OTHER INFORMATION: HK14 N2 Wild-type

<400> SEQUENCE: 12

```
Met Asn Pro Asn Gln Lys Ile Ile Thr Ile Gly Ser Val Ser Leu Thr
1                   5                   10                  15

Ile Ser Thr Ile Cys Phe Phe Met Gln Ile Ala Ile Leu Ile Thr Thr
                20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
        50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
        130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
                180                 185                 190

Cys Ile Thr Gly Asp Asp Lys Asn Ala Thr Ala Ser Phe Ile Tyr Asn
                195                 200                 205

Gly Arg Leu Val Asp Ser Val Val Ser Trp Ser Lys Asp Ile Leu Arg
        210                 215                 220

Thr Gln Glu Ser Glu Cys Ile Cys Ile Asn Gly Thr Cys Thr Val Val
225                 230                 235                 240

Met Thr Asp Gly Ser Ala Ser Gly Lys Ala Asp Thr Lys Ile Leu Phe
```

-continued

```
                  245              250              255

Ile Glu Glu Gly Lys Ile Val His Thr Ser Thr Leu Ser Gly Ser Ala
            260              265              270

Gln His Val Glu Glu Cys Ser Cys Tyr Pro Arg Tyr Pro Gly Val Arg
            275              280              285

Cys Val Cys Arg Asp Asn Trp Lys Gly Ser Asn Arg Pro Ile Val Asp
        290              295              300

Ile Asn Ile Lys Asp His Ser Ile Val Ser Ser Tyr Val Cys Ser Gly
305              310              315              320

Leu Val Gly Asp Thr Pro Arg Lys Asn Asp Ser Ser Ser Ser His
            325              330              335

Cys Leu Asp Pro Asn Asn Glu Glu Gly Gly His Gly Val Lys Gly Trp
            340              345              350

Ala Phe Asp Asp Gly Asn Asp Val Trp Met Gly Arg Thr Ile Asn Glu
            355              360              365

Thr Ser Arg Leu Gly Tyr Glu Thr Phe Lys Val Ile Glu Gly Trp Ser
        370              375              380

Asn Pro Lys Ser Lys Leu Gln Thr Asn Arg Gln Val Ile Val Asp Arg
385              390              395              400

Gly Asp Arg Ser Gly Tyr Ser Gly Ile Phe Ser Val Glu Gly Lys Ser
            405              410              415

Cys Ile Asn Arg Cys Phe Tyr Val Glu Leu Ile Arg Gly Arg Lys Glu
            420              425              430

Glu Thr Glu Val Leu Trp Thr Ser Asn Ser Ile Val Val Phe Cys Gly
            435              440              445

Thr Ser Gly Thr Tyr Gly Thr Gly Ser Trp Pro Asp Gly Ala Asp Leu
        450              455              460

Asn Leu Met Pro Ile
465

<210> SEQ ID NO 13
<211> LENGTH: 469
<212> TYPE: PRT
<213> ORGANISM: Artificial Sequence
<220> FEATURE:
<223> OTHER INFORMATION: HK14 N2 L52C

<400> SEQUENCE: 13

Met Asn Pro Asn Gln Lys Ile Ile Thr Ile Gly Ser Val Ser Leu Thr
1               5               10              15

Ile Ser Thr Ile Cys Phe Phe Met Gln Ile Ala Ile Leu Ile Thr Thr
            20              25              30

Val Thr Leu His Phe Lys Gln Tyr Glu Phe Asn Ser Pro Pro Asn Asn
        35              40              45

Gln Val Met Cys Cys Glu Pro Thr Ile Ile Glu Arg Asn Ile Thr Glu
        50              55              60

Ile Val Tyr Leu Thr Asn Thr Thr Ile Glu Lys Glu Ile Cys Pro Lys
65              70              75              80

Pro Ala Glu Tyr Arg Asn Trp Ser Lys Pro Gln Cys Gly Ile Thr Gly
            85              90              95

Phe Ala Pro Phe Ser Lys Asp Asn Ser Ile Arg Leu Ser Ala Gly Gly
            100             105             110

Asp Ile Trp Val Thr Arg Glu Pro Tyr Val Ser Cys Asp Pro Asp Lys
            115             120             125

Cys Tyr Gln Phe Ala Leu Gly Gln Gly Thr Thr Leu Asn Asn Val His
```

```
        130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
                180                 185                 190

Cys Ile Thr Gly Asp Asp Lys Asn Ala Thr Ala Ser Phe Ile Tyr Asn
                195                 200                 205

Gly Arg Leu Val Asp Ser Val Val Ser Trp Ser Lys Asp Ile Leu Arg
                210                 215                 220

Thr Gln Glu Ser Glu Cys Ile Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
                260                 265                 270

Gln His Val Glu Glu Cys Ser Cys Tyr Pro Arg Tyr Pro Gly Val Arg
                275                 280                 285

Cys Val Cys Arg Asp Asn Trp Lys Gly Ser Asn Arg Pro Ile Val Asp
                290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
                340                 345                 350

Ala Phe Asp Asp Gly Asn Asp Val Trp Met Gly Arg Thr Ile Asn Glu
                355                 360                 365

Thr Ser Arg Leu Gly Tyr Glu Thr Phe Lys Val Ile Glu Gly Trp Ser
                370                 375                 380

Asn Pro Lys Ser Lys Leu Gln Thr Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
                420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Leu
                450                 455                 460

Asn Leu Met Pro Ile
465
```

<210> SEQ ID NO 14
<211> LENGTH: 469
<212> TYPE: PRT
<213> ORGANISM: Artificial Sequence
<220> FEATURE:
<223> OTHER INFORMATION: HK14 N2 L52C_E54C

<400> SEQUENCE: 14

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
```

-continued

```
          20                25                30
Val Thr Leu His Phe Lys Gln Tyr Glu Phe Asn Ser Pro Pro Asn Asn
          35                40                45
Gln Val Met Cys Cys Cys Pro Thr Ile Ile Glu Arg Asn Ile Thr Glu
          50                55                60
Ile Val Tyr Leu Thr Asn Thr Thr Ile Glu Lys Glu Ile Cys Pro Lys
65                70                75                80
Pro Ala Glu Tyr Arg Asn Trp Ser Lys Pro Gln Cys Gly Ile Thr Gly
                85                90                95
Phe Ala Pro Phe Ser Lys Asp Asn Ser Ile Arg Leu Ser Ala Gly Gly
              100               105               110
Asp Ile Trp Val Thr Arg Glu Pro Tyr Val Ser Cys Asp Pro Asp Lys
          115               120               125
Cys Tyr Gln Phe Ala Leu Gly Gln Gly Thr Thr Leu Asn Asn Val His
      130               135               140
Ser Asn Asn Thr Val Arg Asp Arg Thr Pro Tyr Arg Thr Leu Leu Met
145               150               155               160
Asn Glu Leu Gly Val Pro Phe His Leu Gly Thr Lys Gln Val Cys Ile
              165               170               175
Ala Trp Ser Ser Ser Ser Cys His Asp Gly Lys Ala Trp Leu His Val
          180               185               190
Cys Ile Thr Gly Asp Asp Lys Asn Ala Thr Ala Ser Phe Ile Tyr Asn
          195               200               205
Gly Arg Leu Val Asp Ser Val Val Ser Trp Ser Lys Asp Ile Leu Arg
      210               215               220
Thr Gln Glu Ser Glu Cys Ile Cys Ile Asn Gly Thr Cys Thr Val Val
225               230               235               240
Met Thr Asp Gly Ser Ala Ser Gly Lys Ala Asp Thr Lys Ile Leu Phe
              245               250               255
Ile Glu Glu Gly Lys Ile Val His Thr Ser Thr Leu Ser Gly Ser Ala
              260               265               270
Gln His Val Glu Glu Cys Ser Cys Tyr Pro Arg Tyr Pro Gly Val Arg
          275               280               285
Cys Val Cys Arg Asp Asn Trp Lys Gly Ser Asn Arg Pro Ile Val Asp
      290               295               300
Ile Asn Ile Lys Asp His Ser Ile Val Ser Ser Tyr Val Cys Ser Gly
305               310               315               320
Leu Val Gly Asp Thr Pro Arg Lys Asn Asp Ser Ser Ser Ser Ser His
              325               330               335
Cys Leu Asp Pro Asn Asn Glu Glu Gly Gly His Gly Val Lys Gly Trp
          340               345               350
Ala Phe Asp Asp Gly Asn Asp Val Trp Met Gly Arg Thr Ile Asn Glu
          355               360               365
Thr Ser Arg Leu Gly Tyr Glu Thr Phe Lys Val Ile Glu Gly Trp Ser
      370               375               380
Asn Pro Lys Ser Lys Leu Gln Thr Asn Arg Gln Val Ile Val Asp Arg
385               390               395               400
Gly Asp Arg Ser Gly Tyr Ser Gly Ile Phe Ser Val Glu Gly Lys Ser
              405               410               415
Cys Ile Asn Arg Cys Phe Tyr Val Glu Leu Ile Arg Gly Arg Lys Glu
          420               425               430
Glu Thr Glu Val Leu Trp Thr Ser Asn Ser Ile Val Val Phe Cys Gly
          435               440               445
```

```
Thr Ser Gly Thr Tyr Gly Thr Gly Ser Trp Pro Asp Gly Ala Asp Leu
    450                 455                 460

Asn Leu Met Pro Ile
465

<210> SEQ ID NO 15
<211> LENGTH: 481
<212> TYPE: PRT
<213> ORGANISM: Artificial Sequence
<220> FEATURE:
<223> OTHER INFORMATION: N1.2

<400> SEQUENCE: 15

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Ser
        35                  40                  45

Leu Val Pro Arg Gly Ser Pro Ser Arg Ile Glu Thr Cys Asn Gln Ser
    50                  55                  60

Val Ile Thr Tyr Glu Asn Asn Thr Trp Val Asn Gln Thr Tyr Val Asn
65                  70                  75                  80

Ile Ser Asn Thr Asn Phe Ala Ala Gly Gln Ser Val Val Ser Val Lys
                85                  90                  95

Leu Ala Gly Asn Ser Ser Leu Cys Pro Val Ser Gly Trp Ala Ile Tyr
            100                 105                 110

Ser Lys Asp Asn Ser Val Arg Ile Gly Ser Lys Gly Asp Val Phe Val
        115                 120                 125

Ile Arg Glu Pro Phe Ile Ser Cys Ser Pro Leu Glu Cys Arg Thr Phe
    130                 135                 140

Phe Leu Thr Gln Gly Ala Leu Leu Asn Asp Lys His Ser Asn Gly Thr
145                 150                 155                 160

Ile Lys Asp Arg Ser Pro Tyr Arg Thr Leu Met Ser Cys Pro Ile Gly
            165                 170                 175

Glu Val Pro Ser Pro Tyr Asn Ser Arg Phe Glu Ser Val Ala Trp Ser
            180                 185                 190

Ala Ser Ala Cys His Asp Gly Ile Asn Trp Leu Thr Ile Gly Ile Ser
        195                 200                 205

Gly Pro Asp Ser Gly Ala Val Ala Val Leu Lys Tyr Asn Gly Ile Ile
    210                 215                 220

Thr Asp Thr Ile Lys Ser Trp Arg Asn Asn Ile Leu Arg Thr Gln Glu
225                 230                 235                 240

Ser Glu Cys Ala Cys Val Asn Gly Ser Cys Phe Thr Ile Met Thr Asp
            245                 250                 255

Gly Pro Ser Asp Gly Gln Ala Ser Tyr Lys Ile Phe Arg Ile Glu Lys
            260                 265                 270

Gly Lys Ile Ile Lys Ser Val Glu Met Lys Ala Pro Asn Tyr His Tyr
        275                 280                 285

Glu Glu Cys Ser Cys Tyr Pro Asp Ser Ser Glu Ile Thr Cys Val Cys
        290                 295                 300

Arg Asp Asn Trp His Gly Ser Asn Arg Pro Trp Val Ser Phe Asn Gln
305                 310                 315                 320

Asn Leu Glu Tyr Gln Met Gly Tyr Ile Cys Ser Gly Val Phe Gly Asp
                325                 330                 335
```

```
Asn Pro Arg Pro Asn Asp Lys Thr Gly Ser Cys Gly Pro Val Ser Ser
        340             345         350

Asn Gly Ala Asn Gly Val Lys Gly Phe Ser Phe Lys Tyr Gly Asn Gly
        355             360         365

Val Trp Ile Gly Arg Thr Lys Ser Ile Ser Ser Arg Lys Gly Phe Glu
        370             375         380

Met Ile Trp Asp Pro Asn Gly Trp Thr Gly Thr Asp Asn Lys Phe Ser
385             390             395             400

Ile Lys Gln Asp Ile Val Gly Ile Asn Glu Trp Ser Gly Tyr Ser Gly
            405             410             415

Ser Phe Val Gln His Pro Glu Leu Thr Gly Leu Asp Cys Ile Arg Pro
        420             425             430

Cys Phe Trp Val Glu Leu Ile Arg Gly Arg Pro Glu Glu Asn Thr Ile
        435             440             445

Trp Thr Ser Gly Ser Ser Ile Ser Phe Cys Gly Val Asn Ser Asp Thr
    450             455             460

Val Gly Trp Ser Trp Pro Asp Gly Ala Glu Leu Pro Phe Thr Ile Asp
465             470             475             480

Lys

<210> SEQ ID NO 16
<211> LENGTH: 481
<212> TYPE: PRT
<213> ORGANISM: Artificial Sequence
<220> FEATURE:
<223> OTHER INFORMATION: N1.3 (C49A - monomer)

<400> SEQUENCE: 16

Met Leu Leu Val Asn Gln Ser His Gln Gly Phe Asn Lys Glu His Thr
1               5               10              15

Ser Lys Met Val Ser Ala Ile Val Leu Tyr Val Leu Leu Ala Ala Ala
        20              25              30

Ala His Ser Ala Phe Ala Ala Asp Pro His His His His His His Ser
        35              40              45

Leu Val Pro Arg Gly Ser Pro Ser Arg Ile Glu Thr Ala Asn Gln Ser
    50              55              60

Val Ile Thr Tyr Glu Asn Asn Thr Trp Val Asn Gln Thr Tyr Val Asn
65              70              75              80

Ile Ser Asn Thr Asn Phe Ala Ala Gly Gln Ser Val Val Ser Val Lys
            85              90              95

Leu Ala Gly Asn Ser Ser Leu Cys Pro Val Ser Gly Trp Ala Ile Tyr
        100             105             110

Ser Lys Asp Asn Ser Val Arg Ile Gly Ser Lys Gly Asp Val Phe Val
        115             120             125

Ile Arg Glu Pro Phe Ile Ser Cys Ser Pro Leu Glu Cys Arg Thr Phe
    130             135             140

Phe Leu Thr Gln Gly Ala Leu Leu Asn Asp Lys His Ser Asn Gly Thr
145             150             155             160

Ile Lys Asp Arg Ser Pro Tyr Arg Thr Leu Met Ser Cys Pro Ile Gly
            165             170             175

Glu Val Pro Ser Pro Tyr Asn Ser Arg Phe Glu Ser Val Ala Trp Ser
        180             185             190

Ala Ser Ala Cys His Asp Gly Ile Asn Trp Leu Thr Ile Gly Ile Ser
        195             200             205
```

-continued

```
Gly Pro Asp Ser Gly Ala Val Ala Val Leu Lys Tyr Asn Gly Ile Ile
    210             215                 220

Thr Asp Thr Ile Lys Ser Trp Arg Asn Asn Ile Leu Arg Thr Gln Glu
225             230                 235                 240

Ser Glu Cys Ala Cys Val Asn Gly Ser Cys Phe Thr Ile Met Thr Asp
            245                 250                 255

Gly Pro Ser Asp Gly Gln Ala Ser Tyr Lys Ile Phe Arg Ile Glu Lys
            260                 265                 270

Gly Lys Ile Ile Lys Ser Val Glu Met Lys Ala Pro Asn Tyr His Tyr
        275                 280                 285

Glu Glu Cys Ser Cys Tyr Pro Asp Ser Ser Glu Ile Thr Cys Val Cys
    290                 295                 300

Arg Asp Asn Trp His Gly Ser Asn Arg Pro Trp Val Ser Phe Asn Gln
305             310                 315                 320

Asn Leu Glu Tyr Gln Met Gly Tyr Ile Cys Ser Gly Val Phe Gly Asp
            325                 330                 335

Asn Pro Arg Pro Asn Asp Lys Thr Gly Ser Cys Gly Pro Val Ser Ser
            340                 345                 350

Asn Gly Ala Asn Gly Val Lys Gly Phe Ser Phe Lys Tyr Gly Asn Gly
        355                 360                 365

Val Trp Ile Gly Arg Thr Lys Ser Ile Ser Ser Arg Lys Gly Phe Glu
    370             375                 380

Met Ile Trp Asp Pro Asn Gly Trp Thr Gly Thr Asp Asn Lys Phe Ser
385             390                 395                 400

Ile Lys Gln Asp Ile Val Gly Ile Asn Glu Trp Ser Gly Tyr Ser Gly
            405                 410                 415

Ser Phe Val Gln His Pro Glu Leu Thr Gly Leu Asp Cys Ile Arg Pro
            420                 425                 430

Cys Phe Trp Val Glu Leu Ile Arg Gly Arg Pro Glu Glu Asn Thr Ile
        435                 440                 445

Trp Thr Ser Gly Ser Ser Ile Ser Phe Cys Gly Val Asn Ser Asp Thr
    450                 455                 460

Val Gly Trp Ser Trp Pro Asp Gly Ala Glu Leu Pro Phe Thr Ile Asp
465             470                 475                 480

Lys
```

```
<210> SEQ ID NO 17
<211> LENGTH: 481
<212> TYPE: PRT
<213> ORGANISM: Artificial Sequence
<220> FEATURE:
<223> OTHER INFORMATION: N1.4 (T48C)

<400> SEQUENCE: 17

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Ser
        35                  40                  45

Leu Val Pro Arg Gly Ser Pro Ser Arg Ile Glu Cys Cys Asn Gln Ser
    50                  55                  60

Val Ile Thr Tyr Glu Asn Asn Thr Trp Val Asn Gln Thr Tyr Val Asn
65                  70                  75                  80

Ile Ser Asn Thr Asn Phe Ala Ala Gly Gln Ser Val Val Ser Val Lys
```

-continued

```
                        85                    90                    95

Leu Ala Gly Asn Ser Ser Leu Cys Pro Val Ser Gly Trp Ala Ile Tyr
            100                   105                   110

Ser Lys Asp Asn Ser Val Arg Ile Gly Ser Lys Gly Asp Val Phe Val
            115                   120                   125

Ile Arg Glu Pro Phe Ile Ser Cys Ser Pro Leu Glu Cys Arg Thr Phe
            130                   135                   140

Phe Leu Thr Gln Gly Ala Leu Leu Asn Asp Lys His Ser Asn Gly Thr
145                   150                   155                   160

Ile Lys Asp Arg Ser Pro Tyr Arg Thr Leu Met Ser Cys Pro Ile Gly
            165                   170                   175

Glu Val Pro Ser Pro Tyr Asn Ser Arg Phe Glu Ser Val Ala Trp Ser
            180                   185                   190

Ala Ser Ala Cys His Asp Gly Ile Asn Trp Leu Thr Ile Gly Ile Ser
            195                   200                   205

Gly Pro Asp Ser Gly Ala Val Ala Val Leu Lys Tyr Asn Gly Ile Ile
            210                   215                   220

Thr Asp Thr Ile Lys Ser Trp Arg Asn Asn Ile Leu Arg Thr Gln Glu
225                   230                   235                   240

Ser Glu Cys Ala Cys Val Asn Gly Ser Cys Phe Thr Ile Met Thr Asp
            245                   250                   255

Gly Pro Ser Asp Gly Gln Ala Ser Tyr Lys Ile Phe Arg Ile Glu Lys
            260                   265                   270

Gly Lys Ile Ile Lys Ser Val Glu Met Lys Ala Pro Asn Tyr His Tyr
            275                   280                   285

Glu Glu Cys Ser Cys Tyr Pro Asp Ser Ser Glu Ile Thr Cys Val Cys
            290                   295                   300

Arg Asp Asn Trp His Gly Ser Asn Arg Pro Trp Val Ser Phe Asn Gln
305                   310                   315                   320

Asn Leu Glu Tyr Gln Met Gly Tyr Ile Cys Ser Gly Val Phe Gly Asp
            325                   330                   335

Asn Pro Arg Pro Asn Asp Lys Thr Gly Ser Cys Gly Pro Val Ser Ser
            340                   345                   350

Asn Gly Ala Asn Gly Val Lys Gly Phe Ser Phe Lys Tyr Gly Asn Gly
            355                   360                   365

Val Trp Ile Gly Arg Thr Lys Ser Ile Ser Ser Arg Lys Gly Phe Glu
            370                   375                   380

Met Ile Trp Asp Pro Asn Gly Trp Thr Gly Thr Asp Asn Lys Phe Ser
385                   390                   395                   400

Ile Lys Gln Asp Ile Val Gly Ile Asn Glu Trp Ser Gly Tyr Ser Gly
            405                   410                   415

Ser Phe Val Gln His Pro Glu Leu Thr Gly Leu Asp Cys Ile Arg Pro
            420                   425                   430

Cys Phe Trp Val Glu Leu Ile Arg Gly Arg Pro Glu Glu Asn Thr Ile
            435                   440                   445

Trp Thr Ser Gly Ser Ser Ile Ser Phe Cys Gly Val Asn Ser Asp Thr
            450                   455                   460

Val Gly Trp Ser Trp Pro Asp Gly Ala Glu Leu Pro Phe Thr Ile Asp
465                   470                   475                   480

Lys
```

<210> SEQ ID NO 18
<211> LENGTH: 481

-continued

```
<212> TYPE: PRT
<213> ORGANISM: Artificial Sequence
<220> FEATURE:
<223> OTHER INFORMATION: N1.5 (N50C)

<400> SEQUENCE: 18

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Ser
            35                  40                  45

Leu Val Pro Arg Gly Ser Pro Ser Arg Ile Glu Thr Cys Cys Gln Ser
        50                  55                  60

Val Ile Thr Tyr Glu Asn Asn Thr Trp Val Asn Gln Thr Tyr Val Asn
65                  70                  75                  80

Ile Ser Asn Thr Asn Phe Ala Ala Gly Gln Ser Val Val Ser Val Lys
                85                  90                  95

Leu Ala Gly Asn Ser Ser Leu Cys Pro Val Ser Gly Trp Ala Ile Tyr
                100                 105                 110

Ser Lys Asp Asn Ser Val Arg Ile Gly Ser Lys Gly Asp Val Phe Val
            115                 120                 125

Ile Arg Glu Pro Phe Ile Ser Cys Ser Pro Leu Glu Cys Arg Thr Phe
        130                 135                 140

Phe Leu Thr Gln Gly Ala Leu Leu Asn Asp Lys His Ser Asn Gly Thr
145                 150                 155                 160

Ile Lys Asp Arg Ser Pro Tyr Arg Thr Leu Met Ser Cys Pro Ile Gly
                165                 170                 175

Glu Val Pro Ser Pro Tyr Asn Ser Arg Phe Glu Ser Val Ala Trp Ser
                180                 185                 190

Ala Ser Ala Cys His Asp Gly Ile Asn Trp Leu Thr Ile Gly Ile Ser
            195                 200                 205

Gly Pro Asp Ser Gly Ala Val Ala Val Leu Lys Tyr Asn Gly Ile Ile
        210                 215                 220

Thr Asp Thr Ile Lys Ser Trp Arg Asn Asn Ile Leu Arg Thr Gln Glu
225                 230                 235                 240

Ser Glu Cys Ala Cys Val Asn Gly Ser Cys Phe Thr Ile Met Thr Asp
                245                 250                 255

Gly Pro Ser Asp Gly Gln Ala Ser Tyr Lys Ile Phe Arg Ile Glu Lys
                260                 265                 270

Gly Lys Ile Ile Lys Ser Val Glu Met Lys Ala Pro Asn Tyr His Tyr
            275                 280                 285

Glu Glu Cys Ser Cys Tyr Pro Asp Ser Ser Glu Ile Thr Cys Val Cys
        290                 295                 300

Arg Asp Asn Trp His Gly Ser Asn Arg Pro Trp Val Ser Phe Asn Gln
305                 310                 315                 320

Asn Leu Glu Tyr Gln Met Gly Tyr Ile Cys Ser Gly Val Phe Gly Asp
                325                 330                 335

Asn Pro Arg Pro Asn Asp Lys Thr Gly Ser Cys Gly Pro Val Ser Ser
            340                 345                 350

Asn Gly Ala Asn Gly Val Lys Gly Phe Ser Phe Lys Tyr Gly Asn Gly
            355                 360                 365

Val Trp Ile Gly Arg Thr Lys Ser Ile Ser Ser Arg Lys Gly Phe Glu
        370                 375                 380
```

-continued

```
Met Ile Trp Asp Pro Asn Gly Trp Thr Gly Thr Asp Asn Lys Phe Ser
385                 390                 395                 400

Ile Lys Gln Asp Ile Val Gly Ile Asn Glu Trp Ser Gly Tyr Ser Gly
                405                 410                 415

Ser Phe Val Gln His Pro Glu Leu Thr Gly Leu Asp Cys Ile Arg Pro
                420                 425                 430

Cys Phe Trp Val Glu Leu Ile Arg Gly Arg Pro Glu Glu Asn Thr Ile
            435                 440                 445

Trp Thr Ser Gly Ser Ser Ile Ser Phe Cys Gly Val Asn Ser Asp Thr
        450                 455                 460

Val Gly Trp Ser Trp Pro Asp Gly Ala Glu Leu Pro Phe Thr Ile Asp
465                 470                 475                 480

Lys

<210> SEQ ID NO 19
<211> LENGTH: 481
<212> TYPE: PRT
<213> ORGANISM: Artificial Sequence
<220> FEATURE:
<223> OTHER INFORMATION: N1.6 (T48C+N50C)

<400> SEQUENCE: 19

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro His His His His His His Ser
            35                  40                  45

Leu Val Pro Arg Gly Ser Pro Ser Arg Ile Glu Cys Cys Cys Gln Ser
        50                  55                  60

Val Ile Thr Tyr Glu Asn Asn Thr Trp Val Asn Gln Thr Tyr Val Asn
65                  70                  75                  80

Ile Ser Asn Thr Asn Phe Ala Ala Gly Gln Ser Val Val Ser Val Lys
                85                  90                  95

Leu Ala Gly Asn Ser Ser Leu Cys Pro Val Ser Gly Trp Ala Ile Tyr
                100                 105                 110

Ser Lys Asp Asn Ser Val Arg Ile Gly Ser Lys Gly Asp Val Phe Val
            115                 120                 125

Ile Arg Glu Pro Phe Ile Ser Cys Ser Pro Leu Glu Cys Arg Thr Phe
        130                 135                 140

Phe Leu Thr Gln Gly Ala Leu Leu Asn Asp Lys His Ser Asn Gly Thr
145                 150                 155                 160

Ile Lys Asp Arg Ser Pro Tyr Arg Thr Leu Met Ser Cys Pro Ile Gly
                165                 170                 175

Glu Val Pro Ser Pro Tyr Asn Ser Arg Phe Glu Ser Val Ala Trp Ser
                180                 185                 190

Ala Ser Ala Cys His Asp Gly Ile Asn Trp Leu Thr Ile Gly Ile Ser
            195                 200                 205

Gly Pro Asp Ser Gly Ala Val Ala Val Leu Lys Tyr Asn Gly Ile Ile
        210                 215                 220

Thr Asp Thr Ile Lys Ser Trp Arg Asn Asn Ile Leu Arg Thr Gln Glu
225                 230                 235                 240

Ser Glu Cys Ala Cys Val Asn Gly Ser Cys Phe Thr Ile Met Thr Asp
                245                 250                 255

Gly Pro Ser Asp Gly Gln Ala Ser Tyr Lys Ile Phe Arg Ile Glu Lys
```

-continued

```
              260             265             270

Gly Lys Ile Ile Lys Ser Val Glu Met Lys Ala Pro Asn Tyr His Tyr
              275             280             285

Glu Glu Cys Ser Cys Tyr Pro Asp Ser Ser Glu Ile Thr Cys Val Cys
              290             295             300

Arg Asp Asn Trp His Gly Ser Asn Arg Pro Trp Val Ser Phe Asn Gln
305             310             315             320

Asn Leu Glu Tyr Gln Met Gly Tyr Ile Cys Ser Gly Val Phe Gly Asp
              325             330             335

Asn Pro Arg Pro Asn Asp Lys Thr Gly Ser Cys Gly Pro Val Ser Ser
              340             345             350

Asn Gly Ala Asn Gly Val Lys Gly Phe Ser Phe Lys Tyr Gly Asn Gly
              355             360             365

Val Trp Ile Gly Arg Thr Lys Ser Ile Ser Ser Arg Lys Gly Phe Glu
              370             375             380

Met Ile Trp Asp Pro Asn Gly Trp Thr Gly Thr Asp Asn Lys Phe Ser
385             390             395             400

Ile Lys Gln Asp Ile Val Gly Ile Asn Glu Trp Ser Gly Tyr Ser Gly
              405             410             415

Ser Phe Val Gln His Pro Glu Leu Thr Gly Leu Asp Cys Ile Arg Pro
              420             425             430

Cys Phe Trp Val Glu Leu Ile Arg Gly Arg Pro Glu Glu Asn Thr Ile
              435             440             445

Trp Thr Ser Gly Ser Ser Ile Ser Phe Cys Gly Val Asn Ser Asp Thr
              450             455             460

Val Gly Trp Ser Trp Pro Asp Gly Ala Glu Leu Pro Phe Thr Ile Asp
465             470             475             480

Lys
```

```
<210> SEQ ID NO 20
<211> LENGTH: 481
<212> TYPE: PRT
<213> ORGANISM: Artificial Sequence
<220> FEATURE:
<223> OTHER INFORMATION: N1.7 (A76C)

<400> SEQUENCE: 20

Met Leu Leu Val Asn Gln Ser His Gln Gly Phe Asn Lys Glu His Thr
1               5               10              15

Ser Lys Met Val Ser Ala Ile Val Leu Tyr Val Leu Leu Ala Ala Ala
              20              25              30

Ala His Ser Ala Phe Ala Ala Asp Pro His His His His His His Ser
              35              40              45

Leu Val Pro Arg Gly Ser Pro Ser Arg Ile Glu Thr Cys Asn Gln Ser
              50              55              60

Val Ile Thr Tyr Glu Asn Asn Thr Trp Val Asn Gln Thr Tyr Val Asn
65              70              75              80

Ile Ser Asn Thr Asn Phe Ala Cys Gly Gln Ser Val Val Ser Val Lys
              85              90              95

Leu Ala Gly Asn Ser Ser Leu Cys Pro Val Ser Gly Trp Ala Ile Tyr
              100             105             110

Ser Lys Asp Asn Ser Val Arg Ile Gly Ser Lys Gly Asp Val Phe Val
              115             120             125

Ile Arg Glu Pro Phe Ile Ser Cys Ser Pro Leu Glu Cys Arg Thr Phe
              130             135             140
```

-continued

```
Phe Leu Thr Gln Gly Ala Leu Leu Asn Asp Lys His Ser Asn Gly Thr
145                 150                 155                 160

Ile Lys Asp Arg Ser Pro Tyr Arg Thr Leu Met Ser Cys Pro Ile Gly
                165                 170                 175

Glu Val Pro Ser Pro Tyr Asn Ser Arg Phe Glu Ser Val Ala Trp Ser
            180                 185                 190

Ala Ser Ala Cys His Asp Gly Ile Asn Trp Leu Thr Ile Gly Ile Ser
        195                 200                 205

Gly Pro Asp Ser Gly Ala Val Ala Val Leu Lys Tyr Asn Gly Ile Ile
    210                 215                 220

Thr Asp Thr Ile Lys Ser Trp Arg Asn Asn Ile Leu Arg Thr Gln Glu
225                 230                 235                 240

Ser Glu Cys Ala Cys Val Asn Gly Ser Cys Phe Thr Ile Met Thr Asp
                245                 250                 255

Gly Pro Ser Asp Gly Gln Ala Ser Tyr Lys Ile Phe Arg Ile Glu Lys
            260                 265                 270

Gly Lys Ile Ile Lys Ser Val Glu Met Lys Ala Pro Asn Tyr His Tyr
        275                 280                 285

Glu Glu Cys Ser Cys Tyr Pro Asp Ser Ser Glu Ile Thr Cys Val Cys
    290                 295                 300

Arg Asp Asn Trp His Gly Ser Asn Arg Pro Trp Val Ser Phe Asn Gln
305                 310                 315                 320

Asn Leu Glu Tyr Gln Met Gly Tyr Ile Cys Ser Gly Val Phe Gly Asp
                325                 330                 335

Asn Pro Arg Pro Asn Asp Lys Thr Gly Ser Cys Gly Pro Val Ser Ser
            340                 345                 350

Asn Gly Ala Asn Gly Val Lys Gly Phe Ser Phe Lys Tyr Gly Asn Gly
        355                 360                 365

Val Trp Ile Gly Arg Thr Lys Ser Ile Ser Ser Arg Lys Gly Phe Glu
    370                 375                 380

Met Ile Trp Asp Pro Asn Gly Trp Thr Gly Thr Asp Asn Lys Phe Ser
385                 390                 395                 400

Ile Lys Gln Asp Ile Val Gly Ile Asn Glu Trp Ser Gly Tyr Ser Gly
                405                 410                 415

Ser Phe Val Gln His Pro Glu Leu Thr Gly Leu Asp Cys Ile Arg Pro
            420                 425                 430

Cys Phe Trp Val Glu Leu Ile Arg Gly Arg Pro Glu Glu Asn Thr Ile
        435                 440                 445

Trp Thr Ser Gly Ser Ser Ile Ser Phe Cys Gly Val Asn Ser Asp Thr
    450                 455                 460

Val Gly Trp Ser Trp Pro Asp Gly Ala Glu Leu Pro Phe Thr Ile Asp
465                 470                 475                 480

Lys
```

```
<210> SEQ ID NO 21
<211> LENGTH: 481
<212> TYPE: PRT
<213> ORGANISM: Artificial Sequence
<220> FEATURE:
<223> OTHER INFORMATION: N1.8 (Q78C)

<400> SEQUENCE: 21

Met Leu Leu Val Asn Gln Ser His Gln Gly Phe Asn Lys Glu His Thr
1               5                   10                  15
```

-continued

```
Ser Lys Met Val Ser Ala Ile Val Leu Tyr Val Leu Leu Ala Ala Ala
        20              25              30

Ala His Ser Ala Phe Ala Ala Asp Pro His His His His His His Ser
        35              40              45

Leu Val Pro Arg Gly Ser Pro Ser Arg Ile Glu Thr Cys Asn Gln Ser
        50              55              60

Val Ile Thr Tyr Glu Asn Asn Thr Trp Val Asn Gln Thr Tyr Val Asn
65              70              75              80

Ile Ser Asn Thr Asn Phe Ala Ala Gly Cys Ser Val Val Ser Val Lys
                85              90              95

Leu Ala Gly Asn Ser Ser Leu Cys Pro Val Ser Gly Trp Ala Ile Tyr
            100             105             110

Ser Lys Asp Asn Ser Val Arg Ile Gly Ser Lys Gly Asp Val Phe Val
            115             120             125

Ile Arg Glu Pro Phe Ile Ser Cys Ser Pro Leu Glu Cys Arg Thr Phe
        130             135             140

Phe Leu Thr Gln Gly Ala Leu Leu Asn Asp Lys His Ser Asn Gly Thr
145             150             155             160

Ile Lys Asp Arg Ser Pro Tyr Arg Thr Leu Met Ser Cys Pro Ile Gly
            165             170             175

Glu Val Pro Ser Pro Tyr Asn Ser Arg Phe Glu Ser Val Ala Trp Ser
            180             185             190

Ala Ser Ala Cys His Asp Gly Ile Asn Trp Leu Thr Ile Gly Ile Ser
        195             200             205

Gly Pro Asp Ser Gly Ala Val Ala Val Leu Lys Tyr Asn Gly Ile Ile
        210             215             220

Thr Asp Thr Ile Lys Ser Trp Arg Asn Asn Ile Leu Arg Thr Gln Glu
225             230             235             240

Ser Glu Cys Ala Cys Val Asn Gly Ser Cys Phe Thr Ile Met Thr Asp
                245             250             255

Gly Pro Ser Asp Gly Gln Ala Ser Tyr Lys Ile Phe Arg Ile Glu Lys
            260             265             270

Gly Lys Ile Ile Lys Ser Val Glu Met Lys Ala Pro Asn Tyr His Tyr
            275             280             285

Glu Glu Cys Ser Cys Tyr Pro Asp Ser Ser Glu Ile Thr Cys Val Cys
        290             295             300

Arg Asp Asn Trp His Gly Ser Asn Arg Pro Trp Val Ser Phe Asn Gln
305             310             315             320

Asn Leu Glu Tyr Gln Met Gly Tyr Ile Cys Ser Gly Val Phe Gly Asp
            325             330             335

Asn Pro Arg Pro Asn Asp Lys Thr Gly Ser Cys Gly Pro Val Ser Ser
            340             345             350

Asn Gly Ala Asn Gly Val Lys Gly Phe Ser Phe Lys Tyr Gly Asn Gly
        355             360             365

Val Trp Ile Gly Arg Thr Lys Ser Ile Ser Ser Arg Lys Gly Phe Glu
        370             375             380

Met Ile Trp Asp Pro Asn Gly Trp Thr Gly Thr Asp Asn Lys Phe Ser
385             390             395             400

Ile Lys Gln Asp Ile Val Gly Ile Asn Glu Trp Ser Gly Tyr Ser Gly
            405             410             415

Ser Phe Val Gln His Pro Glu Leu Thr Gly Leu Asp Cys Ile Arg Pro
            420             425             430

Cys Phe Trp Val Glu Leu Ile Arg Gly Arg Pro Glu Glu Asn Thr Ile
```

-continued

```
                 435                 440                 445

Trp Thr Ser Gly Ser Ser Ile Ser Phe Cys Gly Val Asn Ser Asp Thr
    450                 455                 460

Val Gly Trp Ser Trp Pro Asp Gly Ala Glu Leu Pro Phe Thr Ile Asp
465                 470                 475                 480

Lys

<210> SEQ ID NO 22
<211> LENGTH: 481
<212> TYPE: PRT
<213> ORGANISM: Artificial Sequence
<220> FEATURE:
<223> OTHER INFORMATION: N1.9 (V81C)

<400> SEQUENCE: 22

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Ser
        35                  40                  45

Leu Val Pro Arg Gly Ser Pro Ser Arg Ile Glu Thr Cys Asn Gln Ser
    50                  55                  60

Val Ile Thr Tyr Glu Asn Asn Thr Trp Val Asn Gln Thr Tyr Val Asn
65                  70                  75                  80

Ile Ser Asn Thr Asn Phe Ala Ala Gly Gln Ser Val Cys Ser Val Lys
                85                  90                  95

Leu Ala Gly Asn Ser Ser Leu Cys Pro Val Ser Gly Trp Ala Ile Tyr
            100                 105                 110

Ser Lys Asp Asn Ser Val Arg Ile Gly Ser Lys Gly Asp Val Phe Val
            115                 120                 125

Ile Arg Glu Pro Phe Ile Ser Cys Ser Pro Leu Glu Cys Arg Thr Phe
    130                 135                 140

Phe Leu Thr Gln Gly Ala Leu Leu Asn Asp Lys His Ser Asn Gly Thr
145                 150                 155                 160

Ile Lys Asp Arg Ser Pro Tyr Arg Thr Leu Met Ser Cys Pro Ile Gly
            165                 170                 175

Glu Val Pro Ser Pro Tyr Asn Ser Arg Phe Glu Ser Val Ala Trp Ser
            180                 185                 190

Ala Ser Ala Cys His Asp Gly Ile Asn Trp Leu Thr Ile Gly Ile Ser
            195                 200                 205

Gly Pro Asp Ser Gly Ala Val Ala Val Leu Lys Tyr Asn Gly Ile Ile
    210                 215                 220

Thr Asp Thr Ile Lys Ser Trp Arg Asn Asn Ile Leu Arg Thr Gln Glu
225                 230                 235                 240

Ser Glu Cys Ala Cys Val Asn Gly Ser Cys Phe Thr Ile Met Thr Asp
            245                 250                 255

Gly Pro Ser Asp Gly Gln Ala Ser Tyr Lys Ile Phe Arg Ile Glu Lys
            260                 265                 270

Gly Lys Ile Ile Lys Ser Val Glu Met Lys Ala Pro Asn Tyr His Tyr
            275                 280                 285

Glu Glu Cys Ser Cys Tyr Pro Asp Ser Ser Glu Ile Thr Cys Val Cys
    290                 295                 300

Arg Asp Asn Trp His Gly Ser Asn Arg Pro Trp Val Ser Phe Asn Gln
305                 310                 315                 320
```

-continued

```
Asn Leu Glu Tyr Gln Met Gly Tyr Ile Cys Ser Gly Val Phe Gly Asp
            325                 330                 335

Asn Pro Arg Pro Asn Asp Lys Thr Gly Ser Cys Gly Pro Val Ser Ser
            340                 345                 350

Asn Gly Ala Asn Gly Val Lys Gly Phe Ser Phe Lys Tyr Gly Asn Gly
            355                 360                 365

Val Trp Ile Gly Arg Thr Lys Ser Ile Ser Ser Arg Lys Gly Phe Glu
    370                 375                 380

Met Ile Trp Asp Pro Asn Gly Trp Thr Gly Thr Asp Asn Lys Phe Ser
385                 390                 395                 400

Ile Lys Gln Asp Ile Val Gly Ile Asn Glu Trp Ser Gly Tyr Ser Gly
            405                 410                 415

Ser Phe Val Gln His Pro Glu Leu Thr Gly Leu Asp Cys Ile Arg Pro
            420                 425                 430

Cys Phe Trp Val Glu Leu Ile Arg Gly Arg Pro Glu Glu Asn Thr Ile
            435                 440                 445

Trp Thr Ser Gly Ser Ser Ile Ser Phe Cys Gly Val Asn Ser Asp Thr
    450                 455                 460

Val Gly Trp Ser Trp Pro Asp Gly Ala Glu Leu Pro Phe Thr Ile Asp
465                 470                 475                 480

Lys
```

```
<210> SEQ ID NO 23
<211> LENGTH: 481
<212> TYPE: PRT
<213> ORGANISM: Artificial Sequence
<220> FEATURE:
<223> OTHER INFORMATION: N1.11 (W61C)

<400> SEQUENCE: 23
```

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Ser
            35                  40                  45

Leu Val Pro Arg Gly Ser Pro Ser Arg Ile Glu Thr Cys Asn Gln Ser
    50                  55                  60

Val Ile Thr Tyr Glu Asn Asn Thr Cys Val Asn Gln Thr Tyr Val Asn
65                  70                  75                  80

Ile Ser Asn Thr Asn Phe Ala Ala Gly Gln Ser Val Val Ser Val Lys
            85                  90                  95

Leu Ala Gly Asn Ser Ser Leu Cys Pro Val Ser Gly Trp Ala Ile Tyr
            100                 105                 110

Ser Lys Asp Asn Ser Val Arg Ile Gly Ser Lys Gly Asp Val Phe Val
            115                 120                 125

Ile Arg Glu Pro Phe Ile Ser Cys Ser Pro Leu Glu Cys Arg Thr Phe
    130                 135                 140

Phe Leu Thr Gln Gly Ala Leu Leu Asn Asp Lys His Ser Asn Gly Thr
145                 150                 155                 160

Ile Lys Asp Arg Ser Pro Tyr Arg Thr Leu Met Ser Cys Pro Ile Gly
            165                 170                 175

Glu Val Pro Ser Pro Tyr Asn Ser Arg Phe Glu Ser Val Ala Trp Ser
            180                 185                 190
```

-continued

Ala Ser Ala Cys His Asp Gly Ile Asn Trp Leu Thr Ile Gly Ile Ser
        195                 200                 205

Gly Pro Asp Ser Gly Ala Val Ala Val Leu Lys Tyr Asn Gly Ile Ile
        210                 215                 220

Thr Asp Thr Ile Lys Ser Trp Arg Asn Asn Ile Leu Arg Thr Gln Glu
225                 230                 235                 240

Ser Glu Cys Ala Cys Val Asn Gly Ser Cys Phe Thr Ile Met Thr Asp
                245                 250                 255

Gly Pro Ser Asp Gly Gln Ala Ser Tyr Lys Ile Phe Arg Ile Glu Lys
                260                 265                 270

Gly Lys Ile Ile Lys Ser Val Glu Met Lys Ala Pro Asn Tyr His Tyr
        275                 280                 285

Glu Glu Cys Ser Cys Tyr Pro Asp Ser Ser Glu Ile Thr Cys Val Cys
        290                 295                 300

Arg Asp Asn Trp His Gly Ser Asn Arg Pro Trp Val Ser Phe Asn Gln
305                 310                 315                 320

Asn Leu Glu Tyr Gln Met Gly Tyr Ile Cys Ser Gly Val Phe Gly Asp
                325                 330                 335

Asn Pro Arg Pro Asn Asp Lys Thr Gly Ser Cys Gly Pro Val Ser Ser
                340                 345                 350

Asn Gly Ala Asn Gly Val Lys Gly Phe Ser Phe Lys Tyr Gly Asn Gly
        355                 360                 365

Val Trp Ile Gly Arg Thr Lys Ser Ile Ser Ser Arg Lys Gly Phe Glu
        370                 375                 380

Met Ile Trp Asp Pro Asn Gly Trp Thr Gly Thr Asp Asn Lys Phe Ser
385                 390                 395                 400

Ile Lys Gln Asp Ile Val Gly Ile Asn Glu Trp Ser Gly Tyr Ser Gly
                405                 410                 415

Ser Phe Val Gln His Pro Glu Leu Thr Gly Leu Asp Cys Ile Arg Pro
                420                 425                 430

Cys Phe Trp Val Glu Leu Ile Arg Gly Arg Pro Glu Glu Asn Thr Ile
                435                 440                 445

Trp Thr Ser Gly Ser Ser Ile Ser Phe Cys Gly Val Asn Ser Asp Thr
        450                 455                 460

Val Gly Trp Ser Trp Pro Asp Gly Ala Glu Leu Pro Phe Thr Ile Asp
465                 470                 475                 480

Lys

<210> SEQ ID NO 24
<211> LENGTH: 530
<212> TYPE: PRT
<213> ORGANISM: Artificial Sequence
<220> FEATURE:
<223> OTHER INFORMATION: SMDTF-N1

<400> SEQUENCE: 24

Met Leu Leu Val Asn Gln Ser His Gln Gly Phe Asn Lys Glu His Thr
1                   5                   10                  15

Ser Lys Met Val Ser Ala Ile Val Leu Tyr Val Leu Leu Ala Ala Ala
                20                  25                  30

Ala His Ser Ala Phe Ala Ala Asp Pro His His His His His His Val
        35                  40                  45

Glu Leu Ser Ser Gln Gln Glu Tyr Leu Lys Leu Lys Glu Arg Tyr Asp
        50                  55                  60

Ala Leu Gln Arg Thr Gln Arg Asn Leu Leu Gly Glu Asp Leu Gly Pro

```
65              70              75              80

Leu Ser Thr Lys Glu Leu Glu Ser Leu Glu Arg Gln Leu Asp Ser Ser
            85              90              95

Leu Lys Gln Ile Arg Ala Leu Arg Thr Gln Phe Met Leu Asp Gln Ser
            100             105             110

Lys Glu Arg Met Leu Thr Glu Thr Asn Lys Thr Leu Arg Leu Arg Leu
            115             120             125

Ala Asp Gly Tyr Ser Leu Val Pro Arg Gly Ser Pro Ser Arg Ser Val
        130             135             140

Lys Leu Ala Gly Asn Ser Ser Leu Cys Pro Val Ser Gly Trp Ala Ile
145             150             155             160

Tyr Ser Lys Asp Asn Ser Val Arg Ile Gly Ser Lys Gly Asp Val Phe
            165             170             175

Val Ile Arg Glu Pro Phe Ile Ser Cys Ser Pro Leu Glu Cys Arg Thr
            180             185             190

Phe Phe Leu Thr Gln Gly Ala Leu Leu Asn Asp Lys His Ser Asn Gly
            195             200             205

Thr Ile Lys Asp Arg Ser Pro Tyr Arg Thr Leu Met Ser Cys Pro Ile
        210             215             220

Gly Glu Val Pro Ser Pro Tyr Asn Ser Arg Phe Glu Ser Val Ala Trp
225             230             235             240

Ser Ala Ser Ala Cys His Asp Gly Ile Asn Trp Leu Thr Ile Gly Ile
            245             250             255

Ser Gly Pro Asp Ser Gly Ala Val Ala Val Leu Lys Tyr Asn Gly Ile
            260             265             270

Ile Thr Asp Thr Ile Lys Ser Trp Arg Asn Asn Ile Leu Arg Thr Gln
        275             280             285

Glu Ser Glu Cys Ala Cys Val Asn Gly Ser Cys Phe Thr Ile Met Thr
    290             295             300

Asp Gly Pro Ser Asp Gly Gln Ala Ser Tyr Lys Ile Phe Arg Ile Glu
305             310             315             320

Lys Gly Lys Ile Ile Lys Ser Val Glu Met Lys Ala Pro Asn Tyr His
            325             330             335

Tyr Glu Glu Cys Ser Cys Tyr Pro Asp Ser Ser Glu Ile Thr Cys Val
            340             345             350

Cys Arg Asp Asn Trp His Gly Ser Asn Arg Pro Trp Val Ser Phe Asn
        355             360             365

Gln Asn Leu Glu Tyr Gln Met Gly Tyr Ile Cys Ser Gly Val Phe Gly
    370             375             380

Asp Asn Pro Arg Pro Asn Asp Lys Thr Gly Ser Cys Gly Pro Val Ser
385             390             395             400

Ser Asn Gly Ala Asn Gly Val Lys Gly Phe Ser Phe Lys Tyr Gly Asn
            405             410             415

Gly Val Trp Ile Gly Arg Thr Lys Ser Ile Ser Ser Arg Lys Gly Phe
            420             425             430

Glu Met Ile Trp Asp Pro Asn Gly Trp Thr Gly Thr Asp Asn Lys Phe
            435             440             445

Ser Ile Lys Gln Asp Ile Val Gly Ile Asn Glu Trp Ser Gly Tyr Ser
        450             455             460

Gly Ser Phe Val Gln His Pro Glu Leu Thr Gly Leu Asp Cys Ile Arg
465             470             475             480

Pro Cys Phe Trp Val Glu Leu Ile Arg Gly Arg Pro Glu Glu Asn Thr
            485             490             495
```

-continued

```
Ile Trp Thr Ser Gly Ser Ser Ile Ser Phe Cys Gly Val Asn Ser Asp
        500                 505                 510

Thr Val Gly Trp Ser Trp Pro Asp Gly Ala Glu Leu Pro Phe Thr Ile
        515                 520                 525

Asp Lys
    530
```

```
<210> SEQ ID NO 25
<211> LENGTH: 558
<212> TYPE: PRT
<213> ORGANISM: Artificial Sequence
<220> FEATURE:
<223> OTHER INFORMATION: SPP-N1

<400> SEQUENCE: 25

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Glu
        35                  40                  45

Asn Thr Ser Ser Met Lys Glu Met Ala Thr Leu Leu Thr Ser Leu Gly
    50                  55                  60

Val Ile Gln Ser Ala Gln Glu Phe Glu Ser Ser Arg Asp Ala Ser Tyr
65                  70                  75                  80

Val Phe Ala Arg Arg Ala Leu Lys Ser Ala Asn Tyr Ala Glu Met Thr
                85                  90                  95

Phe Asn Val Cys Gly Leu Ile Leu Ser Ala Glu Lys Ser Ser Ala Arg
            100                 105                 110

Lys Val Asp Glu Asn Lys Gln Leu Leu Lys Ile Gln Glu Ser Val Glu
        115                 120                 125

Ser Phe Arg Asp Ile Tyr Lys Arg Phe Ser Glu Tyr Gln Lys Glu Gln
    130                 135                 140

Asn Ser Leu Leu Met Ser Asn Leu Ser Thr Leu His Ile Ile Thr Asp
145                 150                 155                 160

Ser Leu Val Pro Arg Gly Ser Pro Ser Arg Ser Val Lys Leu Ala Gly
                165                 170                 175

Asn Ser Ser Leu Cys Pro Val Ser Gly Trp Ala Ile Tyr Ser Lys Asp
            180                 185                 190

Asn Ser Val Arg Ile Gly Ser Lys Gly Asp Val Phe Val Ile Arg Glu
        195                 200                 205

Pro Phe Ile Ser Cys Ser Pro Leu Glu Cys Arg Thr Phe Phe Leu Thr
    210                 215                 220

Gln Gly Ala Leu Leu Asn Asp Lys His Ser Asn Gly Thr Ile Lys Asp
225                 230                 235                 240

Arg Ser Pro Tyr Arg Thr Leu Met Ser Cys Pro Ile Gly Glu Val Pro
                245                 250                 255

Ser Pro Tyr Asn Ser Arg Phe Glu Ser Val Ala Trp Ser Ala Ser Ala
            260                 265                 270

Cys His Asp Gly Ile Asn Trp Leu Thr Ile Gly Ile Ser Gly Pro Asp
        275                 280                 285

Ser Gly Ala Val Ala Val Leu Lys Tyr Asn Gly Ile Ile Thr Asp Thr
    290                 295                 300

Ile Lys Ser Trp Arg Asn Asn Ile Leu Arg Thr Gln Glu Ser Glu Cys
305                 310                 315                 320
```

-continued

```
Ala Cys Val Asn Gly Ser Cys Phe Thr Ile Met Thr Asp Gly Pro Ser
            325                 330                 335

Asp Gly Gln Ala Ser Tyr Lys Ile Phe Arg Ile Glu Lys Gly Lys Ile
            340                 345                 350

Ile Lys Ser Val Glu Met Lys Ala Pro Asn Tyr His Tyr Glu Glu Cys
            355                 360                 365

Ser Cys Tyr Pro Asp Ser Ser Glu Ile Thr Cys Val Cys Arg Asp Asn
            370                 375                 380

Trp His Gly Ser Asn Arg Pro Trp Val Ser Phe Asn Gln Asn Leu Glu
385                 390                 395                 400

Tyr Gln Met Gly Tyr Ile Cys Ser Gly Val Phe Gly Asp Asn Pro Arg
                405                 410                 415

Pro Asn Asp Lys Thr Gly Ser Cys Gly Pro Val Ser Ser Asn Gly Ala
            420                 425                 430

Asn Gly Val Lys Gly Phe Ser Phe Lys Tyr Gly Asn Gly Val Trp Ile
            435                 440                 445

Gly Arg Thr Lys Ser Ile Ser Ser Arg Lys Gly Phe Glu Met Ile Trp
        450                 455                 460

Asp Pro Asn Gly Trp Thr Gly Thr Asp Asn Lys Phe Ser Ile Lys Gln
465                 470                 475                 480

Asp Ile Val Gly Ile Asn Glu Trp Ser Gly Tyr Ser Gly Ser Phe Val
                485                 490                 495

Gln His Pro Glu Leu Thr Gly Leu Asp Cys Ile Arg Pro Cys Phe Trp
            500                 505                 510

Val Glu Leu Ile Arg Gly Arg Pro Glu Glu Asn Thr Ile Trp Thr Ser
            515                 520                 525

Gly Ser Ser Ile Ser Phe Cys Gly Val Asn Ser Asp Thr Val Gly Trp
        530                 535                 540

Ser Trp Pro Asp Gly Ala Glu Leu Pro Phe Thr Ile Asp Lys
545                 550                 555

<210> SEQ ID NO 26
<211> LENGTH: 469
<212> TYPE: PRT
<213> ORGANISM: Artificial Sequence
<220> FEATURE:
<223> OTHER INFORMATION: PiLZ-N1

<400> SEQUENCE: 26

Met Leu Leu Val Asn Gln Ser His Gln Gly Phe Asn Lys Glu His Thr
1                   5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Leu
            35                  40                  45

Leu Val Gln Arg Met Asp Ala Lys Leu Asp Leu Ile Leu Ala Leu Ile
        50                  55                  60

Gly Arg Leu Val Arg Gln Ser Ser Leu Val Pro Arg Gly Ser Pro Ser
65                  70                  75                  80

Arg Ser Val Lys Leu Ala Gly Asn Ser Ser Leu Cys Pro Val Ser Gly
            85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
            115                 120                 125
```

-continued

```
Cys Arg Thr Phe Phe Leu Thr Gln Gly Ala Leu Leu Asn Asp Lys His
    130             135             140

Ser Asn Gly Thr Ile Lys Asp Arg Ser Pro Tyr Arg Thr Leu Met Ser
145             150             155             160

Cys Pro Ile Gly Glu Val Pro Ser Pro Tyr Asn Ser Arg Phe Glu Ser
                165             170             175

Val Ala Trp Ser Ala Ser Ala Cys His Asp Gly Ile Asn Trp Leu Thr
            180             185             190

Ile Gly Ile Ser Gly Pro Asp Ser Gly Ala Val Ala Val Leu Lys Tyr
            195             200             205

Asn Gly Ile Ile Thr Asp Thr Ile Lys Ser Trp Arg Asn Asn Ile Leu
    210             215             220

Arg Thr Gln Glu Ser Glu Cys Ala Cys Val Asn Gly Ser Cys Phe Thr
225             230             235             240

Ile Met Thr Asp Gly Pro Ser Asp Gly Gln Ala Ser Tyr Lys Ile Phe
            245             250             255

Arg Ile Glu Lys Gly Lys Ile Ile Lys Ser Val Glu Met Lys Ala Pro
            260             265             270

Asn Tyr His Tyr Glu Glu Cys Ser Cys Tyr Pro Asp Ser Ser Glu Ile
    275             280             285

Thr Cys Val Cys Arg Asp Asn Trp His Gly Ser Asn Arg Pro Trp Val
    290             295             300

Ser Phe Asn Gln Asn Leu Glu Tyr Gln Met Gly Tyr Ile Cys Ser Gly
305             310             315             320

Val Phe Gly Asp Asn Pro Arg Pro Asn Asp Lys Thr Gly Ser Cys Gly
            325             330             335

Pro Val Ser Ser Asn Gly Ala Asn Gly Val Lys Gly Phe Ser Phe Lys
            340             345             350

Tyr Gly Asn Gly Val Trp Ile Gly Arg Thr Lys Ser Ile Ser Ser Arg
            355             360             365

Lys Gly Phe Glu Met Ile Trp Asp Pro Asn Gly Trp Thr Gly Thr Asp
    370             375             380

Asn Lys Phe Ser Ile Lys Gln Asp Ile Val Gly Ile Asn Glu Trp Ser
385             390             395             400

Gly Tyr Ser Gly Ser Phe Val Gln His Pro Glu Leu Thr Gly Leu Asp
            405             410             415

Cys Ile Arg Pro Cys Phe Trp Val Glu Leu Ile Arg Gly Arg Pro Glu
            420             425             430

Glu Asn Thr Ile Trp Thr Ser Gly Ser Ser Ile Ser Phe Cys Gly Val
            435             440             445

Asn Ser Asp Thr Val Gly Trp Ser Trp Pro Asp Gly Ala Glu Leu Pro
    450             455             460

Phe Thr Ile Asp Lys
465
```

```
<210> SEQ ID NO 27
<211> LENGTH: 519
<212> TYPE: PRT
<213> ORGANISM: Artificial Sequence
<220> FEATURE:
<223> OTHER INFORMATION: MPP-N1

<400> SEQUENCE: 27

Met Leu Leu Val Asn Gln Ser His Gln Gly Phe Asn Lys Glu His Thr
1               5               10              15
```

```
Ser Lys Met Val Ser Ala Ile Val Leu Tyr Val Leu Leu Ala Ala Ala
        20              25              30

Ala His Ser Ala Phe Ala Ala Asp Pro His His His His His His Gly
        35              40              45

Asp His Tyr Asp Asp Glu Leu Phe Ser Asp Val Gln Asp Ile Lys Thr
    50              55              60

Ala Leu Ala Lys Ile His Glu Asp Asn Gln Lys Ile Ile Ser Lys Leu
65              70              75              80

Glu Ser Leu Leu Leu Leu Lys Gly Glu Val Glu Ser Ile Lys Lys Gln
                85              90              95

Ile Asn Arg Gln Asn Ile Ser Ile Ser Thr Leu Glu Gly His Leu Ser
            100             105             110

Ser Ile Met Ile Ala Ile Pro Gly Leu Ser Leu Val Pro Arg Gly Ser
            115             120             125

Pro Ser Arg Ser Val Lys Leu Ala Gly Asn Ser Ser Leu Cys Pro Val
    130             135             140

Ser Gly Trp Ala Ile Tyr Ser Lys Asp Asn Ser Val Arg Ile Gly Ser
145             150             155             160

Lys Gly Asp Val Phe Val Ile Arg Glu Pro Phe Ile Ser Cys Ser Pro
            165             170             175

Leu Glu Cys Arg Thr Phe Phe Leu Thr Gln Gly Ala Leu Leu Asn Asp
            180             185             190

Lys His Ser Asn Gly Thr Ile Lys Asp Arg Ser Pro Tyr Arg Thr Leu
            195             200             205

Met Ser Cys Pro Ile Gly Glu Val Pro Ser Pro Tyr Asn Ser Arg Phe
    210             215             220

Glu Ser Val Ala Trp Ser Ala Ser Ala Cys His Asp Gly Ile Asn Trp
225             230             235             240

Leu Thr Ile Gly Ile Ser Gly Pro Asp Ser Gly Ala Val Ala Val Leu
            245             250             255

Lys Tyr Asn Gly Ile Ile Thr Asp Thr Ile Lys Ser Trp Arg Asn Asn
            260             265             270

Ile Leu Arg Thr Gln Glu Ser Glu Cys Ala Cys Val Asn Gly Ser Cys
            275             280             285

Phe Thr Ile Met Thr Asp Gly Pro Ser Asp Gly Gln Ala Ser Tyr Lys
    290             295             300

Ile Phe Arg Ile Glu Lys Gly Lys Ile Ile Lys Ser Val Glu Met Lys
305             310             315             320

Ala Pro Asn Tyr His Tyr Glu Glu Cys Ser Cys Tyr Pro Asp Ser Ser
            325             330             335

Glu Ile Thr Cys Val Cys Arg Asp Asn Trp His Gly Ser Asn Arg Pro
            340             345             350

Trp Val Ser Phe Asn Gln Asn Leu Glu Tyr Gln Met Gly Tyr Ile Cys
            355             360             365

Ser Gly Val Phe Gly Asp Asn Pro Arg Pro Asn Asp Lys Thr Gly Ser
    370             375             380

Cys Gly Pro Val Ser Ser Asn Gly Ala Asn Gly Val Lys Gly Phe Ser
385             390             395             400

Phe Lys Tyr Gly Asn Gly Val Trp Ile Gly Arg Thr Lys Ser Ile Ser
            405             410             415

Ser Arg Lys Gly Phe Glu Met Ile Trp Asp Pro Asn Gly Trp Thr Gly
            420             425             430
```

-continued

```
Thr Asp Asn Lys Phe Ser Ile Lys Gln Asp Ile Val Gly Ile Asn Glu
        435                 440                 445

Trp Ser Gly Tyr Ser Gly Ser Phe Val Gln His Pro Glu Leu Thr Gly
        450                 455                 460

Leu Asp Cys Ile Arg Pro Cys Phe Trp Val Glu Leu Ile Arg Gly Arg
465                 470                 475                 480

Pro Glu Glu Asn Thr Ile Trp Thr Ser Gly Ser Ser Ile Ser Phe Cys
                485                 490                 495

Gly Val Asn Ser Asp Thr Val Gly Trp Ser Trp Pro Asp Gly Ala Glu
                500                 505                 510

Leu Pro Phe Thr Ile Asp Lys
        515

<210> SEQ ID NO 28
<211> LENGTH: 496
<212> TYPE: PRT
<213> ORGANISM: Artificial Sequence
<220> FEATURE:
<223> OTHER INFORMATION: ACE-N1

<400> SEQUENCE: 28

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Pro His His His His His His Ala
        35                  40                  45

Val Ala Asp Val Gly Asp Pro Phe Leu Leu Trp Lys Gln Gln Met Asp
        50                  55                  60

Lys Trp Gln Asn Glu Tyr Ile Thr Asp Trp Gln Tyr His Phe Glu Gln
65                  70                  75                  80

Tyr Lys Lys Tyr Gln Thr Tyr Arg His Leu Asp Ser Asp Ser Cys Ser
                85                  90                  95

Gly Ser Ser Leu Val Pro Arg Gly Ser Pro Ser Arg Ser Val Lys Leu
                100                 105                 110

Ala Gly Asn Ser Ser Leu Cys Pro Val Ser Gly Trp Ala Ile Tyr Ser
        115                 120                 125

Lys Asp Asn Ser Val Arg Ile Gly Ser Lys Gly Asp Val Phe Val Ile
        130                 135                 140

Arg Glu Pro Phe Ile Ser Cys Ser Pro Leu Glu Cys Arg Thr Phe Phe
145                 150                 155                 160

Leu Thr Gln Gly Ala Leu Leu Asn Asp Lys His Ser Asn Gly Thr Ile
                165                 170                 175

Lys Asp Arg Ser Pro Tyr Arg Thr Leu Met Ser Cys Pro Ile Gly Glu
                180                 185                 190

Val Pro Ser Pro Tyr Asn Ser Arg Phe Glu Ser Val Ala Trp Ser Ala
                195                 200                 205

Ser Ala Cys His Asp Gly Ile Asn Trp Leu Thr Ile Gly Ile Ser Gly
        210                 215                 220

Pro Asp Ser Gly Ala Val Ala Val Leu Lys Tyr Asn Gly Ile Ile Thr
225                 230                 235                 240

Asp Thr Ile Lys Ser Trp Arg Asn Asn Ile Leu Arg Thr Gln Glu Ser
                245                 250                 255

Glu Cys Ala Cys Val Asn Gly Ser Cys Phe Thr Ile Met Thr Asp Gly
        260                 265                 270
```

```
Pro Ser Asp Gly Gln Ala Ser Tyr Lys Ile Phe Arg Ile Glu Lys Gly
        275                 280                 285

Lys Ile Ile Lys Ser Val Glu Met Lys Ala Pro Asn Tyr His Tyr Glu
        290                 295                 300

Glu Cys Ser Cys Tyr Pro Asp Ser Ser Glu Ile Thr Cys Val Cys Arg
305                 310                 315                 320

Asp Asn Trp His Gly Ser Asn Arg Pro Trp Val Ser Phe Asn Gln Asn
                325                 330                 335

Leu Glu Tyr Gln Met Gly Tyr Ile Cys Ser Gly Val Phe Gly Asp Asn
                340                 345                 350

Pro Arg Pro Asn Asp Lys Thr Gly Ser Cys Gly Pro Val Ser Ser Asn
        355                 360                 365

Gly Ala Asn Gly Val Lys Gly Phe Ser Phe Lys Tyr Gly Asn Gly Val
        370                 375                 380

Trp Ile Gly Arg Thr Lys Ser Ile Ser Ser Arg Lys Gly Phe Glu Met
385                 390                 395                 400

Ile Trp Asp Pro Asn Gly Trp Thr Gly Thr Asp Asn Lys Phe Ser Ile
                405                 410                 415

Lys Gln Asp Ile Val Gly Ile Asn Glu Trp Ser Gly Tyr Ser Gly Ser
                420                 425                 430

Phe Val Gln His Pro Glu Leu Thr Gly Leu Asp Cys Ile Arg Pro Cys
        435                 440                 445

Phe Trp Val Glu Leu Ile Arg Gly Arg Pro Glu Glu Asn Thr Ile Trp
        450                 455                 460

Thr Ser Gly Ser Ser Ile Ser Phe Cys Gly Val Asn Ser Asp Thr Val
465                 470                 475                 480

Gly Trp Ser Trp Pro Asp Gly Ala Glu Leu Pro Phe Thr Ile Asp Lys
                485                 490                 495

<210> SEQ ID NO 29
<211> LENGTH: 454
<212> TYPE: PRT
<213> ORGANISM: Artificial Sequence
<220> FEATURE:
<223> OTHER INFORMATION: N1 PR8

<400> SEQUENCE: 29

Met Asn Pro Asn Gln Lys Ile Thr Thr Ile Gly Ser Ile Cys Leu Val
1               5                   10                  15

Val Gly Leu Ile Ser Leu Ile Leu Gln Ile Gly Asn Ile Ile Ser Ile
                20                  25                  30

Trp Ile Ser His Ser Ile Gln Thr Gly Ser Gln Asn His Thr Gly Ile
        35                  40                  45

Cys Asn Gln Asn Ile Ile Thr Tyr Lys Asn Ser Thr Trp Val Lys Asp
        50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
                100                 105                 110

Glu Cys Arg Thr Phe Phe Leu Thr Gln Gly Ala Leu Leu Asn Asp Lys
        115                 120                 125

His Ser Asn Gly Thr Val Lys Asp Arg Ser Pro Tyr Arg Ala Leu Met
        130                 135                 140
```

```
Ser Cys Pro Val Gly Glu Ala Pro Ser Pro Tyr Asn Ser Arg Phe Glu
145             150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
                180                 185                 190

Tyr Asn Gly Ile Ile Thr Glu Thr Ile Lys Ser Trp Arg Lys Lys Ile
            195                 200                 205

Leu Arg Thr Gln Glu Ser Glu Cys Ala Cys Val Asn Gly Ser Cys Phe
        210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Gly Lys
                260                 265                 270

Val Met Cys Val Cys Arg Asp Asn Trp His Gly Ser Asn Arg Pro Trp
            275                 280                 285

Val Ser Phe Asp Gln Asn Leu Asp Tyr Gln Ile Gly Tyr Ile Cys Ser
        290                 295                 300

Gly Val Phe Gly Asp Asn Pro Arg Pro Glu Asp Gly Thr Gly Ser Cys
305                 310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
            340                 345                 350

Arg His Gly Phe Glu Met Ile Trp Asp Pro Asn Gly Trp Thr Glu Thr
        355                 360                 365

Asp Ser Lys Phe Ser Val Arg Gln Asp Val Val Ala Met Thr Asp Trp
    370                 375                 380

Ser Gly Tyr Ser Gly Ser Phe Val Gln His Pro Glu Leu Thr Gly Leu
385                 390                 395                 400

Asp Cys Met Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
                420                 425                 430

Val Asn Ser Asp Thr Val Asp Trp Ser Trp Pro Asp Gly Ala Glu Leu
            435                 440                 445

Pro Phe Ser Ile Asp Lys
        450
```

```
<210> SEQ ID NO 30
<211> LENGTH: 469
<212> TYPE: PRT
<213> ORGANISM: Artificial Sequence
<220> FEATURE:
<223> OTHER INFORMATION: N1_Mich15

<400> SEQUENCE: 30

Met Asn Pro Asn Gln Lys Ile Ile Thr Ile Gly Ser Ile Cys Met Thr
1               5                   10                  15

Ile Gly Met Ala Asn Leu Ile Leu Gln Ile Gly Asn Ile Ile Ser Ile
                20                  25                  30

Trp Val Ser His Ser Ile Gln Ile Gly Asn Gln Ser Gln Ile Glu Thr
            35                  40                  45
```

```
Cys Asn Gln Ser Val Ile Thr Tyr Glu Asn Asn Thr Trp Val Asn Gln
    50                      55                  60

Thr Tyr Val Asn Ile Ser Asn Thr Asn Phe Ala Ala Gly Gln Ser Val
65                      70                  75                  80

Val Ser Val Lys Leu Ala Gly Asn Ser Ser Leu Cys Pro Val Ser Gly
            85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
            115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
            165                 170                 175

Val Ala Trp Ser Ala Ser Ala Cys His Asp Gly Ile Asn Trp Leu Thr
            180                 185                 190

Ile Gly Ile Ser Gly Pro Asp Ser Gly Ala Val Ala Val Leu Lys Tyr
            195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
            245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Ser Ser Glu Ile
            275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
            325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
            355                 360                 365

Lys Gly Phe Glu Met Ile Trp Asp Pro Asn Gly Trp Thr Gly Thr Asp
    370                 375                 380

Asn Lys Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
            405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
            435                 440                 445

Asn Ser Asp Thr Val Gly Trp Ser Trp Pro Asp Gly Ala Glu Leu Pro
    450                 455                 460

Phe Thr Ile Asp Lys
```

-continued

465

<210> SEQ ID NO 31
<211> LENGTH: 453
<212> TYPE: PRT
<213> ORGANISM: Artificial Sequence
<220> FEATURE:
<223> OTHER INFORMATION: N1_WSN

<400> SEQUENCE: 31

```
Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Asn His Thr Gly Ile
        35                  40                  45

Cys Asn Gln Gly Ser Ile Thr Tyr Lys Val Val Ala Gly Gln Asp Ser
    50                  55                  60

Thr Ser Val Ile Leu Thr Gly Asn Ser Ser Leu Cys Pro Ile Arg Gly
65                  70                  75                  80

Trp Ala Ile His Ser Lys Asp Asn Gly Ile Arg Ile Gly Ser Lys Gly
                85                  90                  95

Asp Val Phe Val Ile Arg Glu Pro Phe Ile Ser Cys Ser His Leu Glu
            100                 105                 110

Cys Arg Thr Phe Phe Leu Thr Gln Gly Ala Leu Leu Asn Asp Lys His
            115                 120                 125

Ser Arg Gly Thr Phe Lys Asp Arg Ser Pro Tyr Arg Ala Leu Met Ser
    130                 135                 140

Cys Pro Val Gly Glu Ala Pro Ser Pro Tyr Asn Ser Arg Phe Glu Ser
145                 150                 155                 160

Val Ala Trp Ser Ala Ser Ala Cys His Asp Gly Met Gly Trp Leu Thr
                165                 170                 175

Ile Gly Ile Ser Gly Pro Asp Asp Gly Ala Val Ala Val Leu Lys Tyr
            180                 185                 190

Asn Arg Ile Ile Thr Glu Thr Ile Lys Ser Trp Arg Lys Asn Ile Leu
            195                 200                 205

Arg Thr Gln Glu Ser Glu Cys Thr Cys Val Asn Gly Ser Cys Phe Thr
    210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
                245                 250                 255

Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
            275                 280                 285

Ser Phe Asp Gln Asn Leu Asp Tyr Lys Ile Gly Tyr Ile Cys Ser Gly
    290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
            340                 345                 350

His Gly Phe Glu Met Ile Trp Asp Pro Asn Gly Trp Thr Glu Thr Asp
```

-continued

```
              355               360               365

Ser Arg Phe Ser Met Arg Gln Asp Val Val Ala Ile Thr Asn Arg Ser
    370               375               380

Gly Tyr Ser Gly Ser Phe Val Gln His Pro Glu Leu Thr Gly Leu Asp
385               390               395               400

Cys Met Arg Pro Cys Phe Trp Val Glu Leu Ile Arg Gly Leu Pro Glu
                405               410               415

Glu Asp Ala Ile Trp Thr Ser Gly Ser Ile Ile Ser Phe Cys Gly Val
                420               425               430

Asn Ser Asp Thr Val Asp Trp Ser Trp Pro Asp Gly Ala Glu Leu Pro
                435               440               445

Phe Thr Ile Asp Lys
    450

<210> SEQ ID NO 32
<211> LENGTH: 469
<212> TYPE: PRT
<213> ORGANISM: Artificial Sequence
<220> FEATURE:
<223> OTHER INFORMATION: N2_HK14
<220> FEATURE:
<221> NAME/KEY: MISC_FEATURE
<222> LOCATION: (148)..(148)
<223> OTHER INFORMATION: X is unknown in public database

<400> SEQUENCE: 32

Met Asn Pro Asn Gln Lys Ile Ile Thr Ile Gly Ser Val Ser Leu Thr
1               5                 10                15

Ile Ser Thr Ile Cys Phe Phe Met Gln Ile Ala Ile Leu Ile Thr Thr
                20                25                30

Val Thr Leu His Phe Lys Gln Tyr Glu Phe Asn Ser Pro Pro Asn Asn
            35                40                45

Gln Val Met Leu Cys Glu Pro Thr Ile Ile Glu Arg Asn Ile Thr Glu
    50                55                60

Ile Val Tyr Leu Thr Asn Thr Thr Ile Glu Lys Glu Ile Cys Pro Lys
65                70                75                80

Pro Ala Glu Tyr Arg Asn Trp Ser Lys Pro Gln Cys Gly Ile Thr Gly
                85                90                95

Phe Ala Pro Phe Ser Lys Asp Asn Ser Ile Arg Leu Ser Ala Gly Gly
                100               105               110

Asp Ile Trp Val Thr Arg Glu Pro Tyr Val Ser Cys Asp Pro Asp Lys
            115               120               125

Cys Tyr Gln Phe Ala Leu Gly Gln Gly Thr Thr Leu Asn Asn Val His
    130               135               140

Ser Asn Asn Xaa Val Arg Asp Arg Thr Pro Tyr Arg Thr Leu Leu Met
145               150               155               160

Asn Glu Leu Gly Val Pro Phe His Leu Gly Thr Lys Gln Val Cys Ile
                165               170               175

Ala Trp Ser Ser Ser Ser Cys His Asp Gly Lys Ala Trp Leu His Val
                180               185               190

Cys Ile Thr Gly Asp Asp Lys Asn Ala Thr Ala Ser Phe Ile Tyr Asn
            195               200               205

Gly Arg Leu Val Asp Ser Val Val Ser Trp Ser Lys Asp Ile Leu Arg
    210               215               220

Thr Gln Glu Ser Glu Cys Ile Cys Ile Asn Gly Thr Cys Thr Val Val
225               230               235               240
```

```
Met Thr Asp Gly Ser Ala Ser Gly Lys Ala Asp Thr Lys Ile Leu Phe
            245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
                340                 345                 350

Ala Phe Asp Asp Gly Asn Asp Val Trp Met Gly Arg Thr Ile Asn Glu
                355                 360                 365

Thr Ser Arg Leu Gly Tyr Glu Thr Phe Lys Val Ile Glu Gly Trp Ser
    370                 375                 380

Asn Pro Lys Ser Lys Leu Gln Thr Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
                420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Leu
    450                 455                 460

Asn Leu Met Pro Ile
465
```

```
<210> SEQ ID NO 33
<211> LENGTH: 469
<212> TYPE: PRT
<213> ORGANISM: Artificial Sequence
<220> FEATURE:
<223> OTHER INFORMATION: N2_ck
<220> FEATURE:
<221> NAME/KEY: MISC_FEATURE
<222> LOCATION: (356)..(356)
<223> OTHER INFORMATION: X is unknown in public database

<400> SEQUENCE: 33

Met Asn Pro Asn Gln Lys Ile Ile Ala Leu Gly Ser Ala Ser Leu Thr
1               5                   10                  15

Ile Ala Ile Val Cys Leu Leu Ile Gln Ile Ala Ile Leu Ala Thr Thr
            20                  25                  30

Met Thr Leu His Phe Thr Gln Ser Glu Tyr Thr Asn Ser Ser Thr Asn
        35                  40                  45

Lys Val Val Ser Cys Glu Ser Thr Ile Ile Glu Arg Asn Ile Thr Glu
    50                  55                  60

Ile Val His Leu Asn Gly Thr Ile Ile Glu Arg Glu Ser Cys Pro Lys
65                  70                  75                  80

Ser Ala Glu Tyr Lys Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110
```

```
Asp Ile Trp Val Thr Arg Glu Pro Tyr Val Ser Cys Ser Leu Asn Lys
        115                 120                 125

Cys Tyr Gln Phe Ala Leu Gly Gln Gly Thr Thr Leu Asn Asn Arg His
        130                 135                 140

Ser Asn Gly Thr Thr His Asp Arg Ser Pro Tyr Arg Thr Leu Leu Met
145                 150                 155                 160

Ser Glu Leu Gly Val Pro Phe His Leu Gly Thr Lys Gln Val Cys Ile
                165                 170                 175

Ala Trp Ser Ser Ser Ser Cys His Asp Gly Arg Ala Trp Leu His Val
                180                 185                 190

Cys Val Thr Gly Asp Asp Lys Asn Ala Thr Ala Ser Val Ile Tyr Asp
        195                 200                 205

Gly Met Leu Thr Asp Ser Ile Val Ser Trp Ser Lys Asn Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Met Ala Asp Thr Arg Ile Leu Phe
                245                 250                 255

Ile Arg Glu Gly Lys Ile Val His Ile Ser Pro Leu Ser Gly Ser Ala
        260                 265                 270

Gln His Val Glu Glu Cys Ser Cys Tyr Pro Arg Tyr Pro Glu Val Arg
        275                 280                 285

Cys Val Cys Arg Asp Asn Trp Lys Gly Ser Asn Arg Pro Val Leu Tyr
        290                 295                 300

Ile Asn Met Ala Asp Tyr Asn Ile Asp Ser Asn Tyr Val Cys Ser Gly
305                 310                 315                 320

Leu Val Gly Asp Thr Pro Arg Ser Asp Asp Ser Ser Ser Ser Ser Asn
                325                 330                 335

Cys Arg Asp Pro Asn Asn Glu Arg Gly Gly Pro Gly Val Lys Gly Trp
                340                 345                 350

Ala Phe Asp Xaa Gly Asp Asp Val Trp Met Gly Arg Thr Ile Lys Lys
                355                 360                 365

Asp Ser Arg Ala Gly Tyr Glu Thr Phe Arg Val Val Asp Gly Trp Thr
        370                 375                 380

Val Ala Asn Ser Lys Ser Gln Thr Asn Arg Gln Val Ile Val Glu Ser
385                 390                 395                 400

Asp Asn Arg Ser Gly Tyr Ser Gly Ile Phe Ser Val Glu Gly Lys Thr
                405                 410                 415

Cys Ile Asn Arg Cys Phe Tyr Val Glu Leu Ile Arg Gly Arg Pro Gln
                420                 425                 430

Glu Thr Arg Val Trp Trp Thr Ser Asn Ser Ile Ile Val Phe Cys Gly
        435                 440                 445

Thr Ser Gly Thr Tyr Gly Thr Gly Ser Trp Pro Asp Gly Ala Asn Ile
        450                 455                 460

Asn Phe Met Ser Ile
465
```

```
<210> SEQ ID NO 34
<211> LENGTH: 469
<212> TYPE: PRT
<213> ORGANISM: Artificial Sequence
<220> FEATURE:
<223> OTHER INFORMATION: N3_sw

<400> SEQUENCE: 34
```

```
Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Ile Phe Asn
            20                  25                  30

Thr Val Ile His Glu Lys Ile Gly Asp His Gln Ile Val Thr Tyr Pro
            35                  40                  45

Thr Ile Thr Thr Pro Ala Val Pro Asn Cys Ser Asp Thr Ile Ile Thr
    50                  55                  60

Tyr Asn Asn Thr Val Ile Asn Asn Ile Thr Thr Thr Ile Ile Thr Glu
65                  70                  75                  80

Glu Glu Arg Pro Phe Lys Ser Pro Leu Pro Leu Cys Pro Phe Arg Gly
            85                  90                  95

Phe Phe Pro Phe His Lys Asp Asn Ala Ile Arg Leu Gly Glu Asn Lys
            100                 105                 110

Asp Val Ile Val Thr Arg Glu Pro Tyr Val Ser Cys Asp Asn Asp Asn
            115                 120                 125

Cys Trp Ser Phe Ala Leu Thr Gln Gly Ala Leu Leu Gly Thr Lys His
    130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
            165                 170                 175

Ile Ala Trp Ser Ser Ser Ser Cys Phe Asp Gly Lys Glu Trp Met His
            180                 185                 190

Val Cys Met Thr Gly Asn Asp Asn Ala Ser Ala Gln Ile Ile Tyr
            195                 200                 205

Gly Gly Arg Met Thr Asp Ser Ile Lys Ser Trp Arg Lys Asp Ile Leu
    210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp Tyr Arg Val Tyr
            245                 250                 255

Trp Ile Arg Glu Gly Lys Ile Ile Lys Tyr Glu Asn Val Pro Lys Thr
            260                 265                 270

Lys Ile Gln His Leu Glu Glu Cys Ser Cys Tyr Val Asp Ile Asp Val
            275                 280                 285

Tyr Cys Ile Cys Arg Asp Asn Trp Lys Gly Ser Asn Arg Pro Trp Met
    290                 295                 300

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Thr Met Ser Cys
            325                 330                 335

Asp Ser Pro Ser Asn Val Asn Gly Gly Pro Gly Val Lys Gly Phe Gly
            340                 345                 350

Phe Lys Ala Gly Asp Asp Val Trp Leu Gly Arg Thr Val Ser Thr Ser
            355                 360                 365

Gly Arg Ser Gly Phe Glu Ile Ile Lys Val Thr Glu Gly Trp Ile Asn
    370                 375                 380

Ser Pro Asn His Val Lys Ser Ile Thr Gln Thr Leu Val Ser Asn Asn
385                 390                 395                 400

Asp Trp Ser Gly Tyr Ser Gly Ser Phe Ile Val Lys Ala Lys Asp Cys
            405                 410                 415
```

```
Phe Gln Pro Cys Phe Tyr Val Glu Leu Ile Arg Gly Arg Pro Asn Lys
            420                 425                 430

Asn Asp Asp Val Ser Trp Thr Ser Asn Ser Ile Val Thr Phe Cys Gly
            435                 440                 445

Leu Asp Asn Glu Pro Gly Ser Gly Asn Trp Pro Asp Gly Ser Asn Ile
    450                 455                 460

Gly Phe Met Pro Lys
465

<210> SEQ ID NO 35
<211> LENGTH: 469
<212> TYPE: PRT
<213> ORGANISM: Artificial Sequence
<220> FEATURE:
<223> OTHER INFORMATION: N3_bwt

<400> SEQUENCE: 35

Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Val Phe Asn
            20                  25                  30

Thr Val Ile His Glu Lys Ile Gly Asp His Gln Thr Val Thr His Pro
            35                  40                  45

Thr Ile Thr Thr Pro Ala Ile Pro Asn Cys Ser Asp Thr Ile Ile Thr
    50                  55                  60

Tyr Asn Asn Thr Val Ile Asn Asn Ile Thr Thr Thr Ile Ile Thr Glu
65                  70                  75                  80

Ala Glu Arg Pro Phe Lys Ser Pro Leu Pro Leu Cys Pro Phe Arg Gly
                85                  90                  95

Phe Phe Pro Phe His Lys Asp Asn Ala Ile Arg Leu Gly Glu Asn Lys
            100                 105                 110

Gly Val Ile Val Thr Arg Glu Pro Tyr Ile Ser Cys Asp Asn Asp Asn
            115                 120                 125

Cys Trp Ser Phe Ala Leu Ala Gln Gly Ala Leu Leu Gly Thr Lys His
    130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
                165                 170                 175

Ile Ala Trp Ser Ser Ser Ser Cys Phe Asp Gly Lys Glu Trp Met His
            180                 185                 190

Val Cys Met Thr Gly Asn Asp Asn Asp Ala Ser Ala Gln Ile Ile Tyr
    195                 200                 205

Ala Gly Arg Met Thr Asp Ser Ile Lys Ser Trp Arg Lys Asp Ile Leu
    210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp His Arg Val Tyr
                245                 250                 255

Trp Ile Arg Glu Gly Lys Ile Ile Lys Tyr Glu Asp Val Pro Lys Thr
            260                 265                 270

Lys Ile Gln His Leu Glu Glu Cys Ser Cys Tyr Val Asp Ile Asp Val
    275                 280                 285

Tyr Cys Ile Cys Arg Asp Asn Trp Lys Gly Ser Asn Arg Pro Trp Met
    290                 295                 300
```

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Thr Met Ser Cys
                325                 330                 335

Asp Ser Pro Ser Asn Val Asn Gly Gly Pro Gly Val Lys Gly Phe Gly
            340                 345                 350

Phe Lys Ala Gly Asn Asp Val Trp Leu Gly Arg Thr Val Ser Thr Ser
        355                 360                 365

Gly Arg Ser Gly Phe Glu Ile Ile Lys Val Thr Glu Gly Trp Ile Asn
    370                 375                 380

Ser Pro Asn His Ala Lys Ser Ile Thr Gln Thr Leu Val Ser Asn Asn
385                 390                 395                 400

Asp Trp Ser Gly Tyr Ser Gly Ser Phe Ile Val Lys Thr Lys Asp Cys
                405                 410                 415

Phe Gln Pro Cys Phe Tyr Val Glu Leu Ile Arg Gly Arg Pro Asn Lys
                420                 425                 430

Asn Asp Asp Val Ser Trp Thr Ser Asn Ser Ile Val Thr Phe Cys Gly
            435                 440                 445

Leu Asp Asn Glu Pro Gly Ser Gly Asn Trp Pro Asp Gly Ser Asn Ile
    450                 455                 460

Gly Phe Met Pro Lys
465

<210> SEQ ID NO 36
<211> LENGTH: 469
<212> TYPE: PRT
<213> ORGANISM: Artificial Sequence
<220> FEATURE:
<223> OTHER INFORMATION: N3_duck

<400> SEQUENCE: 36

Met Asn Pro Asn Gln Lys Ile Ile Thr Ile Gly Val Val Asn Thr Thr
1               5                   10                  15

Leu Ser Thr Ile Ala Leu Leu Ile Gly Ile Gly Asn Leu Ile Phe Asn
                20                  25                  30

Thr Val Ile His Glu Lys Ile Gly Val His Gln Thr Val Val Tyr Pro
            35                  40                  45

Thr Ile Thr Pro Pro Val Ile Pro Asn Cys Ser Asp Thr Thr Ile Thr
    50                  55                  60

Tyr Asn Asn Thr Val Val Asn Asn Ile Thr Ala Thr Ile Ile Asn Lys
65                  70                  75                  80

Ala Glu Lys Gln Phe Lys Pro Ser Leu Pro Leu Cys Pro Phe Arg Gly
                85                  90                  95

Phe Phe Pro Phe His Lys Asp Asn Ala Ile Arg Leu Gly Glu Asn Lys
                100                 105                 110

Asp Val Ile Val Thr Arg Glu Pro Tyr Val Ser Cys Asp Asn Asp Asp
            115                 120                 125

Cys Trp Ser Phe Ala Leu Ala Gln Gly Ala Leu Leu Gly Thr Lys His
    130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
                165                 170                 175

Val Ala Trp Ser Ser Ser Ser Cys Phe Asp Gly Lys Glu Trp Met His
            180                 185                 190

-continued

```
Val Cys Met Thr Gly Asn Asp Asn Asp Ala Ser Gly Gln Ile Ile Tyr
        195                 200                 205

Ala Gly Lys Met Thr Asp Ser Ile Lys Ser Trp Arg Arg Asp Ile Leu
        210                 215                 220

Arg Thr Gln Glu Ser Glu Cys Gln Cys Ile Asp Gly Thr Cys Ile Val
225                 230                 235                 240

Ala Val Thr Asp Gly Pro Ala Ala Ser Ser Ala Asp His Arg Ile Tyr
                245                 250                 255

Trp Ile Arg Lys Gly Lys Ile Ile Lys Tyr Glu Asp Ile Pro Lys Thr
                260                 265                 270

Lys Ile Gln His Leu Glu Glu Cys Ser Cys Tyr Val Asp Thr Asp Val
        275                 280                 285

Tyr Cys Ile Cys Arg Asp Asn Trp Lys Gly Ser Asn Arg Pro Trp Met
        290                 295                 300

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Thr Val Ser Cys
                325                 330                 335

Asp Ser Pro Ser Asn Ile Asn Gly Gly Pro Gly Val Lys Gly Phe Gly
                340                 345                 350

Phe Arg Ala Gly Asn Asp Val Trp Leu Gly Arg Thr Val Ser Thr Thr
                355                 360                 365

Gly Arg Ser Gly Phe Glu Val Ile Lys Val Thr Glu Gly Trp Ile Asn
        370                 375                 380

Ser Leu Asn His Ala Lys Ser Ile Thr Gln Thr Leu Val Ser Asn Asn
385                 390                 395                 400

Asp Trp Ser Gly Tyr Ser Gly Ser Phe Ile Val Glu Asn Asn Gly Cys
                405                 410                 415

Phe Gln Pro Cys Phe Tyr Ile Glu Leu Ile Arg Gly Arg Pro Asn Arg
                420                 425                 430

Asn Asp Asp Val Ser Trp Thr Ser Asn Ser Ile Val Thr Phe Cys Gly
                435                 440                 445

Leu Asp Asn Glu Pro Gly Ser Gly Asn Trp Pro Asp Gly Ser Asn Ile
        450                 455                 460

Gly Phe Met Pro Lys
465

<210> SEQ ID NO 37
<211> LENGTH: 470
<212> TYPE: PRT
<213> ORGANISM: Artificial Sequence
<220> FEATURE:
<223> OTHER INFORMATION: N4_duck

<400> SEQUENCE: 37

Met Asn Pro Asn Gln Lys Ile Ile Thr Ile Gly Ser Val Ser Ile Val
1               5                   10                  15

Leu Thr Thr Ile Gly Leu Leu Leu Gln Ile Thr Ser Leu Cys Ser Ile
                20                  25                  30

Trp Phe Ser His Tyr Asn Gln Val Thr Gln Thr Ser Glu Gln Ser Cys
        35                  40                  45

Ser Asn Asn Thr Thr Asn Tyr Tyr Asn Glu Thr Phe Val Asn Val Thr
        50                  55                  60

Asn Val Gln Asn Asn Tyr Thr Thr Ile Thr Glu Pro Ser Ser Pro Gln
65                  70                  75                  80
```

-continued

```
Val Ile His Tyr Ser Ser Gly Arg Asp Leu Cys Pro Val Lys Gly Trp
            85              90              95

Ala Pro Leu Ser Lys Asp Asn Gly Ile Arg Ile Gly Ser Arg Gly Glu
            100             105             110

Val Phe Val Ile Arg Glu Pro Phe Ile Ser Cys Ser Ile Asn Glu Cys
            115             120             125

Arg Thr Phe Phe Leu Thr Gln Gly Ala Leu Leu Asn Asp Lys His Ser
    130             135             140

Asn Gly Thr Val Lys Asp Arg Ser Pro Phe Arg Thr Leu Met Ser Cys
145             150             155             160

Pro Ile Gly Val Ala Pro Ser Pro Ser Asn Ser Arg Phe Glu Ser Val
            165             170             175

Ala Trp Ser Ala Thr Ala Cys Ser Asp Gly Pro Gly Trp Leu Thr Leu
            180             185             190

Gly Ile Thr Gly Pro Asp Ser Thr Ala Val Ala Val Ile Lys Tyr Asn
            195             200             205

Gly Ile Ile Thr Asp Thr Leu Lys Ser Trp Lys Gly Asn Ile Met Arg
    210             215             220

Thr Gln Glu Ser Glu Cys Val Cys Gln Asp Glu Phe Cys Tyr Thr Leu
225             230             235             240

Ile Thr Asp Gly Pro Ser Asp Ala Gln Ala Phe Tyr Lys Ile Leu Lys
            245             250             255

Ile Arg Lys Gly Lys Ile Met Ser Val Lys Asp Val Asp Ala Thr Gly
            260             265             270

Phe His Phe Glu Glu Cys Ser Cys Tyr Pro Ser Gly Glu Asn Val Glu
            275             280             285

Cys Val Cys Arg Asp Asn Trp Arg Gly Ser Asn Arg Pro Trp Ile Arg
    290             295             300

Phe Asn Ser Asp Leu Asp Tyr Gln Ile Gly Tyr Val Cys Ser Gly Val
305             310             315             320

Phe Gly Asp Asn Pro Arg Pro Val Asp Gly Thr Gly Ser Cys Ser Gly
            325             330             335

Pro Ile Asn Asn Gly Lys Gly Arg Tyr Gly Val Lys Gly Phe Ser Phe
            340             345             350

Arg Tyr Gly Asp Gly Val Trp Ile Gly Arg Thr Lys Ser Leu Glu Ser
            355             360             365

Arg Ser Gly Phe Glu Met Val Trp Asp Ala Asn Gly Trp Val Ser Thr
    370             375             380

Asp Lys Asp Ser Asn Gly Val Gln Asp Ile Ile Asp Asn Asp Asn Trp
385             390             395             400

Ser Gly Tyr Ser Gly Ser Phe Ser Ile Arg Gly Glu Thr Thr Gly Lys
            405             410             415

Asn Cys Thr Val Pro Cys Phe Trp Val Glu Met Ile Arg Gly Gln Pro
            420             425             430

Lys Glu Lys Thr Ile Trp Thr Ser Gly Ser Ser Ile Ala Phe Cys Gly
            435             440             445

Val Asp Ser Asp Thr Thr Gly Trp Ser Trp Pro Asp Gly Ala Leu Leu
    450             455             460

Pro Phe Asp Ile Asp Lys
465             470
```

<210> SEQ ID NO 38
<211> LENGTH: 470
<212> TYPE: PRT

<213> ORGANISM: Artificial Sequence
<220> FEATURE:
<223> OTHER INFORMATION: N4_rt

<400> SEQUENCE: 38

Met Asn Pro Asn Gln Lys Ile Ile Thr Ile Gly Ser Val Ser Ile Ile
1                 5                  10                 15

Leu Thr Thr Ile Gly Leu Leu Leu Gln Ile Thr Ser Leu Cys Ser Ile
                20                  25                 30

Trp Phe Ser His Tyr Asn Gln Val Thr Gln Thr His Glu Gln Pro Cys
            35                  40                 45

Ser Asn Asn Thr Thr Asn Tyr Tyr Asn Glu Thr Phe Val Asn Val Thr
    50                  55                 60

Asn Val Gln Asn Asn Tyr Thr Thr Val Thr Glu Pro Ser Thr Pro Asp
65                  70                 75                 80

Val Val His Tyr Ser Ser Gly Arg Asp Leu Cys Pro Ile Arg Gly Trp
                85                  90                 95

Ala Pro Leu Ser Lys Asp Asn Gly Ile Arg Ile Gly Ser Arg Gly Glu
            100                 105                110

Val Phe Val Ile Arg Glu Pro Phe Ile Ser Cys Ser Ile Ser Glu Cys
            115                 120                125

Arg Thr Phe Phe Leu Thr Gln Gly Ala Leu Leu Asn Asp Lys His Ser
    130                 135                140

Asn Gly Thr Val Lys Asp Arg Ser Pro Phe Arg Thr Leu Met Ser Cys
145                 150                155                160

Pro Ile Gly Val Ala Pro Ser Pro Ser Asn Ser Arg Phe Glu Ser Val
                165                 170                175

Ala Trp Ser Ala Thr Ala Cys Ser Asp Gly Pro Gly Trp Leu Thr Leu
            180                 185                190

Gly Ile Thr Gly Pro Asp Thr Thr Ala Val Ala Val Leu Lys Tyr Asn
        195                 200                205

Gly Ile Ile Thr Asp Thr Phe Lys Ser Trp Lys Gly Asn Ile Met Arg
    210                 215                220

Thr Gln Glu Ser Glu Cys Val Cys Gln Asp Glu Phe Cys Tyr Thr Leu
225                 230                235                240

Ile Thr Asp Gly Pro Ser Asp Ala Gln Ala Phe Tyr Lys Ile Leu Lys
                245                 250                255

Ile Arg Lys Gly Lys Ile Val Ser Met Lys Asp Val Asp Ala Thr Gly
            260                 265                270

Phe His Phe Glu Glu Cys Ser Cys Tyr Pro Ser Arg Thr Asp Ile Glu
            275                 280                285

Cys Val Cys Arg Asp Asn Trp Arg Gly Ser Asn Arg Pro Trp Ile Arg
    290                 295                300

Phe Asn Ser Asp Leu Asp Tyr Gln Ile Gly Tyr Val Cys Ser Gly Ile
305                 310                315                320

Phe Gly Asp Asn Pro Arg Pro Val Asp Gly Thr Gly Ser Cys Asn Ser
            325                 330                335

Pro Val Asn Asn Gly Lys Gly Arg Tyr Gly Val Lys Gly Phe Ser Phe
            340                 345                350

Arg Tyr Gly Asp Gly Val Trp Ile Gly Arg Thr Lys Ser Leu Glu Phe
        355                 360                365

Arg Ser Gly Phe Glu Met Val Trp Asp Ala Asn Gly Trp Val Ser Thr
    370                 375                380

Asp Lys Asp Ser Asn Gly Val Gln Asp Ile Ile Asp Asn Asp Asn Trp

-continued

```
385                390                395                400

Ser Gly Tyr Ser Gly Ser Phe Ser Ile Arg Gly Glu Lys Thr Gly Arg
              405                410                415

Asn Cys Thr Val Pro Cys Phe Trp Val Glu Met Ile Arg Gly Gln Pro
              420                425                430

Lys Glu Lys Thr Ile Trp Thr Ser Gly Ser Ser Ile Ala Phe Cys Gly
          435                440                445

Val Asn Ser Asp Thr Thr Gly Trp Ser Trp Pro Asp Gly Ala Leu Leu
      450                455                460

Pro Phe Asp Ile Asp Lys
465                470

<210> SEQ ID NO 39
<211> LENGTH: 473
<212> TYPE: PRT
<213> ORGANISM: Artificial Sequence
<220> FEATURE:
<223> OTHER INFORMATION: N5_aw

<400> SEQUENCE: 39

Met Asn Pro Asn Gln Lys Ile Ile Thr Ile Gly Ser Val Ser Leu Ala
1                5                10                15

Leu Val Val Phe Asn Ile Leu Leu His Ile Ala Ser Ile Val Ile Gly
              20                25                30

Ile Ile Ser Val Thr Lys Glu Ile Ser Val Ser Ser Thr Cys Asn Thr
          35                40                45

Thr Glu Val Tyr Asn Glu Thr Val Arg Leu Glu Thr Ile Thr Ile Pro
      50                55                60

Ile Asn Asn Thr Val Tyr Ile Glu Arg Glu Ser His Gln Glu Pro Glu
65                70                75                80

Phe Leu Asn Asn Thr Glu Pro Leu Cys Asn Val Ser Gly Phe Ala Ile
              85                90                95

Val Ser Lys Asp Asn Gly Ile Arg Ile Gly Ser Arg Gly His Val Phe
          100                105                110

Val Ile Arg Glu Pro Phe Val Ala Cys Gly Pro Thr Glu Cys Arg Thr
          115                120                125

Phe Phe Leu Thr Gln Gly Ala Leu Leu Asn Asp Lys His Ser Asn Asn
      130                135                140

Thr Val Lys Asp Arg Ser Pro Tyr Arg Ala Leu Met Ser Val Pro Leu
145                150                155                160

Gly Ser Ser Pro Asn Ala Tyr Gln Ala Lys Phe Glu Ser Val Ala Trp
              165                170                175

Ser Ala Thr Ala Cys His Asp Gly Lys Gly Trp Leu Ala Val Gly Ile
          180                185                190

Ser Gly Ala Asp Asp Asp Ala Tyr Ala Val Ile His Tyr Gly Gly Met
          195                200                205

Pro Thr Asp Val Val Arg Ser Trp Arg Lys Gln Ile Leu Arg Thr Gln
      210                215                220

Glu Ser Ser Cys Val Cys Met Thr Gly Asn Cys Tyr Trp Val Met Thr
225                230                235                240

Asp Gly Pro Ala Asn Ser Gln Ala Ser Tyr Lys Ile Phe Lys Ser His
              245                250                255

Arg Gly Met Val Thr Asn Glu Arg Glu Val Ser Phe Gln Gly Gly His
          260                265                270

Ile Glu Glu Cys Ser Cys Tyr Pro Asn Leu Gly Lys Val Glu Cys Val
```

-continued

```
                275              280              285

Cys Arg Asp Asn Trp Asn Gly Met Asn Arg Pro Val Leu Thr Phe Asp
    290              295              300

Glu Asp Leu Asn Tyr Glu Val Gly Tyr Leu Cys Ala Gly Ile Pro Thr
305              310              315              320

Asp Thr Pro Arg Val Gln Asp Asn Ser Phe Thr Gly Ser Cys Thr Asn
                325              330              335

Ala Val Gly Gly Ser Gly Thr Asn Asn Tyr Gly Val Lys Gly Phe Gly
                340              345              350

Phe Arg Gln Gly Asn Ser Val Trp Ala Gly Arg Thr Val Ser Ile Ser
                355              360              365

Ser Arg Ser Gly Phe Glu Ile Leu Leu Ile Glu Asp Gly Trp Ile Lys
    370              375              380

Thr Ser Lys Asn Val Val Lys Lys Val Glu Val Leu Asn Asn Lys Asn
385              390              395              400

Trp Ser Gly Tyr Ser Gly Ala Phe Thr Ile Pro Ile Thr Met Thr Ser
                405              410              415

Lys Gln Cys Leu Val Pro Cys Phe Trp Leu Glu Met Ile Arg Gly Lys
                420              425              430

Pro Glu Glu Arg Thr Ser Ile Trp Thr Ser Ser Ser Ser Thr Val Phe
                435              440              445

Cys Gly Val Ser Ser Glu Val Pro Gly Trp Ser Trp Asp Asp Gly Ala
    450              455              460

Ile Leu Pro Phe Asp Ile Asp Lys Met
465              470
```

```
<210> SEQ ID NO 40
<211> LENGTH: 472
<212> TYPE: PRT
<213> ORGANISM: Artificial Sequence
<220> FEATURE:
<223> OTHER INFORMATION: N5_md

<400> SEQUENCE: 40

Met Asn Pro Asn Gln Lys Ile Ile Thr Ile Gly Ser Ile Ser Leu Gly
1               5               10              15

Leu Val Val Phe Asn Ile Leu Leu His Val Ala Ser Ile Val Leu Gly
                20              25              30

Ile Ile Ser Val Thr Lys Asp His Gly Ala Tyr Thr Cys Asn Thr Thr
                35              40              45

Glu Val Tyr Asn Glu Thr Val Arg Val Glu Thr Val Thr Ile Pro Val
    50              55              60

Asn Asn Thr Ile Tyr Ile Glu Arg Glu Leu Thr His Glu Pro Glu Phe
65              70              75              80

Leu Asn Asn Thr Glu Pro Leu Cys Glu Val Ser Gly Phe Ala Ile Val
                85              90              95

Ser Lys Asp Asn Gly Ile Arg Ile Gly Ser Arg Gly His Val Phe Val
                100             105             110

Ile Arg Glu Pro Phe Val Ala Cys Gly Pro Ser Glu Cys Arg Thr Phe
                115             120             125

Phe Leu Thr Gln Gly Ala Leu Leu Asn Asp Lys His Ser Asn Asn Thr
    130             135             140

Val Lys Asp Arg Ser Pro Tyr Arg Ala Leu Met Ser Val Pro Leu Gly
145             150             155             160

Ser Ser Pro Asn Ala Tyr Gln Ala Lys Phe Glu Ser Val Gly Trp Ser
```

-continued

```
                165                 170                 175
Ala Thr Ala Cys His Asp Gly Lys Glu Trp Met Ala Ile Gly Val Ser
            180                 185                 190

Gly Ala Asp Asp Asp Ala Tyr Ala Val Ile His Tyr Gly Gly Ile Pro
            195                 200                 205

Thr Asp Val Val Arg Ser Trp Arg Lys Gln Ile Leu Arg Thr Gln Glu
        210                 215                 220

Ser Ser Cys Val Cys Met Lys Gly Glu Cys Tyr Trp Val Met Thr Asp
    225                 230                 235                 240

Gly Pro Ala Asn Asn Gln Ala Ser Tyr Lys Ile Phe Lys Ser Gln Lys
                245                 250                 255

Gly Leu Val Val Asp Glu Lys Glu Ile Ser Phe Gln Gly Gly His Ile
                260                 265                 270

Glu Glu Cys Ser Cys Tyr Pro Asn Met Gly Lys Val Glu Cys Val Cys
                275                 280                 285

Arg Asp Asn Trp Asn Gly Met Asn Arg Pro Ile Leu Thr Phe Asp Glu
        290                 295                 300

Asn Leu Glu Tyr Glu Val Gly Tyr Leu Cys Ala Gly Ile Pro Thr Asp
    305                 310                 315                 320

Thr Pro Arg Val Gln Asp Ser Ser Phe Thr Gly Ser Cys Thr Asn Ala
                325                 330                 335

Val Gly Gly Ser Gly Thr Asn Asn Tyr Gly Val Lys Gly Phe Gly Phe
                340                 345                 350

Arg Gln Gly Thr Ser Val Trp Ala Gly Arg Thr Ile Ser Ile Ser Ser
                355                 360                 365

Arg Ser Gly Phe Glu Val Leu Leu Ile Lys Asp Gly Trp Ile Arg Pro
        370                 375                 380

Ser Lys Thr Ile Ser Lys Lys Val Glu Val Leu Asp Asn Lys Asn Trp
    385                 390                 395                 400

Ser Gly Tyr Ser Gly Ser Phe Thr Ile Pro Thr Ala Met Thr Ser Lys
                405                 410                 415

Ser Cys Leu Val Pro Cys Phe Trp Leu Glu Met Ile Arg Gly Lys Pro
                420                 425                 430

Glu Glu Arg Thr Ser Ile Trp Thr Ser Ser Ser Ser Thr Val Phe Cys
            435                 440                 445

Gly Val Ser Ser Glu Val Pro Gly Trp Ser Trp Asp Asp Gly Ala Ile
    450                 455                 460

Leu Pro Phe Asp Ile Asp Lys Met
465                 470

<210> SEQ ID NO 41
<211> LENGTH: 459
<212> TYPE: PRT
<213> ORGANISM: Artificial Sequence
<220> FEATURE:
<223> OTHER INFORMATION: N6_Sz

<400> SEQUENCE: 41

Met Asn Pro Asn Gln Lys Ile Thr Cys Ile Ser Ala Thr Gly Val Thr
1               5                   10                  15

Leu Ser Val Val Ser Leu Leu Ile Gly Ile Ala Asn Leu Gly Leu Asn
            20                  25                  30

Ile Gly Leu His Tyr Lys Val Ser Asp Ser Thr Thr Ile Asn Ile Pro
        35                  40                  45

Asn Met Asn Glu Thr Asn Ser Thr Thr Thr Asn Ile Thr Asn Ile Ile
```

-continued

```
        50               55              60

Val Asn Lys Asn Glu Glu Arg Thr Phe Leu Asn Leu Thr Lys Pro Leu
65                  70                  75                  80

Cys Glu Val Asn Ser Trp His Ile Leu Ser Lys Asp Asn Ala Ile Arg
                85                  90                  95

Ile Gly Glu Asp Ala His Ile Leu Val Thr Arg Glu Pro Tyr Leu Ser
                100                 105                 110

Cys Asp Pro Gln Gly Cys Arg Met Phe Ala Leu Ser Gln Gly Thr Thr
                115                 120                 125

Leu Arg Gly Arg His Ala Asn Gly Thr Ile His Asp Arg Gly Pro Phe
        130                 135                 140

Arg Ala Leu Ile Ser Trp Glu Met Gly Gln Ala Pro Ser Pro Tyr Asn
145                 150                 155                 160

Thr Arg Val Glu Cys Ile Gly Trp Ser Ser Thr Ser Cys His Asp Gly
                165                 170                 175

Ile Ser Arg Met Ser Ile Cys Ile Ser Gly Pro Asn Asp Asn Ala Ser
                180                 185                 190

Ala Val Val Trp Tyr Arg Gly Arg Pro Val Thr Glu Ile Pro Ser Trp
                195                 200                 205

Val Gly Asn Ile Leu Arg Thr Gln Glu Ser Glu Cys Val Cys His Lys
        210                 215                 220

Gly Ile Cys Pro Val Val Met Thr Asp Gly Pro Ala Asn Asn Lys Ala
225                 230                 235                 240

Ala Thr Lys Ile Ile Tyr Phe Lys Glu Gly Lys Ile Gln Lys Ile Glu
                245                 250                 255

Glu Leu Gln Gly Asn Ala Gln His Ile Glu Glu Cys Ser Cys Tyr Gly
                260                 265                 270

Ala Ala Gly Met Ile Lys Cys Val Cys Arg Asp Asn Trp Lys Gly Ala
                275                 280                 285

Asn Arg Pro Ile Ile Thr Ile Asp Pro Glu Met Met Thr His Thr Ser
        290                 295                 300

Lys Tyr Leu Cys Ser Lys Ile Leu Thr Asp Thr Ser Arg Pro Asn Asp
305                 310                 315                 320

Pro Thr Asn Gly Asn Cys Asp Ala Pro Ile Thr Gly Gly Ser Pro Asp
                325                 330                 335

Pro Gly Val Lys Gly Phe Ala Phe Leu Asp Gly Glu Asn Ser Trp Leu
                340                 345                 350

Gly Arg Thr Ile Ser Lys Asp Ser Arg Ser Gly Tyr Glu Met Leu Lys
                355                 360                 365

Val Pro Asn Ala Glu Thr Asp Thr Gln Ser Gly Pro Thr Ser Tyr Gln
        370                 375                 380

Leu Ile Val Asn Asn Gln Asn Trp Ser Gly Tyr Ser Gly Ala Phe Ile
385                 390                 395                 400

Asp Tyr Trp Ala Asn Lys Gly Cys Phe Asn Pro Cys Phe Tyr Val Glu
                405                 410                 415

Leu Ile Arg Gly Arg Pro Lys Glu Ile Asp Val Leu Trp Thr Ser Ser
                420                 425                 430

Ser Met Val Ala Leu Cys Gly Ser Arg Glu Arg Leu Gly Ser Trp Ser
                435                 440                 445

Trp His Asp Gly Ala Glu Ile Ile Tyr Phe Lys
        450                 455
```

<210> SEQ ID NO 42

-continued

```
<211> LENGTH: 470
<212> TYPE: PRT
<213> ORGANISM: Artificial Sequence
<220> FEATURE:
<223> OTHER INFORMATION: N6_cs

<400> SEQUENCE: 42

Met Asn Pro Asn Gln Lys Ile Ile Cys Ile Ser Ala Thr Gly Met Thr
1               5                   10                  15

Leu Ser Val Val Ser Leu Leu Ile Gly Ile Ala Asn Leu Gly Leu Asn
            20                  25                  30

Ile Gly Leu His Tyr Lys Val Gly Asp Thr Pro Asp Val Asn Ile Pro
        35                  40                  45

Ser Met Asn Glu Thr Asn Ser Thr Thr Thr Ile Ile Asn Asn Asn Thr
    50                  55                  60

Gln Asn Asn Phe Thr Asn Ile Thr Asn Ile Ile Val Asn Lys Glu Glu
65                  70                  75                  80

Gly Arg Thr Phe Leu Asn Leu Thr Lys Pro Leu Cys Glu Val Asn Ser
            85                  90                  95

Trp His Ile Leu Ser Lys Asp Asn Ala Ile Arg Ile Gly Glu Asp Ala
            100                 105                 110

His Ile Leu Val Thr Arg Glu Pro Tyr Leu Ser Cys Asp Pro Gln Gly
        115                 120                 125

Cys Arg Met Phe Ala Leu Ser Gln Gly Thr Thr Leu Arg Gly Arg His
    130                 135                 140

Ala Asn Gly Thr Ile His Asp Arg Ser Pro Phe Arg Ala Leu Val Ser
145                 150                 155                 160

Trp Glu Met Gly Gln Ala Pro Ser Pro Tyr Asn Val Arg Val Glu Cys
            165                 170                 175

Ile Gly Trp Ser Ser Thr Ser Cys His Asp Gly Ile Ser Arg Met Ser
            180                 185                 190

Ile Cys Met Ser Gly Pro Asn Asn Asn Ala Ser Ala Val Val Trp Tyr
            195                 200                 205

Gly Gly Arg Pro Val Thr Glu Ile Pro Ser Trp Ala Gly Asn Ile Leu
        210                 215                 220

Arg Thr Gln Glu Ser Glu Cys Val Cys His Lys Gly Ile Cys Pro Val
225                 230                 235                 240

Val Met Thr Asp Gly Pro Ala Asn Asn Arg Ala Ala Thr Lys Ile Ile
            245                 250                 255

Tyr Phe Lys Glu Gly Lys Ile Gln Lys Ile Glu Glu Leu Glu Gly Asn
            260                 265                 270

Ala Gln His Ile Glu Glu Cys Ser Cys Tyr Gly Ala Ala Gly Val Ile
        275                 280                 285

Lys Cys Ile Cys Arg Asp Asn Trp Lys Gly Ala Asn Arg Pro Val Ile
    290                 295                 300

Ile Ile Asp Pro Glu Met Met Thr His Thr Ser Lys Tyr Leu Cys Ser
305                 310                 315                 320

Arg Val Leu Thr Asp Thr Ser Arg Pro Asn Asp Pro Thr Ser Gly Asn
            325                 330                 335

Cys Asp Ala Pro Ile Thr Gly Gly Ser Pro Asp Pro Gly Val Lys Gly
            340                 345                 350

Phe Ala Phe Leu Asp Gly Glu Asn Ser Trp Leu Gly Arg Thr Ile Ser
            355                 360                 365

Lys Asp Ser Arg Ser Gly Tyr Glu Met Leu Lys Val Pro Asn Ala Glu
    370                 375                 380
```

-continued

Thr Asp Thr Gln Ser Gly Pro Thr Ser His Gln Val Ile Val Asn Asn
385                 390                 395                 400

Gln Asn Trp Ser Gly Tyr Ser Gly Ala Phe Ile Asp Tyr Trp Ala Asn
                    405                 410                 415

Lys Glu Cys Phe Asn Pro Cys Phe Tyr Val Glu Leu Ile Arg Gly Arg
            420                 425                 430

Pro Lys Glu Ser Ser Val Leu Trp Thr Ser Asn Ser Ile Val Ala Leu
        435                 440                 445

Cys Gly Ser Lys Glu Arg Leu Gly Ser Trp Ser Trp His Asp Gly Ala
        450                 455                 460

Glu Ile Ile Tyr Phe Lys
465                 470

<210> SEQ ID NO 43
<211> LENGTH: 471
<212> TYPE: PRT
<213> ORGANISM: Artificial Sequence
<220> FEATURE:
<223> OTHER INFORMATION: N7_cN

<400> SEQUENCE: 43

Met Asn Pro Asn Gln Lys Leu Phe Ala Leu Ser Gly Val Ala Ile Ala
1               5                   10                  15

Leu Ser Val Leu Asn Leu Leu Ile Gly Ile Ser Asn Val Gly Leu Asn
            20                  25                  30

Val Ser Leu His Leu Lys Glu Lys Gly Pro Lys Gln Glu Glu Asn Leu
        35                  40                  45

Thr Cys Thr Thr Ile Asn Gln Asn Asn Thr Thr Val Val Glu Asn Thr
    50                  55                  60

Tyr Val Asn Asn Thr Thr Ile Ile Thr Lys Gly Thr Asp Leu Lys Thr
65                  70                  75                  80

Pro Ser Tyr Leu Leu Leu Asn Lys Ser Leu Cys Asn Val Glu Gly Trp
                85                  90                  95

Val Val Ile Ala Lys Asp Asn Ala Val Arg Phe Gly Glu Ser Glu Gln
            100                 105                 110

Ile Ile Val Thr Arg Glu Pro Tyr Val Ser Cys Asp Pro Thr Gly Cys
        115                 120                 125

Lys Met Tyr Ala Leu His Gln Gly Thr Thr Ile Arg Asn Lys His Ser
    130                 135                 140

Asn Gly Thr Ile His Asp Arg Thr Ala Phe Arg Gly Leu Ile Ser Thr
145                 150                 155                 160

Pro Leu Gly Thr Pro Pro Thr Val Ser Asn Ser Asp Phe Met Cys Val
                165                 170                 175

Gly Trp Ser Ser Thr Thr Cys His Asp Gly Ile Ala Arg Met Thr Ile
            180                 185                 190

Cys Ile Gln Gly Asn Asn Asp Asn Ala Thr Ala Thr Val Tyr Tyr Asn
        195                 200                 205

Arg Arg Leu Thr Thr Thr Ile Lys Thr Trp Ala Arg Asn Ile Leu Arg
    210                 215                 220

Thr Gln Glu Ser Glu Cys Val Cys His Asn Gly Thr Cys Ala Val Val
225                 230                 235                 240

Met Thr Asp Gly Ser Ala Ser Ser Gln Ala Tyr Thr Lys Val Met Tyr
                245                 250                 255

Phe His Lys Gly Leu Val Val Lys Glu Glu Glu Leu Arg Gly Ser Ala
            260                 265                 270

-continued

```
Arg His Ile Glu Glu Cys Ser Cys Tyr Gly His Asn Gln Lys Val Thr
    275             280             285

Cys Val Cys Arg Asp Asn Trp Gln Gly Ala Asn Arg Pro Ile Ile Glu
    290             295             300

Ile Asp Met Asn Thr Leu Glu His Thr Ser Arg Tyr Val Cys Thr Gly
305             310             315             320

Ile Leu Thr Asp Thr Ser Arg Pro Gly Asp Lys Ser Ser Gly Asp Cys
            325             330             335

Ser Asn Pro Ile Thr Gly Ser Pro Gly Ala Pro Gly Val Lys Gly Phe
            340             345             350

Gly Phe Leu Asn Gly Asp Asn Thr Trp Leu Gly Arg Thr Ile Ser Pro
            355             360             365

Arg Ser Arg Ser Gly Phe Glu Met Leu Lys Ile Pro Asn Ala Gly Thr
    370             375             380

Asp Pro Asn Ser Arg Ile Ala Glu Arg Gln Glu Ile Val Asp Asn Asn
385             390             395             400

Asn Trp Ser Gly Tyr Ser Gly Ser Phe Ile Asp Tyr Trp Asn Asp Asn
            405             410             415

Ser Glu Cys Tyr Asn Pro Cys Phe Tyr Val Glu Leu Ile Arg Gly Arg
            420             425             430

Pro Glu Glu Ala Lys Tyr Val Trp Trp Thr Ser Asn Ser Leu Ile Ala
    435             440             445

Leu Cys Gly Ser Pro Phe Pro Val Gly Pro Gly Ser Phe Pro Asp Gly
    450             455             460

Ala Gln Ile Gln Tyr Phe Ser
465             470
```

```
<210> SEQ ID NO 44
<211> LENGTH: 471
<212> TYPE: PRT
<213> ORGANISM: Artificial Sequence
<220> FEATURE:
<223> OTHER INFORMATION: N7_cG

<400> SEQUENCE: 44
```

```
Met Asn Pro Asn Gln Lys Leu Phe Ala Leu Ser Gly Val Ala Ile Ala
1               5               10              15

Leu Ser Val Leu Asn Leu Leu Ile Gly Ile Ser Asn Val Gly Leu Asn
            20              25              30

Val Ser Leu His Leu Lys Glu Lys Gly Pro Lys Gln Glu Glu Asn Leu
        35              40              45

Thr Cys Thr Thr Ile Asn Gln Asn Asn Thr Thr Val Val Glu Asn Thr
    50              55              60

Tyr Val Asn Asn Thr Thr Ile Ile Thr Lys Gly Thr Asp Leu Lys Thr
65              70              75              80

Pro Ser Tyr Leu Leu Leu Asn Lys Ser Leu Cys Asn Val Glu Gly Trp
            85              90              95

Val Val Ile Ala Lys Asp Asn Ala Val Arg Phe Gly Glu Ser Glu Gln
            100             105             110

Ile Ile Val Thr Arg Glu Pro Tyr Val Ser Cys Asp Pro Thr Gly Cys
        115             120             125

Lys Met Tyr Ala Leu His Gln Gly Thr Thr Ile Arg Asn Lys His Ser
    130             135             140

Asn Gly Thr Ile His Asp Arg Thr Ala Phe Arg Gly Leu Ile Ser Thr
145             150             155             160
```

```
Pro Leu Gly Thr Pro Pro Thr Val Ser Asn Ser Asp Phe Met Cys Val
            165             170             175

Gly Trp Ser Ser Thr Thr Cys His Asp Gly Ile Ala Arg Met Thr Ile
            180             185             190

Cys Ile Gln Gly Asn Asn Asp Asn Ala Thr Ala Thr Val Tyr Tyr Asn
            195             200             205

Arg Arg Leu Thr Thr Thr Ile Lys Thr Trp Ala Arg Asn Ile Leu Arg
    210             215             220

Thr Gln Glu Ser Glu Cys Val Cys His Asn Gly Thr Cys Ala Val Val
225             230             235             240

Met Thr Asp Gly Ser Ala Ser Ser Gln Ala Tyr Thr Lys Val Met Tyr
            245             250             255

Phe His Lys Gly Leu Val Val Lys Glu Glu Glu Leu Arg Gly Ser Ala
            260             265             270

Arg His Ile Glu Glu Cys Ser Cys Tyr Gly His Asn Gln Lys Val Thr
            275             280             285

Cys Val Cys Arg Asp Asn Trp Gln Gly Ala Asn Arg Pro Ile Ile Glu
    290             295             300

Ile Asp Met Asn Thr Leu Glu His Thr Ser Arg Tyr Val Cys Thr Gly
305             310             315             320

Ile Leu Thr Asp Thr Ser Arg Pro Gly Asp Lys Ser Ser Gly Asp Cys
            325             330             335

Ser Asn Pro Ile Thr Gly Ser Pro Gly Ala Pro Gly Val Lys Gly Phe
            340             345             350

Gly Phe Leu Asn Gly Asp Asn Thr Trp Leu Gly Arg Thr Ile Ser Pro
            355             360             365

Arg Ser Arg Ser Gly Phe Glu Met Leu Lys Ile Pro Asn Ala Gly Thr
    370             375             380

Asp Pro Asn Ser Arg Ile Ala Glu Arg Gln Glu Ile Val Asp Asn Asn
385             390             395             400

Asn Trp Ser Gly Tyr Ser Gly Ser Phe Ile Asp Tyr Trp Asn Asp Asn
            405             410             415

Ser Glu Cys Tyr Asn Pro Cys Phe Tyr Val Glu Leu Ile Arg Gly Arg
            420             425             430

Pro Glu Glu Ala Lys Tyr Val Trp Trp Ala Ser Asn Ser Leu Ile Ala
            435             440             445

Leu Cys Gly Ser Pro Phe Pro Val Gly Ser Gly Ser Phe Pro Asp Gly
    450             455             460

Ala Gln Ile Gln Tyr Phe Ser
465             470
```

```
<210> SEQ ID NO 45
<211> LENGTH: 470
<212> TYPE: PRT
<213> ORGANISM: Artificial Sequence
<220> FEATURE:
<223> OTHER INFORMATION: N8_cN

<400> SEQUENCE: 45
```

```
Met Asn Pro Asn Gln Lys Ile Val Thr Ile Gly Ser Ile Ser Leu Gly
1               5               10              15

Leu Val Val Phe Asn Val Leu Leu His Ala Val Ser Ile Ile Leu Thr
            20              25              30

Val Leu Ala Leu Gly Lys Ser Glu Asn Asn Gly Ile Cys Asn Gly Thr
            35              40              45
```

-continued

```
Val Val Arg Glu Tyr Asn Glu Thr Val Arg Ile Glu Lys Val Thr Gln
    50              55              60

Trp Tyr Asn Thr Ser Val Val Glu Tyr Val Pro His Trp Asn Glu Gly
65              70              75              80

Thr Tyr Ile Asn Asn Thr Glu Pro Ile Cys Asp Val Lys Gly Phe Ala
                85              90              95

Pro Phe Ser Lys Asp Asn Gly Ile Arg Val Gly Ser Arg Gly His Ile
            100             105             110

Phe Val Ile Arg Glu Pro Phe Val Ser Cys Ser Pro Val Glu Cys Arg
    115             120             125

Thr Phe Phe Leu Thr Gln Gly Ser Leu Leu Asn Asp Lys His Ser Asn
    130             135             140

Gly Thr Val Lys Asp Arg Ser Pro Phe Arg Thr Leu Met Ser Val Glu
145             150             155             160

Val Gly Gln Ser Pro Asn Val Tyr Gln Ala Arg Phe Glu Ala Val Ala
            165             170             175

Trp Ser Ala Thr Ala Cys His Asp Gly Lys Lys Trp Met Thr Ile Gly
            180             185             190

Val Thr Gly Pro Asp Ser Lys Ala Val Ala Val Val His Tyr Gly Gly
            195             200             205

Val Pro Thr Asp Val Val Asn Ser Trp Ala Gly Asp Ile Leu Arg Thr
    210             215             220

Gln Glu Ser Ser Cys Thr Cys Ile Gln Gly Asn Cys Tyr Trp Val Met
225             230             235             240

Thr Asp Gly Pro Ala Asn Arg Gln Ala Gln Tyr Arg Ile Tyr Lys Ala
            245             250             255

Asn Gln Gly Lys Ile Ile Gly Arg Thr Asp Val Ser Phe Ser Gly Gly
            260             265             270

His Ile Glu Glu Cys Ser Cys Tyr Pro Asn Asp Gly Lys Val Glu Cys
            275             280             285

Val Cys Arg Asp Asn Trp Thr Gly Thr Asn Arg Pro Val Leu Ile Ile
    290             295             300

Ser Pro Asp Leu Ser Tyr Arg Val Gly Tyr Leu Cys Ala Gly Leu Pro
305             310             315             320

Ser Asp Thr Pro Arg Gly Glu Asp Thr Gln Phe Ala Gly Ser Cys Thr
            325             330             335

Ser Pro Met Gly Asn Gln Gly Tyr Gly Val Lys Gly Phe Gly Phe Arg
            340             345             350

Gln Gly Thr Asp Val Trp Val Gly Arg Thr Ile Ser Arg Thr Ser Arg
    355             360             365

Ser Gly Phe Glu Ile Ile Arg Ile Lys Asn Gly Trp Thr Gln Thr Ser
    370             375             380

Lys Glu Gln Ile Arg Arg Gln Val Val Val Asp Asn Ser Asn Trp Ser
385             390             395             400

Gly Tyr Ser Gly Ser Phe Thr Leu Pro Val Glu Leu Ser Gly Arg Glu
            405             410             415

Cys Leu Val Pro Cys Phe Trp Val Glu Met Ile Arg Gly Arg Pro Glu
            420             425             430

Glu Arg Thr Ile Trp Thr Ser Ser Ser Ile Val Met Cys Gly Val
    435             440             445

Asp Tyr Glu Ile Ala Asp Trp Ser Trp His Asp Gly Ala Ile Leu Pro
    450             455             460
```

```
Phe Asp Ile Asp Lys Thr
465                 470

<210> SEQ ID NO 46
<211> LENGTH: 470
<212> TYPE: PRT
<213> ORGANISM: Artificial Sequence
<220> FEATURE:
<223> OTHER INFORMATION: N8_cL

<400> SEQUENCE: 46

Met Asn Pro Asn Gln Lys Ile Ile Thr Ile Gly Ser Val Ser Leu Gly
1               5                   10                  15

Leu Val Val Leu Asn Ile Leu Leu His Ile Val Ser Ile Thr Val Thr
            20                  25                  30

Val Leu Val Leu Pro Arg Asn Gly Asn Asn Gly Ser Cys Asn Glu Thr
        35                  40                  45

Val Ile Arg Glu Tyr Asn Glu Thr Val Arg Val Glu Lys Val Thr Gln
    50                  55                  60

Trp His Asn Thr Asn Val Ile Glu Tyr Ile Glu Arg Pro Glu Asn Asp
65                  70                  75                  80

His Phe Met Asn Asn Thr Glu Ala Leu Cys Asp Ala Lys Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Thr Glu Cys Arg
            115                 120                 125

Thr Phe Phe Leu Thr Gln Gly Ser Leu Leu Asn Asp Lys His Ser Asn
        130                 135                 140

Gly Thr Val Lys Asp Arg Ser Pro Tyr Arg Thr Leu Met Ser Val Glu
145                 150                 155                 160

Ile Gly Gln Ser Pro Asn Val Tyr Gln Ala Arg Phe Glu Ala Val Ala
            165                 170                 175

Trp Ser Ala Thr Ala Cys His Asp Gly Lys Lys Trp Met Thr Ile Gly
            180                 185                 190

Val Thr Gly Pro Asp Ala Lys Ala Val Ala Val Val His Tyr Gly Gly
            195                 200                 205

Ile Pro Thr Asp Val Ile Asn Ser Trp Ala Gly Asp Ile Leu Arg Thr
    210                 215                 220

Gln Glu Ser Ser Cys Thr Cys Ile Gln Gly Glu Cys Phe Trp Val Met
225                 230                 235                 240

Thr Asp Gly Pro Ala Asn Arg Gln Ala Gln Tyr Arg Ala Phe Lys Ala
            245                 250                 255

Lys Gln Gly Lys Ile Val Gly Gln Ala Glu Ile Ser Phe Asn Gly Gly
            260                 265                 270

His Ile Glu Glu Cys Ser Cys Tyr Pro Asn Glu Gly Lys Val Glu Cys
        275                 280                 285

Val Cys Arg Asp Asn Trp Thr Gly Thr Asn Arg Pro Val Leu Val Ile
        290                 295                 300

Ser Pro Asp Leu Ser Tyr Arg Val Gly Tyr Leu Cys Ala Gly Ile Pro
305                 310                 315                 320

Ser Asp Thr Pro Arg Gly Glu Asp Ser Gln Phe Thr Gly Ser Cys Thr
            325                 330                 335

Ser Pro Met Gly Asn Gln Gly Tyr Gly Val Lys Gly Phe Gly Phe Arg
            340                 345                 350
```

-continued

```
Gln Gly Ser Asp Val Trp Met Gly Arg Thr Ile Ser Arg Thr Ser Arg
        355                 360                 365

Ser Gly Phe Glu Ile Leu Lys Val Arg Asn Gly Trp Val Gln Asn Ser
        370                 375                 380

Lys Glu Gln Ile Lys Arg Gln Val Val Val Asp Asn Leu Asn Trp Ser
385                 390                 395                 400

Gly Tyr Ser Gly Ser Phe Thr Leu Pro Val Glu Leu Thr Lys Arg Asn
                405                 410                 415

Cys Leu Val Pro Cys Phe Trp Val Glu Met Ile Arg Gly Lys Pro Glu
                420                 425                 430

Glu Lys Thr Ile Trp Thr Ser Ser Ser Ile Val Met Cys Gly Val
        435                 440                 445

Asp His Glu Ile Ala Asp Trp Ser Trp His Asp Gly Ala Ile Leu Pro
        450                 455                 460

Phe Asp Ile Asp Lys Met
465                 470
```

<210> SEQ ID NO 47
<211> LENGTH: 465
<212> TYPE: PRT
<213> ORGANISM: Artificial Sequence
<220> FEATURE:
<223> OTHER INFORMATION: N9_AH13

<400> SEQUENCE: 47

```
Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
                20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
        50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
                100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
        130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
                180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
        210                 215                 220

Ser Glu Cys Val Cys His Asn Gly Val Cys Pro Val Val Phe Thr Asp
225                 230                 235                 240
```

```
Gly Ser Ala Thr Gly Pro Ala Asp Thr Arg Ile Tyr Tyr Phe Lys Glu
            245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
            275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
            355                 360                 365

Gly Tyr Glu Met Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
            435                 440                 445

Phe Leu Gly Gln Trp Asn Trp Pro Asp Gly Ala Lys Ile Glu Tyr Phe
    450                 455                 460

Leu
465
```

```
<210> SEQ ID NO 48
<211> LENGTH: 465
<212> TYPE: PRT
<213> ORGANISM: Artificial Sequence
<220> FEATURE:
<223> OTHER INFORMATION: N9_ck
```

```
<400> SEQUENCE: 48
```

```
Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
            35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Lys Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
            115                 120                 125
```

-continued

```
Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
            195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
            275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
            355                 360                 365

Gly Tyr Glu Met Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Lys Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
            435                 440                 445

Phe Leu Gly Gln Trp Asn Trp Pro Asp Gly Ala Lys Ile Glu Tyr Phe
    450                 455                 460

Leu
465
```

```
<210> SEQ ID NO 49
<211> LENGTH: 466
<212> TYPE: PRT
<213> ORGANISM: Artificial Sequence
<220> FEATURE:
<223> OTHER INFORMATION: B_Mal

<400> SEQUENCE: 49

Met Leu Pro Ser Thr Ile Gln Thr Leu Thr Leu Phe Leu Thr Ser Gly
1               5                   10                  15
```

-continued

```
Gly Val Leu Leu Ser Leu Tyr Val Ser Ala Ser Leu Ser Tyr Leu Pro
            20                  25                  30

Tyr Ser Asp Ile Leu Leu Lys Phe Pro Ser Thr Glu Ile Thr Ala Pro
            35                  40                  45

Thr Met Pro Leu Asp Cys Ala Asn Ala Ser Asn Val Gln Ala Val Asn
        50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
            115                 120                 125

His Phe Ala Leu Thr His Tyr Ala Ala Gln Pro Gly Gly Tyr Tyr Asn
        130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Ile Lys Tyr Gly Glu
            195                 200                 205

Ala Tyr Thr Asp Thr Tyr His Ser Tyr Ala Asn Asn Ile Leu Arg Thr
        210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Ile Lys Glu Ile Phe Pro Thr Gly Arg Ile Lys
            260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
        290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
            355                 360                 365

Met Ser Lys Thr Lys Arg Met Gly Met Gly Leu Tyr Val Lys Tyr Asp
        370                 375                 380

Gly Asp Pro Trp Ala Asp Ser Asp Ala Leu Ala Phe Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
```

-continued

```
              435               440               445
Met Gly Ser Gly Gln Leu Leu Trp Asp Thr Val Thr Gly Val Asn Met
     450               455               460

Ala Leu
465

<210> SEQ ID NO 50
<211> LENGTH: 6
<212> TYPE: PRT
<213> ORGANISM: Artificial Sequence
<220> FEATURE:
<223> OTHER INFORMATION: His tag

<400> SEQUENCE: 50

His His His His His His
1               5

<210> SEQ ID NO 51
<211> LENGTH: 7
<212> TYPE: PRT
<213> ORGANISM: Artificial Sequence
<220> FEATURE:
<223> OTHER INFORMATION: Cleavage site

<400> SEQUENCE: 51

Leu Val Pro Arg Gly Ser Pro
1               5

<210> SEQ ID NO 52
<211> LENGTH: 7
<212> TYPE: PRT
<213> ORGANISM: Artificial Sequence
<220> FEATURE:
<223> OTHER INFORMATION: Cleavage site
<220> FEATURE:
<221> NAME/KEY: MISC_FEATURE
<222> LOCATION: (7)..(7)
<223> OTHER INFORMATION: X is G or S

<400> SEQUENCE: 52

Glu Asn Leu Tyr Phe Gln Xaa
1               5

<210> SEQ ID NO 53
<211> LENGTH: 102
<212> TYPE: PRT
<213> ORGANISM: Artificial Sequence
<220> FEATURE:
<223> OTHER INFORMATION: PR8 N1 (aa 1-102)

<400> SEQUENCE: 53

Met Asn Pro Asn Gln Lys Ile Thr Thr Ile Gly Ser Ile Cys Leu Val
1               5               10               15

Val Gly Leu Ile Ser Leu Ile Leu Gln Ile Gly Asn Ile Ile Ser Ile
          20               25               30

Trp Ile Ser His Ser Ile Gln Thr Gly Ser Gln Asn His Thr Gly Ile
          35               40               45

Cys Asn Gln Asn Ile Ile Thr Tyr Lys Asn Ser Thr Trp Val Lys Asp
     50               55               60

Thr Thr Ser Val Ile Leu Thr Gly Asn Ser Ser Leu Cys Pro Ile Arg
65               70               75               80

Gly Trp Ala Ile Tyr Ser Lys Asp Asn Ser Ile Arg Ile Gly Ser Lys
               85               90               95
```

-continued

```
Gly Asp Val Phe Val Ile
            100

<210> SEQ ID NO 54
<211> LENGTH: 117
<212> TYPE: PRT
<213> ORGANISM: Artificial Sequence
<220> FEATURE:
<223> OTHER INFORMATION: HK14 N2 (aa 1-117)

<400> SEQUENCE: 54

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr
        115

<210> SEQ ID NO 55
<211> LENGTH: 1539
<212> TYPE: DNA
<213> ORGANISM: Artificial Sequence
<220> FEATURE:
<223> OTHER INFORMATION: N1-MPP (with his tag)

<400> SEQUENCE: 55
atgctgctcg tcaaccaatc ccaccagggc ttcaacaagg aacacacttc taagatggtc      60
tccgctatcg tgctctacgt gctgctcgct gccgctgccc actcagcttt cgctgccgac     120
ccacaccacc accaccacca cggcgatcac tacgacgacg aactgttctc cgacgtgcag     180
gacatcaaga ccgctctggc taagatccac gaggacaacc agaagatcat ctccaagctg     240
gaatccctgc tgctgctgaa gggcgaagtc gagtccatca gaagcagat caaccgccag      300 aacatctcca tctccacctt ggagggtcac ctgtcctcca tcatgatcgc tatccctggc     360
ctgggcggcg gctccgtgaa attagcgggc aattcctctc tctgccctgt tagtggatgg     420
gctatataca gtaaagacaa cagtgtaaga atcggttcca aggggatgt gtttgtcata      480 agggaaccat tcatatcatg ctctcccttg aatgcagaa ccttcttctt gactcaaggg       540
gccttgctaa atgacaaaca ttccaatgga accattaaag acaggagccc ataccgaacc     600
ctaatgagct gtcctattgg tgaagttccc tctccataca actcaagatt tgagtcagtc     660
gcttggtcag caagtgcttg tcatgatggc atcaattggc taacaattgg aatttctggc     720
ccagacagtg gggcagtggc tgtgttaaag tacaatggca ataacagaa cactatcaag      780 agttggagga acaatatatt gagaacacaa gagtctgaat gtgcatgtgt aaatggttct     840
tgctttacca atatgaccga tggaccaagt gatggacagg cctcatacaa aatcttcaga     900
atagaaaagg gaaagataat caaatcagtc gaaatgaaag ccctaatta tcactatgag      960
```

```
gaatgctcct gttaccctga ttctagtgaa atcacatgtg tgtgcaggga taactggcat    1020
ggctcgaatc gaccgtgggt gtctttcaac cagaatctgg aatatcagat gggatacata    1080
tgcagtgggg ttttcggaga caatccacgc cctaatgata agacaggcag ttgtggtcca    1140
gtatcgtcta atggagcaaa tggagtaaaa ggattttcat tcaaatacgg caatggtgtt    1200
tggataggga gaactaaaag cattagttca agaaaaggtt ttgagatgat ttgggatccg    1260
aatggatgga ctgggactga caataaattc tcaataaagc aagatatcgt aggaataaat    1320
gagtggtcag ggtatagcgg gagttttgtt cagcatccag aactaacagg gctggattgt    1380
ataagacctt gcttctgggt tgaactaata agagggcgac ccgaagagaa cacaatctgg    1440
actagcggga gcagcatatc cttttgtggt gtaaacagtg acactgtggg ttggtcttgg    1500
ccagacggtg ctgagttgcc atttaccatt gacaagtaa                           1539
```

```
<210> SEQ ID NO 56
<211> LENGTH: 512
<212> TYPE: PRT
<213> ORGANISM: Artificial Sequence
<220> FEATURE:
<223> OTHER INFORMATION: N1-MPP (with his tag)

<400> SEQUENCE: 56

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Gly
        35                  40                  45

Asp His Tyr Asp Asp Glu Leu Phe Ser Asp Val Gln Asp Ile Lys Thr
    50                  55                  60

Ala Leu Ala Lys Ile His Glu Asp Asn Gln Lys Ile Ile Ser Lys Leu
65                  70                  75                  80

Glu Ser Leu Leu Leu Leu Lys Gly Glu Val Glu Ser Ile Lys Lys Gln
                85                  90                  95

Ile Asn Arg Gln Asn Ile Ser Ile Ser Thr Leu Glu Gly His Leu Ser
            100                 105                 110

Ser Ile Met Ile Ala Ile Pro Gly Leu Gly Gly Gly Ser Val Lys Leu
        115                 120                 125

Ala Gly Asn Ser Ser Leu Cys Pro Val Ser Gly Trp Ala Ile Tyr Ser
    130                 135                 140

Lys Asp Asn Ser Val Arg Ile Gly Ser Lys Gly Asp Val Phe Val Ile
145                 150                 155                 160

Arg Glu Pro Phe Ile Ser Cys Ser Pro Leu Glu Cys Arg Thr Phe Phe
                165                 170                 175

Leu Thr Gln Gly Ala Leu Leu Asn Asp Lys His Ser Asn Gly Thr Ile
            180                 185                 190

Lys Asp Arg Ser Pro Tyr Arg Thr Leu Met Ser Cys Pro Ile Gly Glu
        195                 200                 205

Val Pro Ser Pro Tyr Asn Ser Arg Phe Glu Ser Val Ala Trp Ser Ala
    210                 215                 220

Ser Ala Cys His Asp Gly Ile Asn Trp Leu Thr Ile Gly Ile Ser Gly
225                 230                 235                 240

Pro Asp Ser Gly Ala Val Ala Val Leu Lys Tyr Asn Gly Ile Ile Thr
                245                 250                 255

Asp Thr Ile Lys Ser Trp Arg Asn Asn Ile Leu Arg Thr Gln Glu Ser
```

-continued

```
                 260              265              270

Glu Cys Ala Cys Val Asn Gly Ser Cys Phe Thr Ile Met Thr Asp Gly
            275              280              285

Pro Ser Asp Gly Gln Ala Ser Tyr Lys Ile Phe Arg Ile Glu Lys Gly
        290              295              300

Lys Ile Ile Lys Ser Val Glu Met Lys Ala Pro Asn Tyr His Tyr Glu
305              310              315              320

Glu Cys Ser Cys Tyr Pro Asp Ser Ser Glu Ile Thr Cys Val Cys Arg
                325              330              335

Asp Asn Trp His Gly Ser Asn Arg Pro Trp Val Ser Phe Asn Gln Asn
            340              345              350

Leu Glu Tyr Gln Met Gly Tyr Ile Cys Ser Gly Val Phe Gly Asp Asn
        355              360              365

Pro Arg Pro Asn Asp Lys Thr Gly Ser Cys Gly Pro Val Ser Ser Asn
        370              375              380

Gly Ala Asn Gly Val Lys Gly Phe Ser Phe Lys Tyr Gly Asn Gly Val
385              390              395              400

Trp Ile Gly Arg Thr Lys Ser Ile Ser Ser Arg Lys Gly Phe Glu Met
                405              410              415

Ile Trp Asp Pro Asn Gly Trp Thr Gly Thr Asp Asn Lys Phe Ser Ile
            420              425              430

Lys Gln Asp Ile Val Gly Ile Asn Glu Trp Ser Gly Tyr Ser Gly Ser
        435              440              445

Phe Val Gln His Pro Glu Leu Thr Gly Leu Asp Cys Ile Arg Pro Cys
        450              455              460

Phe Trp Val Glu Leu Ile Arg Gly Arg Pro Glu Glu Asn Thr Ile Trp
465              470              475              480

Thr Ser Gly Ser Ser Ile Ser Phe Cys Gly Val Asn Ser Asp Thr Val
                485              490              495

Gly Trp Ser Trp Pro Asp Gly Ala Glu Leu Pro Phe Thr Ile Asp Lys
            500              505              510
```

```
<210> SEQ ID NO 57
<211> LENGTH: 1521
<212> TYPE: DNA
<213> ORGANISM: Artificial Sequence
<220> FEATURE:
<223> OTHER INFORMATION: N1-MPP (no his tag)

<400> SEQUENCE: 57
atgctgctcg tcaaccaatc ccaccagggc ttcaacaagg aacacacttc taagatggtc     60
tccgctatcg tgctctacgt gctgctcgct gccgctgccc actcagcttt cgctgccgac    120
ccaggcgatc actacgacga cgaactgttc tccgacgtgc aggacatcaa gaccgctctg    180
gctaagatcc acgaggacaa ccagaagatc atctccaagc tggaatccct gctgctgctg    240
aagggcgaag tcgagtccat caagaagcag atcaaccgcc agaacatctc catctccacc    300
ttggagggtc acctgtcctc catcatgatc gctatccctg gcctgggcgg cggctccgtg    360
aaattagcgg gcaattcctc tctctgccct gttagtggat gggctatata cagtaaagac    420
aacagtgtaa gaatcggttc caggggggat gtgtttgtca taagggaacc attcatatca    480
tgctctccct ggaatgcag aaccttcttc ttgactcaag gggccttgct aaatgacaaa    540
cattccaatg gaaccattaa agacaggagc ccataccgaa ccctaatgag ctgtcctatt    600
ggtgaagttc cctctccata caactcaaga tttgagtcag tcgcttggtc agcaagtgct    660
```

-continued

```
tgtcatgatg gcatcaattg gctaacaatt ggaatttctg gcccagacag tggggcagtg    720
gctgtgttaa agtacaatgg cataataaca gacactatca agagttggag gaacaatata    780
ttgagaacac aagagtctga atgtgcatgt gtaaatggtt cttgctttac cataatgacc    840
gatggaccaa gtgatggaca ggcctcatac aaaatcttca gaatagaaaa gggaaagata    900
atcaaatcag tcgaaatgaa agcccctaat tatcactatg aggaatgctc ctgttaccct    960
gattctagtg aaatcacatg tgtgtgcagg gataactggc atggctcgaa tcgaccgtgg    1020
gtgtctttca accagaatct ggaatatcag atgggataca tatgcagtgg ggttttcgga    1080
gacaatccac gccctaatga taagacaggc agttgtggtc cagtatcgtc taatggagca    1140
aatggagtaa aaggattttc attcaaatac ggcaatggtg tttggatagg gagaactaaa    1200
agcattagtt caagaaaagg ttttgagatg atttgggatc cgaatggatg gactgggact    1260
gacaataaat tctcaataaa gcaagatatc gtaggaataa atgagtggtc agggtatagc    1320
gggagttttg ttcagcatcc agaactaaca gggctggatt gtataagacc ttgcttctgg    1380
gttgaactaa taagagggcg acccgaagag aacacaatct ggactagcgg gagcagcata    1440 tcctttttgtg gtgtaaacag tgacactgtg ggttggtctt ggccagacgg tgctgagttg    1500
ccatttacca ttgacaagta a                                             1521
```

```
<210> SEQ ID NO 58
<211> LENGTH: 506
<212> TYPE: PRT
<213> ORGANISM: Artificial Sequence
<220> FEATURE:
<223> OTHER INFORMATION: N1-MPP (no his tag)

<400> SEQUENCE: 58

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp His Tyr Asp Asp Glu
        35                  40                  45

Leu Phe Ser Asp Val Gln Asp Ile Lys Thr Ala Leu Ala Lys Ile His
    50                  55                  60

Glu Asp Asn Gln Lys Ile Ile Ser Lys Leu Glu Ser Leu Leu Leu Leu
65                  70                  75                  80

Lys Gly Glu Val Glu Ser Ile Lys Lys Gln Ile Asn Arg Gln Asn Ile
            85                  90                  95

Ser Ile Ser Thr Leu Glu Gly His Leu Ser Ser Ile Met Ile Ala Ile
            100                 105                 110

Pro Gly Leu Gly Gly Gly Ser Val Lys Leu Ala Gly Asn Ser Ser Leu
            115                 120                 125

Cys Pro Val Ser Gly Trp Ala Ile Tyr Ser Lys Asp Asn Ser Val Arg
        130                 135                 140

Ile Gly Ser Lys Gly Asp Val Phe Val Ile Arg Glu Pro Phe Ile Ser
145                 150                 155                 160

Cys Ser Pro Leu Glu Cys Arg Thr Phe Phe Leu Thr Gln Gly Ala Leu
                165                 170                 175

Leu Asn Asp Lys His Ser Asn Gly Thr Ile Lys Asp Arg Ser Pro Tyr
            180                 185                 190

Arg Thr Leu Met Ser Cys Pro Ile Gly Glu Val Pro Ser Pro Tyr Asn
        195                 200                 205
```

-continued

```
Ser Arg Phe Glu Ser Val Ala Trp Ser Ala Ser Ala Cys His Asp Gly
    210             215                 220

Ile Asn Trp Leu Thr Ile Gly Ile Ser Gly Pro Asp Ser Gly Ala Val
225             230                 235                 240

Ala Val Leu Lys Tyr Asn Gly Ile Ile Thr Asp Thr Ile Lys Ser Trp
                245                 250                 255

Arg Asn Asn Ile Leu Arg Thr Gln Glu Ser Glu Cys Ala Cys Val Asn
            260                 265                 270

Gly Ser Cys Phe Thr Ile Met Thr Asp Gly Pro Ser Asp Gly Gln Ala
            275                 280                 285

Ser Tyr Lys Ile Phe Arg Ile Glu Lys Gly Lys Ile Ile Lys Ser Val
    290                 295                 300

Glu Met Lys Ala Pro Asn Tyr His Tyr Glu Glu Cys Ser Cys Tyr Pro
305                 310                 315                 320

Asp Ser Ser Glu Ile Thr Cys Val Cys Arg Asp Asn Trp His Gly Ser
                325                 330                 335

Asn Arg Pro Trp Val Ser Phe Asn Gln Asn Leu Glu Tyr Gln Met Gly
            340                 345                 350

Tyr Ile Cys Ser Gly Val Phe Gly Asp Asn Pro Arg Pro Asn Asp Lys
            355                 360                 365

Thr Gly Ser Cys Gly Pro Val Ser Ser Asn Gly Ala Asn Gly Val Lys
    370                 375                 380

Gly Phe Ser Phe Lys Tyr Gly Asn Gly Val Trp Ile Gly Arg Thr Lys
385                 390                 395                 400

Ser Ile Ser Ser Arg Lys Gly Phe Glu Met Ile Trp Asp Pro Asn Gly
                405                 410                 415

Trp Thr Gly Thr Asp Asn Lys Phe Ser Ile Lys Gln Asp Ile Val Gly
            420                 425                 430

Ile Asn Glu Trp Ser Gly Tyr Ser Gly Ser Phe Val Gln His Pro Glu
            435                 440                 445

Leu Thr Gly Leu Asp Cys Ile Arg Pro Cys Phe Trp Val Glu Leu Ile
    450                 455                 460

Arg Gly Arg Pro Glu Glu Asn Thr Ile Trp Thr Ser Gly Ser Ser Ile
465                 470                 475                 480

Ser Phe Cys Gly Val Asn Ser Asp Thr Val Gly Trp Ser Trp Pro Asp
                485                 490                 495

Gly Ala Glu Leu Pro Phe Thr Ile Asp Lys
        500                 505
```

<210> SEQ ID NO 59
<211> LENGTH: 1575
<212> TYPE: DNA
<213> ORGANISM: Artificial Sequence
<220> FEATURE:
<223> OTHER INFORMATION: N2-MPP

<400> SEQUENCE: 59

```
atgctgctcg tcaaccaatc ccaccagggc ttcaacaagg aacacacttc taagatggtc        60
tccgctatcg tgctctacgt gctgctcgct gccgctgccc actcagcttt cgctgccgac       120
ccacaccacc accaccacca cggcgatcac tacgacgacg aactgttctc cgacgtgcag       180
gacatcaaga ccgctctggc taagatccac gaggacaacc agaagatcat ctccaagctg       240
gaatccctgc tgctgctgaa gggcgaagtc gagtccatca agaagcagat caaccgccag       300
aacatctcca tctccacctt ggagggtcac ctgtcctcca tcatgatcgc tatccctggc       360
```

-continued

```
ctgtctctcg tgcccagggg atcaccttct agaatatgcc ccaaaccagc agaatacaga       420
aattggtcaa aaccgcaatg tggcattaca ggatttgcac ctttctctaa ggacaattcg       480
attaggcttt ccgctggtgg ggacatctgg gtgacaagag aaccttatgt gtcatgcgat       540
cctgacaagt gttatcaatt tgcccttgga cagggaacaa caataaacaa cgtgcattca       600
aataacacag cacgtgatag gacccctcat cggactctat tgatgaatga gttgggtgtt       660
cctttccatc tggggaccaa gcaagtgtgc atagcatggt ccagctcaag ttgtcacgat       720
ggaaaagcat ggctgcatgt ttgtataacg ggggatgata aaaatgcaac tgctagtttc       780
atttacaatg ggaggcttgt agatagtgtt gtttcatggt ccaaagatat tctcaggacc       840
caggagtcag aatgcgtttg tatcaatgga acttgtacag tagtaatgac tgatggaaat       900
gctacaggaa aagctgatac taaaatatta ttcattgagg aggggaaaat cgttcatact       960
agcaaattgt caggaagtgc tcagcatgtc gaagagtgct cttgctatcc tcgataccct      1020
ggtgtcagat gtgtctgcag agacaactgg aaaggatcca accggcccat cgtagatata      1080
aacataaagg atcatagcat tgtttccagt tatgtgtgtt caggacttgt tggagacaca      1140
cccagaaaaa ccgacagctc cagcagcagc cattgcttga atcctaacaa tgaaaaaggt      1200
ggtcatggag tgaaaggctg ggcctttgat gatggaaatg acgtgtggat ggggagaaca      1260
atcaacgaga cgtcacgctt agggtatgaa accttcaaag tcgttgaagg ctggtccaac      1320
cctaagtcca aattgcagat aaataggcaa gtcatagttg acagaggtga taggtccggt      1380
tattctggta ttttctctgt tgaaggcaaa agctgcatca atcggtgctt ttatgtggag      1440
ttgattaggg gaagaaaaga ggaaactgaa gtcttgtgga cctcaaacag tattgttgtg      1500
ttttgtggca cctcaggtac atatggaaca ggctcatggc ctgatggggc ggacctcaat      1560
ctcatgcata tataa                                                        1575
```

```
<210> SEQ ID NO 60
<211> LENGTH: 524
<212> TYPE: PRT
<213> ORGANISM: Artificial Sequence
<220> FEATURE:
<223> OTHER INFORMATION: N2-MPP

<400> SEQUENCE: 60

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His His Gly
        35                  40                  45

Asp His Tyr Asp Asp Glu Leu Phe Ser Asp Val Gln Asp Ile Lys Thr
    50                  55                  60

Ala Leu Ala Lys Ile His Glu Asp Asn Gln Lys Ile Ile Ser Lys Leu
65                  70                  75                  80

Glu Ser Leu Leu Leu Leu Lys Gly Glu Val Glu Ser Ile Lys Lys Gln
                85                  90                  95

Ile Asn Arg Gln Asn Ile Ser Ile Ser Thr Leu Glu Gly His Leu Ser
            100                 105                 110

Ser Ile Met Ile Ala Ile Pro Gly Leu Ser Leu Val Pro Arg Gly Ser
        115                 120                 125

Pro Ser Arg Ile Cys Pro Lys Pro Ala Glu Tyr Arg Asn Trp Ser Lys
    130                 135                 140
```

-continued

```
Pro Gln Cys Gly Ile Thr Gly Phe Ala Pro Phe Ser Lys Asp Asn Ser
145             150                 155                 160

Ile Arg Leu Ser Ala Gly Gly Asp Ile Trp Val Thr Arg Glu Pro Tyr
            165                 170                 175

Val Ser Cys Asp Pro Asp Lys Cys Tyr Gln Phe Ala Leu Gly Gln Gly
            180             185                 190

Thr Thr Ile Asn Asn Val His Ser Asn Asn Thr Ala Arg Asp Arg Thr
            195                 200                 205

Pro His Arg Thr Leu Leu Met Asn Glu Leu Gly Val Pro Phe His Leu
        210                 215                 220

Gly Thr Lys Gln Val Cys Ile Ala Trp Ser Ser Ser Ser Cys His Asp
225                 230                 235                 240

Gly Lys Ala Trp Leu His Val Cys Ile Thr Gly Asp Asp Lys Asn Ala
                245                 250                 255

Thr Ala Ser Phe Ile Tyr Asn Gly Arg Leu Val Asp Ser Val Val Ser
            260                 265                 270

Trp Ser Lys Asp Ile Leu Arg Thr Gln Glu Ser Glu Cys Val Cys Ile
            275                 280                 285

Asn Gly Thr Cys Thr Val Val Met Thr Asp Gly Asn Ala Thr Gly Lys
        290                 295                 300

Ala Asp Thr Lys Ile Leu Phe Ile Glu Glu Gly Lys Ile Val His Thr
305                 310                 315                 320

Ser Lys Leu Ser Gly Ser Ala Gln His Val Glu Glu Cys Ser Cys Tyr
                325                 330                 335

Pro Arg Tyr Pro Gly Val Arg Cys Val Cys Arg Asp Asn Trp Lys Gly
            340                 345                 350

Ser Asn Arg Pro Ile Val Asp Ile Asn Ile Lys Asp His Ser Ile Val
            355                 360                 365

Ser Ser Tyr Val Cys Ser Gly Leu Val Gly Asp Thr Pro Arg Lys Thr
        370                 375                 380

Asp Ser Ser Ser Ser Ser His Cys Leu Asn Pro Asn Asn Glu Lys Gly
385                 390                 395                 400

Gly His Gly Val Lys Gly Trp Ala Phe Asp Asp Gly Asn Asp Val Trp
                405                 410                 415

Met Gly Arg Thr Ile Asn Glu Thr Ser Arg Leu Gly Tyr Glu Thr Phe
            420                 425                 430

Lys Val Val Glu Gly Trp Ser Asn Pro Lys Ser Lys Leu Gln Ile Asn
            435                 440                 445

Arg Gln Val Ile Val Asp Arg Gly Asp Arg Ser Gly Tyr Ser Gly Ile
        450                 455                 460

Phe Ser Val Glu Gly Lys Ser Cys Ile Asn Arg Cys Phe Tyr Val Glu
465                 470                 475                 480

Leu Ile Arg Gly Arg Lys Glu Glu Thr Glu Val Leu Trp Thr Ser Asn
                485                 490                 495

Ser Ile Val Val Phe Cys Gly Thr Ser Gly Thr Tyr Gly Thr Gly Ser
            500                 505                 510

Trp Pro Asp Gly Ala Asp Leu Asn Leu Met His Ile
            515                 520
```

<210> SEQ ID NO 61
<211> LENGTH: 1578
<212> TYPE: DNA
<213> ORGANISM: Artificial Sequence
<220> FEATURE:
<223> OTHER INFORMATION: B-MPP

<400> SEQUENCE: 61

```
atgctgctcg tcaaccaatc ccaccagggc ttcaacaagg aacacacttc taagatggtc      60
tccgctatcg tgctctacgt gctgctcgct gccgctgccc actcagcttt cgctgccgac     120
ccacaccacc accaccacca cggcgatcac tacgacgacg aactgttctc cgacgtgcag     180
gacatcaaga ccgctctggc taagatccac gaggacaacc agaagatcat ctccaagctg     240
gaatccctgc tgctgctgaa gggcgaagtc gagtccatca agaagcagat caaccgccag     300
aacatctcca tctccacctt ggagggtcac ctgtcctcca tcatgatcgc tatccctggc     360
ctgtctctcg tgcccagggg atcaccttct agacttcttc tcccagaacc ggagtggaca     420
tacccgcgtt tatcttgccc gggctcaacc tttcagaaag cactcctaat tagccctcat     480
agattcggag aaaccaaagg aaactcagct cccttgataa taagggaacc ttttgttgct     540
tgtggaccaa atgaatgcaa acactttgct ttaacccatt atgcagccca accagggga     600 tactacaatg aacaagagg agacagaaac aagctgaggc atctaatttc agtcaaattg     660
ggcaaaatcc caacagtaga gaactccatt ttccacatgg cagcatggag cgggtccgcg     720
tgccatgatg gtaaggaatg gacatatatc ggagttgatg ccctgacaa taatgcattg     780 ctcaaagtaa aatatggaga agcatatact gacacatacc attcctatgc aaacaacatc     840
ctaagaacac aagaaagtgc ctgcaattgc atcggggaa attgttatct aatgataact     900
gatggctcag cttcaggtgt tagtgaatgc agatttctta agattcgaga gggccgaata     960 ataaagaaa tatttccaac aggaagagta aaacacactg aggaatgcac atgcggattt    1020
gccagcaata aaaccataga atgtgcctgt agagacaaca ggtacacagc aaaaagacct    1080
tttgtcaaat taaacgtgga gactgataca gcagaaataa ggttgatgtg cacagatacc    1140
tatttggaca cccccagacc aaatgatgga agcataacag gcccttgtga atctgatggg    1200
gacaaaggga gtggaggcat caagggagga tttgttcatc aaagaatgaa atccaagatt    1260
ggaaggtggt actctcgaac gatgtctcaa actgaaagga tggggatggg actgtatgtc    1320
aagtatggtg agacccatg gctgacagt gatgccctag cttttagtgg agtaatggtt    1380
tcaatgaaag aacctggttg gtattccttt ggcttcgaaa taaaagataa gaaatgcgat    1440
gtcccctgta ttgggataga gatggtacat gatggtggaa aagagacttg cactcagca    1500 gcaacagcca tttactgttt aatgggctca ggacagctgc tgtgggacac tgtcacaggt    1560
gttgacatgg ctctgtaa                                                1578
```

<210> SEQ ID NO 62
<211> LENGTH: 525
<212> TYPE: PRT
<213> ORGANISM: Artificial Sequence
<220> FEATURE:
<223> OTHER INFORMATION: B-MPP

<400> SEQUENCE: 62

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His His His His His Gly
        35                  40                  45

Asp His Tyr Asp Asp Glu Leu Phe Ser Asp Val Gln Asp Ile Lys Thr
    50                  55                  60
```

-continued

```
Ala Leu Ala Lys Ile His Glu Asp Asn Gln Lys Ile Ile Ser Lys Leu
65                  70                  75                  80

Glu Ser Leu Leu Leu Leu Lys Gly Glu Val Glu Ser Ile Lys Lys Gln
                85                  90                  95

Ile Asn Arg Gln Asn Ile Ser Ile Ser Thr Leu Glu Gly His Leu Ser
            100                 105                 110

Ser Ile Met Ile Ala Ile Pro Gly Leu Ser Leu Val Pro Arg Gly Ser
        115                 120                 125

Pro Ser Arg Leu Leu Leu Pro Glu Pro Glu Trp Thr Tyr Pro Arg Leu
    130                 135                 140

Ser Cys Pro Gly Ser Thr Phe Gln Lys Ala Leu Leu Ile Ser Pro His
145                 150                 155                 160

Arg Phe Gly Glu Thr Lys Gly Asn Ser Ala Pro Leu Ile Ile Arg Glu
                165                 170                 175

Pro Phe Val Ala Cys Gly Pro Asn Glu Cys Lys His Phe Ala Leu Thr
            180                 185                 190

His Tyr Ala Ala Gln Pro Gly Gly Tyr Tyr Asn Gly Thr Arg Gly Asp
        195                 200                 205

Arg Asn Lys Leu Arg His Leu Ile Ser Val Lys Leu Gly Lys Ile Pro
    210                 215                 220

Thr Val Glu Asn Ser Ile Phe His Met Ala Ala Trp Ser Gly Ser Ala
225                 230                 235                 240

Cys His Asp Gly Lys Glu Trp Thr Tyr Ile Gly Val Asp Gly Pro Asp
                245                 250                 255

Asn Asn Ala Leu Leu Lys Val Lys Tyr Gly Glu Ala Tyr Thr Asp Thr
            260                 265                 270

Tyr His Ser Tyr Ala Asn Asn Ile Leu Arg Thr Gln Glu Ser Ala Cys
        275                 280                 285

Asn Cys Ile Gly Gly Asn Cys Tyr Leu Met Ile Thr Asp Gly Ser Ala
    290                 295                 300

Ser Gly Val Ser Glu Cys Arg Phe Leu Lys Ile Arg Glu Gly Arg Ile
305                 310                 315                 320

Ile Lys Glu Ile Phe Pro Thr Gly Arg Val Lys His Thr Glu Glu Cys
                325                 330                 335

Thr Cys Gly Phe Ala Ser Asn Lys Thr Ile Glu Cys Ala Cys Arg Asp
            340                 345                 350

Asn Arg Tyr Thr Ala Lys Arg Pro Phe Val Lys Leu Asn Val Glu Thr
        355                 360                 365

Asp Thr Ala Glu Ile Arg Leu Met Cys Thr Asp Thr Tyr Leu Asp Thr
    370                 375                 380

Pro Arg Pro Asn Asp Gly Ser Ile Thr Gly Pro Cys Glu Ser Asp Gly
385                 390                 395                 400

Asp Lys Gly Ser Gly Gly Ile Lys Gly Gly Phe Val His Gln Arg Met
                405                 410                 415

Lys Ser Lys Ile Gly Arg Trp Tyr Ser Arg Thr Met Ser Gln Thr Glu
            420                 425                 430

Arg Met Gly Met Gly Leu Tyr Val Lys Tyr Gly Gly Asp Pro Trp Ala
        435                 440                 445

Asp Ser Asp Ala Leu Ala Phe Ser Gly Val Met Val Ser Met Lys Glu
    450                 455                 460

Pro Gly Trp Tyr Ser Phe Gly Phe Glu Ile Lys Asp Lys Lys Cys Asp
465                 470                 475                 480

Val Pro Cys Ile Gly Ile Glu Met Val His Asp Gly Gly Lys Glu Thr
```

-continued

```
                 485               490               495
Trp His Ser Ala Ala Thr Ala Ile Tyr Cys Leu Met Gly Ser Gly Gln
            500               505               510

Leu Leu Trp Asp Thr Val Thr Gly Val Asp Met Ala Leu
        515               520               525

<210> SEQ ID NO 63
<211> LENGTH: 10
<212> TYPE: PRT
<213> ORGANISM: Artificial Sequence
<220> FEATURE:
<223> OTHER INFORMATION: Cleavage site

<400> SEQUENCE: 63

Ser Leu Val Pro Arg Gly Ser Pro Ser Arg
1               5                   10

<210> SEQ ID NO 64
<211> LENGTH: 393
<212> TYPE: PRT
<213> ORGANISM: Artificial Sequence
<220> FEATURE:
<223> OTHER INFORMATION: Globular head domain of NA of influenza virus
      A/Kansas/14/2017

<400> SEQUENCE: 64

Ile Cys Pro Lys Pro Ala Glu Tyr Arg Asn Trp Ser Lys Pro Gln Cys
1               5                   10                  15

Gly Ile Thr Gly Phe Ala Pro Phe Ser Lys Asp Asn Ser Ile Arg Leu
            20                  25                  30

Ser Ala Gly Gly Asp Ile Trp Val Thr Arg Glu Pro Tyr Val Ser Cys
        35                  40                  45

Asp Pro Asp Lys Cys Tyr Gln Phe Ala Leu Gly Gln Gly Thr Thr Ile
    50                  55                  60

Asn Asn Val His Ser Asn Asn Thr Ala Arg Asp Arg Thr Pro His Arg
65                  70                  75                  80

Thr Leu Leu Met Asn Glu Leu Gly Val Pro Phe His Leu Gly Thr Lys
                85                  90                  95

Gln Val Cys Ile Ala Trp Ser Ser Ser Ser Cys His Asp Gly Lys Ala
            100                 105                 110

Trp Leu His Val Cys Ile Thr Gly Asp Asp Lys Asn Ala Thr Ala Ser
        115                 120                 125

Phe Ile Tyr Asn Gly Arg Leu Val Asp Ser Val Val Ser Trp Ser Lys
    130                 135                 140

Asp Ile Leu Arg Thr Gln Glu Ser Glu Cys Val Cys Ile Asn Gly Thr
145                 150                 155                 160

Cys Thr Val Val Met Thr Asp Gly Asn Ala Thr Gly Lys Ala Asp Thr
                165                 170                 175

Lys Ile Leu Phe Ile Glu Glu Gly Lys Ile Val His Thr Ser Lys Leu
            180                 185                 190

Ser Gly Ser Ala Gln His Val Glu Glu Cys Ser Cys Tyr Pro Arg Tyr
        195                 200                 205

Pro Gly Val Arg Cys Val Cys Arg Asp Asn Trp Lys Gly Ser Asn Arg
    210                 215                 220

Pro Ile Val Asp Ile Asn Ile Lys Asp His Ser Ile Val Ser Ser Tyr
225                 230                 235                 240

Val Cys Ser Gly Leu Val Gly Asp Thr Pro Arg Lys Thr Asp Ser Ser
        245                 250                 255
```

```
Ser Ser Ser His Cys Leu Asn Pro Asn Asn Glu Lys Gly Gly His Gly
            260             265             270

Val Lys Gly Trp Ala Phe Asp Asp Gly Asn Asp Val Trp Met Gly Arg
            275             280             285

Thr Ile Asn Glu Thr Ser Arg Leu Gly Tyr Glu Thr Phe Lys Val Val
            290             295             300

Glu Gly Trp Ser Asn Pro Lys Ser Lys Leu Gln Ile Asn Arg Gln Val
305             310             315             320

Ile Val Asp Arg Gly Asp Arg Ser Gly Tyr Ser Gly Ile Phe Ser Val
            325             330             335

Glu Gly Lys Ser Cys Ile Asn Arg Cys Phe Tyr Val Glu Leu Ile Arg
            340             345             350

Gly Arg Lys Glu Glu Thr Glu Val Leu Trp Thr Ser Asn Ser Ile Val
            355             360             365

Val Phe Cys Gly Thr Ser Gly Thr Tyr Gly Thr Gly Ser Trp Pro Asp
            370             375             380

Gly Ala Asp Leu Asn Leu Met His Ile
385             390

<210> SEQ ID NO 65
<211> LENGTH: 394
<212> TYPE: PRT
<213> ORGANISM: Artificial Sequence
<220> FEATURE:
<223> OTHER INFORMATION: Globular head domain of NA of influenza virus
      B/Colorado/06/2017

<400> SEQUENCE: 65

Leu Leu Leu Pro Glu Pro Glu Trp Thr Tyr Pro Arg Leu Ser Cys Pro
1               5               10              15

Gly Ser Thr Phe Gln Lys Ala Leu Leu Ile Ser Pro His Arg Phe Gly
            20              25              30

Glu Thr Lys Gly Asn Ser Ala Pro Leu Ile Ile Arg Glu Pro Phe Val
            35              40              45

Ala Cys Gly Pro Asn Glu Cys Lys His Phe Ala Leu Thr His Tyr Ala
            50              55              60

Ala Gln Pro Gly Gly Tyr Tyr Asn Gly Thr Arg Gly Asp Arg Asn Lys
65              70              75              80

Leu Arg His Leu Ile Ser Val Lys Leu Gly Lys Ile Pro Thr Val Glu
            85              90              95

Asn Ser Ile Phe His Met Ala Ala Trp Ser Gly Ser Ala Cys His Asp
            100             105             110

Gly Lys Glu Trp Thr Tyr Ile Gly Val Asp Gly Pro Asp Asn Asn Ala
            115             120             125

Leu Leu Lys Val Lys Tyr Gly Glu Ala Tyr Thr Asp Thr Tyr His Ser
            130             135             140

Tyr Ala Asn Asn Ile Leu Arg Thr Gln Glu Ser Ala Cys Asn Cys Ile
145             150             155             160

Gly Gly Asn Cys Tyr Leu Met Ile Thr Asp Gly Ser Ala Ser Gly Val
            165             170             175

Ser Glu Cys Arg Phe Leu Lys Ile Arg Glu Gly Arg Ile Ile Lys Glu
            180             185             190

Ile Phe Pro Thr Gly Arg Val Lys His Thr Glu Glu Cys Thr Cys Gly
            195             200             205

Phe Ala Ser Asn Lys Thr Ile Glu Cys Ala Cys Arg Asp Asn Arg Tyr
```

-continued

```
              210                  215                  220

Thr Ala Lys Arg Pro Phe Val Lys Leu Asn Val Glu Thr Asp Thr Ala
225                 230                 235                 240

Glu Ile Arg Leu Met Cys Thr Asp Thr Tyr Leu Asp Thr Pro Arg Pro
                245                 250                 255

Asn Asp Gly Ser Ile Thr Gly Pro Cys Glu Ser Asp Gly Asp Lys Gly
                260                 265                 270

Ser Gly Gly Ile Lys Gly Gly Phe Val His Gln Arg Met Lys Ser Lys
                275                 280                 285

Ile Gly Arg Trp Tyr Ser Arg Thr Met Ser Gln Thr Glu Arg Met Gly
                290                 295                 300

Met Gly Leu Tyr Val Lys Tyr Gly Gly Asp Pro Trp Ala Asp Ser Asp
305                 310                 315                 320

Ala Leu Ala Phe Ser Gly Val Met Val Ser Met Lys Glu Pro Gly Trp
                325                 330                 335

Tyr Ser Phe Gly Phe Glu Ile Lys Asp Lys Lys Cys Asp Val Pro Cys
                340                 345                 350

Ile Gly Ile Glu Met Val His Asp Gly Gly Lys Glu Thr Trp His Ser
                355                 360                 365

Ala Ala Thr Ala Ile Tyr Cys Leu Met Gly Ser Gly Gln Leu Leu Trp
                370                 375                 380

Asp Thr Val Thr Gly Val Asp Met Ala Leu
385                 390
```

```
<210> SEQ ID NO 66
<211> LENGTH: 388
<212> TYPE: PRT
<213> ORGANISM: Artificial Sequence
<220> FEATURE:
<223> OTHER INFORMATION: Globular head domain of NA of influenza virus
      A/Michigan/45/15

<400> SEQUENCE: 66

Ser Val Lys Leu Ala Gly Asn Ser Ser Leu Cys Pro Val Ser Gly Trp
1               5                   10                  15

Ala Ile Tyr Ser Lys Asp Asn Ser Val Arg Ile Gly Ser Lys Gly Asp
                20                  25                  30

Val Phe Val Ile Arg Glu Pro Phe Ile Ser Cys Ser Pro Leu Glu Cys
                35                  40                  45

Arg Thr Phe Phe Leu Thr Gln Gly Ala Leu Leu Asn Asp Lys His Ser
     50                  55                  60

Asn Gly Thr Ile Lys Asp Arg Ser Pro Tyr Arg Thr Leu Met Ser Cys
65                  70                  75                  80

Pro Ile Gly Glu Val Pro Ser Pro Tyr Asn Ser Arg Phe Glu Ser Val
                85                  90                  95

Ala Trp Ser Ala Ser Ala Cys His Asp Gly Ile Asn Trp Leu Thr Ile
                100                 105                 110

Gly Ile Ser Gly Pro Asp Ser Gly Ala Val Ala Val Leu Lys Tyr Asn
                115                 120                 125

Gly Ile Ile Thr Asp Thr Ile Lys Ser Trp Arg Asn Asn Ile Leu Arg
                130                 135                 140

Thr Gln Glu Ser Glu Cys Ala Cys Val Asn Gly Ser Cys Phe Thr Ile
145                 150                 155                 160

Met Thr Asp Gly Pro Ser Asp Gly Gln Ala Ser Tyr Lys Ile Phe Arg
                165                 170                 175
```

-continued

```
Ile Glu Lys Gly Lys Ile Ile Lys Ser Val Glu Met Lys Ala Pro Asn
            180                 185                 190

Tyr His Tyr Glu Glu Cys Ser Cys Tyr Pro Asp Ser Ser Glu Ile Thr
        195                 200                 205

Cys Val Cys Arg Asp Asn Trp His Gly Ser Asn Arg Pro Trp Val Ser
    210                 215                 220

Phe Asn Gln Asn Leu Glu Tyr Gln Met Gly Tyr Ile Cys Ser Gly Val
225                 230                 235                 240

Phe Gly Asp Asn Pro Arg Pro Asn Asp Lys Thr Gly Ser Cys Gly Pro
                245                 250                 255

Val Ser Ser Asn Gly Ala Asn Gly Val Lys Gly Phe Ser Phe Lys Tyr
                260                 265                 270

Gly Asn Gly Val Trp Ile Gly Arg Thr Lys Ser Ile Ser Ser Arg Lys
            275                 280                 285

Gly Phe Glu Met Ile Trp Asp Pro Asn Gly Trp Thr Gly Thr Asp Asn
            290                 295                 300

Lys Phe Ser Ile Lys Gln Asp Ile Val Gly Ile Asn Glu Trp Ser Gly
305                 310                 315                 320

Tyr Ser Gly Ser Phe Val Gln His Pro Glu Leu Thr Gly Leu Asp Cys
                325                 330                 335

Ile Arg Pro Cys Phe Trp Val Glu Leu Ile Arg Gly Arg Pro Glu Glu
                340                 345                 350

Asn Thr Ile Trp Thr Ser Gly Ser Ser Ile Ser Phe Cys Gly Val Asn
            355                 360                 365

Ser Asp Thr Val Gly Trp Ser Trp Pro Asp Gly Ala Glu Leu Pro Phe
    370                 375                 380

Thr Ile Asp Lys
385
```

RECOMBINANT NEURAMINIDASE AND USES THEREOF

CROSS-REFERENCE TO RELATED APPLICATIONS

This application is a U.S. National Stage Application under 35 U.S.C. § 371 of International Patent Application No. PCT/US2020/056703, filed Oct. 21, 2020, which claims the benefit of U.S. Provisional Patent Application No. 62/924,511, filed Oct. 22, 2019, the disclosure of each of which is incorporated by reference herein in its entirety.

STATEMENT REGARDING FEDERALLY SPONSORED RESEARCH

This invention was made with government support under award HHSN272201400008C, AI097092-07, R01AI145870-01 and 75N93019C00051 awarded by the National Institutes of Health. The government has certain rights in this invention.

SEQUENCE LISTING

This application incorporates by reference in its entirety a Sequence Listing submitted with this application as a text filed entitled "06923-305-228_SEQ_LISTING.txt", created on Oct. 21, 2020, and is 226,341 bytes in size.

1. INTRODUCTION

In one aspect, provided herein are recombinant neuraminidases comprising an ectodomain of influenza virus neuraminidase with amino acid substitutions or insertions of cysteines in the stalk domain to generate a more stable, tetrameric influenza virus neuraminidase. In specific embodiments, the influenza virus neuraminidase further comprises influenza virus neuraminidase transmembrane and cytoplasmic domains. In another aspect, provided herein are recombinant neuraminidase comprising a globular head domain of influenza virus neuraminidase and a tetramerization domain, wherein the recombinant neuraminidase lacks influenza virus neuraminidase stalk, transmembrane and cytoplasmic domains. In another aspect, provided herein are methods of immunizing against influenza virus using such recombinant neuraminidases or compositions thereof.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza A viruses are mainly avians, but influenza A viruses (including those of avian origin) also can infect and cause illness in humans and other animal hosts (bats, canines, pigs, horses, sea mammals, and mustelids). For example, the H5N1 avian influenza A virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high attack rate. In a normal season, influenza can cause between 3-5 million cases of severe illness and up to 500,000 deaths worldwide (World Health Organization (2003) Influenza: Overview; March 2003). In the United States, influenza viruses infect an estimated 10-15% of the population (Glezen and Couch R B (1978) Interpandemic influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated with Influenza and Respiratory Syncytial Virus in the United States. JAMA 289: 179-186; Belshe (2007) Translational research on vaccines: influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957, 1968, and 2009. Due to the lack of pre-formed immunity against the major viral antigen, hemagglutinin (HA), pandemic influenza can affect greater than 50% of the population in a single year and often causes more severe disease than epidemic influenza. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 influenza virus in the late 1990s (Claas et al. (1998) Human influenza A H5N1 virus related to a highly pathogenic avian influenza virus. Lancet 351: 472-7), there have been concerns that it may be the next pandemic virus.

Seasonal vaccination is currently the most effective intervention against influenza (Gross et al., Ann Intern Med, 1995, 123(7): p. 518-27; Ogburn et al., J Reprod Med, 2007, 52(9): p. 753-6; Jefferson et al., Lancet, 2005. 366 (9492): p. 1165-74; Beyer et al., Vaccine, 2013, 31(50): p. 6030-3; Nichol et al., N Engl J Med, 1995. 333 (14): p. 889-93; Jefferson et al., Lancet, 2005. 365 (9461): p. 773-80), yet overall vaccine effectiveness was only 36% in the recent 2017-2018 season (Flannery et al., MMWR Morb Mortal Wkly Rep, 2018. 67 (6): p. 180-185). However, current vaccination approaches rely on achieving a good match between circulating strains and the isolates included in the vaccine. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Often, the predictions of the vaccine strain selection committee are inaccurate, resulting in a substantial drop in the efficacy of vaccination.

The neuraminidase (NA) of influenza viruses is a homo-tetrameric, type II transmembrane protein (Fields S, Winter G, Brownlee G G. 1981. Structure of the neuraminidase gene in human influenza virus A/PR/8/34. Nature 290:213-7; Ward C W, Elleman T C, Azad A A. 1982. Amino acid sequence of the Pronase-released heads of neuraminidase subtype N2 from the Asian strain A/Tokyo/3/67 of influenza virus. Biochem J 207:91-5). The tetrameric form of the NA has the enzymatic function of removing sialic acids from mucus, which is crucial to prevent immobilization of the virus in the respiratory tract, and to release virus progenies from infected cells (Palese P, Tobita K, Ueda M, Compans R W. 1974. Characterization of temperature sensitive influenza virus mutants defective in neuraminidase. Virology 61:397-410). Four identical monomeric polypeptides each approximately 470 amino acids assemble to form tetrameric NA (McAuley et al., 2019, Frontiers in Microbiology 10: 39). The four monomers each have four distinct structural domains: the cytoplasmic tail, the transmembrane region, the stalk, and the catalytic head (id.). The ectodomain of NA is composed of the globular head domain and stalk domain of NA.

Antiviral drugs that target the enzymatic function of NA have been shown to reduce virus load (Moscona A. 2005. Neuraminidase inhibitors for influenza. N Engl J Med 353: 1363-73; Gubareva L V, Kaiser L, Hayden F G. 2000. Influenza virus neuraminidase inhibitors. Lancet 355:827-35). The influenza virus NA is also an excellent immune target as the NA harbors conserved epitopes (Chen Y Q, Wohlbold T J, Zheng N Y, Huang M, Huang Y, Neu K E, Lee J, Wan H, Rojas K T, Kirkpatrick E, Henry C, Palm A E, Stamper C T, Lan L Y, Topham D J, Treanor J, Wrammert J, Ahmed R, Eichelberger M C, Georgiou G, Krammer F, Wilson P C. 2018. Influenza Infection in Humans Induces Broadly Cross-Reactive and Protective Neuraminidase-Reactive Antibodies. Cell 173:417-429.e10; Wohlbold T J, Podolsky K A, Chromikova V, Kirkpatrick E, Falconieri V, Meade P, Amanat F, Tan J, tenOever B R, Tan G S, Subramaniam S, Palese P, Krammer F. 2017. Broadly protective murine monoclonal antibodies against influenza B virus target highly conserved neuraminidase epitopes. Nat Microbiol 2:1415-1424). Therefore, antibodies that inhibit neuraminidase activity and bind to the protein would likely be protective. Indeed, several studies have shown that N A-specific antibodies that are neuraminidase inhibitory (NAI) correlate with protection against influenza viruses in both animals and humans (Jacobsen H, Rajendran M, Choi A, Sjursen H, Brokstad K A, Cox R J, Palese P, Krammer F, Nachbagauer R. 2017. Influenza Virus Hemagglutinin Stalk-Specific Antibodies in Human Serum are a Surrogate Marker for In Vivo Protection in a Serum Transfer Mouse Challenge Model. MBio 8; Monto A S, Petrie J G, Cross R T, Johnson E, Liu M, Zhong W, Levine M, Katz J M, Ohmit S E. 2015. Antibody to Influenza Virus Neuraminidase: An Independent Correlate of Protection. J Infect Dis 212:1191-9; Kilbourne E D, Johansson B E, Grajower B. 1990. Independent and disparate evolution in nature of influenza A virus hemagglutinin and neuraminidase glycoproteins. Proc Natl Acad Sci USA 87:786-90; Couch R B, Atmar R L, Franco L M, Quarles J M, Wells J, Arden N, Nino D, Belmont J W. 2013. Antibody correlates and predictors of immunity to naturally occurring influenza in humans and the importance of antibody to the neuraminidase. J Infect Dis 207:974-81; Walz L, Kays S K, Zimmer G, von Messling V. 2018. Neuraminidase-Inhibiting Antibody Titers Correlate with Protection from Heterologous Influenza Virus Strains of the Same Neuraminidase Subtype. J Virol 92). Antibodies against NA have been shown to reduce viral shedding in infected individuals (Maier H E, Nachbagauer R, Kuan G, Ng S, Lopez R, Sanchez N, Stadlbauer D, Gresh L, Schiller A, Rajabhathor A, Ojeda S, Guglia A F, Amanat F, Balmaseda A, Krammer F, Gordon A. 2019. Pre-existing anti-neuraminidase antibodies are associated with shortened duration of influenza A (H1N1) pdm virus shedding and illness in naturally infected adults. Clin Infect Dis.) and guinea pigs (McMahon M, Kirkpatrick E, Stadlbauer D, Strohmeier S, Bouvier N M, Krammer F. 2019. Mucosal Immunity against Neuraminidase Prevents Influenza B Virus Transmission in Guinea Pigs. MBio 10). However, current inactivated influenza virus vaccines (IIVs) induce limited NA-specific antibody responses, while most of the immune response is against the HA. This is likely due to the lower immunogenicity of the NA compared to that of HA in the context of IIVs and the lack of standardization of the NA content during vaccine production (Wohlbold T J, Nachbagauer R, Xu H, Tan G S, Hirsh A, Brokstad K A, Cox R J, Palese P, Krammer F. 2015. Vaccination with Adjuvanted Recombinant Neuraminidase Induces Broad Heterologous, but Not Heterosubtypic, Cross-Protection against Influenza Virus Infection in Mice. MBio 6; Krammer F, Fouchier R A M, Eichelberger M C, Webby R J, Shaw-Saliba K, Wan H, Wilson P C, Compans R W, Skountzou I, Monto A S. 2018. NAction! How Can Neuraminidase-Based Immunity Contribute to Better Influenza Virus Vaccines? MBio 9). It was not clear whether the in-correctly folded monomeric NA could elicit protective antibody responses. But it is speculated that a correctly folded tetrameric NA is required, as anti-N1 or N2 titers have been observed to correlate with enzymatically active forms of the NAs in the vaccines (Krammer F, Fouchier R A M, Eichelberger M C, Webby R J, Shaw-Saliba K, Wan H, Wilson P C, Compans R W, Skountzou I, Monto A S. 2018. NAction! How Can Neuraminidase-Based Immunity Contribute to Better Influenza Virus Vaccines? MBio 9; Marcelin G, Sandbulte M R, Webby R J. 2012. Contribution of antibody production against neuraminidase to the protection afforded by influenza vaccines. Rev Med Virol 22:267-79).

Thus, there is a need for therapies to prevent and treat influenza virus infections and influenza virus diseases.

3. SUMMARY

In one aspect, provided herein is are recombinant neuraminidases comprising a mutated influenza virus neuraminidase ectodomain, wherein the mutated ectodomain comprises an influenza virus neuraminidase ectodomain comprising one, two or more amino acid substitutions to cysteine at one, two or more amino acid residues found in the stalk domain of the ectodomain. In one embodiment, provided herein is a recombinant neuraminidase comprising a mutated influenza virus neuraminidase ectodomain, wherein the mutated ectodomain comprises an influenza virus neuraminidase ectodomain comprising an amino acid substitution to cysteine at amino acid residue 48 or 50 of an N1 subtype or at an amino acid residue corresponding to amino acid residue 48 or 50 of influenza virus A/Puerto Rico/08/1934. In another embodiment, provided herein is a recombinant neuraminidase comprising a mutated influenza virus neuraminidase ectodomain, wherein the mutated ectodomain comprises an influenza virus neuraminidase ectodomain comprising amino acid substitutions to cysteine at amino acid residues 48 and 50 of an N1 subtype or at amino acid residues corresponding to amino acid residues 48 and 50 of influenza virus A/Puerto Rico/08/1934. In certain embodiments, the influenza virus neuraminidase ectodomain is of subtype N1 or N2. In other embodiments, the influenza virus neuraminidase ectodomain is of subtype N3, N4, N5, N6, N7, N8 or N9 subtype. In some embodiments, the recombinant neuraminidase further comprises the influenza virus neuraminidase transmembrane and cytoplasmic domains. In other embodiments, the recombinant neuraminidase further comprises a tetramerization domain. In a specific embodiment, the tetramerization domain comprises a measles virus phosphoprotein tetramerization domain or a Sendai virus phosphoprotein tetramerization domain.

In another embodiment, provided herein is a recombinant neuraminidase comprising a mutated influenza virus neuraminidase ectodomain, wherein the mutated ectodomain comprises an influenza virus neuraminidase ectodomain comprising an amino acid substitution to cysteine at amino acid residue 61 of an N1 subtype or at an amino acid residue corresponding to amino acid residue 61 of influenza virus A/Puerto Rico/08/1934. In some embodiments, the mutated influenza virus neuraminidase ectodomain further comprises an amino acid substitution to a cysteine at amino acid residue 48 of an N1 subtype or at an amino acid residue corresponding to amino acid residue 48 of influenza virus A/Puerto Rico/08/1934. In certain embodiments, the influenza virus neuraminidase ectodomain is of subtype N1 or N2. In other embodiments, the influenza virus neuraminidase ectodomain is of subtype N3, N4, N5, N6, N7, N8 or N9 subtype. In some embodiments, the recombinant neuraminidase further comprises the influenza virus neuraminidase transmembrane and cytoplasmic domains. In other embodiments, the recombinant neuraminidase further comprises a tetramerization domain. In a specific embodiment, the tetramerization domain comprises a measles virus phosphoprotein tetramerization domain or a Sendai virus phosphoprotein tetramerization domain.

In another embodiment, provided herein is a recombinant neuraminidase comprising a mutated influenza virus neuraminidase ectodomain and a tetramerization domain, wherein the mutated ectodomain comprises an influenza virus neuraminidase ectodomain comprising an amino acid substitution to a cysteine at amino acid residue 48 of an N1 subtype or at an amino acid residue corresponding to amino acid residue 48 of influenza virus A/Puerto Rico/08/1934. In certain embodiments, the tetramerization domain comprises a measles virus phosphoprotein tetramerization domain or a Sendai virus phosphoprotein tetramerization domain. In certain embodiments, the influenza virus neuraminidase ectodomain is of subtype N1 or N2. In other embodiments, the influenza virus neuraminidase ectodomain is of subtype N3, N4, N5, N6, N7, N8 or N9 subtype.

In another embodiment, provided herein is a recombinant neuraminidase comprising a mutated influenza virus neuraminidase ectodomain, wherein the mutated ectodomain comprises an influenza virus neuraminidase ectodomain comprising an amino acid substitution to cysteine at amino acid residue 52 of an N2 subtype or at an amino acid residue corresponding to amino acid residue 52 of influenza virus A/Hong Kong/4801/2014, wherein the ectodomain is from an influenza A virus N2, N3, N4, N5, N6, N7, N8 or N9 subtype. In certain embodiments, the mutated ectodomain further comprises an amino acid substitution to cysteine at amino acid residue 54 of an N2 subtype or at amino acid residue corresponding to amino acid residue 54 of A/Hong Kong/4801/2014. In another embodiment, provided herein is a recombinant neuraminidase comprising a mutated influenza virus neuraminidase ectodomain, wherein the mutated ectodomain comprises an influenza virus neuraminidase ectodomain comprising an amino acid substitution to cysteine at amino acid residue 54 of an N2 subtype or at an amino acid residue corresponding to amino acid residue 54 of A/Hong Kong/4801/2014, wherein the ectodomain is from an influenza A virus N2, N3, N4, N5, N6, N7, N8 or N9 subtype. In some embodiments, the recombinant neuraminidase further comprises the influenza virus neuraminidase transmembrane and cytoplasmic domains. In other embodiments, the recombinant neuraminidase further comprises a tetramerization domain. In a specific embodiment, the tetramerization domain comprises a measles virus phosphoprotein tetramerization domain or a Sendai virus phosphoprotein tetramerization domain.

In another aspect, provided herein is a recombinant neuraminidase comprising an influenza virus neuraminidase globular head domain and a tetramerization domain, wherein the recombinant neuraminidase lacks all or a portion of the influenza virus neuraminidase stalk (e.g., 25, 30, 35, 40, 45, 50, 55, 60 or more amino acid residues of the influenza neuraminidase stalk, or 25-50, 30-50, 40-50, 30-60, 40-60 or 50-60 amino acid residues of the influenza neuraminidase stalk), the transmembrane domain and the cytoplasmic domain. In one embodiment, the tetramerization domain comprises a paramyxovirus protein tetramerization domain. In specific embodiments, the paramyxovirus protein tetramerization domain is a tetramerization domain of a paramyxovirus phosphoprotein (e.g., a Nipah virus phosphoprotein, a Hendra virus phosphoprotein, a respiratory syncytial virus phosphoprotein, human parainfluenza virus (hPIV) phosphoprotein, bovine parainfluenza virus phosphoprotein, a mumps virus phosphoprotein, a Cedar virus phosphoprotein, a Ghana virus phosphoprotein, a Newcastle disease virus phosphoprotein, a canine distemper virus phosphoprotein, or a Peste des petits ruminants virus (PPRV) phosphoprotein). In another embodiment, provided herein is a recombinant neuraminidase comprising an influenza virus neuraminidase globular head domain and a tetramerization domain, wherein the recombinant neuraminidase lacks all or a portion of the influenza virus neuraminidase stalk (e.g., 25, 30, 35, 40, 45, 50, 55, 60 or more amino acid residues of the influenza neuraminidase stalk, or 25-50, 30-50, 40-50, 30-60, 40-60 or 50-60 amino acid residues of the influenza neuraminidase stalk), the transmembrane domain and the cytoplasmic domain, and wherein the tetramerization domain comprises a measles virus phosphoprotein tetramerization domain or a Sendai virus phosphoprotein tetramerization domain. In certain embodiments, the influenza virus neuraminidase ectodomain is of subtype N1 or N2. In other embodiments, the influenza virus neuraminidase ectodomain is of subtype N3, N4, N5, N6, N7, N8 or N9 subtype.

In another aspect, provided herein is a recombinant neuraminidase comprising an influenza virus neuraminidase globular head domain and a tetramerization domain, wherein the recombinant neuraminidase lacks influenza virus neuraminidase stalk, transmembrane and cytoplasmic domains. In one embodiment, the tetramerization domain comprises a paramyxovirus phosphoprotein tetramerization domain. In another embodiment, provided herein is a recombinant neuraminidase comprising an influenza virus neuraminidase globular head domain and a paramyxovirus protein tetramerization domain (e.g., a paramyxovirus protein tetramerization domain), wherein the recombinant neuraminidase lacks of influenza virus neuraminidase stalk domain, transmembrane domain and cytoplasmic domain. In specific embodiments, the paramyxovirus phosphoprotein is a Nipah virus phosphoprotein, a Hendra virus phosphoprotein, a respiratory syncytial virus phosphoprotein, human parainfluenza virus (hPIV) phosphoprotein, bovine parainfluenza virus phosphoprotein, a mumps virus phosphoprotein, a Cedar virus phosphoprotein, a Ghana virus phosphoprotein, a Newcastle disease virus phosphoprotein, a canine distemper virus phosphoprotein, or a Peste des petits ruminants virus (PPRV) phosphoprotein. In another embodiment, provided herein is a recombinant neuraminidase comprising an influenza virus neuraminidase globular head domain and a tetramerization domain, wherein the recombinant neuraminidase lacks of influenza virus neuraminidase stalk domain, transmembrane domain and cytoplasmic domain, and wherein the tetramerization domain comprises a measles virus phosphoprotein tetramerization domain or a Sendai virus phosphoprotein tetramerization domain. In certain embodiments, the influenza virus neuraminidase ectodomain is of subtype N1 or N2. In other embodiments, the influenza virus neuraminidase ectodomain is of subtype N3, N4, N5, N6, N7, N8 or N9 subtype.

In certain embodiments, a recombinant neuraminidase described herein comprises a signal peptide. In some embodiments, a recombinant neuraminidase described herein comprises a histidine tag, a Flag tag, or other purification tag. In certain embodiments, a recombinant neuraminidase described herein comprises a cleavage site, such as described in, e.g., Section 6, infra. In some embodiments, a recombinant neuraminidase described herein comprises a cleavage site, such as described in, e.g., Section 6, infra and a histidine tag, a Flag tag, or other purification tag. In specific embodiments, a recombinant neuraminidase described herein is isolated.

In certain embodiments, provided herein is a recombinant neuraminidase comprising the amino acid sequence of SEQ ID NO: 27, 56, 58, 60 or 62. In a specific embodiment, a recombinant neuraminidase comprises the amino acid sequence of SEQ ID NO: 27, 56 or 58.

In another aspect, provided herein is a nucleic acid sequence comprising a nucleotide sequence encoding a recombinant neuraminidase described herein. In a specific embodiment, the nucleic acid sequence is isolated.

In certain embodiments, provided herein is a nucleic acid sequence comprising the nucleotide sequence of SEQ ID NO: 55, 57, 59, or 61. In a specific embodiment, a nucleic acid sequence provided herein comprises the nucleic acid sequence comprises the nucleotide sequence of SEQ ID NO: 55 or 57.

In another aspect, provided herein is an expression vector comprising a nucleic acid sequence that comprises a nucleotide sequence encoding a recombinant neuraminidase described herein. In a specific embodiment, the expression vector facilitates expression of the recombinant neuraminidase in a suitable substrate.

In certain embodiments, provided herein is an expression vector comprising a nucleic acid sequence, wherein the nucleic acid sequence comprises the nucleotide sequence of SEQ ID NO: 55, 57, 59, or 61. In a specific embodiment, provided herein is an expression vector comprising a nucleic acid sequence, wherein the nucleic acid sequence comprises the nucleotide sequence of SEQ ID NO: 55 or 57.

In another aspect, provided herein are host cells capable of expressing a nucleic acid sequence comprising a nucleotide sequence encoding a recombinant neuraminidase described herein. In a specific embodiment, provided herein is a host cell expressing the nucleic acid sequence comprising a nucleotide sequence encoding a recombinant neuraminidase described herein.

In another aspect, provided herein is a recombinant influenza virus comprising a recombinant neuraminidase described herein. In one embodiment, provided herein is a recombinant influenza virus comprising a genome, wherein the genome comprises a gene segment comprising a nucleic acid sequence encoding the recombinant neuraminidase described herein such that the recombinant neuraminidase is expressed by a cell infected with the recombinant influenza virus. In another embodiment, provided herein is a recombinant influenza virus comprising a neuraminidase, wherein the neuraminidase comprises a mutated influenza virus neuraminidase ectodomain, wherein the mutated ectodomain comprises an influenza virus neuraminidase ectodomain comprising an amino acid substitution to cysteine at amino acid residue 48 of an N1 subtype or at an amino acid residue corresponding to amino acid residue 48 of influenza virus A/Puerto Rico/08/1934. In another aspect, provided herein is a recombinant influenza virus comprising a genome, wherein the genome comprises a gene segment comprising a nucleotide sequence encoding a neuraminidase such that the neuraminidase is expressed by an infected cell, wherein the neuraminidase comprises a mutated influenza virus neuraminidase ectodomain, wherein the mutated ectodomain comprises an influenza virus neuraminidase ectodomain comprising an amino acid substitution to cysteine at amino acid residue 48 of an N1 subtype or at amino acid residue corresponding to amino acid residue 48 of influenza virus A/Puerto Rico/08/1934. In certain embodiments, a recombinant influenza virus described herein is inactivated. In specific embodiments, a recombinant influenza virus described herein is split. In other embodiments, a recombinant influenza virus described herein is a live attenuated influenza virus. In some embodiments, a recombinant influenza virus described herein is a recombinant influenza A virus. In a specific embodiment, a recombinant influenza virus described herein is an H1 or H3 subtype. In other embodiments, a recombinant influenza virus described herein is an influenza B virus.

In another aspect, provided herein is an immunogenic composition comprising the neuraminidase described herein. In some embodiments, the immunogenic composition further comprises a trivalent inactivated influenza vaccine (TIV), quadrivalent inactivated influenza virus vaccine (QIV), or recombinant influenza virus vaccine. In some embodiments, the immunogenic composition further comprises an adjuvant.

In another aspect, provided herein is an immunogenic composition comprising a nucleic acid sequence that comprises a nucleotide sequence encoding a recombinant neuraminidase described herein. In some embodiments, the immunogenic composition further comprises an adjuvant.

In another aspect, provided herein is an immunogenic composition comprising the recombinant influenza virus described herein. In some embodiments, the immunogenic composition further comprises an adjuvant.

In another aspect, provided herein is a method of immunizing against influenza virus, comprising administering a subject a dose of the immunogenic composition described herein. In another aspect, provided herein is a method of inducing an immune response against influenza virus, comprising administering a subject a dose of the immunogenic composition described herein. In some embodiments, the subject is administered a further dose of the immunogenic composition as a boost. In a specific embodiment, the subject is human. In another specific embodiment, the immunogenic composition is administered intramuscularly to the subject.

3.1 Terminology

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. In a specific embodiment, the nucleic acid may be self-replicating RNA.

As used herein, the terms "purified" and "isolated" when used in the context of a polypeptide (including an antibody) that is obtained from a natural source, e.g., cells, refers to a polypeptide which is substantially free of contaminating materials from the natural source, e.g., minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including an antibody) that is chemically synthesized refers to a polypeptide which is substantially free of chemical precursors or other chemicals which are involved in the syntheses of the polypeptide. In a specific embodiment, a recombinant influenza virus NA is chemically synthesized. In another specific embodiment, a recombinant influenza virus NA is isolated.

As used herein, terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

As used herein, the term "premature human infant" refers to a human infant born at less than 37 weeks of gestational age.

As used herein, the term "seasonal influenza virus strain" refers to a strain of influenza virus to which a subject population is exposed to on a seasonal basis. In specific embodiments, the term seasonal influenza virus strain refers to a strain of influenza A virus. In specific embodiments, the term seasonal influenza virus strain refers to a strain of influenza virus that belongs to the H1 or the H3 subtype, i.e., the two subtypes that presently persist in the human subject population. In other embodiments, the term seasonal influenza virus strain refers to a strain of influenza B virus.

The terms "tertiary structure" and "quaternary structure" have the meanings understood by those of skill in the art. Tertiary structure refers to the three-dimensional structure of a single polypeptide chain. Quaternary structure refers to the three dimensional structure of a polypeptide having multiple polypeptide chains.

As used herein, in some embodiments, the phrase "wild-type" in the context of a viral polypeptide refers to a viral polypeptide that is found in nature and is associated with a naturally occurring virus.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. DESCRIPTION OF THE FIGURES

FIGS. 1A-1C. Reducing (FIG. 1A), non-reducing (FIG. 1B) and cross-linked (FIG. 1C) SDS-PAGE of measles virus phosphoprotein (MPP-N1) or the Sendai virus phosphoprotein (SPP-N1) tetramerization domain fused to N1 as well as a SEPPALLATA-like MADS domain transcription factor from Arabidopsis tetramerization domain fused to N1 (SMDTF-N1). VASP-N1 serves as positive control. MPP-N1, SPP-N1 and VASP-N1 are maintained as tetramers when cross-linked.

FIG. 2. NA activity of constructs with the measles virus phosphoprotein (MPP-N1) or the Sendai virus phosphoprotein (SPP-N1) tetramerization domain fused to N1. VASP-N1 serves as positive control, and irrelevant FIG. 3. Human NI active antibodies, including pan-NA mAb 1G01, recognize MPP-1 in an ELISA on Ni-NTA plates.

FIG. 4. Protective effect of the measles virus phosphoprotein (MPP-N1) or the Sendai virus phosphoprotein (SPP-N1) tetramerization domain fused to N1 as vaccine in the mouse model. VASP-N1 serves as positive control, and irrelevant proteins served as negative control. % in parentheses indicates survival.

FIG. 5. NA activity of different NA-stalk cysteine mutants in an NA-Star assay. Area under the curve is shown as quantification of the activity.

FIGS. 6A-6B. NA contents of inactivated purified PR8 H1N1 viruses. (FIG. 6A) NA contents of inactivated purified viruses expressing WT, I48C, N50C, I48C_N50C, W61 insertC or V62 insertC NA were examined by western blot. (FIG. 6B) A combination of I48C with W61 insertC results in more tetrameric and less trimeric contents of NA than other mutants. NA contents of inactivated purified viruses expressing WT, I48C, I48C_N50C, I48C W61 insert C NA were examined by western blot. The viral proteins in A and B were resolved on 10% SDS-PAGE. NR: non-reducing; R: reducing FIG. 7. Amino acid sequence alignment of PR8 N1 and HK14 N2 (N1, aa 1-102 (SEQ ID NO:53); N2, aa 1-117 (SEQ ID NO:54)) to identify corresponding residues for cysteine substitutions in HK14 N2. The natural cysteines in N1 (C49) and N2 (C53) are boxed.

FIGS. 8A-8B. NA contents and NA activity of inactivated purified HK14 H3N2 viruses. (FIG. 8A) NA contents of WT, L52C and L52C_E54C viruses were examined by western blot. The viral proteins were resolved on 8%-16% SDS-PAGE. (FIG. 8B) NA activity of virus preparations. A NA-fluor neuraminidase activity assay was used to measure potential NA activity from 5 ng of each virus.

FIGS. 9A-9D. Alignment of the neuraminidases of the following influenza viruses A/PR/8/34 (N1 PR8; SEQ ID NO:29), A/Michigan/45/15 (N1_Mich15; SEQ ID NO:30), A/WSN/33 (N1_WSN; SEQ ID NO:31), A/Hong Kong/4801/14 (N2_HK14; SEQ ID NO:32), A/chicken/Bangladesh/19870/13 (N2_ck; SEQ ID NO:33), A/swine/Missouri/4296424/06A (N3_sw; SEQ ID NO:34), A/blue-winged teal/Guatemala/CIP049H113-74/13 (N3_bwt; SEQ ID NO:35), A/duck/Jiangxi/22676/13 (N3_duck; SEQ ID NO:36), A/duck/Hokkaido/222/14 (N4_duck; SEQ ID NO:37), A/ruddy turnstone/Delaware/AI03-378/03 (N4_rt; SEQ ID NO:38), A/American wigeon/California/HS007B/15 (N5_aw; SEQ ID NO:39), A/migratory duck/Jiangxi/6847/03 (N5_md; SEQ ID NO:40), A/Shenzhen/1/16 (N6_Sz; SEQ ID NO:41), A/Caspian seal/Russia/T1/12 (N6_cs; SEQ ID NO:42), A/chicken/Netherlands/1/03 (N7_cN; SEQ ID NO:43), A/chicken/Germany/R28/03 (N7_cG; SEQ ID NO:44), A/chicken/Netherlands/14015531/14 (N8_cN; SEQ ID NO:45), A/chicken/Laos/A0573/07 (N8_cL; SEQ ID NO:46), A/Anhui/2/13 (N9_AH13; SEQ ID NO:47), A/chicken/Dongguan/1143/14 (N9_ck; SEQ ID NO:48), and B/Malaysia/2506/04 (B_Mal; SEQ ID NO:49). C49 is shown in bold and underlined for N1_PR8.

FIG. 10. This figure depicts the immunization protocol administered to a female 6-8 week old BALB/c mice. In particular, recombinant N1-MPP (SEQ ID NO:27) was tested as a vaccine in a mouse model. The table in the figure lists the antigen administered for the various groups. Group 1 received recombinant N1-MPP at a 3 μg dose intramuscularly twice in a three week interval. Group 2 received the same antigen but mixed with the adjuvant AddaVax (see the depiction in the figure with the mice). Group 3 received recombinant N1-MPP admixed to a 1 μg dose (based on H1 HA) of a current seasonal quadrivalent influenza virus vaccine (QIV, brand: Flucelvax) twice. Group 4 received recombinant N1-MPP in one leg and the QIV in the second leg based on the assumption that mixing NA and QIV could render the NA immunosubdominant. Group 5 received QIV twice and group 6 received an irrelevant recombinant protein as negative control. Animals were bled after the prime and after the boost. Four weeks post boost, animals were challenged with 25× or 400×LD$_{50}$ of A/Singapore/GP1908/2015 IVR-180 (H1N1).

FIGS. 11A-11C. FIG. 11A depicts the results from an ELISA measuring the binding of sera from mice immunized in accordance with the protocol provided in the legend for FIG. 10 for groups 1 to 6 to recombinant N1-VASP, which comprises the globular head domain of influenza virus A/Michigan/45/15 NA and the human VASP tetramerization domain. FIG. 11B depicts the results from an ELISA measuring the binding of sera from mice immunized in accordance with the protocol provided in the legend for FIG. 10 for groups 1 to 6 to recombinant H1. FIG. 11C depicts the results from functional neuraminidase inhibition assays. In particular, the ability of sera from mice immunized in accordance with the protocol provided in the legend for FIG. 10 for groups 1 to 6 to inhibit the neuraminidase function of an H7N1 re-assortant virus that contains a matched N1 NA (influenza virus A/Michigan/45/15 NA), an H7 HA and PR8 sequences.

FIGS. 12A-12B. FIG. 12A depicts the weight loss of mice in groups 1 to 6 immunized as described in the legend for FIG. 10 and challenged as described in the legend for FIG. 10 with 25×LD$_{50}$ of A/Singapore/GP1908/2015 IVR-180 (H1N1). FIG. 12B depicts the survival of mice in groups 1 to 6 immunized as described in the legend for FIG. 10 and challenged as described in the legend for FIG. 10 with 25×LD$_{50}$ of A/Singapore/GP1908/2015 IVR-180 (H1N1).

FIGS. 13A-13B. FIG. 13A depicts the weight loss of mice in groups 2, 4, 5 and 6 immunized as described in the legend for FIG. 10 and challenged as described in the legend for FIG. 10 with 400×LD$_{50}$ of A/Singapore/GP1908/2015 IVR-180 (H1N1). FIG. 12B depicts the survival of mice in groups 2, 4, 5 and 6 immunized as described in the legend for FIG.

10 and challenged as described in the legend for FIG. 10 with 400×LD$_{50}$ of A/Singapore/GP1908/2015 IVR-180 (H1N1).

FIGS. 14A-14E. Recombinant N2-MPP (comprising the MPP tetramerization domain and globular head domain of influenza virus A/Kansas/14/2017 (H3N2) N2; SEQ ID NO:60) and recombinant B-MPP (comprising the MPP tetramerization domain and globular head domain of influenza virus B/Colorado/06/2017 NA; SEQ ID NO: 62). FIG. 14A shows the reactivity of broadly reactive anti-influenza B virus NA monoclonal antibodies to recombinant B-MPP. FIG. 14B shows the reactivity of broadly reactive anti-influenza A virus N2 NA monoclonal antibodies to recombinant N2-MPP. FIG. 14C shows the NA activity of recombinant N1-MPP (SEQ ID NO: 27), recombinant N2-MPP (SEQ ID NO:60), and recombinant B-MPP (SEQ ID NO:62) in an NA-star assay. FIG. 14D shows recombinant N1-MPP (SEQ ID NO: 27), recombinant N2-MPP (SEQ ID NO:60), and recombinant B-MPP (SEQ ID NO:62) in a reducing SDS-PAGE. FIG. 14E shows recombinant N1-MPP (SEQ ID NO: 27), recombinant N2-MPP (SEQ ID NO:60), and recombinant B-MPP (SEQ ID NO:62) in a cross-linking SDS-PAGE.

FIG. 15. This figure provides the immunization regimen used to immunize mice with recombinant N1-MPP, recombinant N2-MPP, or recombinant B-MPP. With respect to the study of each of the three recombinant NA proteins (recombinant N1-MPP, recombinant N2-MPP, and recombinant B-MPP), three groups of mice were immunized. Mice in groups 1 and 2 were vaccinated with 3 μg of recombinant NA protein (recombinant N1-MPP, recombinant N2-MPP, or recombinant B-MPP, as indicated) intramuscularly twice in a three week interval. For one group, the recombinant NA was always given unadjuvanted, for the second group adjuvanted with AddaVax. A third group received irrelevant recombinant protein as a negative control. Three weeks after the boost the animals were challenged with 25×LD$_{50}$ of the specified challenge viruses.

FIGS. 16A-16D. FIG. 16A depicts the weight loss of mice vaccinated with N1-MPP as described in the legend for FIG. 15 and challenged as described in the legend for FIG. 15 with 25×LD$_{50}$ of A/Singapore/GP1908/2015 (H1N1). FIG. 16B depicts the survival of mice vaccinated with N1-MPP as described in the legend for FIG. 15 and challenged as described in the legend for FIG. 15 with 25×LD$_{50}$ of A/Singapore/GP1908/2015 (H1N1). FIG. 16C depicts the results from an ELISA measuring the binding of sera from mice immunized in accordance with the protocol provided in FIG. 15 and the legend for FIG. 15 for groups 1 to 3 to recombinant N1-VASP (which comprises the globular head domain of influenza virus A/Michigan/45/15 NA and the human VASP tetramerization domain). FIG. 16D depicts the results from functional neuraminidase inhibition assays. In particular, the ability of sera from mice vaccinated with N1-MPP as described in the legend for FIG. 15 to inhibit the neuraminidase function of an H7N1 re-assortant virus that contains a matched N1 NA was assessed.

FIG. 17A-17C. FIG. 17A depicts the weight loss of mice vaccinated with N2-MPP as described in the legend for FIG. 15 and challenged as described in the legend for FIG. 15 with 25×LD$_{50}$ of A/Switzerland/9715293/2013 (H3N2, mouse adapted). FIG. 17B depicts the survival of mice vaccinated with N2-MPP as described in the legend for FIG. 15 and challenged as described in the legend for FIG. 15 with 25×LD$_{50}$ of A/Switzerland/9715293/2013 (H3N2, mouse adapted). FIG. 17C depicts the results from an ELISA measuring the binding of sera from mice immunized in accordance with the protocol provided in FIG. 15 and the legend for FIG. 15 for groups 1 to 3 to recombinant N2-VASP (which comprises the globular head domain of influenza virus A/Kansas/14/2017 NA and the human VASP tetramerization domain).

FIGS. 18A-18C. FIG. 18A depicts the weight loss of mice vaccinated with B-MPP as described in the legend for FIG. 15 and challenged as described in the legend for FIG. 15 with $25 \times LD_{50}$ of B/New York/PV01181/2018. FIG. 18B depicts the survival of mice vaccinated with B-MPP as described in the legend for FIG. 15 and challenged as described in the legend for FIG. 15 with $25 \times LD_{50}$ of B/New York/PV01181/2018. FIG. 18C depicts the results from an ELISA measuring the binding of sera from mice immunized in accordance with the protocol provided in FIG. 15 and the legend for FIG. 15 for groups 1 to 3 to recombinant B-VASP (which comprises the globular head domain of influenza virus B/Colorado/06/2017 NA and the human VASP tetramerization domain).

4.1 SEQUENCE INFORMATION

| SEQ ID NO. | NAME | SEQUENCE |
|---|---|---|
| 1 | Tetramerization domain from SEPPALLATA-like MADS domain transcription factor from *Arabidopsis thaliana* (SMDTF) | VELSSQQEYLKLKERYDALQRTQRNLLGEDLGPLSTKE LESLERQLDSSLKQIRALRTQFMLDQSKERMLTETNKT LRLRLADGY |
| 2 | Sendai virus phosphoprotein tetramerization domain (SPP) | ENTSSMKEMATLLTSLGVIQSAQEFESSRDASYVFARR ALKSANYAEMTFNVCGLILSAEKSSARKVDENKQLLKI QESVESFRDIYKRFSEYQKEQNSLLMSNLSTLHIITD |
| 3 | PiLZ structure from *Xhantomonas campestris* | LLVQRMDAKLDLILALIGRLVRQS |
| 4 | Measles virus phosphoprotein tetramerization domain (MPP) | GDHYDDELFSDVQDIKTALAKIHEDNQKIISKLESLLLL KGEVESIKKQFNRQNISISTLEGHLSSIMIAIPGL |
| 5 | *Dictyocaulus viviparus* ACE tetramerization domain | AVADVGDPFLLWKQQMDKWQNEYITDWQYHFEQYK KYQTYRHLDSDSCSGS |
| 6 | PR8 N1 Wild-type | MNPNQKITTIGSICLVVGLISLILQIGNIISIWISHSIQTGS QNHTGICNQNIITYKNSTWVKDTTSVILTGNSSLCPIRG WAIYSKDNSIRIGSKGDVFVIREPFISCSHLECRTFFLTQ GALLNDKHSNGTVKDRSPYRALMSCPVGEAPSPYNSR FESVAWSASACHDGMGWLTIGISGPDNGAVAVLKYN GIITETIKSWRKKILRTQESECACVNGSCFTIMTDGPSD GLASYKIFKIEKGKVTKSIELNAPNSHYEECSCYPDTGK VMCVCRDNWHGSNRPWVSFDQNLDYQIGYICSGVFG DNPRPEDGTGSCGPVYVDGANGVKGFSYRYGNGVWI GRTKSHSSRHGFEMIWDPNGWTETDSKFSVRQDVVA MTDWSGYSGSFVQHPELTGLDCMRPCFWVELIRGRPK EKTIWTSASSISFCGVNSDTVDWSWPDGAELPFSIDK* |
| 7 | PR8 N1 I48C | MNPNQKITTIGSICLVVGLISLILQIGNIISIWISHSIQTGS QNHTGCCNQNIITYKNSTWVKDTTSVILTGNSSLCPIRG WAIYSKDNSIRIGSKGDVFVIREPFISCSHLECRTFFLTQ GALLNDKHSNGTVKDRSPYRALMSCPVGEAPSPYNSR FESVAWSASACHDGMGWLTIGISGPDNGAVAVLKYN GIITETIKSWRKKILRTQESECACVNGSCFTIMTDGPSD GLASYKIFKIEKGKVTKSIELNAPNSHYEECSCYPDTGK VMCVCRDNWHGSNRPWVSFDQNLDYQIGYICSGVFG DNPRPEDGTGSCGPVYVDGANGVKGFSYRYGNGVWI GRTKSHSSRHGFEMIWDPNGWTETDSKFSVRQDVVA MTDWSGYSGSFVQHPELTGLDCMRPCFWVELIRGRPK EKTIWTSASSISFCGVNSDTVDWSWPDGAELPFSIDK* |
| 8 | PR8 N1 N50C | MNPNQKITTIGSICLVVGLISLILQIGNIISIWISHSIQTGS QNHTGICCQNIITYKNSTWVKDTTSVILTGNSSLCPIRG WAIYSKDNSIRIGSKGDVFVIREPFISCSHLECRTFFLTQ GALLNDKHSNGTVKDRSPYRALMSCPVGEAPSPYNSR FESVAWSASACHDGMGWLTIGISGPDNGAVAVLKYN GIITETIKSWRKKILRTQESECACVNGSCFTIMTDGPSD |

| SEQ ID NO. | NAME | SEQUENCE |
|---|---|---|
| | | GLASYKIFKIEKGKVTKSIELNAPNSHYEECSCYPDTGK |
| | | VMCVCRDNWHGSNRPWVSFDQNLDYQIGYICSGVFG |
| | | DNPRPEDGTGSCGPVYVDGANGVKGFSYRYGNGVWI |
| | | GRTKSHSSRHGFEMIWDPNGWTETDSKFSVRQDVVA |
| | | MTDWSGYSGSFVQHPELTGLDCMRPCFWVELIRGRPK |
| | | EKTIWTSASSISFCGVNSDTVDWSWPDGAELPFSIDK* |
| 9 | PR8 N1 61insertC | MNPNQKITTIGSICLVVGLISLILQIGNIISIWISHSIQTGS |
| | | QNHTGICNQNIITYKNSTWCVKDTTSVILTGNSSLCPIR |
| | | GWAIYSKDNSIRIGSKGDVFVIREPFISCSHLECRTFFLT |
| | | QGALLNDKHSNGTVKDRSPYRALMSCPVGEAPSPYNS |
| | | RFESVAWSASACHDGMGWLTIGISGPDNGAVAVLKYN |
| | | GIITETIKSWRKKILRTQESECACVNGSCFTIMTDGPSD |
| | | GLASYKIFKIEKGKVTKSIELNAPNSHYEECSCYPDTGK |
| | | VMCVCRDNWHGSNRPWVSFDQNLDYQIGYICSGVFG |
| | | DNPRPEDGTGSCGPVYVDGANGVKGFSYRYGNGVWI |
| | | GRTKSHSSRHGFEMIWDPNGWTETDSKFSVRQDVVA |
| | | MTDWSGYSGSFVQHPELTGLDCMRPCFWVELIRGRPK |
| | | EKTIWTSASSISFCGVNSDTVDWSWPDGAELPFSIDK* |
| 10 | PR8N1 I48C_N50C | MNPNQKITTIGSICLVVGLISLILQIGNIISIWISHSIQTGS |
| | | QNHTGCCCQNIITYKNSTWVKDTTSVILTGNSSLCPIRG |
| | | WAIYSKDNSIRIGSKGDVFVIREPFISCSHLECRTFFLTQ |
| | | GALLNDKHSNGTVKDRSPYRALMSCPVGEAPSPYNSR |
| | | FESVAWSASACHDGMGWLTIGISGPDNGAVAVLKYN |
| | | GIITETIKSWRKKILRTQESECACVNGSCFTIMTDGPSD |
| | | GLASYKIFKIEKGKVTKSIELNAPNSHYEECSCYPDTGK |
| | | VMCVCRDNWHGSNRPWVSFDQNLDYQIGYICSGVFG |
| | | DNPRPEDGTGSCGPVYVDGANGVKGFSYRYGNGVWI |
| | | GRTKSHSSRHGFEMIWDPNGWTETDSKFSVRQDVVA |
| | | MTDWSGYSGSFVQHPELTGLDCMRPCFWVELIRGRPK |
| | | EKTIWTSASSISFCGVNSDTVDWSWPDGAELPFSIDK* |
| 11 | PR8N1 I48C_61insertC | MNPNQKITTIGSICLVVGLISLILQIGNIISIWISHSIQTGS |
| | | QNHTGCCNQNIITYKNSTWCVKDTTSVILTGNSSLCPIR |
| | | GWAIYSKDNSIRIGSKGDVFVIREPFISCSHLECRTFFLT |
| | | QGALLNDKHSNGTVKDRSPYRALMSCPVGEAPSPYNS |
| | | RFESVAWSASACHDGMGWLTIGISGPDNGAVAVLKYN |
| | | GIITETIKSWRKKILRTQESECACVNGSCFTIMTDGPSD |
| | | GLASYKIFKIEKGKVTKSIELNAPNSHYEECSCYPDTGK |
| | | VMCVCRDNWHGSNRPWVSFDQNLDYQIGYICSGVFG |
| | | DNPRPEDGTGSCGPVYVDGANGVKGFSYRYGNGVWI |
| | | GRTKSHSSRHGFEMIWDPNGWTETDSKFSVRQDVVA |
| | | MTDWSGYSGSFVQHPELTGLDCMRPCFWVELIRGRPK |
| | | EKTIWTSASSISFCGVNSDTVDWSWPDGAELPFSIDK* |
| 12 | HK14 N2 Wild-type | MNPNQKIITIGSVSLTISTICFFMQIAILITTVTLHFKQYE |
| | | FNSPPNNQVMLCEPTIIERNITEIVYLTNTTIEKEICPKPA |
| | | EYRNWSKPQCGITGFAPFSKDNSIRLSAGGDIWVTREP |
| | | YVSCDPDKCYQFALGQGTTLNNVHSNNTVRDRTPYRT |
| | | LLMNELGVPFHLGTKQVCIAWSSSSCHDGKAWLHVCI |
| | | TGDDKNATASFIYNGRLVDSVVSWSKDILRTQESECICI |
| | | NGTCTVVMTDGSASGKADTKILFIEEGKIVHTSTLSGSA |
| | | QHVEECSCYPRYPGVRCVCRDNWKGSNRPIVDINIKDH |
| | | SIVSSYVCSGLVGDTPRKNDSSSSSHCLDPNNEEGGHG |
| | | VKGWAFDDGNDVWMGRTINETSRLGYETFKVIEGWS |
| | | NPKSKLQTNRQVIVDRGDRSGYSGIFSVEGKSCINRCFY |
| | | VELIRGRKEETEVLWTSNSIVVFCGTSGTYGTGSWPDG |
| | | ADLNLMPI* |
| 13 | HK14 N2 L52C | MNPNQKIITIGSVSLTISTICFFMQIAILITTVTLHFKQYE |
| | | FNSPPNNQVMCCEPTIIERNITEIVYLTNTTIEKEICPKPA |
| | | EYRNWSKPQCGITGFAPFSKDNSIRLSAGGDIWVTREP |
| | | YVSCDPDKCYQFALGQGTTLNNVHSNNTVRDRTPYRT |
| | | LLMNELGVPFHLGTKQVCIAWSSSSCHDGKAWLHVCI |
| | | TGDDKNATASFIYNGRLVDSVVSWSKDILRTQESECICI |
| | | NGTCTVVMTDGSASGKADTKILFIEEGKIVHTSTLSGSA |
| | | QHVEECSCYPRYPGVRCVCRDNWKGSNRPIVDINIKDH |
| | | SIVSSYVCSGLVGDTPRKNDSSSSSHCLDPNNEEGGHG |
| | | VKGWAFDDGNDVWMGRTINETSRLGYETFKVIEGWS |
| | | NPKSKLQTNRQVIVDRGDRSGYSGIFSVEGKSCINRCFY |
| | | VELIRGRKEETEVLWTSNSIVVFCGTSGTYGTGSWPDG |
| | | ADLNLMPI* |

-continued

| SEQ ID NO. | NAME | SEQUENCE |
|---|---|---|
| 14 | HK14 N2 L52C_E54C | MNPNQKIITIGSVSLTISTICFFMQIAILITTVTLHFKQYE FNSPPNNQVMCCCPTIIERNITEIVYLTNTTIEKEICPKPA EYRNWSKPQCGITGFAPFSKDNSIRLSAGGDIWVTREP YVSCDPDKCYQFALGQGTTLNNVHSNNTVRDRTPYRT LLMNELGVPFHLGTKQVCIAWSSSSCHDGKAWLHVCI TGDDKNATASFIYNGRLVDSVVSWSKDILRTQESECICI NGTCTVVMTDGSASGKADTKILFIEEGKIVHTSTLSGSA QHVEECSCYPRYPGVRCVCRDNWKGSNRPIVDINIKDH SIVSSYVCSGLVGDTPRKNDSSSSSHCLDPNNEEGGHG VKGWAFDDGNDVWMGRTINETSRLGYETFKVIEGWS NPKSKLQTNRQVIVDRGDRSGYSGIFSVEGKSCINRCFY VELIRGRKEETEVLWTSNSIVVFCGTSGTYGTGSWPDG ADLNLMPI* |
| 15 | N1.2 | MLLVNQSHQGFNKEHTSKMVSAIVLYVLLAAAAHSAF AADPHHHHHHSLVPRGSPSRIETCNQSVITYENNTWVN QTYVNISNTNFAAGQSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWT SGSSISFCGVNSDTVGWSWPDGAELPFTIDK* |
| 16 | N1.3 (C49A-monomer) | MLLVNQSHQGFNKEHTSKMVSAIVLYVLLAAAAHSAF AADPHHHHHHSLVPRGSPSRIETANQSVITYENNTWVN QTYVNISNTNFAAGQSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWT SGSSISFCGVNSDTVGWSWPDGAELPFTIDK* |
| 17 | N1.4 (T48C) | MLLVNQSHQGFNKEHTSKMVSAIVLYVLLAAAAHSAF AADPHHHHHHSLVPRGSPSRIECCNQSVITYENNTWVN QTYVNISNTNFAAGQSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWTSGSSISFCGV NSDTVGWSWPDGAELPFTIDK* |
| 18 | N1.5 (N50C) | MLLVNQSHQGFNKEHTSKMVSAIVLYVLLAAAAHSAF AADPHHHHHHSLVPRGSPSRIETCCQSVITYENNTWVN QTYVNISNTNFAAGQSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWT SGSSISFCGVNSDTVGWSWPDGAELPFTIDK* |
| 19 | N1.6 (T48C + N50C) | MLLVNQSHQGFNKEHTSKMVSAIVLYVLLAAAAHSAF AADPHHHHHHSLVPRGSPSRIECCCQSVITYENNTWVN QTYVNISNTNFAAGQSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS |

-continued

| SEQ ID NO. | NAME | SEQUENCE |
|---|---|---|
| | | ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWTSGSSISFCGV NSDTVGWSWPDGAELPFTIDK* |
| 20 | N1.7(A76C) | MLLVNQSHQGFNKEHTSKMVSAIVLYVLLAAAAHSAF AADPHHHHHHSLVPRGSPSRIETCNQSVITYENNTWVN QTYVNISNTNFACGQSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWTSGSSISFCGV NSDTVGWSWPDGAELPFTIDK* |
| 21 | N1.8 (Q78C) | MLLVNQSHQGFNKEHTSKMVSAIVLYVLLAAAAHSAF AADPHHHHHHSLVPRGSPSRIETCNQSVITYENNTWVN QTYVNISNTNFAAGCSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWTSGSSISFCGV NSDTVGWSWPDGAELPFTIDK* |
| 22 | N1.9 (V81C) | MLLVNQSHQGFNKEHTSKMVSAIVLYVLLAAAAHSAF AADPHHHHHHSLVPRGSPSRIETCNQSVITYENNTWVN QTYVNISNTNFAAGQSVCSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWTSGSSISFCGV NSDTVGWSWPDGAELPFTIDK* |
| 23 | N1.11 (W61C) | MLLVNQSHQGFNKEHTSKMVSAIVLYVLLAAAAHSAF AADPHHHHHHSLVPRGSPSRIETCNQSVITYENNTCVN QTYVNISNTNFAAGQSVVSVKLAGNSSLCPVSGWAIYS KDNSVRIGSKGDVFVIREPFISCSPLECRTFFLTQGALLN DKHSNGTIKDRSPYRTLMSCPIGEVPSPYNSRFESVAWS ASACHDGINWLTIGISGPDSGAVAVLKYNGIITDTIKSW RNNILRTQESECACVNGSCFTIMTDGPSDGQASYKIFRI EKGKIIKSVEMKAPNYHYEECSCYPDSSEITCVCRDNW HGSNRPWVSFNQNLEYQMGYICSGVFGDNPRPNDKTG SCGPVSSNGANGVKGFSFKYGNGVWIGRTKSISSRKGF EMIWDPNGWTGTDNKFSIKQDIVGINEWSGYSGSFVQ HPELTGLDCIRPCFWVELIRGRPEENTIWTSGSSISFCGV NSDTVGWSWPDGAELPFTIDK* |
| 24 | SMDTF-N1 | MLLVNQSHQGFNKEHTSKMVSAIVLYVLLAAAAHSAF AADPHHHHHHVELSSQQEYLKLKERYDALQRTQRNLL GEDLGPLSTKELESLERQLDSSLKQIRALRTQFMLDQS KERMLTETNKTLRLRLADGYSLVPRGSPSRSVKLAGNS SLCPVSGWAIYSKDNSVRIGSKGDVFVIREPFISCSPLEC RTFFLTQGALLNDKHSNGTIKDRSPYRTLMSCPIGEVPS PYNSRFESVAWSASACHDGINWLTIGISGPDSGAVAVL KYNGIITDTIKSWRNNILRTQESECACVNGSCFTIMTDG PSDGQASYKIFRIEKGKIIKSVEMKAPNYHYEECSCYPD SSEITCVCRDNWHGSNRPWVSFNQNLEYQMGYICSGV FGDNPRPNDKTGSCGPVSSNGANGVKGFSFKYGNGV |

-continued

| SEQ ID NO. | NAME | SEQUENCE |
|---|---|---|
| | | WIGRTKSISSRKGFEMIWDPNGWTGTDNKFSIKQDIVGI<br>NEWSGYSGSFVQHPELTGLDCIRPCFWVELIRGRPEEN<br>TIWTSGSSISFCGVNSDTVGWSWPDGAELPFTIDK* |
| 25 | SPP-N1 | MLLVNQSHQGFNKEHTSKMVSAIVLYVLLAAAAHSAF<br>AADPHHHHHHENTSSMKEMATLLTSLGVIQSAQEFESS<br>RDASYVFARRALKSANYAEMTFNVCGLILSAEKSSAR<br>KVDENKQLLKIQESVESFRDIYKRFSEYQKEQNSLLMS<br>NLSTLHIITDSLVPRGSPSRSVKLAGNSSLCPVSGWAIYS<br>KDNSVRIGSKGDVFVIREPFISCSPLECRTFFLTQGALLN<br>DKHSNGTIKDRSPYRTLMSCPIGEVPSPYNSRFESVAWS<br>ASACHDGINWLTIGISGPDSGAVAVLKYNGIITDTIKSW<br>RNNILRTQESECACVNGSCFTIMTDGPSDGQASYKIFRI<br>EKGKIIKSVEMKAPNYHYEECSCYPDSSEITCVCRDNW<br>HGSNRPWVSFNQNLEYQMGYICSGVFGDNPRPNDKTG<br>SCGPVSSNGANGVKGFSFKYGNGVWIGRTKSISSRKGF<br>EMIWDPNGWTGTDNKFSIKQDIVGINEWSGYSGSFVQ<br>HPELTGLDCIRPCFWVELIRGRPEENTIWTSGSSISFCGV<br>NSDTVGWSWPDGAELPFTIDK* |
| 26 | PiLZ-N1 | MLLVNQSHQGFNKEHTSKMVSAIVLYVLLAAAAHSAF<br>AADPHHHHHHLLVQRMDAKLDLILALIGRLVRQSSLV<br>PRGSPSRSVKLAGNSSLCPVSGWAIYSKDNSVRIGSKG<br>DVFVIREPFISCSPLECRTFFLTQGALLNDKHSNGTIKDR<br>SPYRTLMSCPIGEVPSPYNSRFESVAWSASACHDGINW<br>LTIGISGPDSGAVAVLKYNGIITDTIKSWRNNILRTQESE<br>CACVNGSCFTIMTDGPSDGQASYKIFRIEKGKIIKSVEM<br>KAPNYHYEECSCYPDSSEITCVCRDNWHGSNRPWVSF<br>NQNLEYQMGYICSGVFGDNPRPNDKTGSCGPVSSNGA<br>NGVKGFSFKYGNGVWIGRTKSISSRKGFEMIWDPNGW<br>TGTDNKFSIKQDIVGFNEWSGYSGSFVQHPELTGLDCIR<br>PCFWVELIRGRPEENTIWTSGSSISFCGVNSDTVGWSW<br>PDGAELPFTIDK* |
| 27 | MPP-N1 | MLLVNQSHQGFNKEHTSKMVSAIVLYVLLAAAAHSAF<br>AADPHHHHHGDHYDDELFSDVQDIKTALAKIHEDNQ<br>KIISKLESLLLLKGEVESIKKQINRQNISISTLEGHLSSIMI<br>AIPGLSLVPRGSPSRSVKLAGNSSLCPVSGWAIYSKDNS<br>VRIGSKGDVFVIREPFISCSPLECRTFFLTQGALLNDKHS<br>NGTIKDRSPYRTLMSCPIGEVPSPYNSRFESVAWSASAC<br>HDGINWLTIGISGPDSGAVAVLKYNGIITDTIKSWRNNI<br>LRTQESECACVNGSCFTIMTDGPSDGQASYKIFRIEKGK<br>IIKSVEMKAPNYHYEECSCYPDSSEITCVCRDNWHGSN<br>RPWVSFNQNLEYQMGYICSGVFGDNPRPNDKTGSCGP<br>VSSNGANGVKGFSFKYGNGVWIGRTKSISSRKGFEMI<br>WDPNGWTGTDNKFSIKQDIVGINEWSGYSGSFVQHPE<br>LTGLDCIRPCFWVELIRGRPEENTIWTSGSSISFCGVNS<br>DTVGWSWPDGAELPFTIDK* |
| 28 | ACE-N1 | MLLVNQSHQGFNKEHTSKMVSAFVLYVLLAAAAHSAF<br>AADPHHHHHHAVADVGDPFLLWKQQMDKWQNEYIT<br>DWQYHFEQYKKYQTYRHLDSDSCSGSSLVPRGSPSRS<br>VKLAGNSSLCPVSGWAIYSKDNSVRIGSKGDVFVIREP<br>FISCSPLECRTFFLTQGALLNDKHSNGTIKDRSPYRTLM<br>SCPIGEVPSPYNSRFESVAWSASACHDGINWLTIGISGP<br>DSGAVAVLKYNGIITDTIKSWRNNILRTQESECACVNG<br>SCFTIMTDGPSDGQASYKIFRIEKGKIIKSVEMKAPNYH<br>YEECSCYPDSSEITCVCRDNWHGSNRPWVSFNQNLEY<br>QMGYICSGVFGDNPRPNDKTGSCGPVSSNGANGVKGF<br>SFKYGNGVWIGRTKSISSRKGFEMIWDPNGWTGTDNK<br>FSIKQDIVGINEWSGYSGSFVQHPELTGLDCIRPCFWVE<br>LIRGRPEENTIWTSGSSISFCGVNSDTVGWSWPDGAELP<br>FTIDK* |
| 29-49 | Influenza virus<br>neuraminidase of<br>different strains | See FIGS. 9A-9D |
| 50 | His tag | HHHHHH |
| 51 | Cleavage site | LVPRGSP |
| 52 | Cleavage site | ENLYFQX (X = G/S) |

-continued

| SEQ ID NO. | NAME | SEQUENCE |
|---|---|---|
| 53 | PR8N1 (aa 1-102) | MNPNQKITTIGSICLVVGLISLILQIGNIISIWISHSIQTGS QNHTGICNQNIITYKNSTWVKDTTSVILTGNSSLCPIRG WAIYSKDNSIRIGSKGDVFVI |
| 54 | HK14 N2 (aa 1-117) | MNPNQKIITIGSVSLTISTICFFMQIAILITTVTLHFKQYE FNSPPNNQVMLCEPTIIERNITEIVYLTNTTIEKEICPKPA EYRNWSKPQCGITGFAPFSKDNSIRLSAGGDIWVT |
| 55 | N1-MPP (with his tag) | atgctgctcgtcaaccaatcccaccagggcttcaacaaggaacacacttctaagatggt ctccgctatcgtgctctacgtgctgctcgctgccgctgcccactcagctttcgctgccga cccacaccaccaccaccaccacggcgatcactacgacgacgaactgttctccgacgt gcaggacatcaagaccgctctggctaagatccacgaggacaaccagaagatcatctc caagctggaatccctgctgctgctgaagggcgaagtcgagtccatcaagaagcagatc aaccgccagaacatctccatctccaccttggagggtcacctgtcctccatcatgatcgct atccctggcctgGGCGGCGGCTCCGTGAAATTAGCGGGCA ATTCCTCTCTCTGCCCTGTTAGTGGATGGGCTATATA CAGTAAAGACAACAGTGTAAGAATCGGTTCCAAGGG GGATGTGTTTGTCATAAGGGAACCATTCATATCATG CTCTCCCTTGGAATGCAGAACCTTCTTCTTGACTCAA GGGGCCTTGCTAAATGACAAACATTCCAATGGAACC ATTAAAGACAGGAGCCCATACCGAACCCTAATGAGC TGTCCTATTGGTGAAGTTCCCTCTCCATACAACTCAA GATTTGAGTCAGTCGCTTGGTCAGCAAGTGCTTGTCA TGATGGCATCAATTGGCTAACAATTGGAATTTCTGG CCCAGACAGTGGGGCAGTGGCTGTGTTAAAGTACAA TGGCATAATAACAGACACTATCAAGAGTTGGAGGAA CAATATATTGAGAACACAAGAGTCTGAATGTGCATG TGTAAATGGTTCTTGCTTTACCATAATGACCGATGGA CCAAGTGATGGACAGGCCTCATACAAAATCTTCAGA ATAGAAAAGGGAAAGATAATCAAATCAGTCGAAAT GAAAGCCCCTAATTATCACTATGAGGAATGCTCCTG TTACCCTGATTCTAGTGAAATCACATGTGTGTGCAGG GATAACTGGCATGGCTCGAATCGACCGTGGGTGTCT TTCAACCAGAATCTGGAATATCAGATGGGATACATA TGCAGTGGGGTTTTCGGAGACAATCCACGCCCTAAT GATAAGACAGGCAGTTGTGGTCCAGTATCGTCTAAT GGAGCAAATGGAGTAAAAGGATTTTCATTCAAATAC GGCAATGGTGTTTGGATAGGGAGAACTAAAAGCATT AGTTCAAGAAAAGGTTTTGAGATGATTTGGGATCCG AATGGATGGACTGGGACTGACAATAAATTCTCAATA AAGCAAGATATCGTAGGAATAAATGAGTGGTCAGG GTATAGCGGGAGTTTTGTTCAGCATCCAGAACTAAC AGGGCTGGATTGTATAAGACCTTGCTTCTGGGTTGA ACTAATAAGAGGGCGACCCGAAGAGAACACAATCT GGACTAGCGGGAGCAGCATATCCTTTTGTGGTGTAA ACAGTGACACTGTGGGTTGGTCTTGGCCAGACGGTG CTGAGTTGCCATTTACCATTGACAAGTAA |
| 56 | N1-MPP (with his tag) | MLLVNQSHQGFNKEHTSKMVSAIVLYVLLAAAAHSAF AADPHHHHHHGDHYDDELFSDVQDIKTALAKIHEDNQ KIISKLESLLLLKGEVESIKKQINRQNISISTLEGHLSSIMI AIPGLGGGSVKLAGNSSLCPVSGWAIYSKDNSVRIGSK GDVFVIREPFISCSPLECRTFFLTQGALLNDKHSNGTIKD RSPYRTLMSCPIGEVPSPYNSRFESVAWSASACHDGIN WLTIGISGPDSGAVAVLKYNGIITDTIKSWRNNILRTQE SECACVNGSCFTIMTDGPSDQOASYKIFRIEKGKIIKSVE MKAPNYHYEECSCYPDSSEITCVCRDNWHGSNRPWVS FNQNLEYQMGYICSGVFGDNPRPNDKTGSCGPVSSNG ANGVKGFSFKYGNGVWIGRTKSISSRKGFEMIWDPNG WTGTDNKFSIKQDIVGINEWSGYSGSFVQHPELTGLDC IRPCFWVELIRGRPEENTIWTSGSSISFCGVNSDTVGWS WPDGAELPFTIDK* |
| 57 | N1-MPP (no his tag) | atgctgctcgtcaaccaatcccaccagggcttcaacaaggaacacacttctaagatggt ctccgctatcgtgctctacgtgctgctcgctgccgctgcccactcagctttcgctgccga cccaggcgatcactacgacgacgaactgttctccgacgtgcaggacatcaagaccgct ctggctaagatccacgaggacaaccagaagatcatctccaagctggaatccctgctgc tgctgaagggcgaagtcgagtccatcaagaagcagatcaaccgccagaacatctccat ctccaccttggagggtcacctgtcctccatcatgatcgctatccctggcctgGGCGG CGGCTCCGTGAAATTAGCGGGCAATTCCTCTCTCTGC CCTGTTAGTGGATGGGCTATATACAGTAAAGACAAC AGTGTAAGAATCGGTTCCAAGGGGGATGTGTTTGTC ATAAGGGAACCATTCATATCATGCTCTCCCTTGGAAT GCAGAACCTTCTTCTTGACTCAAGGGGCCTTGCTAA ATGACAAACATTCCAATGGAACCATTAAAGACAGGA |

-continued

| SEQ ID NO. | NAME | SEQUENCE |
|---|---|---|
| | | GCCCATACCGAACCCTAATGAGCTGTCCTATTGGTG |
| | | AAGTTCCCTCTCCATACAACTCAAGATTTGAGTCAGT |
| | | CGCTTGGTCAGCAAGTGCTTGTCATGATGGCATCAA |
| | | TTGGCTAACAATTGGAATTTCTGGCCCAGACAGTGG |
| | | GGCAGTGGCTGTGTTAAAGTACAATGGCATAATAAC |
| | | AGACACTATCAAGAGTTGGAGGAACAATATATTGAG |
| | | AACACAAGAGTCTGAATGTGCATGTGTAAATGGTTC |
| | | TTGCTTTACCATAATGACCGATGGACCAAGTGATGG |
| | | ACAGGCCTCATACAAAATCTTCAGAATAGAAAAGGG |
| | | AAAGATAATCAAATCAGTCGAAATGAAAGCCCCTAA |
| | | TTATCACTATGAGGAATGCTCCTGTTACCCTGATTCT |
| | | AGTGAAATCACATGTGTGTGCAGGGATAACTGGCAT |
| | | GGCTCGAATCGACCGTGGGTGTCTTTCAACCAGAAT |
| | | CTGGAATATCAGATGGGATACATATGCAGTGGGGTT |
| | | TTCGGAGACAATCCACGCCCTAATGATAAGACAGGC |
| | | AGTTGTGGTCCAGTATCGTCTAATGGAGCAAATGGA |
| | | GTAAAAGGATTTTCATTCAAATACGGCAATGGTGTT |
| | | TGGATAGGGAGAACTAAAAGCATTAGTTCAAGAAA |
| | | AGGTTTTGAGATGATTTGGGATCCGAATGGATGGAC |
| | | TGGGACTGACAATAAATTCTCAATAAAGCAAGATAT |
| | | CGTAGGAATAAATGAGTGGTCAGGGTATAGCGGGA |
| | | GTTTTGTTCAGCATCCAGAACTAACAGGGCTGGATT |
| | | GTATAAGACCTTGCTTCTGGGTTGAACTAATAAGAG |
| | | GGCGACCCGAAGAGAACACAATCTGGACTAGCGGG |
| | | AGCAGCATATCCTTTTGTGGTGTAAACAGTGACACT |
| | | GTGGGTTGGTCTTGGCCAGACGGTGCTGAGTTGCCA |
| | | TTTACCATTGACAAGTAA |
| 58 | N1-MPP (no his tag) | MLLVNQSHQGFNKEHTSKMVSAIVLYVLLAAAAHSAF |
| | | AADPGDHYDDELFSDVQDIKTALAKIHEDNQKIISKLES |
| | | LLLLKGEVESIKKQINRQNISISTLEGHLSSIMIAIPGLGG |
| | | GSVKLAGNSSLCPVSGWAIYSKDNSVRIGSKGDVFVIR |
| | | <u>EPFISCSPLECRTFFLTQGALLNDKHSNGTIKDRSPYRTL</u> |
| | | <u>MSCPIGEVPSPYNSRFESVAWSASACHDGINWLTIGISG</u> |
| | | <u>PDSGAVAVLKYNGIITDTIKSWRNNILRTQESECACVN</u> |
| | | <u>GSCFTIMTDGPSDGQASYKIFRIEKGKIIKSVEMKAPNY</u> |
| | | <u>HYEECSCYPDSSEITCVCRDNWHGSNRPWVSFNQNLE</u> |
| | | <u>YQMGYICSGVFGDNPRPNDKTGSCGPVSSNGANGVKG</u> |
| | | <u>FSFKYGNGVWIGRTKSISSRKGFEMIWDPNGWTGTDN</u> |
| | | <u>KFSIKQDIVGINEWSGYSGSFVQHPELTGLDCIRPCFWV</u> |
| | | <u>ELIRGRPEENTIWTSGSSISFCGVNSDTVGWSWPDGAEL</u> |
| | | <u>PFTIDK</u>* |
| 59 | N2-MPP | atgctgctcgtcaaccaatcccaccagggcttcaacaaggaacacacttctaagatggt |
| | | ctccgctatcgtgctctacgtgctgctcgctgccgctgcccactcagctttcgctgccga |
| | | cccacaccaccaccaccacggcgatcactacgacgacgaactgttctccgacgt |
| | | gcaggacatcaagaccgctctggctaagatccacgaggacaaccagaagatcatctc |
| | | caagctggaatccctgctgctgctgaagggcgaagtcgagtccatcaagaagcagatc |
| | | aaccgccagaacatctccatctccaccttggagggtcacctgtcctccatcatgatcgct |
| | | atccctggcctgtctctcgtgcccaggggatcaccttctagaATATGCCCCAA |
| | | ACCAGCAGAATACAGAAATTGGTCAAAACCGCAATG |
| | | TGGCATTACAGGATTTGCACCTTTCTCTAAGGACAAT |
| | | TCGATTAGGCTTTCCGCTGGTGGGGACATCTGGGTG |
| | | ACAAGAGAACCTTATGTGTCATGCGATCCTGACAAG |
| | | TGTTATCAATTTGCCCTTGGACAGGGAACAACAATA |
| | | AACAACGTGCATTCAAATAACACAGCACGTGATAGG |
| | | ACCCCTCATCGGACTCTATTGATGAATGAGTTGGGT |
| | | GTTCCTTTCCATCTGGGGACCAAGCAAGTGTGCATA |
| | | GCATGGTCCAGCTCAAGTTGTCACGATGGAAAGCA |
| | | TGGCTGCATGTTTGTATAACGGGGGATGATAAAAAT |
| | | GCAACTGCTAGTTTCATTTACAATGGGAGGCTTGTA |
| | | GATAGTGTTGTTTCATGGTCCAAAGATATTCTCAGGA |
| | | CCCAGGAGTCAGAATGCGTTTGTATCAATGGAACTT |
| | | GTACAGTAGTAATGACTGATGGAAATGCTACAGGAA |
| | | AAGCTGATACTAAAATATTATTCATTGAGGAGGGGA |
| | | AAATCGTTCATACTAGCAAATTGTCAGGAAGTGCTC |
| | | AGCATGTCGAAGAGTGCTCTTGCTATCCTCGATACCC |
| | | TGGTGTCAGATGTGTCTGCAGAGACAACTGGAAAGG |
| | | ATCCAACCGGCCCATCGTAGATATAAACATAAAGGA |
| | | TCATAGCATTGTTTCCAGTTATGTGTGTTCAGGACTT |
| | | GTTGGAGACACACCCAGAAAAACCGACAGCTCCAGC |
| | | AGCAGCCATTGCTTGAATCCTAACAATGAAAAAGGT |
| | | GGTCATGGAGTGAAAGGCTGGGCCTTTGATGATGGA |
| | | AATGACGTGTGGATGGGGAGAACAATCAACGAGAC |
| | | GTCACGCTTAGGGTATGAAACCTTCAAAGTCGTTGA |
| | | AGGCTGGTCCAACCCTAAGTCCAAATTGCAGATAAA |

| SEQ ID NO. | NAME | SEQUENCE |
|---|---|---|
| | | TAGGCAAGTCATAGTTGACAGAGGTGATAGGTCCGG |
| | | TTATTCTGGTATTTTCTCTGTTGAAGGCAAAAGCTGC |
| | | ATCAATCGGTGCTTTTATGTGGAGTTGATTAGGGGA |
| | | AGAAAAGAGGAAACTGAAGTCTTGTGGACCTCAAAC |
| | | AGTATTGTTGTGTTTTGTGGCACCTCAGGTACATATG |
| | | GAACAGGCTCATGGCCTGATGGGGCGGACCTCAATC |
| | | TCATGCATATATAA |
| 60 | N2-MPP | MLLVNQSHQGFNKEHTSKMVSAIVLYVLLAAAAHSAF |
| | | AADPHHHHHGDHYDDELFSDVQDIKTALAKIHEDNQ |
| | | KIISKLESLLLLKGEVESIKKQINRQNISISTLEGHLSSIMI |
| | | AIPGLSLVPRGSPSRICPKPAEYRNWSKPQCGITGFAPFS |
| | | KDNSIRLSAGGDIWVTREPYVSCDPDKCYQFALGQGTT |
| | | INNVHSNNTARDRTPHRTLLMNELGVPFHLGTKQVCIA |
| | | WSSSSCHDGKAWLHVCITGDDKNATASFIYNGRLVDs |
| | | VVSWSKDILRTQESECVCINGTCTVVMTDGNATGKAD |
| | | TKILFIEEGKIVHTSKLSGSAQHVEECSCYPRYPGVRCV |
| | | CRDNWKGSNRPIVDINIKDHSIVSSYVCSGLVGDTPRK |
| | | TDSSSSSHCLNPNNEKGGHGVKGWAFDDGNDVWMGR |
| | | TINETSRLGYETFKVVEGWSNPKSKLQINRQVIVDRGD |
| | | RSGYSGIFSVEGKSCINRCFYVELIRGRKEETEVLWTSN |
| | | SIVVFCGTSGTYGTGSWPDGADLNLMHI* |
| 61 | B-MPP | atgctgctcgtcaaccaatcccaccagggcttcaacaaggaacacacttctaagatggt |
| | | ctccgctatcgtgctctacgtgctgctcgctgccgctgcccactcagctttcgctgccga |
| | | cccacaccaccaccaccacgcgatcactacgacgacgaactgttctccgacgt |
| | | gcaggacatcaagaccgctctggctaagatccacgaggacaaccagaagatcatctc |
| | | caagctggaatccctgctgctgctgaagggcgaagtcgagtccatcaagaagcagatc |
| | | aaccgccgaacatctccatctccaccttggagggtcacctgtcctccatcatgatcgct |
| | | atccctggcctgtctctcgtgcccaggggatcaccttctagacttcttctcccagaaccg |
| | | gagtggacatacccgcgtttatcttgcccgggctcaacctttcagaaagcactcctaatt |
| | | agccctcatagattcggagagaaaccaaaggaaactcagctcccttgataataagggaac |
| | | cttttgttgcttgtggaccaaatgaatgcaaacactttgctttaacccattatgcagcccaa |
| | | ccagggggatactacaatggaacaagaggagacagaaacaagctgaggcatctaatt |
| | | tcagtcaaattgggcaaaatcccaacagtagagaactccattttccacatggcagcatg |
| | | gagcgggtccgcgtgccatgatggtaaggaatggacatatatcggagttgatggccct |
| | | gacaataatgcattgctcaaagtaaaatatggagaagcatatactgacacataccattcc |
| | | tatgcaaacaacatcctaagaacacaagaaagtgcctgcaattgcatcggggggaaatt |
| | | gttatctaatgataactgatggctcagcttcaggtgttagtgaatgcagatttcttaagattc |
| | | gagagggccgaataataaaagaaatatttccaacaggaagagtaaaacacactgagg |
| | | aatgcacatgcgcggatttgccagcaataaaaccatagaatgtgcctgtagagacaacag |
| | | gtacacagcaaaaagacctttgtcaaattaaacgtggagactgatacagcagaataa |
| | | ggttgatgtgcacagatacctatttggacacccccagaccaaatgatggaagcataaca |
| | | ggcccttgtgaatctgatggggacaaagggagtggaggcatcaagggaggatttgttc |
| | | atcaaagaatgaaatccaagattggaaggtggtactctcgaacgatgtctcaaactgaa |
| | | aggatggggatgggactgtatgtcaagtatggtggagacccatgggctgacagtgatg |
| | | ccctagcttttagtggagtaatggtttcaatgaaagaacctggttggtattcctttggcttcg |
| | | aaataaaagataagaaatgcgatgtcccctgtattgggatagagatggtacatgatggt |
| | | ggaaaagagacttggcactcagcagcggccatttactgtttaatgggctcaggaca |
| | | gctgctgtgggacactgtcacaggtgttgacatggctctgtaa |
| 62 | B-MPP | MLLVNQSHQGFNKEHTSKMVSAFVLYVLLAAAAHSAF |
| | | AADPHHHHHGDHYDDELFSDVQDIKTALAKIHEDNQ |
| | | KIISKLESLLLLKGEVESIKKQINRQNISISTLEGHLSSIMI |
| | | AIPGLSLVPRGSPSRLLLPEPEWTYPRLSCPGSTFQKALL |
| | | ISPHRFGETKGNSAPLIIREPFVACGPNECKHFALTHYA |
| | | AQPGGYYNGTRGDRNKLRHLISVKLGKIPTVENSIFHM |
| | | AAWSGSACHDGKEWTYIGVDGPDNNALLKVKYGEAY |
| | | TDTYHSYANNILRTQESACNCIGGNCYLMITDGSASGV |
| | | SECRFLKIREGRIIKEIFPTGRVKHTEECTCGFASNKTIEC |
| | | ACRDNRYTAKRPFVKLNVETDTAEIRLMCTDTYLDTP |
| | | RPNDGSITGPCESDGDKGSGGIKGGFVHQRMKSKIGR |
| | | WYSRTMSQTERMGMGLYVKYGGDPWADSDALAFSG |
| | | VMVSMKEPGWYSFGFEIKDKKCDVPCIGIEMVHDGGK |
| | | ETWHSAATAIYCLMGSGQLLWDTVTGVDMAL* |
| 63 | Cleavage site | SLVPRGSPSR |
| 64 | Globular head domain of NA of influenza virus A/Kansas/14/2017 | ICPKPAEYRNWSKPQCGITGFAPFSKDNSIRLSAGGDIW |
| | | VTREPYVSCDPDKCYQFALGQGTTINNVHSNNTARDR |
| | | TPHRTLLMNELGVPFHLGTKQVCIAWSSSSCHDGKAW |
| | | LHVCITGDDKNATASFIYNGRLVDSVVSWSKDILRTQE |
| | | SECVCINGTCTVVMTDGNATGKADTKILFIEEGKIVHTS |
| | | KLSGSAQHVEECSCYPRYPGVRCVCRDNWKGSNRPIV |
| | | DINIKDHSIVSSYVCSGLVGDTPRKTDSSSSSHCLNPNN |
| | | EKGGHGVKGWAFDDGNDVWMGRTINETSRLGYETFK |

-continued

| SEQ ID NO. | NAME | SEQUENCE |
|---|---|---|
| | | VVEGWSNPKSKLQINRQVIVDRGDRSGYSGIFSVEGKS |
| | | CINRCFYVELIRGRKEETEVLWTSNSIVVFCGTSGTYGT |
| | | GSWPDGADLNLMHI |
| 65 | Globular head domain of NA of influenza virus B/Colorado/06/2017 | LLLPEPEWTYPRLSCPGSTFQKALLISPHRFGETKGNSA PLIIREPFVACGPNECKHFALTHYAAQPGGYYNGTRGD RNKLRHLISVKLGKIPTVENSIFHMAAWSGSACHDGKE WTYIGVDGPDNNALLKVKYGEAYTDTYHSYANNILRT QESACNCIGGNCYLMITDGSASGVSECRFLKIREGRIIK EIFPTGRVKHTEECTCGFASNKTIECACRDNRYTAKRPF VKLNVETDTAEIRLMCTDTYLDTPRPNDGSITGPCESD GDKGSGGIKGGFVHQRMKSKIGRWYSRTMSQTERMG MGLYVKYGGDPWADSDALAFSGVMVSMKEPGWYSF GFEIKDKKCDVPCIGIEMVHDGGKETWHSAATAIYCL MGSGQLLWDTVTGVDMAL* |
| 66 | Globular head domain of NA of influenza virus A/Michigan/45/15 | SVKLAGNSSLCPVSGWAIYSKDNSVRIGSKGDVFVIRE PFISCSPLECRTFFLTQGALLNDKHSNGTIKDRSPYRTL MSCPIGEVPSPYNSRFESVAWSASACHDGINWLTIGISG PDSGAVAVLKYNGIITDTIKSWRNNILRTQESECACVN GSCFTIMTDGPSDGQASYKIFRIEKGKIIKSVEMKAPNY HYEECSCYPDSSEITCVCRDNWHGSNRPWVSFNQNLE YQMGYICSGVFGDNPRPNDKTGSCGPVSSNGANGVKG FSFKYGNGVWIGRTKSISSRKGFEMIWDPNGWTGTDN KFSIKQDIVGINEWSGYSGSFVQHPELTGLDCIRPCFWV ELIRGRPEENTIWTSGSSISFCGVNS DTVGWSWPDGAELPFTIDK* |

5. DETAILED DESCRIPTION

In one aspect, provided herein are recombinant neuraminidases which form stable tetramers and are immunogenic. The recombinant neuraminidases may be used to immunize a subject against influenza virus.

5.1 Recombinant Influenza Virus Neuraminidase

Provided herein are recombinant influenza virus neuraminidases (NA), which may be used as immunogens. In a specific embodiment, a recombinant neuraminidase has the amino acid sequence of a neuraminidase described in Section 6.1 or 6.2, infra. In another specific embodiment, a recombinant neuraminidase has the amino acid sequence of a neuraminidase described in Section 6.1, infra, without one, two or more of the following: the signal sequence, histidine tag, or cleavage site.

In certain embodiments, a recombinant neuraminidase described herein retains one, two, or more, or all of the functions of a wild-type influenza virus neuraminidase. In a specific embodiment, a recombinant neuraminidase described herein cleaves sialic acid. Assays known to one skilled in the art can be utilized to assess the ability of a recombinant neuraminidase to cleave sialic acid.

It will be understood by those of skill in the art that a recombinant neuraminidase provided herein can be prepared according to any technique known by and deemed suitable to those of skill in the art, including the techniques described herein. In certain embodiments a recombinant neuraminidase described herein is isolated.

5.1.1 Recombinant Influenza Virus Neuraminidase with Mutated Ectodomains

In specific aspects, provided herein are recombinant neuraminidases comprising an influenza neuraminidase ectodomain with one, two or more amino acid substitutions to cysteine at one, two or more amino acid residues in the stalk domain of the ectodomain. In one embodiment, provided herein is a recombinant neuraminidase comprising an influenza virus neuraminidase globular head domain and stalk domain with one, two or more amino acid substitutions to cysteine at one, two or more amino acid residues in the stalk domain. In another embodiment, provided herein is a recombinant neuraminidase comprising an influenza virus neuraminidase globular head domain and stalk domain with one, two or more amino acid substitutions to cysteine at one, two or more amino acid residues in the region between the first cysteine of the globular head domain of the influenza virus neuraminidase and the transmembrane of the influenza virus neuraminidase. Those amino acid residues may include one, two or more of amino acid residues 48, 50, 61, 76, 78, and 81 of an N1 subtype or amino acid residues corresponding to one, two or more of amino acid residues 48, 50, 61, 76, 78, and 81 of influenza virus A/Puerto Rico/8/1934 neuraminidase. Alternatively, those amino acid residues may include one or both of amino acid residues 52 and 54 of an N2 subtype or amino acid residues corresponding to one or both of amino acid residues 52 and 54 of influenza virus A/Hong Kong/5738/2014. Without being bound by any theory, one or more amino acid substitutions resulting in one or more additional cysteines in the stalk domain of influenza virus neuraminidase result in the formation of disulfide bonds that increase the stability of the protein.

Those of skill in the art will recognize that the delineation of the domains of an influenza virus neuraminidase may be determined from, e.g., crystal structure and/or by using structure prediction software (for example, the website for the Center for Biological Sequence Analysis, Technical University of Denmark DTU, or Pymol) in conjunction with protein alignments. In a specific embodiment, the first cysteine of the globular head domain of influenza virus neuraminidase corresponds to the amino acid residue indicated by the bold and underlined asterisk in FIGS. 9A-9D.

The amino acid residues in the stalk domain of an influenza virus NA corresponding to particular amino acid residues (e.g., amino acid residues 48, 50, 61, 76, 78, and/or 81 of influenza virus A/Puerto Rico/8/1934 neuraminidase, or amino acid residues 52 and/or 54 of influenza virus A/Hong Kong//4801/2014) in another influenza virus NA may be identified using techniques known to one skilled in the art. In specific embodiments, the amino acid residues in the stalk domain of an influenza virus NA corresponding particular amino acid residues (e.g., amino acid residues 48, 50, 61, 76, 78, and/or 81 of influenza virus A/Puerto Rico/8/1934 neuraminidase, or amino acid residues 52 and/or 54 of influenza virus A/Hong Kong//4801/2014) are identified by comparing the amino acid sequences and/or structural information (e.g., crystal structures) of influenza virus NAs. In particular embodiments, alignments of the amino acid sequences of NA of influenza viruses (e.g., using ClustalO-mega) as well as assessing the NAs for structural similarity enables the skilled person in the art to select the amino acid residues in the influenza virus NA that correspond to par-ticular amino acid residues in stalk domain (e.g., amino acid residues 48, 50, 61, 76, 78, and/or 81 of influenza virus A/Puerto Rico/8/1934 neuraminidase, or amino acid resi-dues 52 and/or 54 of influenza virus A/Hong Kong//4801/2014). See, e.g., the sequence alignments in FIGS. 9A-9D. In certain embodiments, one might want to refrain from substituting amino acid residues in the influenza virus NA stalk domain that impact the structure of the NA with cysteine since such an amino acid substitution may impact the folding of the NA. In other embodiments, any amino acid residue in the stalk domain of an influenza virus neuramini-dase may be substituted with cysteine.

In one aspect, provided herein is a recombinant neuraminidase comprising a mutated influenza virus neuraminidase ectodomain, wherein the mutated ectodo-main comprises an amino acid substitution to cysteine at amino acid residue 48, 50, 61, 76, 78, or 81 of an N1 subtype or at an amino acid residue corresponding to amino acid residue 48, 50, 61, 76, 78, or 81 of influenza virus A/Puerto Rico/8/1934 neuraminidase. In one embodiment, provided herein is a recombinant neuraminidase comprising a mutated influenza virus neuraminidase ectodomain, wherein the mutated ectodomain comprises an amino acid substitution to cysteine at amino acid residue 48 of an N1 subtype or at an amino acid residue corresponding to amino acid residue 48 of influenza virus A/Puerto Rico/8/1934 neuraminidase. In another embodiment, provided herein is a recombinant neuraminidase comprising a mutated influenza virus neuraminidase ectodomain, wherein the mutated ectodo-main comprises an amino acid substitution to cysteine at amino acid residue 50 of an N1 subtype or at an amino acid residue corresponding to amino acid residue 50 of influenza virus A/Puerto Rico/8/1934 neuraminidase. In another embodiment, provided herein is a recombinant neuramini-dase comprising a mutated influenza virus neuraminidase ectodomain, wherein the mutated ectodomain comprises an amino acid substitution to cysteine at amino acid residue 61 of an N1 subtype or at an amino acid residue corresponding to amino acid residue 61 of influenza virus A/Puerto Rico/8/1934 neuraminidase. In another embodiment, provided herein is a recombinant neuraminidase comprising a mutated influenza virus neuraminidase ectodomain, wherein the mutated ectodomain comprises an amino acid substitution to cysteine at amino acid residue 76 of an N1 subtype or at an amino acid residue corresponding to amino acid residue 76 of influenza virus A/Puerto Rico/8/1934 neuraminidase. In another embodiment, provided herein is a recombinant neuraminidase comprising a mutated influenza virus neuraminidase ectodomain, wherein the mutated ectodo-main comprises an amino acid substitution to cysteine at amino acid residue 81 of an N1 subtype or at an amino acid residue corresponding to amino acid residue 81 of influenza virus A/Puerto Rico/8/1934 neuraminidase. In specific embodiments, the mutated ectodomain, aside from the amino acid residue substitutions described herein, comprises the amino acid residues corresponding to the wild-type influenza virus ectodomain.

In another aspect, provided herein is a recombinant neuraminidase comprising a mutated influenza virus neuraminidase ectodomain, wherein the mutated ectodo-main comprises amino acid substitutions to cysteine at two, three, or more of amino acid residues 48, 50, 61, 76, 78, and 81 of an N1 subtype or at amino acid residues corresponding to two, three or more of amino acid residues 48, 50, 61, 76, 78, and 81 of influenza virus A/Puerto Rico/8/1934 neuraminidase. In a specific embodiment, provided herein is a recombinant influenza virus comprising a mutated influ-enza virus neuraminidase ectodomain, wherein the mutated ectodomain comprises amino acid substitutions to cysteine at amino acid residues 48 and 50 of an N1 subtype or amino acid residues corresponding to amino acid residues 48 and 50 of influenza virus A/Puerto Rico/8/1934 neuraminidase. In specific embodiments, the mutated ectodomain, aside from the amino acid residue substitutions described herein, comprises the amino acid residues corresponding to the wild-type influenza virus neuraminidase ectodomain.

In another aspect, provided herein is a recombinant neuraminidase comprising a mutated influenza virus neuraminidase ectodomain, wherein the mutated ectodo-main comprises an amino acid substitution to cysteine at amino acid residue 48, 50, 61, 76, 78, or 81 of influenza virus A/Michigan/45/2015 neuraminidase or at an amino acid residue corresponding to amino acid residue 48, 50, 61, 76, 78, or 81 of influenza virus A/Michigan/45/2015 neuraminidase. In one embodiment, provided herein is a recombinant neuraminidase comprising a mutated influenza virus neuraminidase ectodomain, wherein the mutated ectodomain comprises an amino acid substitution to cysteine at amino acid residue 48 of influenza virus A/Michigan/45/2015 neuraminidase or at an amino acid residue correspond-ing to amino acid residue 48 of influenza virus A/Michigan/45/2015 neuraminidase. In another embodiment, provided herein is a recombinant neuraminidase comprising a mutated influenza virus neuraminidase ectodomain, wherein the mutated ectodomain comprises an amino acid substitution to cysteine at amino acid residue 50 of influenza virus A/Michigan/45/2015 neuraminidase or at an amino acid residue corresponding to amino acid residue 50 of influenza virus A/Michigan/45/2015 neuraminidase. In another embodiment, provided herein is a recombinant neuramini-dase comprising a mutated influenza virus neuraminidase ectodomain, wherein the mutated ectodomain comprises an amino acid substitution to cysteine at amino acid residue 61 of influenza virus A/Michigan/45/2015 neuraminidase or at an amino acid residue corresponding to amino acid residue 61 of influenza virus A/Michigan/45/2015 neuraminidase. In another embodiment, provided herein is a recombinant neuraminidase comprising a mutated influenza virus neuraminidase ectodomain, wherein the mutated ectodo-main comprises an amino acid substitution to cysteine at amino acid residue 76 of influenza virus A/Michigan/45/2015 neuraminidase or at an amino acid residue correspond-ing to amino acid residue 76 of influenza virus A/Michigan/45/2015 neuraminidase. In another embodiment, provided herein is a recombinant neuraminidase comprising a mutated influenza virus neuraminidase ectodomain, wherein the mutated ectodomain comprises an amino acid substitution to cysteine at amino acid residue 81 of influenza virus A/Michigan/45/2015 neuraminidase or at an amino acid residue corresponding to amino acid residue 81 of influenza virus A/Michigan/45/2015 neuraminidase. In specific embodiments, the mutated ectodomain, aside from the amino acid residue substitutions described herein, comprises the amino acid residues corresponding to the wild-type influenza virus A/Michigan/45/2015 neuraminidase ectodomain.

In another aspect, provided herein is a recombinant neuraminidase comprising a mutated influenza A virus neuraminidase ectodomain, wherein the mutated ectodomain comprises an amino acid substitution to cysteine at amino acid residue 52 or 54 of an N2 subtype or at an amino acid residue corresponding to amino acid residue 52 or 54 of influenza virus A/Hong Kong/5738/2014. In a specific embodiment, provided herein is a recombinant neuraminidase comprising a mutated ectodomain, wherein the mutated ectodomain comprises amino acid substitutions at one, two or more of amino acid residues of the influenza virus A/Hong Kong/5738/2014 neuraminidase that correspond to amino acid residues 61, 76, 78 and/or 81 of A/Puerto Rico/8/1934 neuraminidase. In a specific embodiment, provided herein is a recombinant neuraminidase comprising a mutated influenza A virus neuraminidase ectodomain, wherein the mutated ectodomain comprises an amino acid substitution to cysteine at amino acid residue 52 of an N2 subtype or at an amino acid residue corresponding to amino acid residue 52 of influenza virus A/Hong Kong/5738/2014. In another specific embodiment, provided herein is a recombinant neuraminidase comprising a mutated influenza A virus neuraminidase ectodomain, wherein the mutated ectodomain comprises an amino acid substitution to cysteine at amino acid residue 54 of an N2 subtype or at an amino acid residue corresponding to amino acid residue 54 of influenza virus A/Hong Kong/5738/2014. In another specific embodiment, provided herein is a recombinant neuraminidase comprising a mutated influenza A virus neuraminidase ectodomain, wherein the mutated ectodomain comprises amino acid substitutions to cysteine at amino acid residues 52 and 54 of an N2 subtype or at amino acid residues corresponding to amino acid residues 52 and 54 of influenza virus A/Hong Kong/5738/2014. In specific embodiments, the mutated ectodomain, aside from the amino acid residue substitutions described herein, comprises the amino acid residues corresponding to the wild-type influenza virus neuraminidase ectodomain.

In another aspect, provided herein are recombinant neuraminidases comprising an influenza neuraminidase ectodomain with one, two or more insertions of a cysteine at one, two or more amino acid residues in the stalk domain of the ectodomain. In one embodiment, provided herein is a recombinant neuraminidase comprising an influenza virus neuraminidase globular head domain and stalk domain with one, two or more insertions of a cysteine at one, two or more amino acid residues in the stalk domain. In another embodiment, provided herein is a recombinant neuraminidase comprising an influenza virus neuraminidase globular head domain and stalk domain with one, two or more amino acid substitutions to cysteine at one, two or more amino acid residues in the region between the first cysteine of the globular head domain of the influenza virus neuraminidase and the transmembrane of the influenza virus neuraminidase. Those insertions may occur at amino acid residues 48, 50, 61, 76, 78, and 81 of an N1 subtype or at amino acid residues corresponding to one, two or more of amino acid residues 48, 50, 61, 76, 78, and 81 of influenza virus A/Puerto Rico/8/1934 neuraminidase. In specific embodiments, the mutated ectodomain, aside from the insertion of one or more cysteines described herein, comprises the amino acid residues corresponding to the wild-type influenza virus neuraminidase ectodomain.

In one embodiment, provided herein is a recombinant neuraminidase comprising a mutated influenza virus neuraminidase ectodomain, wherein the mutated ectodomain comprises an insertion of a cysteine at amino acid residue 48, 50, 61, 76, 78, or 81 of an N1 subtype or at an amino acid residue corresponding to amino acid residue 48, 50, 61, 76, 78, or 81 of influenza virus A/Puerto Rico/8/1934 neuraminidase. In one embodiment, provided herein is a recombinant neuraminidase comprising a mutated influenza virus neuraminidase ectodomain, wherein the mutated ectodomain comprises an insertion of a cysteine at amino acid residue 61 of an N1 subtype or at an amino acid residue corresponding to amino acid residue 61 of influenza virus A/Puerto Rico/8/1934 neuraminidase. In specific embodiments, the mutated ectodomain, aside from the insertion of one or more cysteines described herein, comprises the amino acid residues corresponding to the wild-type influenza virus neuraminidase ectodomain.

The location to insert cysteine in the stalk domain of an influenza virus NA may be identified using techniques known to one skilled in the art. In specific embodiments, the location to insert cysteine in the stalk domain of an influenza virus NA are identified by comparing the amino acid sequences and/or structural information (e.g., crystal structures) of influenza virus NAs. In particular embodiments, alignments of the amino acid sequences of NA of influenza viruses (e.g., using ClustalOmega) as well as assessing the NAs for structural similarity enables the skilled person in the art to select the location to insert cysteine.

In another aspect, provided herein are recombinant neuraminidases comprising an influenza neuraminidase ectodomain with one, two or more insertions of a cysteine at particular amino acid residues in the stalk domain of the ectodomain and one, two or more amino acid substitutions to cysteine at particular amino acid residues in the stalk domain of the ectodomain. In one embodiment, provided herein is a recombinant neuraminidase comprising an influenza virus neuraminidase globular head domain and stalk domain with one, two or more insertions of a cysteine at particular amino acid residues in the stalk domain and one, two or more amino acid substitutions to cysteine at particular amino acid residues in the stalk domain of ectodomain. Those insertions, amino acid substitutions or both may occur at amino acid residues 48, 50, 61, 76, 78, and 81 of an N1 subtype or at amino acid residues corresponding to one, two or more of amino acid residues 48, 50, 61, 76, 78, and 81 of influenza virus A/Puerto Rico/8/1934 neuraminidase. In one embodiment, provided herein is a recombinant neuraminidase comprising a mutated influenza virus neuraminidase ectodomain, wherein the mutated ectodomain comprises (1) an insertion of a cysteine at amino acid residue 61 of an N1 subtype or at an amino acid residue corresponding to amino acid residue 61 of influenza virus A/Puerto Rico/8/1934 neuraminidase; and (2) an amino acid substitution to cysteine at amino acid residue 48 of an N1 subtype or at an amino acid residue corresponding to amino acid residue 48 of influenza virus A/Puerto Rico/8/1934 neuraminidase. In specific embodiments, the mutated ectodomain, aside from the insertion of one or more cysteines described herein and the amino acid residue substitutions described herein, comprises the amino acid residues corresponding to the wild-type influenza virus ectodomain.

In specific embodiments, a mutated influenza virus ectodomain is based on, from or derived from an influenza A virus neuraminidase ectodomain, such as, e.g., an N1, N2, N3, N4, N5, N6, N7, N8 or N9 subtype ectodomain. In some embodiments, a mutated influenza virus ectodomain is based on, from or derived from N1, N2, N3, N4, N5, N6, N7, N8, N9, N10 or N11 ectodomain. In certain embodiments, a mutated influenza virus ectodomain is based on, from or derived from an influenza A virus neuraminidase ectodomain that has 70%, 75%, 80%, or 85% identity to the ectodomain of an influenza A virus neuraminidase described herein or known in the art. In some embodiments, a mutated influenza virus ectodomain is based on, from or derived from an influenza A virus neuraminidase ectodomain that has 90%, 95%, or 98% identity to the ectodomain of an influenza A virus neuraminidase described herein or known in the art. In other embodiments, a mutated influenza virus ectodomain is based on, from or derived from an influenza B virus neuraminidase ectodomain. In certain embodiments, a mutated influenza virus ectodomain is based on, from or derived from an influenza B virus neuraminidase ectodomain that has 70%, 75%, 80%, or 85% identity to the ectodomain of an influenza B virus neuraminidase described herein or known in the art. In some embodiments, a mutated influenza virus ectodomain is based on, from or derived from an influenza B virus neuraminidase ectodomain that has 90%, 95%, or 98% identity to the ectodomain of an influenza B virus neuraminidase described herein or known in the art. Techniques known to one of skill in the art can be used to determine the percent identity between two amino acid sequences or between two nucleotide sequences. Generally, to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions ×100%). In one embodiment, the two sequences are the same length. In a certain embodiment, the percent identity is determined over the entire length of an amino acid sequence or nucleotide sequence. The determination of percent identity between two sequences (e.g., amino acid sequences or nucleic acid sequences) can also be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to nucleic acid molecules described herein. BLAST protein searches can be performed with the)(BLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of) (BLAST and NBLAST) can be used (see, e.g., National Center for Biotechnology Information (NCBI) on the world-wide web, ncbi.nlm.nih.gov). In another non-limiting example of a mathematical algorithm utilized for the comparison of sequences is the algorithm of Myers and Miller, 1988, CABIOS 4: 11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some embodiments, a recombinant neuraminidase provided herein further comprises an influenza virus neuraminidase transmembrane domain, cytoplasmic domain or both. In a specific embodiment, a recombinant neuraminidase provided herein comprises a mutated influenza virus neuraminidase ectodomain described herein and an influenza virus neuraminidase transmembrane domain, cytoplasmic domain or both. In certain embodiments, the transmembrane domain, cytoplasmic domain or both are based on, from or derived from an influenza A virus neuraminidase, such as, e.g., an N1, N2, N3, N4, N5, N6, N7, N8 or N9 subtype. In some embodiments, the transmembrane domain, cytoplasmic domain or both are based on, from or derived from N1, N2, N3, N4, N5, N6, N7, N8, N9, N10 or N11. In certain embodiments, the transmembrane domain, cytoplasmic domain or both are based on, from or derived from the transmembrane domain, cytoplasmic domain or both of an influenza A virus neuraminidase that has 70%, 75%, 80%, or 85% identity to the transmembrane domain, cytoplasmic domain or both of an influenza A virus neuraminidase described herein or known in the art. In some embodiments, the transmembrane domain, cytoplasmic domain or both are based on, from or derived from the transmembrane domain, cytoplasmic domain or both of an influenza A virus neuraminidase that has 90%, 95%, or 98% identity to the transmembrane domain, cytoplasmic domain or both of an influenza A virus neuraminidase described herein or known in the art. In other embodiments, the transmembrane domain, cytoplasmic domain or both based on, from or derived from an influenza B virus neuraminidase. In some embodiments, the transmembrane domain, cytoplasmic domain or both are based on, from or derived from the transmembrane domain, cytoplasmic domain or both of an influenza B virus neuraminidase that has 70%, 75%, 80%, or 85% identity to the transmembrane domain, cytoplasmic domain or both of an influenza B virus neuraminidase described herein or known in the art. In certain embodiments, the transmembrane domain, cytoplasmic domain or both are based on, from or derived from the transmembrane domain, cytoplasmic domain or both of an influenza B virus neuraminidase that has 70%, 75%, 80%, or 85% identity to the transmembrane domain, cytoplasmic domain or both of an influenza B virus neuraminidase described herein or known in the art. In a specific embodiment, a recombinant neuraminidase provided herein further comprises an influenza virus neuraminidase transmembrane domain, cytoplasmic domain or both, which is based on, from or derived from the same influenza virus neuraminidase as the mutated ectodomain. In another embodiment, a recombinant neuraminidase provided herein further comprises an influenza virus neuraminidase transmembrane domain, cytoplasmic domain or both, which is based on, from or derived from the same influenza virus neuraminidase subtype as the mutated ectodomain.

In certain embodiments, a recombinant neuraminidase provided herein is a soluble. In other embodiments, a recombinant neuraminidase provided herein is not soluble.

In certain embodiments, a recombinant neuraminidase provided herein comprises a tetramerization domain. In a specific embodiment, a recombinant neuraminidase provided herein comprises a mutated influenza virus neuraminidase ectodomain described herein and a tetramerization domain. In some embodiments, the tetramerization domain comprises a tetramerization domain from a GCN4 leucine zipper, a bacterial tetrabrachion tetramerization domain or the human vasodilator stimulated phosphoprotein (VASP) tetramerization domain. In certain embodiments, the tetramerization domain comprises the tetramerization domain from SEPPALLATA-like MADS domain transcription factor from *Arabidopsis thaliana* (SMDTF), PiLZ structure from *Xanthomonas campestris*, or Dictyocaulus viviparus ACE tetramerization domain. In other embodiments, the tetramerization domain comprises a tetramerization domain from a paramyxovirus phosphoprotein (e.g., a Nipah virus phosphoprotein, a Hendra virus phosphoprotein, a respiratory syncytial virus phosphoprotein, human parainfluenza virus (hPIV) phosphoprotein, bovine parainfluenza virus phosphoprotein, a mumps virus phosphoprotein, a Cedar virus phosphoprotein, a Ghana virus phosphoprotein, a Newcastle disease virus phosphoprotein, a canine distemper virus phosphoprotein, or a Peste des petits ruminants virus (PPRV) phosphoprotein). In a specific embodiment, the tetramerization domain is a tetramerization from a measles virus phosphoprotein tetramerization domain or a Sendai virus phosphoprotein tetramerization domain. In another specific embodiment, the tetramerization domain comprises the amino acid sequence of SEQ ID NO: 1, 2, 3, 4 or 5.

In certain embodiments, the tetramerization used has been modified. For example, a tetramerization domain, such as those noted above, has been immunologically silenced by, e.g., adding N-linked glycans to epitopes (e.g., immunodominant epitopes). The epitopes (e.g., immunodominant epitopes) of a tetramerization domain, such as those noted above, may be dampened by adding N-linked glycosylation sites (e.g., Asn-Xaa-Ser/Thr, wherein Xaa is any amino acid, or Asn-Xaa-Ser/Thr, wherein Xaa is any amino acid except Pro) to the domain. In certain embodiments, one, two or more non-naturally occurring glycosylation sites are introduced into the tetramerization domain. The locations of the non-naturally occurring glycosylation sites may be chosen so they cover the immunodominant epitopes of the tetramerization domain. The presence of N-linked glycans may make the covered epitopes immunologically inert.

In certain embodiments, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with an amino acid substitution to cysteine at amino acid residue 48, 50, 61, 76, 78, or 81 of an N1 subtype or at an amino acid residue corresponding to amino acid residue 48, 50, 61, 76, 78, or 81 of influenza virus A/Puerto Rico/8/1934 neuraminidase. In other embodiments, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with amino acid substitutions to cysteine at two, three or more of amino acid residues 48, 50, 61, 76, 78, and 81 of an N1 subtype or at amino acid residues corresponding to two, three or more of amino acid residues 48, 50, 61, 76, 78, and 81 of influenza virus A/Puerto Rico/8/1934 neuraminidase. In certain embodiments, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with amino acid substitutions to cysteine at amino acid residues 48 and 50 of an N1 subtype or at amino acid residues corresponding to amino acid residues 48 and 50 of influenza virus A/Puerto Rico/8/1934 neuraminidase. In some embodiments, the recombinant neuraminidase further comprises a transmembrane domain, a cytoplasmic domain or both from an influenza virus NA subtype that is the same as the NA subtype of the influenza virus ectodomain. In certain embodiments, the recombinant neuraminidase further comprises a transmembrane domain, a cytoplasmic domain or both from the same influenza A virus neuraminidase as the ectodomain. In other embodiments, the recombinant neuraminidase further comprises a tetramerization domain, such as described herein.

In certain embodiments, provided herein is a recombinant neuraminidase comprising a mutated influenza virus ectodomain which comprises an influenza B virus neuraminidase ectodomain with an amino acid substitution to cysteine at an amino acid residue corresponding to amino acid residue 48, 50, 61, 76, 78, or 81 of influenza virus A/Puerto Rico/8/1934 neuraminidase. In a specific embodiment, provided herein is a recombinant neuraminidase comprising a mutated influenza virus ectodomain which comprises an influenza B virus neuraminidase ectodomain with amino acid substitutions to cysteine at amino acid residues corresponding to two, three or more of amino acid residues 48, 50, 61, 76, 78, and 81 of influenza virus A/Puerto Rico/8/1934 neuraminidase. In some embodiments, the recombinant neuraminidase further comprises a transmembrane domain, a cytoplasmic domain or both from an influenza virus NA linage that is the same as the NA lineage of the influenza virus ectodomain. In certain embodiments, the recombinant neuraminidase further comprises a transmembrane domain, a cytoplasmic domain or both from the same influenza B virus neuraminidase as the ectodomain. In other embodiments, the recombinant neuraminidase further comprises a tetramerization domain, such as described herein.

In certain embodiments, provided herein is a recombinant neuraminidase comprising a mutated influenza A virus neuraminidase ectodomain which comprises an influenza A virus neuraminidase ectodomain, such as, e.g., an N1, N2, N3, N4, N5, N6, N7, N8 or N9 subtype ectodomain, with an amino acid substitution to cysteine at an amino acid residue corresponding to amino acid residue 52 or 54 of influenza virus A/Hong Kong/5738/2014 neuraminidase. In some embodiments, provided herein is a recombinant neuraminidase comprising a mutated influenza A virus neuraminidase ectodomain which comprises an influenza A virus neuraminidase ectodomain, such as, e.g., an N1, N2, N3, N4, N5, N6, N7, N8 or N9 subtype ectodomain, with amino acid substitutions to cysteine at amino acid residues corresponding to amino acid residues 52 and 54 of influenza virus A/Hong Kong/5738/2014 neuraminidase. In some embodiments, the recombinant neuraminidase further comprises a transmembrane domain, a cytoplasmic domain or both from an influenza virus NA subtype that is the same as the NA subtype of the influenza virus ectodomain. In certain embodiments, the recombinant neuraminidase further comprises a transmembrane domain, a cytoplasmic domain or both from the same influenza A virus neuraminidase as the ectodomain. In other embodiments, the recombinant neuraminidase further comprises a tetramerization domain, such as described herein.

In certain embodiments, provided herein is a recombinant neuraminidase comprising a mutated influenza B virus neuraminidase ectodomain which comprises an influenza B virus neuraminidase ectodomain with an amino acid substitution to cysteine at an amino acid residue corresponding to amino acid residue 52 or 54 of influenza virus A/Hong Kong/5738/2014 neuraminidase. In some embodiments, provided herein is a recombinant neuraminidase comprising a mutated influenza B virus neuraminidase ectodomain which comprises an influenza B virus neuraminidase ectodomain with amino acid substitutions to cysteine at amino acid residues corresponding to amino acid residues 52 and 54 of influenza virus A/Hong Kong/5738/2014 neuraminidase. In some embodiments, the recombinant neuraminidase further comprises a transmembrane domain, a cytoplasmic domain or both from an influenza virus NA lineage that is the same as the NA lineage of the influenza virus ectodomain. In certain embodiments, the recombinant neuraminidase further comprises a transmembrane domain, a cytoplasmic domain or both from the same influenza B virus neuraminidase as the ectodomain. In other embodiments, the recombinant neuraminidase further comprises a tetramerization domain, such as described herein.

In certain embodiments, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with an insertion of a cysteine at amino acid residue 48, 50, 61, 76, 78, or 81 of an N1 subtype or at an amino acid residue corresponding to amino acid residue 48, 50, 61, 76, 78, or 81 of influenza virus A/Puerto Rico/8/1934 neuraminidase. In other embodiments, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with an insertion of a cysteine at two, three or more of amino acid residues 48, 50, 61, 76, 78, and 81 of an N1 subtype or at amino acid residues corresponding to two, three or more of amino acid residues 48, 50, 61, 76, 78, and 81 of influenza virus A/Puerto Rico/8/1934 neuraminidase. In some embodiments, the recombinant neuraminidase further comprises a transmembrane domain, a cytoplasmic domain or both from an influenza virus NA subtype that is the same as the NA subtype of the influenza virus ectodomain. In certain embodiments, the recombinant neuraminidase further comprises a transmembrane domain, a cytoplasmic domain or both from the same influenza A virus neuraminidase as the ectodomain. In other embodiments, the recombinant neuraminidase further comprises a tetramerization domain, such as described herein.

In certain embodiments, provided herein is a recombinant neuraminidase comprising a mutated influenza virus ectodomain which comprises an influenza B virus neuraminidase ectodomain with an insertion of a cysteine at an amino acid residue corresponding to amino acid residue 48, 50, 61, 76, 78, or 81 of influenza virus A/Puerto Rico/8/1934 neuraminidase. In other embodiments, provided herein is a recombinant neuraminidase comprising a mutated influenza virus ectodomain which comprises an influenza B virus neuraminidase ectodomain with an insertion of a cysteine at amino acid residues corresponding to two, three or more of amino acid residues 48, 50, 61, 76, 78, and 81 of influenza virus A/Puerto Rico/8/1934 neuraminidase. In some embodiments, the recombinant neuraminidase further comprises a transmembrane domain, a cytoplasmic domain or both from an influenza virus NA lineage that is the same as the NA lineage of the influenza virus ectodomain. In certain embodiments, the recombinant neuraminidase further comprises a transmembrane domain, a cytoplasmic domain or both from the same influenza B virus neuraminidase as the ectodomain. In other embodiments, the recombinant neuraminidase further comprises a tetramerization domain, such as described herein.

In certain embodiments, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with (1) an insertion of a cysteine at amino acid residue 48, 50, 61, 76, 78, or 81 of an N1 subtype or at an amino acid residue corresponding to amino acid residue 48, 50, 61, 76, 78, or 81 of influenza virus A/Puerto Rico/8/1934 neuraminidase, and (2) an amino acid substitution to cysteine at amino acid residue 48, 50, 61, 76, 78, or 81 of an N1 subtype or at an amino acid residue corresponding to amino acid residue 48, 50, 61, 76, 78, or 81 of influenza virus A/Puerto Rico/8/1934 neuraminidase. In other embodiments, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with (1) an insertion of a cysteine at one, two, three or more of amino acid residues 48, 50, 61, 76, 78, and 81 of an N1 subtype or at amino acid residues corresponding to one, two, three or more of amino acid residues 48, 50, 61, 76, 78, and 81 of influenza virus A/Puerto Rico/8/1934 neuraminidase; and (2) an amino acid substitution to cysteine at one, two, three or more of amino acid residues 48, 50, 61, 76, 78, and 81 of an N1 subtype or at amino acid residues corresponding to one, two, three or more of amino acid residues 48, 50, 61, 76, 78, and 81 of influenza virus A/Puerto Rico/8/1934 neuraminidase. In a specific embodiment, provided herein is a recombinant neuraminidase comprising a mutated influenza virus ectodomain which comprises an influenza A virus neuraminidase ectodomain, such as, e.g., an N1, N2, N3, N4, N5, N6, N7, N8 or N9 subtype ectodomain, with (1) an insertion of a cysteine at amino acid residue 61 of an N1 subtype or at an amino acid residue corresponding to amino acid residue 61 of influenza virus A/Puerto Rico/8/1934 neuraminidase, and (2) an amino acid substitution to cysteine at amino acid residue 48 of an N1 subtype or at an amino acid residue corresponding to amino acid residue 48 of influenza virus A/Puerto Rico/8/1934 neuraminidase. In some embodiments, the recombinant neuraminidase further comprises a transmembrane domain, a cytoplasmic domain or both from an influenza virus NA subtype that is the same as the NA subtype of the influenza virus ectodomain. In certain embodiments, the recombinant neuraminidase further comprises a transmembrane domain, a cytoplasmic domain or both from the same influenza A virus neuraminidase as the ectodomain. In other embodiments, the recombinant neuraminidase further comprises a tetramerization domain, such as described herein.

In certain embodiments, provided herein is a recombinant neuraminidase comprising a mutated influenza virus ectodomain which comprises an influenza B virus neuraminidase ectodomain with (1) an insertion of a cysteine at an amino acid residue corresponding to amino acid residue 48, 50, 61, 76, 78, or 81 of influenza virus A/Puerto Rico/8/1934 neuraminidase, and (2) an amino acid substitution to cysteine at amino acid residue corresponding to amino acid residue 48, 50, 61, 76, 78, or 81 of influenza virus A/Puerto Rico/8/1934 neuraminidase. In other embodiments, provided herein is a recombinant neuraminidase comprising a mutated influenza virus ectodomain which comprises an influenza B virus neuraminidase ectodomain with (1) an insertion of a cysteine at amino acid residues corresponding to one, two, three or more of amino acid residues 48, 50, 61, 76, 78, and 81 of influenza virus A/Puerto Rico/8/1934 neuraminidase, and (2) an amino acid substitution to cysteine at one, two, three or more of amino acid residues corresponding to one, two, three or more of amino acid residues 48, 50, 61, 76, 78, and 81 of influenza virus A/Puerto Rico/8/1934 neuraminidase. In some embodiments, the recombinant neuraminidase further comprises a transmembrane domain, a cytoplasmic domain or both from an influenza virus NA lineage that is the same as the NA lineage of the influenza virus ectodomain. In certain embodiments, the recombinant neuraminidase further comprises a transmembrane domain, a cytoplasmic domain or both from the same influenza B virus neuraminidase as the ectodomain. In other embodiment, the recombinant neuraminidase further comprises a tetramerization domain, such as described herein.

In certain embodiments, an influenza virus neuraminidase is a human influenza virus neuraminidase. Human influenza virus neuraminidases are known in the art. In certain embodiments, an influenza virus neuraminidase is a swine influenza virus neuraminidase. Swine influenza virus neuraminidases are known in the art. In certain embodiments, an influenza virus neuraminidase is an equine influenza virus neuraminidase. Equine influenza virus neuraminidases are known in the art. In certain embodiments, an influenza virus neuraminidase is an avian influenza virus neuraminidase. Avian influenza virus neuraminidases are known in the art. In certain embodiments, an influenza virus neuraminidase is a seal influenza virus neuraminidase. Seal influenza virus neuraminidases are known in the art. Examples of specific influenza A virus neuraminidases include the neuraminidase of an influenza A virus strains described herein. In a specific embodiment, the influenza A virus neuraminidase is influenza A/Brisbane/02/2018 (H1N1) pdm09-like virus neuraminidase, influenza A/Kansas/14/2017 (H3N2)-like virus neuraminidase, influenze A/Brisbane/02/2018 (H1N1) pdm09-like virus neuraminidase, or influenza A/South Australia/34/2019 (H3N2)-like virus neuraminidase.

In certain embodiments, an influenza B virus neuraminidase is a human influenza B virus neuraminidase. Human influenza B virus neuraminidases are known in the art. In certain embodiments, an influenza B virus neuraminidase is a seal influenza B virus neuraminidase. Seal influenza B virus neuraminidases are known in the art. Examples of specific influenza B virus neuraminidases include the neuraminidase of an influenza B/Yamagata/16/88-lineage virus or an influenza virus B/Victoria/2/87-lineage virus. In a specific embodiment, the influenza B virus neuraminidase is influenza a B/Colorado/06/2017-like virus (B/Victoria/2/87 lineage) neuraminidase, influenza B/Phuket/3073/2013-like virus (B/Yamagata/16/88 lineage) neuraminidase, influenza B/Washington/02/2019-like (B/Victoria lineage) virus neuraminidase, or influenza B/Phuket/3073/2013-like (B/Yamagata lineage) virus neuraminidase.

GenBank™ Accession No. AAA43397.1 provides an exemplary amino acid sequence for a human influenza virus neuraminidase. GenBank™ Accession No. ABG23658.1 (GI: 108946273), GenBank™ Accession No. NP 040981.1 (GI: 8486128), GenBank™ Accession No. AAA43412.1 (GI: 324508), GenBank™ Accession No. ABE97720.1 (GI: 93008579), GenBank™ Accession No. ABE97719.1 (GI: 93008577), and GenBank™ Accession No. ABE97718.1 (GI: 93008575) provide exemplary amino acid sequences for human influenza virus neuraminidases. GenBank™ Accession No. CRI06477.1 provides an exemplary amino acid sequence for a swine influenza virus neuraminidase. GenBank™ Accession No. AAQ90293.1 provides an exemplary amino acid sequence for an equine influenza virus neuraminidase. GenBank™ Accession No. AEX30531.1 (GI: 371449652), GenBank™ Accession No. AEX30532.1 (GI: 371449654), GenBank™ Accession No. AIA62041.1 (GI: 641454926), GenBank™ Accession No. AII30325.1 (GI: 670605039), GenBank™ Accession No. AGO18161.1 (GI: 513130855), and GenBank™ Accession No. AAS89005.1 (GI: 46360357) provide exemplary amino acid sequences for avian influenza virus neuraminidases. Sequences of influenza virus genes may also be found in the Influenza Research Database. For example, influenza virus neuraminidase sequences may be found in the Influenza Research Database under Accession No. FJ66084 and Accession No. KF90392.

In a specific embodiment, a recombinant neuraminidase provided herein has the amino acid sequence of SEQ ID NO: 7, 8, 9, 10, 11, 13 or 14. In another specific embodiment, a recombinant neuraminidase provided herein has the amino acid sequence of SEQ ID NO: 16, 17, 18, 19, 20, 21, 22, or 23. In another specific embodiment, a recombinant neuraminidase provided herein has the amino acid sequence of SEQ ID NO: 16, 17, 18, 19, 20, 21, 22, or 23 without one, two or all of the following: signal peptide, hexa-histidine tag and thrombin cleavage site.

In certain embodiments, a recombinant neuraminidase provided herein further comprise one or more polypeptide domains. Useful polypeptide domains include domains that facilitate purification, folding and cleavage of portions of a polypeptide. For example, a His tag (His-His-His-His-His-His) (SEQ ID NO:50), FLAG epitope or other purification tag can facilitate purification of an neuraminidase polypeptide provided herein. In some embodiments, the His tag has the sequence, (His)n, wherein n is 2, 3, 4, 5, 6, 7, 8, 9, 10, 11, 12, 13, 14, 15, 16, 17, 18, 19, 20 or greater. Cleavage sites can be used to facilitate cleavage of a portion of a polypeptide, for example cleavage of a purification tag. Useful cleavage sites include a thrombin cleavage site, for example one with the sequence LVPRGSP (SEQ ID NO:51). In a specific embodiment, the cleavage site comprises the amino acid sequence of SLVPRGSPSR (SEQ ID NO:63). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:52)).

In certain embodiments, a recombinant neuraminidase provided herein exists in one, two, three or all of the following forms: monomeric, dimeric, trimeric or tetrameric. In specific embodiments, a recombinant neuraminidase provided herein is tetrameric as assessed by techniques known in the art or described herein.

In specific embodiments, a recombinant neuraminidase provided herein are capable of forming a three-dimensional structure that is similar to the three-dimensional structure of a native influenza neuraminidase. Structural similarity might be evaluated based on any technique deemed suitable by those of skill in the art. For instance, reaction, e.g. under non-denaturing conditions, of a recombinant neuraminidase with a neutralizing antibody or antiserum that recognizes a native influenza neuraminidase might indicate structural similarity. Useful neutralizing antibodies or antisera are described in, e.g., Shoji et al., Hum. Vaccines, 2011, 7:199-204, Wan et al., J. Virol. 2013, 87:9290-9300, Doyle et al. Antivir. Res. 2013, 100:567-574, Doyle et al., Biochem. Biophys. Res. Commun. 2013, 441:226-229, and Wohlbold et al., 2017, Nat. Microbiol. 2(10): 1415-1424, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a neuraminidase.

When designing a recombinant neuraminidase, care should be taken to maintain the stability of the resulting protein. In this regard, it is recommended that cysteine residues capable of forming disulfide bonds be maintained since they contribute to the stability of the neuraminidase protein. See, e.g., Basler et al., 1999, Journal of Virology, 73(10):8095-8103 for non-limiting examples of influenza virus neuraminidase cysteine residues capable of forming disulfide bonds. The stability of a recombinant neuraminidase described herein can be assessed using techniques known in the art, such as sensitivity of the neuraminidase molecules to Ca', as described in, e.g., Baker and Gandhi, 1976, Archives of Virology, 52:7-18. The stability of a recombinant neuraminidase may be assessed by any method described herein (e.g., in Section 6, infra).

5.1.2 Recombinant Neuraminidase with Tetramerization Domain

In one aspect, provided herein are recombinant neuraminidases comprising an influenza virus neuraminidase globular head domain and a tetramerization domain. In a specific embodiment, provided herein is a recombinant neuraminidase comprising an influenza virus neuraminidase globular head domain and a tetramerization domain, wherein the recombinant neuraminidase lacks influenza virus neuraminidase transmembrane and cytoplasmic domains. In specific embodiments, the recombinant neuraminidase does not have any transmembrane domain. In certain embodiments, the recombinant neuraminidase includes a stalk domain or a fragment thereof of the same influenza virus neuraminidase as the globular head domain. The fragment of the stalk domain of the influenza virus neuraminidase may consist of or comprise 2, 3, 4, 5, 6, 7, 8, 9, 10, 11, 12, 13, 14, 15, 16, 17, 18, 19, 20, 25, 30, 35, 40, 45, or 50 amino acid residues of the stalk domain of the influenza virus neuraminidase. Alternatively, the fragment of the stalk domain of the influenza virus neuraminidase may consist of or comprise 2 to 5, 5 to 10, 5 to 15, 10 to 15, 5 to 20, 10 to 20, 15 to 20, 20 to 30, 20 to 40, 25 to 30, 25 to 40, 25 to 45, 25 to 50, 30 to 40, or 40 to 50 amino acid residues of the stalk domain of the influenza virus neuraminidase. In specific embodiments, the recombinant neuraminidase does not include the stalk domain of an influenza virus neuraminidase.

Those of skill in the art will recognize that the delineation of the domains of an influenza virus neuraminidase may be determined from, e.g., crystal structure and/or by using structure prediction software (for example, the website for the Center for Biological Sequence Analysis, Technical University of Denmark DTU, or Pymol) in conjunction with protein alignments. In a specific embodiment, the first cysteine of the globular head domain of influenza virus neuraminidase corresponds to the amino acid residue indicated by the bold and underlined asterisk in FIGS. 9A-9D.

In a specific embodiment, provided herein is a recombinant neuraminidase comprising an influenza virus neuraminidase globular head domain and a tetramerization domain, wherein the recombinant neuraminidase lacks influenza virus neuraminidase stalk, transmembrane and cytoplasmic domains. In specific embodiments, the recombinant neuraminidase does not include any transmembrane. In certain embodiments, the tetramerization domain comprises the tetramerization domain from SEPPALLATA-like MADS domain transcription factor from *Arabidopsis thaliana* (SMDTF), PiLZ structure from *Xanthomonas campestris*, or Dictyocaulus viviparus ACE tetramerization domain. In other embodiments, the tetramerization domain comprises a tetramerization domain from a paramyxovirus phosphoprotein (e.g., a Nipah virus phosphoprotein, a Hendra virus phosphoprotein, a respiratory syncytial virus phosphoprotein, human parainfluenza virus (hPIV) phosphoprotein, bovine parainfluenza virus phosphoprotein, a mumps virus phosphoprotein, a Cedar virus phosphoprotein, a Ghana virus phosphoprotein, a Newcastle disease virus phosphoprotein, a canine distemper virus phosphoprotein, or a Peste des petits ruminants virus (PPRV) phosphoprotein). In certain embodiments, the tetramerization domain is not a GCN4 leucine zipper, a bacterial tetrabrachion tetramerization domain or the human vasodilator stimulated phosphoprotein (VASP) tetramerization domain. In a specific embodiment, the tetramerization domain is a tetramerization from a measles virus phosphoprotein tetramerization domain or a Sendai virus phosphoprotein tetramerization domain. In another specific embodiment, the tetramerization domain comprises the amino acid sequence of SEQ ID NO: 1, 2, 3, 4 or 5.

In a particular embodiment, provided herein is a recombinant neuraminidase comprising an influenza virus neuraminidase globular head domain and a tetramerization domain, wherein the recombinant neuraminidase lacks influenza virus neuraminidase stalk, transmembrane and cytoplasmic domains, and wherein the tetramerization domain comprises a measles virus phosphoprotein tetramerization domain or a Sendai virus phosphoprotein tetramerization domain. In a specific embodiment, provided herein is a recombinant neuraminidase comprising or consisting of the amino acid sequence of SEQ ID NO: 24, 25, 26, 27 or 28. In another specific embodiment, provided herein is a recombinant neuraminidase comprising or consisting of the amino acid sequence of SEQ ID NO: 24, 25, 26, 27 or 28 without the signal sequence, histidine tag or both.

In another embodiment, provided herein is a recombinant neuraminidase comprising or consisting of the amino acid sequence of SEQ ID NO: 27, 56, 58, 60 or 62. In another embodiment, provided herein is a recombinant neuraminidase comprising or consisting of the amino acid sequence of SEQ ID NO: 27, 56, 58, 60 or 62 without the signal sequence, histidine tag or both. In a specific embodiment, provided herein is a recombinant neuraminidase comprising or consisting of the amino acid sequence of SEQ ID NO: 27, 56 or 58. In another specific embodiment, provided herein is a recombinant neuraminidase comprising or consisting of the amino acid sequence of SEQ ID NO: 27 without one, two or all of the following: the signal sequence, histidine tag or thrombin cleavage site. In certain embodiments, a recombinant neuraminidase provided herein comprises or consists of the amino acid sequence that is encoded by the nucleotide sequence set forth in SEQ ID NO: 55, 57, 59 or 61.

In certain embodiments, an influenza virus neuraminidase is a human influenza virus neuraminidase. Human influenza virus neuraminidases are known in the art. In certain embodiments, an influenza virus neuraminidase is a swine influenza virus neuraminidase. Swine influenza virus neuraminidases are known in the art. In certain embodiments, an influenza virus neuraminidase is an equine influenza virus neuraminidase. Equine influenza virus neuraminidases are known in the art. In certain embodiments, an influenza virus neuraminidase is an avian influenza virus neuraminidase. Avian influenza virus neuraminidases are known in the art. In certain embodiments, an influenza virus neuraminidase is a seal influenza virus neuraminidase. Seal influenza virus neuraminidases are known in the art.

In some embodiments, an influenza virus neuraminidase is an influenza A virus neuraminidase. In specific embodiments, an influenza virus neuraminidase is an N1, N2, N3, N4, N5, N6, N7, N8 or N9 subtype. Examples of specific influenza A virus neuraminidases include the neuraminidase of an influenza A virus strains described herein. In a specific embodiment, the influenza A virus neuraminidase is influenza A/Brisbane/02/2018 (H1N1) pdm09-like virus neuraminidase, influenza A/Kansas/14/2017 (H3N2)-like virus neuraminidase, influenze A/Brisbane/02/2018 (H1N1) pdm09-like virus neuraminidase, or influenza A/South Australia/34/2019 (H3N2)-like virus neuraminidase.

In some embodiments, an influenza virus neuraminidase is an influenza B virus neuraminidase. In certain embodiments, an influenza B virus neuraminidase is a human influenza B virus neuraminidase. Human influenza B virus neuraminidases are known in the art. In certain embodiments, an influenza B virus neuraminidase is a seal influenza B virus neuraminidase. Seal influenza B virus neuraminidases are known in the art. Examples of specific influenza B virus neuraminidases include the neuraminidase of an influenza B/Yamagata/16/88-lineage virus or an influenza virus B/Victoria/2/87-lineage virus. In a specific embodiment, the influenza B virus neuraminidase is influenza a B/Colorado/06/2017-like virus (B/Victoria/2/87 lineage) neuraminidase, influenza B/Phuket/3073/2013-like virus (B/Yamagata/16/88 lineage) neuraminidase, influenza B/Washington/02/2019-like (B/Victoria lineage) virus neuraminidase, or influenza B/Phuket/3073/2013-like (B/Yamagata lineage) virus neuraminidase.

GenBank™ Accession No. AAA43397.1 provides an exemplary amino acid sequence for a human influenza virus neuraminidase. GenBank™ Accession No. ABG23658.1 (GI: 108946273), GenBank™ Accession No. NP 040981.1 (GI: 8486128), GenBank™ Accession No. AAA43412.1 (GI: 324508), GenBank™ Accession No. ABE97720.1 (GI: 93008579), GenBank™ Accession No. ABE97719.1 (GI: 93008577), and GenBank™ Accession No. ABE97718.1 (GI: 93008575) provide exemplary amino acid sequences for human influenza virus neuraminidases. GenBank™ Accession No. CRI06477.1 provides an exemplary amino acid sequence for a swine influenza virus neuraminidase. GenBank™ Accession No. AAQ90293.1 provides an exemplary amino acid sequence for an equine influenza virus neuraminidase. GenBank™ Accession No. AEX30531.1 (GI: 371449652), GenBank™ Accession No. AEX30532.1 (GI: 371449654), GenBank™ Accession No. AIA62041.1 (GI: 641454926), GenBank™ Accession No. AI130325.1 (GI: 670605039), GenBank™ Accession No. AGO18161.1 (GI: 513130855), and GenBank™ Accession No. AAS89005.1 (GI: 46360357) provide exemplary amino acid sequences for avian influenza virus neuraminidases. Sequences of influenza virus genes may also be found in the Influenza Research Database. For example, influenza virus neuraminidase sequences may be found in the Influenza Research Database under Accession No. FJ66084 and Accession No. KF90392.

In certain embodiments, an influenza virus neuraminidase globular head domain has 70%, 75%, 80%, or 85% identity to the globular head domain of an influenza A virus neuraminidase described herein (e.g., SEQ ID NO: 64 or 66) or known in the art. In some embodiments, an influenza virus neuraminidase globular head domain has 90%, 95%, or 98% identity to the globular head domain of an influenza A virus neuraminidase described herein (e.g., SEQ ID NO: 64 or 66) or known in the art. In certain embodiments, an influenza virus neuraminidase globular head domain has 70%, 75%, 80%, or 85% identity to the globular head domain of an influenza B virus neuraminidase described herein (e.g., SEQ ID NO:65) or known in the art. In some embodiments, an influenza virus neuraminidase globular head domain has 90%, 95%, or 98% identity to the globular head domain of an influenza B virus neuraminidase described herein (e.g., SEQ ID NO:65) or known in the art. In some embodiments, an influenza virus neuraminidase globular head domain comprises or consists of the amino acid sequence of SEQ ID NO:64, 65 or 66.

In certain embodiments, a recombinant neuraminidase provided herein further comprise one or more polypeptide domains. Useful polypeptide domains include domains that facilitate purification, folding and cleavage of portions of a polypeptide. For example, a His tag (His-His-His-His-His-His) (SEQ ID NO:50), FLAG epitope or other purification tag can facilitate purification of an neuraminidase polypeptide provided herein. In some embodiments, the His tag has the sequence, (His)n, wherein n is 2, 3, 4, 5, 6, 7, 8, 9, 10, 11, 12, 13, 14, 15, 16, 17, 18, 19, 20 or greater. Cleavage sites can be used to facilitate cleavage of a portion of a polypeptide, for example cleavage of a purification tag. Useful cleavage sites include a thrombin cleavage site, for example one with the sequence LVPRGSP (SEQ ID NO:51). In a specific embodiment, the cleavage site comprises the amino acid sequence SLVPRGSPSR (SEQ ID NO:63). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:52)). In certain embodiments, a recombinant neuraminidase provided herein does not include a cleavage site. In some embodiments, a recombinant neuraminidase provided herein comprises a signal peptide and a tag (e.g., a histidine tag). In certain embodiments, a recombinant neuraminidase provided herein comprises a signal peptide, a tag (e.g., a histidine tag), and a cleavage site (e.g., a cleavage site described herein).

In a specific embodiment, a recombinant neuraminidase provided herein includes in order a signal peptide, histidine tag or other purification tag, a tetramerization domain (e.g., MPP or another tetramerization domain described herein or known to one of skill in the art), a cleavage site (e.g., SEQ ID NO:63 or another cleavage site described herein or known to one of skill in the art), and a globular head domain of an influenza virus NA. In another specific embodiment, a recombinant neuraminidase provided herein includes in order a signal peptide, histidine tag or other purification tag, a tetramerization domain (e.g., MPP or another tetramerization domain described herein or known to one of skill in the art), and a globular head domain of an influenza virus NA. In another specific embodiment, a recombinant neuraminidase provided herein includes in order a signal peptide, a tetramerization domain (e.g., MPP or another tetramerization domain described herein or known to one of skill in the art), and a globular head domain of an influenza virus NA. In another specific embodiment, a recombinant neuraminidase described herein comprises the components of a signal peptide, histidine tag or other purification tag, a tetramerization domain (e.g., MPP or another tetramerization domain described herein or known to one of skill in the art), a cleavage site (e.g., SEQ ID NO:63 or another cleavage site described herein or known to one of skill in the art), and a globular head domain of an influenza virus NA in the order described in Section 6, infra. In another specific embodiment, a recombinant neuraminidase described herein comprises the components of a signal peptide, histidine tag or other purification tag, a tetramerization domain (e.g., MPP or another tetramerization domain described herein or known to one of skill in the art), and a globular head domain of an influenza virus NA in the order described in Section 6, infra. In another specific embodiment, a recombinant neuraminidase described herein comprises the components of a signal peptide, a tetramerization domain (e.g., MPP or another tetramerization domain described herein or known to one of skill in the art), and a globular head domain of an influenza virus NA in the order described in Section 6, infra.

In certain embodiments, a recombinant neuraminidase provided herein exists in one, two, three or all of the following forms: monomeric, dimeric, trimeric or tetrameric. In specific embodiments, a recombinant neuraminidase provided herein is tetrameric as assessed by techniques known in the art or described herein.

In specific embodiments, a recombinant neuraminidase provided herein are capable of forming a three-dimensional structure that is similar to the three-dimensional structure of a native influenza neuraminidase. Structural similarity might be evaluated based on any technique deemed suitable by those of skill in the art. For instance, reaction, e.g. under non-denaturing conditions, of a recombinant neuraminidase with a neutralizing antibody or antiserum that recognizes a native influenza neuraminidase might indicate structural similarity. Useful neutralizing antibodies or antisera are described in, e.g., Shoji et al., Hum. Vaccines, 2011, 7:199-204, Wan et al., J. Virol. 2013, 87:9290-9300, Doyle et al. Antivir. Res. 2013, 100:567-574, Doyle et al., Biochem. Biophys. Res. Commun. 2013, 441:226-229, and Wohlbold et al., 2017, Nat. Microbiol. 2(10): 1415-1424, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a neuraminidase.

When designing a recombinant neuraminidase, care should be taken to maintain the stability of the resulting protein. In this regard, it is recommended that cysteine residues capable of forming disulfide bonds be maintained since they contribute to the stability of the neuraminidase protein. See, e.g., Basler et al., 1999, Journal of Virology, 73(10):8095-8103 for non-limiting examples of influenza virus neuraminidase cysteine residues capable of forming disulfide bonds. The stability of a recombinant neuraminidase described herein can be assessed using techniques known in the art, such as sensitivity of the neuraminidase molecules to $Ca^{2+}$, as described in, e.g., Baker and Gandhi, 1976, Archives of Virology, 52:7-18. The stability of a recombinant neuraminidase may be assessed by any method described herein (e.g., in Section 6, infra).

5.2 Nucleic Acid Sequences

Provided herein are nucleic acid sequences that encode recombinant neuraminidase described herein. Due to the degeneracy of the genetic code, any nucleic acid sequence that encodes a recombinant neuraminidase described herein is encompassed herein. In specific embodiments, provided herein is a nucleic acid sequence comprising a nucleotide sequence encoding a recombinant neuraminidase (with or without a signal peptide). In certain embodiment, the nucleotide sequence encoding the recombinant neuraminidase comprises a nucleotide sequence encoding a signal peptide (e.g., a signal peptide/membrane anchor from the NA of the same influenza virus as the influenza virus engineered to express the recombinant neuraminidase polypeptide). In some embodiments, the nucleic acid sequence further comprises the 5' non-coding region and 3' non-coding region of an influenza virus NA (e.g., the 5' non-coding region and 3' non-coding region from the NA of the same influenza virus as the influenza virus engineered to express the recombinant neuraminidase). In certain embodiments, the nucleic acid sequence further comprises the packaging signals of an influenza virus NA gene segment. In certain embodiments, the nucleic acid sequence further comprises the packaging signals of an influenza virus gene segment other than an influenza virus NA gene segment, such as described in, e.g., International Patent Application Publication No. WO 2011/014645; Gao & Palese 2009, PNAS 106:15891-15896; U.S. Pat. No. 8,828,406, each of which is incorporated herein in its entirety. In some embodiments, the nucleic acid sequences provided herein are codon optimized.

In certain embodiments, provided herein is a nucleic acid sequence comprising the nucleotide sequence set forth in SEQ ID NO: 55, 57, 59 or 61. In a specific embodiment, provided herein is a nucleic acid sequence comprising the nucleotide sequence set forth in SEQ ID NO: 55 or 57.

Also provided herein are nucleic acid sequences capable of hybridizing to a nucleic acid encoding a recombinant neuraminidase. In some embodiments, provided herein is a nucleic acid sequence capable of hybridizing to the nucleotide sequence set forth in SEQ ID NO:55, 57, 60 or 61. In certain embodiments, provided herein are nucleic acid sequences capable of hybridizing to a fragment of a nucleic acid sequence encoding a recombinant neuraminidase. In some embodiments, provided herein is a nucleic acid sequence capable of hybridizing to a fragment (e.g., comprising or consisting of 250, 300, 350, 400, 450, 500, 550, 600 or more nucleotides, or between 300 to 600, 400 to 600 or 500 to 700 nucleotides) of SEQ ID NO: 55, 57, 60 or 61. In other embodiments, provided herein are nucleic acid sequences capable of hybridizing to the full length of a nucleic acid sequence encoding a recombinant neuraminidase. General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C. below the melting temperature of the nucleic acid(s), a high salt concentration (e.g., greater than 1000 mM) and the absence of co-solvents.

In some embodiments, a nucleic acid sequence comprising a nucleotide sequence encoding a recombinant neuraminidase is isolated. In certain embodiments, an "isolated" nucleic acid sequence refers to a nucleic acid molecule which is separated from other nucleic acid molecules which are present in the natural source of the nucleic acid. In other words, the isolated nucleic acid sequence can comprise heterologous nucleic acids that are not associated with it in nature. In other embodiments, an "isolated" nucleic acid sequence, such as a cDNA or RNA sequence, can be substantially free of other cellular material, or culture medium when produced by recombinant techniques, or substantially free of chemical precursors or other chemicals when chemically synthesized. The term "substantially free of cellular material" includes preparations of nucleic acid sequences in which the nucleic acid sequence is separated from cellular components of the cells from which it is isolated or recombinantly produced. Thus, nucleic acid sequence that is substantially free of cellular material includes preparations of nucleic acid sequence having less than about 30%, 20%, 10%, or 5% (by dry weight) of other nucleic acids. The term "substantially free of culture medium" includes preparations of nucleic acid sequence in which the culture medium represents less than about 50%, 20%, 10%, or 5% of the volume of the preparation. The term "substantially free of chemical precursors or other chemicals" includes preparations in which the nucleic acid sequence is separated from chemical precursors or other chemicals which are involved in the synthesis of the nucleic acid sequence. In specific embodiments, such preparations of the nucleic acid sequence have less than about 50%, 30%, 20%, 10%, 5% (by dry weight) of chemical precursors or compounds other than the nucleic acid sequence of interest.

5.3 Expression of Recombinant Neuraminidase

Provided herein are vectors, including expression vectors, containing a nucleic acid sequence comprising a nucleotide sequence encoding a recombinant neuraminidase (NA) described herein. In a specific embodiment, the vector is an expression vector that is capable of directing the expression of a nucleic acid sequence encoding a recombinant neuraminidase. Non-limiting examples of expression vectors include, but are not limited to, plasmids and viral vectors, such as replication defective retroviruses, adenoviruses, vesicular stomatitis virus (VSV), Newcastle disease virus (NDV), vaccinia (e.g., Modified Vaccinia Ankara virus), adeno-associated viruses and baculoviruses. Techniques known to one of skill in the art may be used to engineer such viral vectors to express a recombinant neuraminidase described herein. Expression vectors also may include, without limitation, transgenic animals and non-mammalian cells/organisms, e.g., non-mammalian cells/organisms that have been engineered to perform mammalian N-linked glycosylation.

In some embodiments, provided herein are expression vectors encoding components of a recombinant neuraminidase (e.g., the stalk domain and the globular head domain, or portions of either domain). Such vectors may be used to express the components in one or more host cells and the components may be isolated and conjugated together with a linker using techniques known to one of skill in the art.

An expression vector comprises a nucleic acid sequence comprising a nucleotide sequence encoding a recombinant neuraminidase described herein and in a form suitable for expression of the nucleic acid sequence in a host cell. In a specific embodiment, an expression vector includes one or more regulatory sequences, selected on the basis of the host cells to be used for expression, which is operably linked to the nucleic acid sequence to be expressed. Within an expression vector, "operably linked" is intended to mean that a nucleic acid sequence of interest is linked to the regulatory sequence(s) in a manner which allows for expression of the nucleic acid sequence (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid sequence in many types of host cells, those which direct expression of the nucleic acid sequence only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid sequence and the progeny or potential progeny of such a cell. Progeny of such a cell may not be identical to the parent cell transformed or transfected with the nucleic acid sequence due to mutations or environmental influences that may occur in succeeding generations or integration of the nucleic acid sequence into the host cell genome. In specific embodiments, the host cell is a cell line. Examples of host cells (e.g., yeat, avian, insect, plant and/or mammalian cells) that may be used to express a nucleic acid sequence are provided herein.

Expression vectors can be designed for expression of a recombinant neuraminidase described herein using prokaryotic (e g., E. coli) or eukaryotic cells (e.g., insect cells (using baculovirus expression vectors, see, e.g., Treanor et al., 2007, JAMA, 297(14):1577-1582 incorporated by reference herein in its entirety), yeast cells, plant cells, algae, avian, or mammalian cells). Examples of yeast host cells include, but are not limited to S. pombe and S. cerevisiae and examples, infra. An example of avian cells includes, but is not limited to EB66 cells. Examples of mammalian host cells include, but are not limited to, A549 cells, Crucell Per.C6 cells, Vero cells, CHO cells, VERO cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, Sf21, *Trichoplusia ni, Spodoptera frugiperda* and *Bombyx mori*. In a particular embodiment, a mammalian cell culture system (e.g. Chinese hamster ovary or baby hamster kidney cells) is used for expression of a recombinant neuraminidase. In another embodiment, a plant cell culture system is used for expression of a recombinant neuraminidase. See, e.g., U.S. Pat. Nos. 7,504,560; 6,770, 799; 6,551,820; 6,136,320; 6,034,298; 5,914,935; 5,612, 487; and 5,484,719, and U.S. patent application publication Nos. 2009/0208477, 2009/0082548, 2009/0053762, 2008/ 0038232, 2007/0275014 and 2006/0204487 for plant cells and methods for the production of proteins utilizing plant cell culture systems. In specific embodiments, plant cell culture systems are not used for expression of a recombinant neuraminidase. The host cells comprising a nucleic acid sequence that encodes a recombinant neuraminidase described herein can be isolated, i.e., the cells are outside of the body of a subject. In certain embodiments, the cells are engineered to express a nucleic acid sequence that encodes a recombinant neuraminidase described herein. In particular embodiments, the cells are engineered to express a recombinant neuraminidase described herein. In specific embodiments, the host cells are cells from a cell line.

In certain embodiments, provided herein is host cell(s) comprising a nucleic acid sequence that comprises a nucleotide sequence encoding a recombinant neuraminidase described herein. In some embodiments, provided herein is a host cell(s) engineered to express a express a recombinant neuraminidase described herein. Host cells include those cells, including cell lines, described herein.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid sequence encoding a recombinant neuraminidase. In other embodiments, a host cell is stably transfected with an expression vector containing a nucleic acid sequence encoding a recombinant neuraminidase.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid sequence can be identified by drug selection (e.g., cells that have incorporated the selectable marker gene will survive, while the other cells die).

As an alternative to recombinant expression of a recombinant neuraminidase using a host cell, an expression vector containing a nucleic acid sequence encoding a recombinant neuraminidase can be transcribed and translated in vitro using, e.g., T7 promoter regulatory sequences and T7 polymerase. In a specific embodiment, a coupled transcription/ translation system, such as Promega TNT®, or a cell lysate or cell extract comprising the components necessary for transcription and translation may be used to produce a recombinant neuraminidase.

Once a recombinant neuraminidase has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins.

Accordingly, provided herein are methods for producing a recombinant neuraminidase. In one embodiment, the method comprises culturing a host cell containing a nucleic acid sequence comprising a nucleotide sequence encoding a recombinant neuraminidase in a suitable medium such that the recombinant neuraminidase is produced. In some embodiments, the method further comprises isolating the recombinant neuraminidase from the medium or the host cell.

Also provided herein are methods for producing a virus (e.g., an influenza virus (see Section 5.4, infra) or a non-influenza virus vector (e.g., a baculovirus) comprising a recombinant neuraminidase described herein, comprising propagating the virus in any substrate that allows the virus to grow to titers that permit their use in accordance with the methods described herein. In one embodiment, the substrate allows the viruses to grow to titers comparable to those determined for the corresponding wild-type viruses. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In some embodiments, the virus is propagated in embryonated eggs (e.g., chicken eggs) that are interferon (IFN)-deficient. In some embodiments, the virus is propagated in embryonated eggs (e.g., chicken eggs) that are impaired in interferon (IFN) expression. In certain embodiments, the virus is propagated in MDCK cells, Vero cells, 293T cells, or other cell lines known in the art. See, e.g., Section 5.3, supra, for examples of cell lines. In certain embodiments, the virus is propagated in cells derived from embryonated eggs. In certain embodiments, the virus is propagated in an embryonated egg (e.g., chicken eggs) and then in MDCK cells, Vero cells, 293T cells, or other cell lines known in the art.

5.4 Influenza Viruses

In one aspect, provided herein are influenza viruses containing a recombinant neuraminidase (NA) described herein. In specific embodiments, the influenza viruses described are recombinantly produced. In a specific embodiment, a recombinant neuraminidase is incorporated into the virion of the influenza virus. The influenza viruses may be conjugated to moieties that target the viruses to particular cell types, such as immune cells. In some embodiments, the virions of the influenza virus have incorporated into them or express a heterologous polypeptide in addition to a recombinant neuraminidase. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing a recombinant neuraminidase may be produced by supplying in trans the recombinant neuraminidase during production of virions using techniques known to one skilled in the art, such as reverse genetics and helper-free plasmid rescue. Alternatively, the replication of a parental influenza virus comprising a genome engineered to express a recombinant neuraminidase in cells susceptible to infection with the virus. In certain embodiments, the neuraminidase function is provided in trans to produce progeny influenza viruses.

In another aspect, provided herein are influenza viruses comprising a genome engineered to express a recombinant neuraminidase. In a specific embodiment, the genome of a parental influenza virus is engineered to encode a recombinant neuraminidase, which is expressed by progeny influenza virus. In another specific embodiment, the genome of a parental influenza virus is engineered to encode a recombinant neuraminidase, which is expressed and incorporated into the virions of progeny influenza virus. Thus, the progeny influenza virus resulting from the replication of the parental influenza virus contain a recombinant neuraminidase. In specific embodiments, the parental influenza virus is an influenza A virus. In other specific embodiments, the parental influenza virus is an influenza B virus.

In some embodiments, the virions of the parental influenza virus have incorporated into them a heterologous polypeptide. In certain embodiments, the genome of a parental influenza virus is engineered to encode a heterologous polypeptide and a recombinant neuraminidase, which are expressed by progeny influenza virus. In specific embodiments, the recombinant neuraminidase, the heterologous polypeptide or both are incorporated into virions of the progeny influenza virus.

Since the genome of influenza A and B viruses consist of eight (8) single-stranded, negative sense segments, the genome of a parental influenza virus may be engineered to express a recombinant neuraminidase (and any other polypeptide, such as a heterologous polypeptide) using a recombinant segment and techniques known to one skilled in the art, such a reverse genetics and helper-free plasmid rescue. In one embodiment, provided herein is a recombinant segment comprising a nucleic acid sequence encoding a recombinant neuraminidase, as well as the 3' and 5' incorporation signals which are required for proper replication, transcription and packaging of the vRNAs (Fujii et al, 2003, Proc. Natl. Acad. Sci. USA 100:2002-2007; Zheng, et al., 1996, Virology 217:242-251, International Publication No. WO 2011/014645, all of which are incorporated by reference herein in their entireties). In a specific embodiment, the recombinant segment uses the 3' and 5' noncoding and/or nontranslated sequences of segments of influenza viruses that are from a different or the same type, subtype/lineage or strain as the parental influenza virus. In some embodiments, the recombinant segment comprises the 3' noncoding region of an influenza virus NA, the untranslated regions of an influenza virus NA, and the 5' non-coding region of an influenza virus NA. In specific embodiments, the recombinant segment comprises packaging signals, such as the 5' and 3' non-coding regions of the NA segment of an influenza virus, from the same type, lineage, or strain as the influenza virus backbone. For example, if the recombinant neuraminidase is engineered to be expressed from an influenza A virus, then the nucleotide sequence encoding the recombinant neuraminidase (NA) comprises the 5' and 3' non-coding regions of the NA segment of the influenza A virus. In certain embodiments, the recombinant segment encoding the recombinant neuraminidase may replace the NA segment of a parental influenza virus.

In some embodiments, an NA gene segment encodes a recombinant neuraminidase. In specific embodiments, the influenza virus NA gene segment and at least one other influenza virus gene segment comprise packaging signals that enable the influenza virus NA gene segment and at least one other gene segment to segregate together during replication of a recombinant influenza virus (see, Gao & Palese 2009, PNAS 106:15891-15896; U.S. Pat. No. 8,828,406; and International Application Publication No. WO11/014645, each of which is incorporated herein by reference in its entirety).

In some embodiments, the genome of a parental influenza virus may be engineered to express a recombinant neuraminidase using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which is hereby incorporated by reference in its entirety). See also, e.g., U.S. Pat. Nos. 6,887,699, 6,001,634, 5,854,037 and 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238). Thus, in certain embodiments, a parental influenza virus is engineered to contain a bicistronic RNA segment that expresses the recombinant neuraminidase and another polypeptide, such as a gene expressed by the parental influenza virus. In some embodiments, the parental influenza virus gene is the NA gene.

Techniques known to one skilled in the art may be used to produce an influenza virus containing a recombinant neuraminidase and an influenza virus comprising a genome engineered to express a recombinant neuraminidase. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152, 845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780475A1 published Jun. 25, 1997, each of which is incorporated by reference herein in its entirety.

Alternatively, helper-free plasmid technology may be used to produce an influenza virus containing a recombinant neuraminidase and an influenza virus comprising a genome engineered to express a recombinant neuraminidase. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951, 754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, each of which is incorporated herein by reference in its entirety. In a specific embodiment, a method analogous to that described in Section 6 is used to construct a recombinant neuraminidase described herein. In a specific embodiment, a method analogous to that described in Section 6 is used to construct an influenza virus containing and expressing a recombinant neuraminidase. In a specific embodiment, a method analogous to that described in Section 6 is used to construct and propagate a recombinant neuraminidase.

In some embodiments, a recombinant influenza virus is produced by reverse genetics, using a DNA plasmid(s) that expresses a recombinant neuraminidase, which is co-transfected with plasmids for the other 7 genes of influenza virus in a mammalian cell line, such as HEK293T cells. In a specific embodiment, the recombinant influenza virus replicates in embryonated chicken eggs without apparent disadvantages over the influenza viruses that do not have a recombinant neuraminidase described herein. For example, the recombinant influenza virus described herein replicates to comparable titers as the corresponding wild-type influenza virus in a particular cell line.

The influenza viruses described herein may be propagated in any substrate that allows the virus to grow to titers that permit their use in accordance with the methods described herein. Thus, in certain embodiments, provided herein is a method for producing a virus described herein comprising propagating the virus in a substrate. In one embodiment, the substrate allows the viruses to grow to titers comparable to those determined for the corresponding wild-type viruses. In certain embodiments, the substrate is one which is biologically relevant to the influenza virus. In a specific embodiment, an attenuated influenza virus by virtue of, e.g., a mutation in the NS1 gene, may be propagated in an IFN-deficient substrate. For example, a suitable IFN-deficient substrate may be one that is defective in its ability to produce or respond to interferon, or is one which an IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In some embodiments, the virus is propagated in embryonated eggs (e.g., chicken eggs) that are IFN-deficient. In certain embodiments, the virus is propagated in MDCK cells, Vero cells, 293T cells, or other cell lines known in the art. See, e.g., Section 5.3, supra, for examples of cell lines. In certain embodiments, the virus is propagated in cells derived from embryonated eggs.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from a single influenza A virus subtype/lineage or strain. In other embodiments, the influenza viruses, or influenza virus polypeptides, genes or genome segments for use as described herein are obtained or derived from two or more influenza A virus subtypes or strains. In a specific embodiment, the influenza A virus is an influenza virus of the H1, H2, H3, H4, H5, H6, H7, H8, H9, H10, H11, H12, H13, H14, H15, H16, H17, or H18 subtype. In a specific embodiment, the influenza A virus is an influenza virus of the H2, H4, H5, H6, H7, H8, H9, H10, H11, H12, H13, H14, H15, H16, H17, or H18 subtype. In a specific embodiment, the influenza A virus is an influenza virus of the H1 or H3 subtype. In a specific embodiment, the influenza A virus is an influenza virus of the H5, H7, H9 or H10 subtype.

Non-limiting examples of influenza A viruses include subtype H10N4, subtype H10N5, subtype H10N8, subtype, H14N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/Victoria/361/2011 (H3N2); A/California/4/2009 (H1N1); A/California/7/2009 (H1N1); A/Perth/16/2009 (H3N2); A/Brisbane/59/2007 (H1N1); A/Brisbane/10/2007 (H3N2); A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1), A/turkey/Germany/3/91 (H1N1); A/sw/Germany/8533/91 (H1N1); A/sw/Belgium/220/92 (H3N2); A/sw/Gent/V230/92 (H1N1); A/sw/Leipzig/145/92 (H3N2); A/sw/Re220/92 hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2), A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1), A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2); A/sw/Haselünne/2617/03 hp (H1N1); A/sw/Löningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N1), A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/

IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dötlingen/IDT3780/05 (H1N2); A/sw/Dötlingen/IDT4735/05 (H1N2), A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S/IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/sw/Voglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2). In a specific embodiment, an influenza A virus is influenza A/Brisbane/02/2018 (H1N1) pdm09-like virus, influenza A/Kansas/14/2017 (H3N2)-like virus, influenze A/Brisbane/02/2018 (H1N1) pdm09-like virus, or influenza A/South Australia/34/2019 (H3N2)-like virus.

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1) A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

In certain embodiments, the influenza viruses, or influenza virus polypeptides, genes or genome segments for use as described herein are obtained or derived from an influenza B virus. In certain embodiments, the influenza viruses, or influenza virus polypeptides, genes or genome segments for use as described herein are obtained or derived from a single influenza B virus subtype/lineage or strain. In other embodiments, the influenza viruses, or influenza virus polypeptides, genes or genome segments for use as described herein are obtained or derived from two or more influenza B virus subtypes or strains.

Non-limiting examples of influenza B viruses include strain Aichi/5/88, strain B/Brisbane/60/2008; Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, strain B/Wisconsin/1/2010; and strain Rochester/02/2001. In a specific embodiment, an influenza B virus is influenza a B/Colorado/06/2017-like virus (B/Victoria/2/87 lineage), influenza B/Phuket/3073/2013-like virus (B/Yamagata/16/88 lineage), influenza B/Washington/02/2019-like (B/Victoria lineage) virus, or influenza B/Phuket/3073/2013-like (B/Yamagata lineage) virus.

Other examples of influenza viruses may be found elsewhere in the application, such as in, e.g., Section 6 below. In a specific embodiment, a seasonal influenza virus strain may be used.

In certain embodiments, the influenza viruses provided herein have an attenuated phenotype. In specific embodiments, the attenuated influenza virus is based on influenza A virus. In specific embodiments, the attenuated influenza virus comprises, encodes, or both, a recombinant neuraminidase and has a backbone of an influenza A virus. In some embodiments, the attenuated influenza virus is based on influenza B virus. In specific embodiments, the attenuated influenza virus comprises, encodes, or both, a recombinant neuraminidase and has a backbone of an influenza B virus.

In specific embodiments, attenuation of influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function (e.g., truncated NS1 protein (see, e.g., Hai et al., 2008, Journal of Virology 82(21):10580-10590, which is incorporated by reference herein in its entirety) or NS1 deletion (see, e.g., Wressnigg et al., 2009, Vaccine 27:2851-2857, which is incorporated by reference herein in its entirety)), or selecting for conditional virus mutants (e.g., cold-adapted viruses, see, e.g., Alexandrova et al., 1990, Vaccine, 8:61-64, which is incorporated by reference herein in its entirety). Alternatively, naturally occurring attenuated influenza viruses may be used as influenza virus backbones for the influenza virus vectors.

In a specific embodiment, the influenza A virus A/Puerto Rico/8/34 strain is used as the backbone to express a recombinant neuraminidase described herein. In another specific embodiment, the virion of the influenza A virus A/Puerto Rico/8/34 strain contains a recombinant neuraminidase described herein. In another specific embodiment, the influenza A virus A/Puerto Rico/8/34 strain is used to express a recombinant neuraminidase described herein and the virion of the A/Puerto Rico/8/34 strain contains the recombinant neuraminidase.

In a specific embodiment, an influenza A virus lacking the NS1 protein (e.g., a delNS1 virus, such as described, e.g., in U.S. Pat. No. 6,468,544; Garcia-Sastre et al., 1998, Virology 252: 324; or Mossier et al., 2013, Vaccine 31: 6194) is used as the backbone to express a recombinant neuraminidase described herein. In another specific embodiment, the virion of an influenza virus lacking the NS1 protein (e.g., a delNS1 virus, such as described, e.g., in U.S. Pat. No. 6,468,544; Garcia-Sastre et al., 1998, Virology 252: 324; or Mössler et al., 2013, Vaccine 31: 6194) contains a recombinant neuraminidase described herein. In another specific embodiment, an influenza virus lacking the NS1 protein (e.g., a delNS1 virus, such as described, e.g., in U.S. Pat. No. 6,468,544; Garcia-Sastre et al., 1998, Virology 252: 324; or Mossier et al., 2013, Vaccine 31: 6194) is used to express a recombinant neuraminidase described herein and the virion of such a virus contains the recombinant neuraminidase.

In a specific embodiment, a cold-adapted influenza A virus strain is used as the backbone to express a recombinant neuraminidase described herein. In another specific embodiment, the virion of the cold-adapted strain contains a recombinant neuraminidase described herein. In another specific embodiment, the cold-adapted influenza A virus is used to express a recombinant neuraminidase described herein and the virion of the cold-adapted influenza virus contains the recombinant neuraminidase. In one embodiment, the cold-adapted influenza A virus is A/Ann Arbor/6/60. In another embodiment, the cold-adapted influenza A virus is A/Leningrad/134/17/57. In another embodiment, a seasonal influenza virus strain is used as the backbone to express a recombinant neuraminidase described herein.

In certain embodiments, an influenza virus comprising a recombinant neuraminidase described herein has one, two, or more of the functions of an influenza virus comprising a wild-type influenza virus NA. A nonlimiting example of a function of a wild-type influenza virus NA include cleavage of sialic acid. In a specific embodiment, an influenza virus comprising a recombinant neuraminidase described herein cleaves sialic acid. Assays known to one skilled in the art can be utilized to assess the ability of a recombinant neuraminidase to cleave sialic acid.

5.5 Compositions

In one aspect, provided herein are compositions comprising a recombinant neuraminidase described herein. An influenza virus comprising a recombinant neuraminidase described herein may be incorporated into a composition. In a particular embodiment, an influenza virus described herein (e.g., in Section 5.4 or 6) is incorporated into a composition. In a specific embodiment, a composition is a pharmaceutical composition, such as an immunogenic composition (e.g., a vaccine formulation). The pharmaceutical compositions provided herein can be in any form that allows for the composition to be administered to a subject. In a specific embodiment, the pharmaceutical compositions are suitable for veterinary and/or human administration. The compositions may be used in methods of preventing an influenza virus disease. The compositions may be used in methods to induce an immune response against influenza virus. The compositions may be used in methods to immunize against influenza virus.

In a specific embodiment, a pharmaceutical composition (e.g., immunogenic composition) comprises a recombinant neuraminidase described herein, and optionally an adjuvant. In another specific embodiment, a pharmaceutical composition (e.g., immunogenic composition) comprises a recombinant neuraminidase described herein in an admixture with a pharmaceutically acceptable carrier. In a specific embodiment, a pharmaceutical composition (e.g., immunogenic composition) comprises an adjuvant (e.g., an adjuvant described herein) and a recombinant neuraminidase described herein, in an admixture with a pharmaceutically acceptable carrier.

In a specific embodiment, a pharmaceutical composition (e.g., immunogenic composition) comprises a nucleic acid sequence comprising a nucleotide sequence encoding a recombinant neuraminidase described herein or a vector (e.g., an expression vector) comprising a nucleic acid sequence encoding a recombinant neuraminidase described herein, and optionally an adjuvant. In another specific embodiment, a pharmaceutical composition (e.g., immunogenic composition) comprises a nucleic acid sequence comprising a nucleotide sequence encoding a recombinant neuraminidase described herein or a vector (e.g., an expression vector) comprising a nucleic acid sequence encoding a recombinant neuraminidase described herein in an admixture with a pharmaceutically acceptable carrier. In a specific embodiment, a pharmaceutical composition (e.g., immunogenic composition) comprises an adjuvant (e.g., an adjuvant described herein) and a nucleic acid sequence comprising a nucleotide sequence encoding a recombinant neuraminidase described herein or a vector (e.g., an expression vector) comprising a nucleic acid sequence encoding a recombinant neuraminidase described herein, in an admixture with a pharmaceutically acceptable carrier. In some embodiments, an immunogenic composition comprises a nucleic acid sequence or vector described herein contained in or associated with a lipid particle, nanoparticle or a liposomal particle.

In a specific embodiment, a pharmaceutical composition (e.g., immunogenic composition) comprises an influenza virus comprising a recombinant neuraminidase described herein, and optionally an adjuvant. In another specific embodiment, a pharmaceutical composition (e.g., immunogenic composition) comprises an influenza virus comprising a recombinant neuraminidase described herein in an admixture with a pharmaceutically acceptable carrier. In a specific embodiment, a pharmaceutical composition (e.g., immunogenic composition) comprises an adjuvant (e.g., an adjuvant described herein) and an influenza virus comprising a recombinant neuraminidase described herein, in an admixture with a pharmaceutically acceptable carrier.

In another specific embodiment, a pharmaceutical composition (e.g., immunogenic composition) comprises an influenza virus (e.g., a seasonal influenza virus strain) and a recombinant neuraminidase described herein in an admixture with a pharmaceutically acceptable carrier. In a specific embodiment, a pharmaceutical composition (e.g., immunogenic composition) comprises an adjuvant (e.g., an adjuvant described herein), an influenza virus (e.g., a seasonal influenza virus strain), and a recombinant neuraminidase described herein, in an admixture with a pharmaceutically acceptable carrier. The influenza virus may be live attenuated or inactivated. In addition, the composition may comprise more than one influenza virus, which is live attenuated or inactivated, and more than one recombinant neuraminidase described herein. The influenza virus composition may be trivalent or quadrivalent. In some embodiments, the composition further comprises an adjuvant.

In another specific embodiment, provided herein is trivalent inactivated influenza virus vaccine supplemented with a recombinant neuraminidase described herein. In another specific embodiment, provided herein is a quadrivalent inactivated influenza virus vaccine supplemented with a recombinant neuraminidase described herein. In another specific embodiment, provided herein is a live attenuated influenza virus vaccine supplemented with a recombinant neuraminidase described herein. In some embodiments, the composition further comprises an adjuvant.

In a specific embodiment, a pharmaceutical composition (e.g., immunogenic composition) comprises a live virus (e.g., a live attenuated virus) comprising a recombinant neuraminidase described herein, and optionally an adjuvant. In another specific embodiment, a pharmaceutical composition (e.g., immunogenic composition) comprises an inactivated virus comprising a recombinant neuraminidase described herein, and optionally an adjuvant. In another specific embodiment, a pharmaceutical composition (e.g., immunogenic composition) comprises a nucleic acid sequence comprising a nucleotide sequence encoding a recombinant neuraminidase described herein, and optionally an adjuvant. In another specific embodiment, a pharmaceutical composition (e.g., immunogenic composition) comprises a vector comprising a nucleic acid sequence encoding a recombinant neuraminidase described herein, and optionally an adjuvant.

In a specific embodiment, provided herein is a composition comprising an antibody that binds to influenza virus neuraminidase, which was generated using a recombinant neuraminidase or an influenza virus described herein.

In certain embodiments, a pharmaceutical composition (e.g., an immunogenic composition) may comprise one or more other therapies in addition to a therapy that utilizes a recombinant neuraminidase described herein described herein. In some embodiments, a pharmaceutical composition (e.g., an immunogenic composition) may comprise one or more other therapies in addition to a therapy that utilizes an influenza virus comprising a recombinant neuraminidase described herein. In certain embodiments, a pharmaceutical composition (e.g., an immunogenic composition) may comprise one or more other therapies in addition to a therapy that utilizes a nucleic acid sequence comprising a nucleotide sequence encoding a recombinant neuraminidase described herein or a vector comprising a nucleic acid sequence encoding a recombinant neuraminidase described herein.

As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration. In a specific embodiment, the pharmaceutical composition may be formulated for intramuscular administration. In another specific embodiment, the pharmaceutical composition may be formulated for subcutaneous administration. In another specific embodiment, the pharmaceutical composition may be formulated for intranasal administration.

In specific embodiments, immunogenic compositions described herein are monovalent formulations. In other embodiments, immunogenic compositions described herein are multivalent formulations. In one example, a multivalent formulation comprises more than one influenza virus comprising a recombinant neuraminidase described herein.

In certain embodiments, an immunogenic composition described herein comprises more than one recombinant neuraminidase described herein. For example, an immunogenic composition may comprise 2, 3 or 4 recombinant neuraminidase described herein (e.g., a recombinant N1 and a recombinant influenza B virus NA).

An immunogenic composition described herein may be used to immunize a subject against influenza virus. An immunogenic composition described herein may also be used to prevent an influenza virus disease in a subject. In a specific embodiment, an immunogenic composition described herein may be used in a method described herein.

In certain embodiments, the pharmaceutical compositions (e.g., immunogenic compositions) described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions (e.g., immunogenic compositions) described herein additionally comprise one or more buffers, e.g., phosphate buffer and sucrose phosphate glutamate buffer. In other embodiments, the pharmaceutical compositions described herein do not comprise buffers.

The pharmaceutical compositions (e.g., immunogenic compositions) described herein can be included in a container, pack, or dispenser together with instructions for administration.

The pharmaceutical compositions (e.g., immunogenic compositions) described herein can be stored before use, e.g., the pharmaceutical compositions can be stored frozen (e.g., at about −20° C. or at about −70° C.); stored in refrigerated conditions (e.g., at about 4° C.); or stored at room temperature (see International Application No. PCT/IB2007/001149 published as International Publication No. WO 07/110776, which is herein incorporated by reference in its entirety, for methods of storing compositions comprising influenza vaccines without refrigeration).

In a specific embodiment, an immunogenic composition is an inactivated vaccine comprising an adjuvant (e.g., an adjuvant described in Section 5.5.3 below) and a recombinant neuraminidase (NA). The inactivated vaccine may be a whole virus inactivated vaccine or split virion vaccine. Techniques for producing such vaccines are known to one of skill in the art. In a specific embodiment, an immunogenic composition comprises formalin-inactivated whole virus particles for vaccination through the intramuscular route.

5.5.1 Live Virus Vaccines

In one embodiment, provided herein are immunogenic compositions (e.g., vaccines) comprising live virus containing a recombinant neuraminidase described herein. In another embodiment, provided herein are immunogenic compositions (e.g., vaccines) comprising live virus that is engineered to encode a recombinant neuraminidase described herein, which is expressed by progeny virus produced in the subjects administered the compositions. In specific embodiments, the recombinant neuraminidase is membrane-bound. In other specific embodiments, the recombinant neuraminidase is not membrane-bound, i.e., it is soluble. In particular embodiments, the live virus is an influenza virus, such as described in Section 5.4. In some embodiments, the live virus is attenuated. In a specific embodiment, the live virus is a live attenuated influenza virus.

In a specific embodiment, the live virus that contains a recombinant neuraminidase is propagated in embryonated chicken eggs before its use in an immunogenic composition described herein. In another specific embodiment, the live virus that contains a recombinant neuraminidase is not propagated in embryonated chicken eggs before its use in an immunogenic composition described herein. In another specific embodiment, the live virus that contains a recombinant neuraminidase is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and therefore, confer substantial, long lasting immunity.

5.5.2 Inactivated Virus Vaccines

In one embodiment, provided herein are immunogenic compositions (e.g., vaccines) comprising an inactivated virus containing a recombinant neuraminidase. In specific embodiments, the recombinant neuraminidase is membrane-bound. In particular embodiments, the inactivated virus is an influenza virus, such as described in Section 5.4 or 6. In certain embodiments, the inactivated virus immunogenic compositions comprise one or more adjuvants.

Techniques known to one of skill in the art may be used to inactivate viruses containing a recombinant neuraminidase. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In a specific embodiment, an immunogenic composition described herein is a split vaccine. Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100-A registered trademark of Union Carbide, Co.) producing a "split virus." The split virus is then further purified by chemical means and suspended in sodium phosphate-buffered isotonic sodium chloride solution.

In a specific embodiment, the inactivated virus that contains a recombinant neuraminidase was propagated in embryonated chicken eggs before its inactivation and subsequent use in an immunogenic composition described herein. In another specific embodiment, the inactivated virus that contains a recombinant neuraminidase was not propagated in embryonated chicken eggs before its inactivation and subsequent use in an immunogenic composition described herein. In another specific embodiment, the inactivated virus that contains a recombinant neuraminidase was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/M2007/003536 published as International Publication No. WO 08/032219 which is herein incorporated by reference in its entirety) before its inactivation and subsequent use in an immunogenic composition described herein.

5.5.3 Adjuvants

In certain embodiments, the compositions described herein comprise, or are administered in combination with, an adjuvant. The adjuvant for administration in combination with a composition described herein may be administered before, concomitantly with, or after administration of said composition. In some embodiments, the adjuvant enhance or boosts an immune response to influenza virus and does not produce an allergy or other adverse reaction. Adjuvants can enhance an immune response by several mechanisms including, e.g., lymphocyte recruitment, stimulation of B and/or T cells, and stimulation of macrophages.

In certain embodiments, an adjuvant augments the intrinsic response to a recombinant neuraminidase without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057, 540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents. An adjuvant may be AddaVax. Another adjuvant is one described in Section 6.1 or 6.2, infra.

5.6 Prophylactic and Therapeutic Uses

In one aspect, provided herein are methods for inducing an immune response in a subject utilizing a recombinant neuraminidase described herein or a composition thereof. In a specific embodiment, a method for inducing an immune response to an influenza virus in a subject comprises administering to a subject in need thereof an effective amount of an immunogenic composition described herein.

In another aspect, provided herein are methods for inducing an immune response in a subject utilizing a nucleic acid sequence comprising a nucleotide sequence encoding a recombinant neuraminidase described herein, or a composition thereof. In a specific embodiment, a method for inducing an immune response to an influenza virus in a subject comprises administering to a subject in need thereof an effective amount of a composition comprising a nucleic acid sequence comprising a nucleotide sequence encoding a recombinant neuraminidase described herein. In another specific embodiment, a method for inducing an immune response to an influenza virus in a subject comprises administering to a subject in need thereof an effective amount of a composition comprising a vector that comprises a nucleic acid sequence encoding a recombinant neuraminidase described herein.

In another aspect, provided herein are methods for inducing an immune response in a subject utilizing an influenza virus containing, engineered to express a recombinant neuraminidase described herein, or both, or a composition described herein In a specific embodiment, a method for inducing an immune response to an influenza virus in a subject comprises administering to a subject in need thereof an effective amount of an influenza virus containing, engineered to express a recombinant neuraminidase described herein, or both, or an immunogenic composition thereof.

In a specific embodiment, a method for inducing an immune response to an influenza virus in a subject comprises administering to a subject in need thereof a live virus vaccine described herein. In particular embodiments, the live virus vaccine comprises an attenuated virus. In another embodiment, a method for inducing an immune response to an influenza virus in a subject comprises administering to a subject in need thereof an inactivated virus vaccine described herein. In another embodiment, a method for inducing an immune response to an influenza virus in a subject comprises administering to a subject in need thereof a split virus vaccine described herein.

In another aspect, provided herein are methods for immunizing against influenza virus in a subject utilizing a recombinant neuraminidase described herein or a composition thereof. In a specific embodiment, a method for immunizing against influenza virus comprises administering to a subject in need thereof an effective amount of an immunogenic composition described herein.

In one aspect, provided herein are methods for immunizing against influenza virus in a subject utilizing a nucleic acid sequence comprising a nucleotide sequence encoding a recombinant neuraminidase described herein, or a composition thereof. In a specific embodiment, a method for immunizing against influenza virus comprises administering to a subject in need thereof an effective amount of a composition comprising a nucleic acid sequence comprising a nucleotide sequence encoding a recombinant neuraminidase described herein. In another specific embodiment, a method for immunizing against influenza virus in a subject comprises administering to a subject in need thereof an effective amount of a composition comprising a vector (e.g., an expression vector) that comprises a nucleic acid sequence encoding a recombinant neuraminidase described herein.

In another aspect, provided herein are methods for immunizing against influenza virus in a subject utilizing an influenza virus containing, engineered to express a recombinant neuraminidase described herein, or both, or a composition described herein In a specific embodiment, a method for immunizing against influenza virus comprises administering to a subject in need thereof an effective amount of an influenza virus containing, engineered to express a recombinant neuraminidase described herein, or both, or an immunogenic composition thereof.

In a specific embodiment, a method for immunizing against influenza virus comprises administering to a subject in need thereof a live virus vaccine described herein. In particular embodiments, the live virus vaccine comprises an attenuated virus. In another embodiment, a method for immunizing against influenza virus comprises administering to a subject in need thereof an inactivated virus vaccine described herein. In another embodiment, a method for immunizing against influenza virus in a subject comprises administering to a subject in need thereof a split virus vaccine described herein.

In another aspect, provided herein is a method for immunizing against influenza virus, comprising administering to the subject an immunogenic composition described herein (e.g., in Section 5.5 above) and administering to the subject an adjuvant described herein. In one embodiment, provided herein is a method for immunizing against influenza virus in a subject, comprising administering to the subject an immunogenic composition described herein (e.g., in Section 5.5 above) in combination with an adjuvant described herein. The immunogenic composition may be administered to the subject concurrently with, prior to (e.g., less than 5 minutes, less than 10 minutes, less than 15 minutes, less than 30 minutes, less than 45 minutes, less than 60 minutes, less than 1.5 hours, or less than 2 hours prior to), or subsequent to (e.g., less than 5 minutes, less than 10 minutes, less than 15 minutes, less than 30 minutes, less than 45 minutes, less than 60 minutes, less than 1.5 hours, or less than 2 hours after) the administration of an adjuvant described herein. In a specific embodiment, the immunogenic composition and the adjuvant described herein are administered via the same route of administration. In other embodiments, the immunogenic composition and the adjuvant are administered via different routes of administration. In a specific embodiment, the immunogenic composition comprises an inactivated influenza virus containing a recombinant NA described herein. In another specific embodiment, the immunogenic composition comprises a split influenza virus, wherein the split influenza virus comprises a recombinant NA described herein. In some embodiments, the immunogenic composition does not comprise an adjuvant.

In another embodiment, provided herein are immunization regimens involving a first immunization (e.g., priming) with an immunogenic composition (e.g., a vaccine) described herein followed by one, two, or more additional immunizations (e.g., boostings) with an immunogenic composition (e.g., a vaccine). In one embodiment, an immunogenic regimen involves a first immunization (e.g., priming) with an immunogenic composition (e.g., a vaccine) described herein followed by one additional immunizations (e.g., boost) with an immunogenic composition (e.g., a vaccine). In a specific embodiment, the immunogenic composition (e.g., a vaccine) used in the first immunization is the same type of an immunogenic composition (e.g., a vaccine) used in one, two or more additional immunizations. For example, if the immunogenic composition (e.g., vaccine) used in the first immunization is an inactivated influenza virus vaccine formulation, the immunogenic composition (e.g., vaccine) used for the one, two or more additional immunizations may be the same type of vaccine formulation, i.e., an inactivated influenza virus vaccine formulation. In other specific embodiments, the immunogenic composition (e.g., vaccine) used in the first immunization is different from the type of immunogenic composition (e.g., vaccine) used in one, two or more additional immunizations. For example, if the immunogenic composition (e.g., vaccine) used in the first immunization is a live influenza virus vaccine formulation, the immunogenic composition (e.g., vaccine) used in the one, two or more additional immunizations is another type of vaccine formulation, such as an inactivated influenza virus. In another example, if the immunogenic composition (e.g., vaccine) used in the first immunization is a live attenuated influenza virus vaccine formulation, the immunogenic composition (e.g., vaccine) used in the one, two or more additional immunizations is another type of vaccine formulation, such as an inactivated influenza virus. In certain embodiments, the vaccine formulation used in the additional immunizations changes. For example, if a live attenuated influenza virus vaccine formulation is used for one additional immunization, then one or more additional immunizations may use a different vaccine formulation, such as an inactivated vaccine formulation. In a particular embodiment, a live influenza virus vaccine formulation is administered to a subject followed by an inactivated vaccine formulation (e.g., split virus vaccine or subunit vaccine). In a specific embodiment, an immunization regimen is analogous to the regimen described in Section 6, infra (e.g., Example 1 or 3, infra).

In a specific embodiment, in accordance with the methods described herein a subject may be administered one, two or more doses of an immunogenic composition described herein.

In a specific embodiment, a subject is immunized in accordance with a method described herein prior, during or both flu season. In a specific embodiment, flu season in the U.S. may be from September or October of one year through March or April of the next year.

In some embodiments, the immune response induced by an immunogenic composition described herein is effective to prevent an influenza virus disease caused by one, two, or more subtypes of influenza A virus. In some embodiments, the immune response induced by an immunogenic composition described herein is effective to prevent an influenza virus disease caused by one, two, three or more strains of influenza virus. In certain embodiments, the immune response induced by an immunogenic composition described herein is effective to prevent an influenza virus disease caused by a subtype of influenza virus that belongs to one NA group and not another NA group. In some embodiments, the immune response induced by an immunogenic composition described herein is effective to prevent an influenza virus disease caused by one or more strains within the same subtype of influenza A virus. In certain embodiments, the immune response induced by an immunogenic composition described herein is effective to prevent an influenza virus disease caused by one, two, three or more strains within the same subtype of influenza A virus.

In some embodiments, the immune response induced by an immunogenic composition described herein is effective to reduce the number of symptoms resulting from an influenza virus disease/infection. In certain embodiments, the immune response induced by an immunogenic composition described herein is effective to reduce the duration of one or more symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an immunogenic composition described herein is effective to reduce the hospitalization of a subject suffering from an influenza virus disease/infection. In some embodiments, the immune response induced by an immunogenic composition described herein is effective to reduce the duration of hospitalization of a subject suffering from an influenza virus disease/infection.

In a specific embodiment, the immune response induced by an immunogenic composition described herein induces NA-specific antibodies (e.g., IgG). In another specific embodiment, the immune response induced by an immunogenic composition described herein induces antibodies with ADCC activity as assessed by a technique known to one of skill in the art or described herein. In another specific embodiment, the immune response induced by an immunogenic composition described herein induces antibodies with neuraminidase inhibition activity as assessed by a technique known to one of skill in the art or described herein. In another specific embodiment, the immune response induced by an immunogenic composition described herein induces antibodies with (1) ADCC activity as assessed by a technique known to one of skill in the art; and (2) neuraminidase inhibition activity as assessed by a technique known to one of skill in the art or described herein.

In another aspect, provided herein are methods for preventing an influenza virus disease in a subject utilizing an immunogenic composition described herein. In a specific embodiment, a method for preventing an influenza virus disease in a subject comprises administering to a subject in need thereof a recombinant neuraminidase described herein. In a specific embodiment, a method for preventing an influenza virus disease in a subject comprises administering to a subject in need thereof a nucleic acid sequence comprising a nucleotide sequence encoding a recombinant neuraminidase, or a vector comprising a nucleic acid sequence encoding a recombinant neuraminidase. In a specific embodiment, a method for preventing an influenza virus disease in a subject comprises administering to a subject in need thereof a live virus vaccine, an inactivated virus vaccine, or a split virus vaccine described herein. In a specific embodiment, a method for preventing an influenza virus disease in a subject comprises administering to a subject in need thereof a live virus vaccine described herein. In particular embodiments, the live virus vaccine comprises an attenuated virus. In another embodiment, a method for preventing an influenza virus disease in a subject comprises administering to a subject in need thereof an inactivated virus vaccine described herein. In another embodiment, a method for preventing or an influenza virus disease in a subject comprises administering to a subject in need thereof a split virus vaccine described herein. In another embodiment, a method for preventing an influenza virus disease in a subject comprises administering to a subject in need thereof an immunogenic composition described herein.

In another aspect, provided herein are methods for preventing an influenza virus disease, or treating an influenza virus infection or an influenza virus disease in a subject comprising administering to a subject an anti-influenza virus NA antibody(ies), wherein the anti-influenza virus NA antibody(ies) was generated utilizing an immunogenic composition described herein. For example, an immunogenic composition described herein may be administered to a non-human subject (e.g., a non-human subject that expresses or is capable of expression human antibody) to generate anti-influenza virus NA antibody(ies). In a specific embodiment, provided herein is a method for preventing an influenza virus disease in a human subject comprising administering the subject a human or humanized anti-influenza virus NA antibody(ies), wherein the anti-influenza virus NA antibody(ies) was generated utilizing an immunogenic composition described herein.

In certain embodiments, the methods for preventing an influenza virus disease, or treating an influenza virus infection or an influenza virus disease in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. In specific embodiments, the methods for preventing an influenza virus disease, or treating an influenza virus infection or an influenza virus disease in a subject (e.g., a human or non-human animal) provided herein result in a reduction of the titer of an influenza virus detected in the subject. In specific embodiments, the methods for preventing an influenza virus disease, or treating an influenza virus infection or an influenza virus disease in a subject results in one, two, or more of the following: (1) reduces the number of symptoms of the infection/disease, (2) reduces the severity of the symptoms of the infection/disease, (3) reduces the length of the infection/disease, (4) reduces hospitalization or complications resulting from the infection/disease, (5) reduces the length of hospitalization of the subject, (6) reduces organ failure associated with the influenza virus infection/disease, and (7) increases survival of the subject. In a specific embodiment, the methods for preventing an influenza virus disease, or treating an influenza virus infection or an influenza virus disease in a subject inhibits the development or onset of an influenza virus disease or one or more symptoms thereof.

In certain embodiments, provided herein are methods for generating antibodies comprising administering an influenza virus containing, engineered to express a recombinant neuraminidase described herein, or both, or composition described herein may be administered to a subject (e.g., a non-human subject). In some embodiments, an influenza virus containing, engineered to express a recombinant neuraminidase described herein, or both, or composition described herein may be administered to a subject (e.g., a non-human subject) and the antibodies may be isolated. The isolated antibodies may be cloned. The antibodies may be humanized and/or optimized. In some embodiments, hybridomas are produced which produce a particular antibody of interest. In certain embodiments, the non-human subject administered a recombinant neuraminidase described herein or a composition described herein is capable of producing human antibodies. Techniques for isolating, cloning, humanizing, optimizing and for generating hybridomas are known to one of skill in the art. In a specific embodiment, antibodies generated by a method described herein may be utilized in assays (e.g., assays described herein) as well as in passive immunization of a subject (e.g., a human subject). Thus, provided herein, in certain embodiments, are methods for treating influenza virus infection or preventing influenza virus disease, comprising administering antibodies generated by a method described herein.

In another aspect, a recombinant neuraminidase described herein may be used to assess antibodies directed to influenza virus neuraminidase in assays, such as immunoassays.

5.6.1 Combination Therapies

In various embodiments, (1) a recombinant neuraminidase described herein, (2) a nucleic acid sequence comprising a nucleotide sequence encoding a recombinant neuraminidase described herein, (3) a vector comprising a nucleic acid sequence encoding a recombinant neuraminidase, or (4) an influenza virus containing, engineered to express a recombinant neuraminidase described herein, or both may be administered to a subject in combination with one or more other therapies (e.g., an antiviral, antibacterial, or immunomodulatory therapies). In some embodiments, a pharmaceutical composition (e.g., an immunogenic composition) described herein may be administered to a subject in combination with one or more therapies (e.g., an antiviral, antibacterial, or immunomodulatory therapies). The one or more other therapies may be beneficial in the prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patient visit.

5.6.2 Patient Populations

In certain embodiments, a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein may be administered to a naïve subject, i.e., a subject that does not have a disease caused by influenza virus infection or has not been and is not currently infected with an influenza virus infection. In one embodiment, a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is administered to a naïve subject that is at risk of acquiring an influenza virus infection.

In another embodiment, a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is administered to a subject that does not have a disease caused by the specific influenza virus, or has not been and is not infected with the specific influenza virus to which the recombinant neuraminidase induces an immune response.

In another embodiment, a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein may also be administered to a subject that is, has been, or is and has been infected with the influenza virus or another type, subtype/ lineage or strain of the influenza virus to which the recombinant neuraminidase induces an immune response.

In certain embodiments, a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is administered to a patient who has been diagnosed with an influenza virus infection. In some embodiments, a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is administered to a patient infected with an influenza virus before symptoms manifest or symptoms become severe (e.g., before the patient requires hospitalization).

In some embodiments, a subject administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In specific embodiments, a subject administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is a human infant. As used herein, the term "human infant" refers to a newborn to 1 year old human.

In specific embodiments, a subject administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or composition described herein is a human child. As used herein, the term "human child" refers to a human that is 1 year to 18 years old.

In specific embodiments, a subject administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is a human adult. As used herein, the term "human adult" refers to a human that is 18 years or older.

In specific embodiments, a subject administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is an elderly human. As used herein, the term "elderly human" refers to a human 65 years or older.

In some embodiments, the human subject to be administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is any individual at increased risk of influenza virus infection or disease resulting from influenza virus infection (e.g., an immunocompromised or immunodeficient individual).

In some embodiments, the human subject to be administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is any individual in close contact with an individual with increased risk of influenza virus infection or disease resulting from influenza virus infection (e.g., immunocompromised or immunosuppressed individuals).

In some embodiments, the human subject to be administered a recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is an individual affected by any condition that increases susceptibility to influenza virus infection or complications or disease resulting from influenza virus infection. In other embodiments, recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein is administered to a subject in whom an influenza virus infection has the potential to increase complications of another condition that the individual is affected by, or for which they are at risk.

5.6.3 Routes of Delivery

A recombinant neuraminidase; a nucleic acid sequence comprising a nucleotide sequence encoding a recombinant neuraminidase; a vector comprising a nucleic acid sequence encoding a recombinant neuraminidase; an influenza virus, which contains or is engineered to express a recombinant neuraminidase described herein, or both; or a composition described herein may be delivered to a subject by a variety of routes. These include, but are not limited to, intranasal, pulmonary, intratracheal, oral, intradermal, intramuscular, intraperitoneal, transdermal, intravenous, conjunctival and subcutaneous routes as well as other routes described herein. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In specific embodiments for live virus vaccines, the vaccine is formulated for administration by a route other than injection.

In one embodiment, a live attenuated influenza virus vaccine is administered intranasally. In another embodiment, an inactivated influenza virus vaccine (e.g., an inactivated whole virus vaccine or a split influenza virus vaccine) is administered intramuscularly.

5.6.4 Dosage

The amount of a recombinant neuraminidase; a nucleic acid sequence comprising a nucleotide sequence encoding a recombinant neuraminidase; a vector (e.g., an expression vector) comprising a nucleic acid sequence encoding a recombinant neuraminidase; an influenza virus, which contains or is engineered to express a recombinant neuraminidase described herein, or both; or a composition described herein, which will be effective in the prevention of an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but non-human mammals including transgenic mammals can also be treated. Treatment dosages are optimally titrated to optimize safety and efficacy.

As used herein, the term "effective amount" in the context of administering a therapy to a subject refers to the amount of a therapy which may have a prophylactic effect(s), therapeutic effect(s), or both a prophylactic and therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; (ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (viii) prevent or reduce the spread of an influenza virus from one subject to another subject; (ix) reduce organ failure associated with an influenza virus infection; (x) reduce hospitalization of a subject; (xi) reduce hospitalization length; (xii) increase the survival of a subject with an influenza virus infection or disease associated therewith; (xiii) eliminate an influenza virus infection or disease associated therewith; (xiv) inhibit or reduce influenza virus replication; (xv) inhibit or reduce the entry of an influenza virus into a host cell(s); (xvi) inhibit or reduce replication of the influenza virus genome; (xvii) inhibit or reduce synthesis of influenza virus proteins; (xviii) inhibit or reduce assembly of influenza virus particles; (xix) inhibit or reduce release of influenza virus particles from a host cell(s); (xx) reduce influenza virus titer; and/or (xxi) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject with an influenza virus infection. In certain embodiments, the effective amount results in a 0.5 fold, 1 fold, 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject with an influenza virus infection. In some embodiments, the effective amount results in a reduction in titer of influenza virus relative to an untreated subject with an influenza virus infection of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

In certain embodiments, an effective amount of a therapy (e.g., a composition thereof) results in an anti-influenza virus NA titer in a blood sample from a subject administered the effective amount 0.5 fold to 10 fold, 0.5 fold to 4 fold, 0.5 fold to 3 fold, 0.5 fold to 2 fold, 0.5 fold, 1 fold, 1.5 fold, 2 fold, 3 fold, 4 fold, 5 fold, 6 fold, 7 fold, 8 fold, 9 fold, 10 fold higher post-immunization relative to the anti-influenza virus NA titer in a blood sample from the subject prior to immunization. In certain embodiments, an effective amount of a therapy (e.g., a composition thereof) results in an anti-influenza virus NA stalk titer in a blood sample from a subject administered the effective amount 0.5 fold to 10 fold, 0.5 fold to 4 fold, 0.5 fold to 3 fold, 0.5 fold to 2 fold, 0.5 fold, 1 fold, 1.5 fold, 2 fold, 3 fold, 4 fold, 5 fold, 6 fold, 7 fold, 8 fold, 9 fold, 10 fold higher post-immunization relative to the anti-influenza virus NA stalk titer in a blood sample from the subject prior to immunization.

In certain embodiments, a dose of an influenza virus described herein may be $10^4$ plaque forming units (PFU) to $10^8$ PFU. In some embodiments, a dose of a recombinant neuraminidase may contain 5 to 15 μg of the recombinant neuraminidase described herein. In certain embodiments, an inactivated vaccine is formulated such that it contains 5 to 15 μg of hemagglutinin (HA) polypeptide described herein. In some embodiments, a dose of a nucleic acid sequence or vector described herein may contain 25 micrograms to 1 milligram of the nucleic acid sequence or vector.

5.7 Biological Assays

Also provided herein are biological assays that may be used to characterize a recombinant NA, and viruses containing, expressing, or both such mutated influenza virus NA polypeptide. See, also, Section 6. In a specific embodiment, an assay described in Section 6 is used to characterize a recombinant NA or virus containing, expressing, or both such a recombinant NA. In another specific embodiment, an assay described in Section 6 is used to characterize the neuraminidase inhibition activity of antibodies induced by an immunogenic composition described herein. In another specific embodiment, the immunogenicity or effectiveness of an immunogenic composition described herein is assessed using one, two, or more assays described in Section 6.

5.7.1 Assays for Testing Activity of Recombinant Neuraminidase

Assays for testing the expression of a recombinant neuraminidase disclosed herein may be conducted using any assay known in the art. For example, an immunoassay, such as a Western blot, may be used to assess the expression of a recombinant neuraminidases. An assay for incorporation of recombinant neuraminidase into a viral vector may comprise growing a virus as described herein, purifying the viral particles by centrifugation through a sucrose cushion, and subsequent analysis for the recombinant neuraminidase expression by an immunoassay, such as Western blotting, using methods well known in the art.

In another embodiment, a recombinant neuraminidase disclosed herein is assayed for proper folding by determination of the structure or conformation of the recombinant neuraminidase using any method known in the art such as, e.g., NMR, X-ray crystallographic methods, or secondary structure prediction methods, e.g., circular dichroism.

In another embodiment, a recombinant neuraminidase disclosed herein is tested for the ability to form tetramers using a technique known in the art or described herein (e.g., in Section 6, infra). In another embodiment, a recombinant neuraminidase disclosed herein or a virus containing or expressing a recombinant neuraminidase disclosed herein is assessed for influenza virus neuraminidase activity using a technique known to one of skill in the art or described herein (e.g., in Section 6, infra).

5.8 Kits

In one aspect, provided herein is a pharmaceutical pack or kit for immunizing against an influenza virus in a subject comprising one or more containers filled with one or more of the ingredients of a pharmaceutical composition described herein (e.g., immunogenic compositions described herein), such as an influenza virus (e.g., a live attenuated influenza virus or an inactivated virus), or a recombinant neuraminidase, or a nucleic acid sequence comprising a nucleotide sequence encoding a recombinant neuraminidase, or a vector comprising a nucleic acid sequence encoding a recombinant neuraminidase. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein. In one embodiment, a kit comprises a recombinant neuraminidase described herein (such as described in Section 5.1 above or Section 6), in one or more containers. In another embodiment, a kit comprises an influenza virus described herein containing a recombinant neuraminidase (such as described in Section 5.4 above or Section 6), in one or more containers. In another embodiment, a kit comprises a nucleic acid sequence comprising a nucleotide sequence encoding a recombinant neuraminidase, in one or more containers. In another embodiment, a kit comprises a vector comprising a nucleic acid sequence encoding a recombinant neuraminidase, in one or more containers. In another embodiment, a kit comprises one or more immunogenic compositions described herein in one or more containers. In certain embodiments, a kit comprises a vaccine described herein, e.g., an inactivated influenza virus vaccine or a live influenza virus vaccine, wherein said vaccine comprises a recombinant neuraminidase described herein and optionally, an adjuvant described herein (e.g., in Section 5.5.3 or Section 6).

In certain embodiments, a kit described herein comprises: (a) a first container comprising an immunogenic composition described herein (e.g., described in Section 5.5 or Section 6); and (b) a second container comprising an adjuvant described herein (e.g., in Section 5.5.3). In specific embodiments, the immunogenic composition is an inactivated whole virus vaccine. In specific embodiments, the immunogenic composition is a split virus vaccine. In specific embodiment, the immunogenic composition is a live attenuated virus vaccine.

In certain embodiments, a kit described herein comprises: (a) a first container comprising an immunogenic composition comprising a recombinant neuraminidase described herein; and (b) a second container comprising an inactivated trivalent influenza virus vaccine, an inactivated quadrivalent influenza virus vaccine or a live attenuated influenza virus vaccine. In some embodiments, the immunogenic composition further comprises an adjuvant.

6. EXAMPLE 1: USE OF NATURAL TETRAMERIZATION DOMAINS AND CYSTEINE MUTANTS TO PRODUCE TETRAMERIC RECOMBINANT NEURAMINIDASE-BASED VACCINE CANDIDATES

6.1.1 Introduction

Trivalent and quadrivalent inactivated influenza virus vaccines (TIV, QIV) induce narrow, strain specific immune responses that target the immunodominant head domain of the viral hemagglutinin (HA). Current vaccines are not efficient at inducing an immune response to the influenza virus NA (1, 2). The reasons for the lack of NA immunogenicity in TIV and QIV are not completely understood, but three major factors may contribute: 1) Low/non-standardized amounts of NA in the vaccine (1), 2) NA in TIV and QIV might not display conserved conformational epitopes correctly due to denaturation during the vaccine production process, and 3) NA is immunosubdominant to HA, especially when attached physically to HA (e.g. via the hydrophobic HA and NA transmembrane domains) (3, 4). A potential solution to this problem is to supplement the current TIV or QIV (or the recombinant influenza vaccine—RIV4) with correctly folded, stable, tetrameric recombinant protein (see FIG. 5 of reference (5)). Two ways exist to produce recombinant NA: i) recombinant expression of full length NA followed by membrane extraction and ii) expression of a soluble version of the NA followed by purification from the cell supernatant. Recombinant expression of the full length NA in cells followed by membrane extraction (6), unfortunately, results in relatively low yields and the hypervariable stalk of the NA might lead to instability over time.

Expression of the head domain only (which houses the protective epitopes) is a good alternative. However, if only the NA head is expressed, no tetramer is formed, and the resulting antigen is not protective. To form a stable, functional and correctly folded tetramer, a tetramerization domain needs to be attached to the NA head domain. This has had been attempted with variable success in the past. To date, a GCN4 leucine zipper, a bacterial tetrabrachion tetramerization domain and the human vasodilator stimulated phosphoprotein (VASP) tetramerization domain have been used, with the latter providing excellent results in vaccine studies (1). However, the GNC4 leucine zipper construct does not express well and has homologies to human proteins and the VASP domain is derived from a human protein raising concerns about autoimmunity. As such, these constructs may be incompatible with GMP production and human clinical trials.

This example describes the production of a stable, immunogenic recombinant neuraminidase comprising a globular head domain of an influenza virus neuraminidase and a tetramerization. This example demonstrates that vaccination with such a stable, immunogenic recombinant neuraminidase confers complete protection against a stringent $10 \times LD_{50}$ challenge.

In addition, this example describes the construction of cysteine mutants to form natural trimers without trimerization domains. When NA is expressed with its stalk domain it forms dimers via a disulfide bridge between two monomers. When the NA is naturally anchored in a lipid membrane, this then leads to tetramer formation (12). However, this is not the case when NA is expressed as recombinant protein (without the transmembrane domain). In this case only dimers are formed. By mutating in additional cysteines, additional disulfide bonds may be formed that then may connect two dimers to form a tetramer.

6.1.2 Materials and Methods

Design and Generation of Recombinant Neuraminidase Constructs

The measles virus phosphoprotein tetramerization domain (MPP) (7), the Sendai virus phosphoprotein tetramerization domain (SPP) (8), a tetramerization domain from SEPPALLATA-like MADS domain transcription factor from *Arabidopsis thaliana* (SMDTF) (9), a PiLZ structure from *Xanthomonas campestris* (10) and Dictyocaulus viviparus ACE tetramerization domain (11) N1 fusion proteins were generated by cloning the respective codon optimized tetramerization domains into a pFastBacDual expression vector. The vector contains the N-terminal signal peptide sequence, a hexa-histidine purification tag as well as a thrombin cleavage site. Then, the globular head domain of A/Michigan/45/15 N1 was directly inserted behind the tetramerization domain.

The Following Sequences were Used:

Italicized and bold: signal peptide and his tag

Underlined and bold: respective tetramerization domains

Bold: N1 NA

Double underlined and bold: thrombin cleavage site plus two amino acid residues

>SMDTF-N1

(SEQ ID NO: 24)

*MLLVNQSHQGFNKEHTSKMVSAIVLYVLLAAAAHSAFAADPHHHHHH*VEL          50

SSQQEYLKLKERYDALQRTQRNLLGEDLGPLSTKELESLERQLDSSLKQI          100

RALRTQFMLDQSKERMLTETNKTLRLRLADGYSLVPRGSPSRSVKLAGNS          150

SLCPVSGWAIYSKDNSVRIGSKGDVFVIREPFISCSPLECRTFFLTQGAL          200

LNDKHSNGTIKDRSPYRTLMSCPIGEVPSPYNSRFESVAWSASACHDGIN          250

WLTIGISGPDSGAVAVLKYNGIITDTIKSWRNNILRTQESECACVNGSCF          300

TIMTDGPSDGQASYKIFRIEKGKIIKSVEMKAPNYHYEECSCYPDSSEIT          350

CVCRDNWHGSNRPWVSFNQNLEYQMGYICSGVFGDNPRPNDKTGSCGPVS          400

SNGANGVKGFSFKYGNGVWIGRTKSISSRKGFEMIWDPNGWTGTDNKFSI          450

KQDIVGINEWSGYSGSFVQHPELTGLDCIRPCFWVELIRGRPEENTIWTS          500

GSSISFCGVNSDTVGWSWPDGAELPFTIDK*

>SPP-N1

(SEQ ID NO: 25)

*MLLVNQSHQGFNKEHTSKMVSAIVLYVLLAAAAHSAADPHHHHHH*ENT          50

SSMKEMATLLTSLGVIQSAQEFESSRDASYVFARRALKSANYAEMTFNVC          100

GLILSAEKSSARKVDENKQLLKIQESVESFRDIYKRFSEYQKEQNSLLMS          150

NLSTLHIITDSLVPRGSPSRSVKLAGNSSLCPVSGWAIYSKDNSVRIGSK          200

GDVFVIREPFISCSPLECRTFFLTQGALLNDKHSNGTIKDRSPYRTLMSC          250

PIGEVPSPYNSRFESVAWSASACHDGINWLTIGISGPDSGAVAVLKYNGI          300

ITDTIKSWRNNILRTQESECACVNGSCFTIMTDGPSDGQASYKIFRIEKG          350

KIIKSVEMKAPNYHYEECSCYPDSSEITCVCRDNWHGSNRPWVSFNQNLE          400

YQMGYICSGVFGDNPRPNDKTGSCGPVSSNGANGVKGFSFKYGNGVWIGR          450

TKSISSRKGFEMIWDPNGWTGTDNKFSIKQDIVGINEWSGYSGSFVQHPE          500

LTGLDCIRPCFWVELIRGRPEENTIWTSGSSISFCGVNSDTVGWSWPDGA          550

ELPFTIDK*

>PiLZ-N1

(SEQ ID NO: 26)

*MLLVNQSHQGFNKEHTSKMVSAIVLYVLLAAAAHSAFAADPHHHHHH*LLV          50

QRMDAKLDLILALIGRLVRQSSLVPRGSPSRSVKLAGNSSLCPVSGWAIY          100

SKDNSVRIGSKGDVFVIREPFISCSPLECRTFFLTQGALLNDKHSNGTIK          150

DRSPYRTLMSCPIGEVPSPYNSRFESVAWSASACHDGINWLTIGISGPDS          200

GAVAVLKYNGIITDTIKSWRNNILRTQESECACVNGSCFTIMTDGPSDGQ          250

ASYKIFRIEKGKIIKSVEMKAPNYHYEECSCYPDSSEITCVCRDNWHGSN          300

RPWVSFNQNLEYQMGYICSGVFGDNPRPNDKTGSCGPVSSNGANGVKGFS          350

FKYGNGVWIGRTKSISSRKGFEMIWDPNGWTGTDNKFSIKQDIVGINEWS          400

GYSGSFVQHPELTGLDCIRPCFWVELIRGRPEENTIWTSGSSISFCGVNS          450

DTVGWSWPDGAELPFTIDK*

>MPP-N1

(SEQ ID NO: 27)

*MLLVNQSHQGFNKEHTSKMVAIVLYVLLAAAAHSAFAADPHHHHHH*GDH          50

YDDELFSDVQDIKTALAKIHEDNQKIISKLESLLLLKGEVESIKKQINRQ          100

NISISTLEGHLSSIMIAIPGLSLVPRGSPSRSVKLAGNSSLCPVSGWAIY          150

SKDNSVRIGSKGDVFVIREPFISCSPLECRTFFLTQGALLNDKHSNGTIK          200

-continued

```
DRSPYRTLMSCPIGEVPSPYNSRFESVAWSASACHDGINWLTIGISGPDS        250

GAVAVLKYNGIITDTIKSWRNNILRTQESECACVNGSCFTIMTDGPSDGQ        300

ASYKIFRIEKGKIIKSVEMKAPNYHYEECSCYPDSSEITCVCRDNWHGSN        350

RPWVSFNQNLEYQMGYICSGVFGDNPRPNDKTGSCGPVSSNGANGVKGFS        400

FKYGNGVWIGRTKSISSRKGFEMIWDPNGWTGTDNKFSIKQDIVGINEWS        450

GYSGSFVQHPELTGLDCIRPCFWVELIRGRPEENTIWTSGSSISFCGVNS        500

DTVGWSWPDGAELPFTIDK*
```

>ACE-N1
```
                                             (SEQ ID NO: 28)
MLLVNQSHQGFNKEHTSKMVSAIVLYVLLAAAAHSAFAADPHHHHHHAVA        50

DVGDPFLLWKQQMDKWQNEYITDWQYHFEQYKKYQTYRHLDSDSCSGSSL        100

VPRGSPSRSVKLAGNSSLCPVSGWAIYSKDNSVRIGSKGDVFVIREPFIS        150

CSPLECRTFFLTQGALLNDKHSNGTIKDRSPYRTLMSCPIGEVPSPYNSR        200

FESVAWSASACHDGINWLTIGISGPDSGAVAVLKYNGIITDTIKSWRNNI        250

LRTQESECACVNGSCFTIMTDGPSDGQASYKIFRIEKGKIIKSVEMKAPN        300

YHYEECSCYPDSSEITCVCRDNWHGSNRPWVSFNQNLEYQMGYICSGVFG        350

DNPRPNDKTGSCGPVSSNGANGVKGFSFKYGNGVWIGRTKSISSRKGFEM        400

IWDPNGWTGTDNKFSIKQDIVGINEWSGYSGSFVQHPELTGLDCIRPCFW        450

VELIRGRPEENTIWTSGSSISFCGVNSDTVGWSWPDGAELPFTIDK*
```

The N1 cysteine mutants, which contain cysteines at different positions in the N1 stalk domain, were cloned into the expression vector pFastBacDual without tetramerization domain. However, the vector still contains the N-terminal signal peptide, the hexa-histidine purification tag as well as the thrombin cleavage site. The construct N1.2 contains part of the stalk domain including the crucial cysteine at position 49 (C49, N1 numbering) which is known to be essential for the formation of stable dimers/tetramers. Construct N1.3 has a mutation at C49, switching the cysteine to alanine resulting in a monomeric protein. The constructs N1.4 (T48C), N1.5 (N50C), N1.6 (T48C+N50C), N1.7 (A76C), N1.8 (Q78C), N1.9 (V81C) and N1.11 (W61C), contain cysteine bonds at different positions in the N1 stalk domain additionally to C49. The construct N1.10 serves as a tetramer control, since it contains a VASP tetramerization domain (1).

The Following Sequences were Used:

Underlined: signal peptide, hexa-histidine tag and thrombin cleavage site

Italics: NA stalk

Bold: introduced mutations

N1.2
```
                                             (SEQ ID NO: 15)
MLLVNQSHQGFNKEHTSKMVSAIVLYVLLAAAAHSAFAADPHHHHHHSLV        50

PRGSPSRIETCNQSVITYENNTWVNQTYVNISNTNFAAGQSVVSVKLAGN        100

SSLCPVSGWAIYSKDNSVRIGSKGDVFVIREPFISCSPLECRTFFLTQGA        150

LLNDKHSNGTIKDRSPYRTLMSCPIGEVPSPYNSRFESVAWSASACHDGI        200

NWLTIGISGPDSGAVAVLKYNGIITDTIKSWRNNILRTQESECACVNGSC        250

FTIMTDGPSDGQASYKIFRIEKGKIIKSVEMKAPNYHYEECSCYPDSSEI        300

TCVCRDNWHGSNRPWVSFNQNLEYQMGYICSGVFGDNPRPNDKTGSCGPV        350

SSNGANGVKGFSFKYGNGVWIGRTKSISSRKGFEMIWDPNGWTGTDNKFS        400

IKQDIVGINEWSGYSGSFVQHPELTGLDCIRPCFWVELIRGRPEENTIWT        450

SGSSISFCGVNSDTVGWSWPDGAELPFTIDK*
```

-continued

N1.3 (C49 A-monomer)
                                              (SEQ ID NO: 16)
MLLVNQSHQGFNKEHTSKMVSAIVLYVLLAAAAHSAFAADPHHHHHHSLV        50

PRGSPSRIET*A*NQSVITYENNTWVNQTYVNISNTNFAAGQSVVSVKLAGN       100

SSLCPVSGWAIYSKDNSVRIGSKGDVFVIREPFISCSPLECRTFFLTQGA        150

LLNDKHSNGTIKDRSPYRTLMSCPIGEVPSPYNSRFESVAWSASACHDGI        200

NWLTIGISGPDSGAVAVLKYNGIITDTIKSWRNNILRTQESECACVNGSC        250

FTIMTDGPSDGQASYKIFRIEKGKIIKSVEMKAPNYHYEECSCYPDSSEI        300

TCVCRDNWHGSNRPWVSFNQNLEYQMGYICSGVFGDNPRPNDKTGSCGPV        350

SSNGANGVKGFSFKYGNGVWIGRTKSISSRKGFEMIWDPNGWTGTDNKFS        400

IKQDIVGINEWSGYSGSFVQHPELTGLDCIRPCFWVELIRGRPEENTIWT        450

SGSSISFCGVNSDTVGWSWPDGAELPFTIDK*

N1.4 (T48C)
                                              (SEQ ID NO: 17)
MLLVNQSHQGFNKEHTSKMVSAIVLYVLLAAAAHSAFAADPHHHHHHSLV        50

PRGSPSRIE*C*CNQSVITYENNTWVNQTYVNISNTNFAAGQSVVSVKLAGN       100

SSLCPVSGWAIYSKDNSVRIGSKGDVFVIREPFISCSPLECRTFFLTQGA        150

LLNDKHSNGTIKDRSPYRTLMSCPIGEVPSPYNSRFESVAWSASACHDGI        200

NWLTIGISGPDSGAVAVLKYNGIITDTIKSWRNNILRTQESECACVNGSC        250

FTIMTDGPSDGQASYKIFRIEKGKIIKSVEMKAPNYHYEECSCYPDSSEI        300

TCVCRDNWHGSNRPWVSFNQNLEYQMGYICSGVFGDNPRPNDKTGSCGPV        350

SSNGANGVKGFSFKYGNGVWIGRTKSISSRKGFEMIWDPNGWTGTDNKFS        400

IKQDIVGINEWSGYSGSFVQHPELTGLDCIRPCFWVELIRGRPEENTIWT        450

SGSSISFCGVNSDTVGWSWPDGAELPFTIDK*

N1.5 (N50C)
                                              (SEQ ID NO: 18)
MLLVNQSHQGFNKEHTSKMVSAIVLYVLLAAAAHSAFAADPHHHHHHSLV        50

PRGSPSRIETC*C*QSVITYENNTWVNQTYVNISNTNFAAGQSVVSVKLAGN       100

SSLCPVSGWAIYSKDNSVRIGSKGDVFVIREPFISCSPLECRTFFLTQGA        150

LLNDKHSNGTIKDRSPYRTLMSCPIGEVPSPYNSRFESVAWSASACHDGI        200

NWLTIGISGPDSGAVAVLKYNGIITDTIKSWRNNILRTQESECACVNGSC        250

FTIMTDGPSDGQASYKIFRIEKGKIIKSVEMKAPNYHYEECSCYPDSSEI        300

TCVCRDNWHGSNRPWVSFNQNLEYQMGYICSGVFGDNPRPNDKTGSCGPV        350

SSNGANGVKGFSFKYGNGVWIGRTKSISSRKGFEMIWDPNGWTGTDNKFS        400

IKQDIVGINEWSGYSGSFVQHPELTGLDCIRPCFWVELIRGRPEENTIWT        450

SGSSISFCGVNSDTVGWSWPDGAELPFTIDK*

N1.6 (T48C + N50C)
                                              (SEQ ID NO: 19)
MLLVNQSHQGFNKEHTSKMVSAIVLYVLLAAAAHSAFAADPHHHHHHSLV        50

PRGSPSRIE*C*C*C*QSVITYENNTWVNQTYVNISNTNFAAGQSVVSVKLAGN      100

SSLCPVSGWAIYSKDNSVRIGSKGDVFVIREPFISCSPLECRTFFLTQGA        150

LLNDKHSNGTIKDRSPYRTLMSCPIGEVPSPYNSRFESVAWSASACHDGI        200

NWLTIGISGPDSGAVAVLKYNGIITDTIKSWRNNILRTQESECACVNGSC        250

FTIMTDGPSDGQASYKIFRIEKGKIIKSVEMKAPNYHYEECSCYPDSSEI        300

-continued

TCVCRDNWHGSNRPWVSFNQNLEYQMGYICSGVFGDNPRPNDKTGSCGPV          350

SSNGANGVKGFSFKYGNGVWIGRTKSISSRKGFEMIWDPNGWTGTDNKFS          400

IKQDIVGINEWSGYSGSFVQHPELTGLDCIRPCFWVELIRGRPEENTIWT          450

SGSSISFCGVNSDTVGWSWPDGAELPFTIDK*

N1.7 (A76C)
                                                   (SEQ ID NO: 20)
MLLVNQSHQGFNKEHTSKMVSAIVLYVLLAAAAHSAFAADPHHHHHHSLV          50

PRGSPSRIETCNQSVITYENNTWVNQTYVNISNTNFACGQSVVSVKLAGN          100

SSLCPVSGWAIYSKDNSVRIGSKGDVFVIREPFISCSPLECRTFFLTQGA          150

LLNDKHSNGTIKDRSPYRTLMSCPIGEVPSPYNSRFESVAWSASACHDGI          200

NWLTIGISGPDSGAVAVLKYNGIITDTIKSWRNNILRTQESECACVNGSC          250

FTIMTDGPSDGQASYKIFRIEKGKIIKSVEMKAPNYHYEECSCYPDSSEI          300

TCVCRDNWHGSNRPWVSFNQNLEYQMGYICSGVFGDNPRPNDKTGSCGPV          350

SSNGANGVKGFSFKYGNGVWIGRTKSISSRKGFEMIWDPNGWTGTDNKFS          400

IKQDIVGINEWSGYSGSFVQHPELTGLDCIRPCFWVELIRGRPEENTIWT          450

SGSSISFCGVNSDTVGWSWPDGAELPFTIDK*

N1.8 (Q78C)
                                                   (SEQ ID NO: 21)
MLLVNQSHQGFNKEHTSKMVSAIVLYVLLAAAAHSAFAADPHHHHHHSLV          50

PRGSPSRIETCNQSVITYENNTWVNQTYVNISNTNFAAGCSVVSVKLAGN          100

SSLCPVSGWAIYSKDNSVRIGSKGDVFVIREPFISCSPLECRTFFLTQGA          150

LLNDKHSNGTIKDRSPYRTLMSCPIGEVPSPYNSRFESVAWSASACHDGI          200

NWLTIGISGPDSGAVAVLKYNGIITDTIKSWRNNILRTQESECACVNGSC          250

FTIMTDGPSDGQASYKIFRIEKGKIIKSVEMKAPNYHYEECSCYPDSSEI          300

TCVCRDNWHGSNRPWVSFNQNLEYQMGYICSGVFGDNPRPNDKTGSCGPV          350

SSNGANGVKGFSFKYGNGVWIGRTKSISSRKGFEMIWDPNGWTGTDNKFS          400

IKQDIVGINEWSGYSGSFVQHPELTGLDCIRPCFWVELIRGRPEENTIWT          450

SGSSISFCGVNSDTVGWSWPDGAELPFTIDK*

N1.9 (V81C)
                                                   (SEQ ID NO: 22)
MLLVNQSHQGFNKEHTSKMVSAIVLYVLLAAAAHSAFAADPHHHHHHSLV          50

PRGSPSRIETCNQSVITYENNTWVNQTYVNISNTNFAAGQSVCSVKLAGN          100

SSLCPVSGWAIYSKDNSVRIGSKGDVFVIREPFISCSPLECRTFFLTQGA          150

LLNDKHSNGTIKDRSPYRTLMSCPIGEVPSPYNSRFESVAWSASACHDGI          200

NWLTIGISGPDSGAVAVLKYNGIITDTIKSWRNNILRTQESECACVNGSC          250

FTIMTDGPSDGQASYKIFRIEKGKIIKSVEMKAPNYHYEECSCYPDSSEI          300

TCVCRDNWHGSNRPWVSFNQNLEYQMGYICSGVFGDNPRPNDKTGSCGPV          350

SSNGANGVKGFSFKYGNGVWIGRTKSISSRKGFEMIWDPNGWTGTDNKFS          400

IKQDIVGINEWSGYSGSFVQHPELTGLDCIRPCFWVELIRGRPEENTIWT          450

SGSSISFCGVNSDTVGWSWPDGAELPFTIDK*

N1.11 (W61C)
                                                   (SEQ ID NO: 23)
MLLVNQSHQGFNKEHTSKMVSAIVLYVLLAAAAHSAFAADPHHHHHHSLV          50

PRGSPSRIETCNQSVITYENNTCVNQTYVNISNTNFAAGQSVVSVKAAGN          100

SSLCPVSGWAIYSKDNSVRIGSKGDVFVIREPFISCSPLECRTFFLTQGA          150

-continued

```
LLNDKHSNGTIKDRSPYRTLMSCPIGEVPSPYNSRFESVAWSASACHDGI        200

NWLTIGISGPDSGAVAVLKYNGIITDTIKSWRNNILRTQESECACVNGSC        250

FTIMTDGPSDGQASYKIFRIEKGKIIKSVEMKAPNYHYEECSCYPDSSEI        300

TCVCRDNWHGSNRPWVSFNQNLEYQMGYICSGVFGDNPRPNDKTGSCGPV        350

SSNGANGVKGFSFKYGNGVWIGRTKSISSRKGFEMIWDPNGWTGTDNKFS        400

IKQDIVGINEWSGYSGSFVQHPELTGLDCIRPCFWVELIRGRPEENTIWT        450

SGSSISFCGVNSDTVGWSWPDGAELPFTIDK*
```

After being cloned into the pFastBacDual expression vector, the constructs were transformed into competent *E. coli* DH10 bacs and the isolated DNA used to transfect Sf9 (*Spodoptera frupperda*) insect cells, following an established protocol (13). The obtained baculoviruses, were then passaged in Sf9 cells to reach higher titers using 3% TNM-FH media (Gemini Bioproducts; 3% Fetal bovine serum (Gibco)). After passaging the virus for three times, the resulting stock solutions were used to infect HighFive cells to express the recombinant neuraminidases. The cells were infected for 3 days at 27° C. without $CO_2$ using ExpressFive media (Gibco), supplemented with 10% L-glutamine (Gibco) and 1% penicillin/streptomycin (Gibco). Afterwards, the cell supernatant containing the respective soluble neuraminidases was separated from the cells by centrifugation and the protein purified by using an established protocol (13, 14). The proteins were stored at −80° C. until further usage.

Sodium Dodecyl Sulfate-Polyacrylamide Gel Electrophoresis (SDS-PAGE)

In order to perform a reducing SDS-PAGE, 1 ug of recombinant protein was mixed with 4× Laemmli sample buffer (Biorad) containing 10% β-mercaptoethanol (BME). The samples were heated for 10 minutes at 98° C. and were afterwards loaded on a SDS gradient gel (4-20% Mini-PROTEAN® TGX™ Precast Protein Gels, Biorad). The gel was run for 30 minutes at 200V and was afterwards stained with Coomassie blue fast stain solution for 1 h, shaking at RT. The staining solution was removed and the gel destained by using distilled water.

For performing a non-reducing SDS-Page, the samples were mixed with 4× Laemmli sample buffer and then treated the same way as mentioned above. To cross-link the recombinant proteins, B S3 cross linker (Sigma-Aldrich) was used (13). For thus, the proteins were mixed with the crosslinking reagent as described in the manufacturers manual. Afterwards, the samples were treated the same way as mentioned above.

NA-Star Assay

To determine potential neuraminidase activity of the different recombinant N1 constructs, an NA-star assay (Thermo Fisher) was performed. The recombinant proteins were diluted to a starting concentration of 10 μg in the provided assay buffer followed by a 1:2 serial dilution. The plates were incubated for 15 minutes at room temperature. The substrate was added and the plates kept in the dark for 30 minutes at 37° C. Afterwards, the provided enhancer solution was added to the wells and the plate immediately read based on luminescence activity using a Synergy Hybrid Reader (BioTek).

Enzyme-Linked Immunosorbent Assay (ELISA)

To determine the binding activity of the recombinant N1 constructs to a panel of human neuraminidase antibodies, an ELISA was performed. To ensure correct folding of the proteins as well as full accessibility of the respective epitopes, Ni-NTA plates (Qiagen) were used to perform the assay. Therefore, the plates were coated overnight at 4° C. with 50 μl/well of 2 μg/ml recombinant protein diluted in Phosphate-buffered saline (PBS). The following day, the coating solution was removed and the plates blocked with 100 μl/well of 3% milk/PBS-0.01% Tween (PBST) for 1 h at RT. The blocking solution was removed and the primary antibody dilutions prepared at a starting concentration of 30 ug/ml in 1% milk/PBST. A 1:3 serial dilution was performed and the antibodies incubated on the plate for 2 h at RT. Afterwards, the plates were washed 3× with PBST and then incubated with an anti-human IgG secondary HRP labelled antibody (1:3000 in 1% milk/PBST) for 1 h at RT. The plates were washed and 100 μl/well of o-phenylenediamine (OPD) developing solution was added for 10 min at RT. The reaction was stopped by adding 50/well of 3M HCL solution and the plates read at an OD of 490 nm using a Synergy Hybrid Reader (BioTek).

Mouse Vaccination and Challenge Studies

The protective efficacy of recombinant neuraminidase vaccine candidates was tested in 6-8 week old female BALB/c mice (n=5 per group). The mice were vaccinated intramuscular with 3 ug of the respective recombinant protein (in 50 μl PBS) adjuvanted 1:1 with AddaVax (InvivoGen). An irrelevant hemagglutinin protein (from B/Malaysia/2506/04) was administered to one of the groups as negative control and an N1 protein, containing a VASP tetramerization domain, which has been shown to be protective in vivo challenge studies was included as a positive control. The mice were vaccinated twice in an interval of 3 weeks. Four weeks after the second vaccination, the mice were challenged with 25×mLD$_{50}$ (murine lethal dose 50%) of A/Singapore/GP1908/2015 (IVR-180). Survival as well as the weight loss were monitored over 14 days. Mice that lost more than 25% of their initial body weight were humanely euthanized.

6.1.3 Results

Novel Tetramerization Domains

First, three of the constructs plus the positive control (VASP-N1) were expressed and purified. MPP-N1 and SMDTF-N1 (e.g., N1 with a leucine zipper from SEPPAL-LATA-like MADS domain transcription factor from *Arabidopsis thaliana* (9)) showed no degradation when analysed on a reducing and non-reducing SDS-PAGE, while SPP-N1 showed slight degradation (FIGS. 1A and 1B). Second, the constructs were tested for formation of tetramers. This was observed for MPP-N1 and SPP-N1 (and the positive control), with MPP-N1 again showing no degradation or secondary bands when cross-linked and run on an SDS-PAGE (FIG. 1C). MPP-N1 behaved identical to VASP-N1 in this assay. Furthermore, successful constructs must have NA activity similar to an N1 tetramer with a known and functional tetramerization domain (VASP-N1 as control). Both the SPP-N1 and MPP-N1 constructs showed similar NA activity. Although the NA activity of MPP-N1 was slightly lower than that of SPP-N1 and VASP-N1, it was still robust (FIG. 2).

Finally, MPP-N1 was tested for recognition by human neuraminidase inhibition active N1 monoclonal antibodies, which was the case (FIG. 3). Both SPP-N1 and MPP-N1 were then moved forward to efficacy testing in animals.

In a simple prime-boost regimen, 3 μg of NA was given to mice intramuscularly twice in a three-week interval (with AddaVax as adjuvant). Both constructs provided complete protection against weight loss and mortality comparable to the VASP-N1 constructs when the animals were challenged with 10 50% lethal doses of homologous virus (FIG. 4). The rationale for the 3 μg dose per mouse is based on the typical dose of 1 μg of HA when inactivated vaccines are used in mice. In humans, the dose of recombinant HA in RIV4 is three times higher than in QIV, therefore a three times higher dose of recombinant NA was chosen.

Cysteine Mutants

The different cysteine mutants described in the methods section were expressed and tested. Neuraminidase activity in an NA-Star assay was used as proxy for tetramer formation. A monomer (N1.3), a dimer (N1.2) and a VASP-stabilized tetramer (N1.10) were used as controls. One construct, N1.6 (T48C+N50C) showed activity comparable to the tetramer (FIG. 5).

6.1.4 Discussion

Natural tetramerization domains including the measles virus phosphoprotein tetramerization domain (MPP) (7), the Sendai virus phosphoprotein tetramerization domain (SPP) (8), a tetramerization domain from SEPPALLATA-like MADS domain transcription factor from *Arabidopsis thaliana* (SMDTF) (9), a PiLZ structure from *Xanthomonas campestris* (10) and a Dictyocaulus viviparus ACE tetramerization domain (11), all fused to the head domain of the A/Michigan/45/15 N1 (H1N1) were screened. These constructs were characterized based on expression, tetramerization, stability and immunogenicity.

In conclusion, two novel constructs with tetramerization domains from the measles and the Sendai virus phosphoprotein that support formation of functional NA tetramers have been identified. These constructs also provide protection as vaccines in an influenza virus challenge mouse model. Vaccination with the MPP tetramerization domain construct in the mouse model conferred complete protection against a stringent $10 \times mLD_{50}$ challenge.

Furthermore, a neuraminidase stalk cysteine double mutant with NA activity comparable to a corresponding recombinant NA stabilized with a VASP tetramerization domain has been identified. The strong activity of this mutant indicates that it forms a tetramer and could also provide protection as a vaccine in vivo.

Both types of constructs are expressed with a hexa-histidine tag to aid purification but versions of the constructs may be expressed without this tag. A tag-less protein is harder to purify but is more suitable for human clinical trials.

6.1.5 References Cited in Example 1 and Background

1. Wohlbold T J, Nachbagauer R, Xu H, Tan G S, Hirsh A, Brokstad K A, Cox R J, Palese P, Krammer F. 2015.

Vaccination with Adjuvanted Recombinant Neuraminidase Induces Broad Heterologous, but Not Heterosubtypic, Cross-Protection against Influenza Virus Infection in Mice. MBio 6.

2. Krammer F, Fouchier R A M, Eichelberger M C, Webby R J, Shaw-Saliba K, Wan H, Wilson P C, Compans R W, Skountzou I, Monto A S. 2018. NAction! How Can Neuraminidase-Based Immunity Contribute to Better Influenza Virus Vaccines? MBio 9.

3. Johansson B E, Moran™, Kilbourne E D. 1987. Antigen-presenting B cells and helper T cells cooperatively mediate intravirionic antigenic competition between influenza A virus surface glycoproteins. Proc Natl Acad Sci USA 84:6869-73.

4. Johansson B E, Kilbourne E D. 1993. Dissociation of influenza virus hemagglutinin and neuraminidase eliminates their intravirionic antigenic competition. J Virol 67:5721-3.

5. Krammer F, Palese P. 2015. Advances in the development of influenza virus vaccines. Nat Rev Drug Discov 14:167-82.

6. Dalakouras T, Smith B, Platis D, Cox M, Labrou N. 2006. Development of recombinant protein-based influenza vaccine. Expression and affinity purification of H1N1 influenza virus neuraminidase. J Chromatogr A 1136:48-56.

7. Communie G, Crépin T, Maurin D, Jensen M R, Blackledge M, Ruigrok R W. 2013. Structure of the tetramerization domain of measles virus phosphoprotein. J Virol 87:7166-9.

8. Tarbouriech N, Curran J, Ruigrok R W, Burmeister W P. 2000. Tetrameric coiled coil domain of Sendai virus phosphoprotein. Nat Struct Biol 7:777-81.

9. Rümpler F, Theißen G, Melzer R. 2018. A conserved leucine zipper-like motif accounts for strong tetramerization capabilities of SEPALLATA-like MADS-domain transcription factors. J Exp Bot 69:1943-1954.

10. Li T N, Chin K H, Fung K M, Yang M T, Wang A H, Chou S H. 2011. A novel tetrameric PilZ domain structure from xanthomonads. PLoS One 6:e22036.

11. Matthews J B, Lazari O, Davidson A J, Warren S, Selkirk M E. 2006. A tryptophan amphiphilic tetramerization domain-containing acetylcholinesterase from the bovine lungworm, Dictyocaulus viviparus. Parasitology 133:381-7.

12. da Silva D V, Nordholm J, Madjo U, Pfeiffer A, Daniels R. 2013. Assembly of subtype 1 influenza neuraminidase is driven by both the transmembrane and head domains. J Biol Chem 288:644-53.

13. Krammer F, Margine I, Tan G S, Pica N, Krause J C, Palese P. 2012. A carboxy-terminal trimerization domain stabilizes conformational epitopes on the stalk domain of soluble recombinant hemagglutinin substrates. PLoS One 7:e43603.

14. Margine I, Palese P, Krammer F. 2013. Expression of Functional Recombinant Hemagglutinin and Neuraminidase Proteins from the Novel H7N9 Influenza Virus Using the Baculovirus Expression System. J Vis Exp.

6.2 Example 2: Stabilization of Neuraminidase (NA) Tetramers of Influenza A Viruses Through Introducing Additional Cysteines to the Stalk Domain of the NA This example demonstrates the production of recombinant influenza viruses engineered to express a recombinant neuraminidase in which additional disulfide bonds were introduced into the stalk region of the viral NA through cysteine substitution(s) or insertion(s). This example demonstrates that introduction of cysteines appears to stabilize the tetrameric neuraminidase of the inactivated purified A/Puerto Rico/08/1934 (PR8) H1N1 virus under conditions, when the viral proteins are resolved on a SDS-PAGE. This observation also holds true for a more clinically relevant A/Hong Kong/4801/2014 (HK14) H3N2 strain.

6.2.1 Materials and Methods

Plasmids

To introduce additional cysteine(s) into the stalk region of NA, amino acid substitution(s) or insertion were performed through PCR mutagenesis using pDZ N1 plasmid for the A/Puerto Rico/08/1934 or pDZ N2 plasmid for the A/Hong Kong/4801/2014 strain as templates. The modified NA gene segments were cloned into linearized vector, which was generated by SapI restriction enzyme (New England Biolabs, Inc.) digestion of the pDZ ambisense plasmid (1). In-Fusion cloning (Takara Bio, Kusatsu, Shiga Prefecture, Japan) was performed. The recombination products were transformed into *Escherichia coli* DH5a competent cells (Thermo Fisher Scientific) and plasmids were purified using QIAprep Spin Miniprep kit (Qiagen). The pRS PR8 6 segment plasmid used to rescue recombinant influenza viruses was generated through deleting NA cassette from pRS PR8 7 segment plasmid which has been described previously (2). Briefly, the pRS PR8 7 segment was digested using NotI (New England Biolabs, Inc.) to specifically remove the NA cassette, the linearized plasmid was re-ligated using T4 DNA ligase (New England Biolabs, Inc.) and transformed into MAX Efficiency Stbl2 Competent cells (Invitrogen) according to the manufacturers' protocols. Plasmids were purified from subsequent colonies using the QIAprep spin miniprep kit (Qiagen).

Sequences

Amino acid sequences of the wild type (WT) and mutant PR8 N1 or HK14 N2 are shown below. These sequences include signal peptide. The amino acid substitutions are in bold and underlined. The amino acid insertions are in bold, italics and underlined. C49 in PR8 N1 and C53 in HK14 N2 are double underlined and italicized.

```
>PR8 N1 WT
                                           (SEQ ID NO: 6)
MNPNQKITTIGSICLVVGLISLILQIGNIISIWISHSIQTGSQNHTGICN       50

QNIITYKNSTWVKDTTSVILTGNSSLCPIRGWAIYSKDNSIRIGSKGDVF      100
VIREPFISCSHLECRTFFLTQGALLNDKHSNGTVKDRSPYRALMSCPVGE      150
APSPYNSRFESVAWSASACHDGMGWLTIGISGPDNGAVAVLKYNGIITET      200
IKSWRKKILRTQESECACVNGSCFTIMTDGPSDGLASYKIFKIEKGKVTK      250
SIELNAPNSHYEECSCYPDTGKVMCVCRDNWHGSNRPWVSFDQNLDYQIG      300
YICSGVFGDNPRPEDGTGSCGPVYVDGANGVKGFSYRYGNGVWIGRTKSH      350
SSRHGFEMIWDPNGWTETDSKFSVRQDVVAMTDWSGYSGSFVQHPELTGL      400
DCMRPCFWVELIRGRPKEKTIWTSASSISFCGVNSDTVDWSWPDGAELPF      450
SIDK*

>PR8 N1 I48C
                                           (SEQ ID NO: 7)
MNPNQKITTIGSICLVVGLISLILQIGNIISIWISHSIQTGSQNHTGCCN       50

QNIITYKNSTWVKDTTSVILTGNSSLCPIRGWAIYSKDNSIRIGSKGDVF      100
VIREPFISCSHLECRTFFLTQGALLNDKHSNGTVKDRSPYRALMSCPVGE      150
APSPYNSRFESVAWSASACHDGMGWLTIGISGPDNGAVAVLKYNGIITET      200
IKSWRKKILRTQESECACVNGSCFTIMTDGPSDGLASYKIFKIEKGKVTK      250
SIELNAPNSHYEECSCYPDTGKVMCVCRDNWHGSNRPWVSFDQNLDYQIG      300
YICSGVFGDNPRPEDGTGSCGPVYVDGANGVKGFSYRYGNGVWIGRTKSH      350
SSRHGFEMIWDPNGWTETDSKFSVRQDVVAMTDWSGYSGSFVQHPELTGL      400
DCMRPCFWVELIRGRPKEKTIWTSASSISFCGVNSDTVDWSWPDGAELPF      450
SIDK*

>PR8 N1 N50C
                                           (SEQ ID NO: 8)
MNPNQKITTIGSICLVVGLISLILQIGNIISIWISHSIQTGSQNHTGICC       50

QNIITYKNSTWVKDTTSVILTGNSSLCPIRGWAIYSKDNSIRIGSKGDVF      100
VIREPFISCSHLECRTFFLTQGALLNDKHSNGTVKDRSPYRALMSCPVGE      150
APSPYNSRFESVAWSASACHDGMGWLTIGISGPDNGAVAVLKYNGIITET      200
IKSWRKKILRTQESECACVNGSCFTIMTDGPSDGLASYKIFKIEKGKVTK      250
SIELNAPNSHYEECSCYPDTGKVMCVCRDNWHGSNRPWVSFDQNLDYQIG      300
YICSGVFGDNPRPEDGTGSCGPVYVDGANGVKGFSYRYGNGVWIGRTKSH      350
SSRHGFEMIWDPNGWTETDSKFSVRQDVVAMTDWSGYSGSFVQHPELTGL      400
DCMRPCFWVELIRGRPKEKTIWTSASSISFCGVNSDTVDWSWPDGAELPF      450
SIDK*

>PR8 N1 61insertC
                                           (SEQ ID NO: 9)
MNPNQKITTIGSICLVVGLISLILQIGNIISIWISHSIQTGSQNHTGICN       50

QNIITYKNSTWCVKDTTSVILTGNSSLCPIRGWAIYSKDNSIRIGSKGDV      100

FVIREPFISCSHLECRTFFLTQGALLNDKHSNGTVKDRSPYRALMSCPVG      150
EAPSPYNSRFESVAWSASACHDGMGWLTIGISGPDNGAVAVLKYNGIITE      200
TIKSWRKKILRTQESECACVNGSCFTIMTDGPSDGLASYKIFKIEKGKVT      250
KSIELNAPNSHYEECSCYPDTGKVMCVCRDNWHGSNRPWVSFDQNLDYQI      300
```

-continued

```
GYICSGVFGDNPRPEDGTGSCGPVYVDGANGVKGFSYRYGNGVWIGRTKS        350
HSSRHGFEMIWDPNGWTETDSKFSVRQDVVAMTDWSGYSGSFVQHPELTG        400
LDCMRPCFWVELIRGRPKEKTIWTSASSISFCGVNSDTVDWSWPDGAELP        450
FSIDK*
```

>PR8 N1 I48C_N50C

```
                                           (SEQ ID NO: 10)
MNPNQKITTIGSICLVVGLISLILQIGNIISIWISHSIQTGSQNHTGCCC          50

QNIITYKNSTWVKDTTSVILTGNSSLCPIRGWAIYSKDNSIRIGSKGDVF        100
VIREPFISCSHLECRTFFLTQGALLNDKHSNGTVKDRSPYRALMSCPVGE        150
APSPYNSRFESVAWSASACHDGMGWLTIGISGPDNGAVAVLKYNGIITET        200
IKSWRKKILRTQESECACVNGSCFTIMTDGPSDGLASYKIFKIEKGKVTK        250
SIELNAPNSHYEECSCYPDTGKVMCVCRDNWHGSNRPWVSFDQNLDYQIG        300
YICSGVFGDNPRPEDGTGSCGPVYVDGANGVKGFSYRYGNGVWIGRTKSH        350
SSRHGFEMIWDPNGWTETDSKFSVRQDVVAMTDWSGYSGSFVQHPELTGL        400
DCMRPCFWVELIRGRPKEKTIWTSASSISFCGVNSDTVDWSWPDGAELPF        450
SIDK*
```

>PR8 N1 I48C_61insertC

```
                                           (SEQ ID NO: 11)
MNPNQKITTIGSICLVVGLISLILQIGNIISIWISHSIQTGSQNHTGCCN          50

QNIITYKNSTWCVKDTTSVILTGNSSLCPIRGWAIYSKDNSIRIGSKGDV        100

FVIREPFISCSHLECRTFFLTQGALLNDKHSNGTVKDRSPYRALMSCPVG        150
EAPSPYNSRFESVAWSASACHDGMGWLTIGISGPDNGAVAVLKYNGIITE        200
TIKSWRKKILRTQESECACVNGSCFTIMTDGPSDGLASYKIFKIEKGKVT        250
KSIELNAPNSHYEECSCYPDTGKVMCVCRDNWHGSNRPWVSFDQNLDYQI        300
GYICSGVFGDNPRPEDGTGSCGPVYVDGANGVKGFSYRYGNGVWIGRTKS        350
HSSRHGFEMIWDPNGWTETDSKFSVRQDVVAMTDWSGYSGSFVQHPELTG        400
LDCMRPCFWVELIRGRPKEKTIWTSASSISFCGVNSDTVDWSWPDGAELP        450
FSIDK*
```

>HK14 N2 WT

```
                                           (SEQ ID NO: 12)
MNPNQKIITIGSVSLTISTICFFMQIAILITTVTLHFKQYEFNSPPNNQV          50
MLCEPTIIERNITEIVYLTNTTIEKEICPKPAEYRNWSKPQCGITGFAPF        100

SKDNSIRLSAGGDIWVTREPYVSCDPDKCYQFALGQGTTLNNVHSNNTVR        150
DRTPYRTLLMNELGVPFHLGTKQVCIAWSSSSCHDGKAWLHVCITGDDKN        200
ATASFIYNGRLVDSVVSWSKDILRTQESECICINGTCTVVMTDGSASGKA        250
DTKILFIEEGKIVHTSTLSGSAQHVEECSCYPRYPGVRCVCRDNWKGSNR        300
PIVDINIKDHSIVSSYVCSGLVGDTPRKNDSSSSSHCLDPNNEEGGHGVK        350
GWAFDDGNDVWMGRTINETSRLGYETFKVIEGWSNPKSKLQTNRQVIVDR        400
GDRSGYSGIFSVEGKSCINRCFYVELIRGRKEETEVLWTSNSIVVFCGTS        450
GTYGTGSWPDGADLNLMPI*
```

>HK14 N2 L52C

```
                                           (SEQ ID NO: 13)
MNPNQKIITIGSVSLTISTICFFMQIAILITTVTLHFKQYEFNSPPNNQV          50
MCCEPTIIERNITEIVYLTNTTIEKEICPKPAEYRNWSKPQCGITGFAPF        100

SKDNSIRLSAGGDIWVTREPYVSCDPDKCYQFALGQGTTLNNVHSNNTVR        150
DRTPYRTLLMNELGVPFHLGTKQVCIAWSSSSCHDGKAWLHVCITGDDKN        200
ATASFIYNGRLVDSVVSWSKDILRTQESECICINGTCTVVMTDGSASGKA        250
DTKILFIEEGKIVHTSTLSGSAQHVEECSCYPRYPGVRCVCRDNWKGSNR        300
PIVDINIKDHSIVSSYVCSGLVGDTPRKNDSSSSSHCLDPNNEEGGHGVK        350
GWAFDDGNDVWMGRTINETSRLGYETFKVIEGWSNPKSKLQTNRQVIVDR        400
GDRSGYSGIFSVEGKSCINRCFYVELIRGRKEETEVLWTSNSIVVFCGTS        450
GTYGTGSWPDGADLNLMPI*
```

>HK14 N2 L52C_E54C

```
                                           (SEQ ID NO: 14)
MNPNQKIITIGSVSLTISTICFFMQIAILITTVTLHFKQYEFNSPPNNQV          50
MCCCPTIIERNITEIVYLTNTTIEKEICPKPAEYRNWSKPQCGITGFAPF        100

SKDNSIRLSAGGDIWVTREPYVSCDPDKCYQFALGQGTTLNNVHSNNTVR        150
DRTPYRTLLMNELGVPFHLGTKQVCIAWSSSSCHDGKAWLHVCITGDDKN        200
ATASFIYNGRLVDSVVSWSKDILRTQESECICINGTCTVVMTDGSASGKA        250
DTKILFIEEGKIVHTSTLSGSAQHVEECSCYPRYPGVRCVCRDNWKGSNR        300
PIVDINIKDHSIVSSYVCSGLVGDTPRKNDSSSSSHCLDPNNEEGGHGVK        350
GWAFDDGNDVWMGRTINETSRLGYETFKVIEGWSNPKSKLQTNRQVIVDR        400
GDRSGYSGIFSVEGKSCINRCFYVELIRGRKEETEVLWTSNSIVVFCGTS        450
GTYGTGSWPDGADLNLMPI*
```

Cells

Human embryonic kidney 293T (HEK 293T) cells were maintained in Dulbecco's Modified Eagle's medium (DMEM; Gibco) containing 10% (vol/vol) fetal bovine serum (FBS) and 100 unit/mL of penicillin/streptomycin (PS; Gibco) at 37° C. with 5% $CO_2$. Madin-Darby canine kidney (MDCK) cells were grown in Minimum Essential Medium (MEM; Gibco) supplemented with 10% (vol/vol) FBS, 2 mM of L-glutamine (Gibco), 0.15% (w/vol) of sodium bicarbonate (Corning), 20 mM of 2-[4-(2-hydroxyethyl)piperazin-1-yl]ethanesulfonic acid (HEPES, Gibco), and 100 unit/mL of PS at 37° C. with 5% $CO_2$.

Rescue of Recombinant Influenza Viruses

Each well of poly-D lysine (Sigma-Aldrich) coated 6-well plates of HEK 293T cells was transfected with 2.1 µg of pRS PR8 6 segment, 0.7 µg of pDZ HA and 0.7 µg modified pDZ NA using TransIT LT1 transfection reagent (Mims Bio). Transfected cells were incubated at 37° C. Forty-eight hours post-transfection, supernatants together with scraped cells were collected and briefly homogenized through several syringe strokes. Two-hundred microliters of cells and super-natant mixture were injected into the allantoic cavity of 8-day old embryonated chicken eggs (Charles River). Injected eggs were incubated at 33° C. for 3 days and then cooled at 4° C. overnight. Allantoic fluids were subsequently collected and clarified by low speed centrifugation. An HA assay was performed using 0.5% turkey red blood cells to examine the presence of rescued virus from the clarified allantoic fluids. HA positive allantoic fluid samples were used to plaque-purify virus on MDCK cells. Plaques grown on MDCK cells were picked and re-suspended in PBS and further amplified again in 10-day old embryonated chicken eggs. RNA was extracted from allantoic fluids containing the plaque-purified virus using QIAamp Viral RNA Mini Kit (Qiagen). One-step RT-PCR was performed to amplify DNA of the NA segment using the SuperScript™ III One-Step RT-PCR System with Platinum™ Taq DNA Polymerase (Thermo Fisher Scientific) and NA specific primers. DNA was gel-purified and sequenced by Sanger sequencing (Ge-newiz). All the H3N2 viruses were also rescued in the PR8 backbone (6 genomic segments except HA and NA are from PR8)

Inactivation and Purification of Influenza Viruses

Influenza viruses were grown in 10-day old embryonated chicken eggs at 37° C. for two days, and were then cooled at 4° C. overnight. Allantoic fluids were collected and clarified by low speed centrifugation. Viruses in the clarified allantoic fluids were inactivated with 0.03% methanol-free formaldehyde for 72 h at 4° C. with rocking. Viruses were then pelleted through a 30% sucrose cushion in NTE buffer (100 mM NaCl, 10 mM Tris-HCl, 1 mM EDTA, pH 7.4) by centrifugation in a Beckman L7-65 ultracentrifuge at 25,000 rpm for 2 h at 4° C. using a Beckman SW28 rotor (Beckman Coulter, Brea, CA, USA). Pellets were collected in PBS (pH 7.4), and protein content was quantified using the bicin-choninic acid (BCA) assay (Thermo Fisher Scientific).

Western Blots

Inactivated purified virus preparations were lysed by mixing with 2× Novex™ Tris-Glycine SDS Sample buffer (Thermo Fisher Scientific). For reducing condition, 10× NuPAGE™ Sample Reducing Agent (Thermo Fisher Scientific) was included. Two micrograms of reducing or non-reducing virus preparations in a total volume of 10 µl were boiled for 5 min to denature the proteins and resolved onto 10% or 8%-16% polyacrylamide gels (Bio-rad Laboratories) under denaturing conditions in the presence of sodium dodecyl sulfate (SDS). Novex™ Sharp Pre-stained Protein Standard (3.5-260 kDa, Thermo Fisher Scientific) or Color Pre-stained Protein Standard, Broad Range standard (10-250 kDa, New England Biolabs, inc.) was used as a protein size marker. The separated viral proteins were then transferred onto polyvinylidene difluoride (PVDF) membranes. The membranes were blocked for 1 h using PBS containing 5% (wt/vol) dry milk powder and were washed three times with PBS containing 0.01% (vol/vol) Tween 20 (PBST). The primary antibodies were mouse anti-N1 monoclonal anti-body 4A5 (3) (1 µg per ml) or anti-N2 polyclonal serum raised in guinea pigs (generated in-house; 1:2,000 dilution). The primary antibodies were diluted in PBS containing 1% (wt/vol) bovine serum albumin (BSA) and incubated on the membranes overnight at 4° C. The membranes were washed three times with PB ST and were incubated for 1 h with secondary horseradish peroxidase (HRP)-labeled antibodies (anti-mouse [GE Healthcare] or anti-guinea pig [Ther-mofisher Fisher]) diluted 1:3,000 in PBS containing 1% (wt/vol) BSA according to the manufacturer's recommen-dations. After three washes with PBST, developing solution (Pierce ECL Western blotting substrate; Thermo Fisher Scientific) was added to the membranes, which were sub-sequently developed in a ChemiDoc MP imaging system (Bio-Rad Laboratories).

NA-Fluor Influenza Neuraminidase Assay

To measure potential neuraminidase activity of different mutant viruses, a fluorescence-based NA activity assay was performed. The viruses were diluted to 2 ng/µl in PBS resulting in 5 ng in 25 µl PBS. Twenty-five microliters of assay buffer (33.3 mM 2-(N-morpholino)ethanesulfonic acid (MES) and 4 mM $CaCl_2$), pH 6.5) were added to each well of a black 96-well plate. Five nanograms of virus in 25 µl of PBS were added to each well in triplicates. The 2(4-Methylumbelliferyl)-$\alpha$-D-N-acetylneuraminic acid (MUNANA) (Sigma-Aldrich) substrate was prepared in assay buffer at a concentration of 200 uM. Fifty microliters of substrate were added to each well and incubated in dark at 37° C. for 1 hour. The reaction was stopped by adding 100 µl of stop solution (0.1 glycine in 20% ethanol, pH 10.7). The plates were read at excitation wavelength 365 nm and emission wavelength 465 nm to measure fluorescence sig-nals using a Synergy Hybrid Reader (BioTek).

6.2.2 Results

Introduction of Additional Cysteines into the Stalk Region of N1 Neuraminidase

It was previously described that natural cysteine(s) in the stalk region contributed to dimer and tetramer formation of the influenza virus NA proteins as well as their enzymatic activity (4, 5). The manufacturing process of IIVs involve possibly harsh physical and chemical treatments (6), which could be potentially detrimental to the structure of the NA. To further stabilize NA tetramers, additional cysteines (dis-ulfide bonds) were introduced into the stalk region by amino acids substitutions or insertions, as such an approach has been shown to benefit tetramer formation of the NA when it was overexpressed in mammalian cells (5). As a proof of principle study, mutagenesis in the PR8 N1 was first per-formed, which included I48C, N50C and I48C_N50C amino acid substitutions as well as insertions of cysteines after W61 and V62 based on our transposons mutagenesis study (unpublished data). Recombinant PR8 cysteine mutant viruses were rescued and amplified in embryonated chicken eggs. Viruses were inactivated using 0.03% formaldehyde and purified through 30% sucrose cushion. To visualize NA contents in virus preparations, 2 µg of each virus were resolved on SDS-PAGE under non-reducing (NR) or reduc-ing (R) conditions. A western blot was performed using N1-specific mouse monoclonal antibody 4A5 (3) (FIG. 6A). Mutant I48C, N50C and I48C_N50C viruses showed more trimeric and tetrameric forms of the NA according to the size of the protein under non-reducing condition. Mutant W61 insertC and V62 insertC viruses showed similar oligomer-ization patterns as the WT virus, most of which are dimers. To further avoid the trimeric form of NA, I48C was com-bined with W61 insertC to generate I48C_W61 insertC mutant. It appears the I48C_W61 insertC mutant had more stable NA tetramers but fewer NA trimers (FIG. 6B).

Introduction of Additional Cysteines into the Stalk Region of N2 Neuraminidase

To apply the same approach to another influenza virus subtype and to a more clinically relevant strain than PR8, an amino acid sequence alignment of the PR8 N1 with HK14 N2 proteins was performed (FIG. 7). The HK14 N2 also has a natural cysteine (C53) that corresponds to the I49C of PR8 N1. Similar mutagenesis was done to generate N2 mutants that are equivalent to N1 I48C and I48C_N50C. These mutants were defined as L52C and L52C_E54C by amino acid sequence alignment (FIG. 7)

The WT and mutant H3N2 viruses were rescued in the PR8 backbone (6 segments are from PR8 except HA and NA). These viruses were inactivated and purified using the same approach described for PR8. Again, the virus preparations were resolved onto non-reducing (NR) and reducing (R) SDS-PAGE followed by a western blot using guinea pig antisera raised against 1-1K14 N2 recombinant protein to detect NA contents (FIG. 8A). Both L52C and L52C_E54C showed more tetrameric contents than the WT virus.

To measure the potential NA activity of H3N2 mutant viruses, a fluorescence-based NA activity assay was used. As plate reader used has a saturation limit for fluorescence signals, the viruses were diluted to 2 ng/μl in PBS, resulting in 5 ng of virus being tested for NA activity. The L52C mutant instead of L52C_E54C mutant exhibited higher fluorescence signals than WT virus (FIG. 8B). However, this is only in the context of formaldehyde inactivation and purification through 30% sucrose, which might not necessarily be the conditions of NA tetramer disruption. virus preparations will be processed as close to industrial manufacturing procedures as possible to identify H1N1 and H3N2 cysteine mutants that have the highest enzymatic activity in the final IIV products.

6.2.3 Discussion

Mutations in the NA stalk region that stabilized the tetrameric form of both N1 and N2 in formaldehyde inactivated purified virus preparations were identified. Those mutants include N1 I48C, N1 N50C, N1 I48C_N50C and N1 I48C_W61 insertC; N2 L52C and N2 L52_E54C. The H3N2 L52C NA mutant seems to show higher NA activity in a fluorescence-based NA activity assay.

6.2.4 References Cited in Example 2

1. Martinez-Sobrido L, Garcia-Sastre A. 2010. Generation of recombinant influenza virus from plasmid DNA. J Vis Exp doi:10.3791/2057.
2. Fulton B O, Sun W, Heaton N S, Palese P. 2018. The Influenza B Virus Hemagglutinin Head Domain Is Less Tolerant to Transposon Mutagenesis than That of the Influenza A Virus. J Virol 92.
3. Wohlbold T J, Nachbagauer R, Xu H, Tan G S, Hirsh A, Brokstad K A, Cox R J, Palese P, Krammer F. 2015. Vaccination with adjuvanted recombinant neuraminidase induces broad heterologous, but not heterosubtypic, cross-protection against influenza virus infection in mice. MBio 6:e02556.
4. Basler C F, Garcia-Sastre A, Palese P. 1999. Mutation of neuraminidase cysteine residues yields temperature-sensitive influenza viruses. J Virol 73:8095-103.
5. da Silva D V, Nordholm J, Madjo U, Pfeiffer A, Daniels R. 2013. Assembly of subtype 1 influenza neuraminidase is driven by both the transmembrane and head domains. J Biol Chem 288:644-53.
6. Kon T C, Onu A, Berbecila L, Lupulescu E, Ghiorgisor A, Kersten G F, Cui Y Q, Amorij J P, Van der Pol L. 2016. Influenza Vaccine Manufacturing: Effect of Inactivation, Splitting and Site of Manufacturing. Comparison of Influenza Vaccine Production Processes. PLoS One 11:e0150700.

6.3 Example 3: Recombinant Neuraminidase-Based Constructs

This example demonstrates the ability of recombinant NA proteins, which comprise the globular head domain of influenza virus NA and the measles virus phosphoprotein tetramerization domain, to induce an immune response in a murine model that is protective against influenza virus challenge.

Recombinant NA proteins. The N1-MPP is described in Example 1. The recombinant N2-MPP protein, which comprises the globular head domain of influenza virus A/Kansas/14/2017 and MPP tetramerization domain, was expressed using a modified pFastBacDual expression vector. Similarly, the recombinant B-MPP protein, which comprises the globular head domain of influenza virus B/Colorado/06/2017 and MPP tetramerization domain, was expressed using the pFastBacDual expression vector. The nucleotide and amino acid sequences of the recombinant N2-MPP and B-MPP proteins are provided below. The amino acid sequence of N1-MPP is provided in SEQ ID NO:27.

| SEQ ID NO: | Construct | Sequence |
|---|---|---|
| 59 | N2-MPP | atgctgctcgtcaaccaatcccaccagggcttcaacaaggaacacacttctaagatggt ctccgctatcgtgctctacgtgctgctcgctgccgctgcccactcagctttcgctgccga cccacaccaccaccaccacggcgatcactacgacgacgaactgttctccgacgt gcaggacatcaagaccgctctggctaagatccacgaggacaaccagaagatcatctc caagctggaatccctgctgctgctgaagggcgaagtcgagtccatcaagaagcagatc aaccgccagaacatctccatctccaccttggagggtcacctgtcctccatcatgatcgct atccctggcctgtctctcgtgcccaggggatcaccttctagaATATGCCCCAA ACCAGCAGAATACAGAAATTGGTCAAAACCGCAATG TGGCATTACAGGATTTGCACCTTTCTCTAAGGACAAT TCGATTAGGCTTTCCGCTGGTGGGGACATCTGGGTG ACAAGAGAACCTTATGTGTCATGCGATCCTGACAAG TGTTATCAATTTGCCCTTGGACAGGGAACAACAATA AACAACGTGCATTCAAATAACACAGCACGTGATAGG ACCCCTCATCGGACTCTATTGATGAATGAGTTGGGT GTTCCTTTCCATCTGGGGACCAAGCAAGTGTGCATA GCATGGTCCAGCTCAAGTTGTCACGATGGAAAAGCA TGGCTGCATGTTTGTATAACGGGGGATGATAAAAAT |

-continued

| SEQ ID NO: | Construct | Sequence |
|---|---|---|

GCAACTGCTAGTTTCATTTACAATGGGAGGCTTGTA
GATAGTGTTGTTTCATGGTCCAAAGATATTCTCAGGA
CCCAGGAGTCAGAATGCGTTTGTATCAATGGAACTT
GTACAGTAGTAATGACTGATGGAAATGCTACAGGAA
AAGCTGATACTAAAATATTATTCATTGAGGAGGGGA
AAATCGTTCATACTAGCAAATTGTCAGGAAGTGCTC
AGCATGTCGAAGAGTGCTCTTGCTATCCTCGATACCC
TGGTGTCAGATGTGTCTGCAGAGACAACTGGAAAGG
ATCCAACCGGCCCATCGTAGATATAAACATAAAGGA
TCATAGCATTGTTTCCAGTTATGTGTGTTCAGGACTT
GTTGGAGACACACCCAGAAAAACCGACAGCTCCAGC
AGCAGCCATTGCTTGAATCCTAACAATGAAAAAGGT
GGTCATGGAGTGAAAGGCTGGGCCTTTGATGATGGA
AATGACGTGTGGATGGGGAGAACAATCAACGAGAC
GTCACGCTTAGGGTATGAAACCTTCAAAGTCGTTGA
AGGCTGGTCCAACCCTAAGTCCAAATTGCAGATAAA
TAGGCAAGTCATAGTTGACAGAGGTGATAGGTCCGG
TTATTCTGGTATTTTCTCTGTTGAAGGCAAAAGCTGC
ATCAATCGGTGCTTTTATGTGGAGTTGATTAGGGGA
AGAAAAGAGGAAACTGAAGTCTTGTGGACCTCAAAC
AGTATTGTTGTGTTTTGTGGCACCTCAGGTACATATG
GAACAGGCTCATGGCCTGATGGGGCGGACCTCAATC
TCATGCATATATAA

60    N2-MPP    *MLLVNQSHQGFNKEHTSKMVSAIVLYVLLAAAAHSAFAAD*
*PHHHHHHGDHYDDELFSDVQDIKTALAKIHEDNQKIIS*
KLESLLLLKGEVESIKKQINRQNISISTLEGHLSSIMIAIP
GLSLVPRGSPSRICPKPAEYRNWSKPQCGITGFAPFS
KDNSIRLSAGGDIWVTREPYVSCDPDKCYQFALGQG
TTINNVHSNNTARDRTPHRTLLMNELGVPFHLGTK
QVCIAWSSSSCHDGKAWLHVCITGDDKNATASFIYN
GRLVDSVVSWSKDILRTQESECVCINGTCTVVMTDG
NATGKADTKILFIEEGKIVHTSKLSGSAQHVEECSCY
PRYPGVRCVCRDNWKGSNRPIVDINIKDHSIVSSYVC
SGLVGDTPRKTDSSSSSHCLNPNNEKGGHGVKGWA
FDDGNDVWMGRTINETSRLGYETFKVVEGWSNPKS
KLQINRQVIVDRGDRSGYSGIFSVEGKSCINRCFYVE
LIRGRKEETEVLWTSNSIVVFCGTSGTYGTGSWPDG
ADLNLMHI*
(signal peptide and his tag are italicized; MPP tetramerization
domain is underlined; thrombin cleavage site plus two amino
acid residues is double underline; NA globular domain of
influenza virus A/Kansas/14/2017 is bold)

61    B-MPP    atgctgctcgtcaaccaatcccaccagggcttcaacaaggaacacacttctaagatggt
ctccgctatcgtgctctacgtgctgctcgctgccgctgcccactcagctttcgctgccga
cccacaccaccaccaccaccacggcgatcactacgacgacgaactgttctccgacgt
gcaggacatcaagaccgctctggctaagatccacgaggacaaccagaagatcatctc
caagctggaatccctgctgctgctgaagggcgaagtcgagtccatcaagaagcagatc
aaccgccgaaacatctccatctccaccttggagggtcacctgtcctccatcatgatcgct
atccctggcctgtctctcgtgcccaggggatcaccttctagacttcttctcccagaaccg
gagtggacatacccgcgtttatcttgcccgggctcaacctttcagaaagcactcctaatt
agccctcatagattcggagaaaccaaaggaaactcagctcccttgataataagggaac
cttttgttgcttgtggaccaaatgaatgcaaacactttgctttaacccattatgcagcccaa
ccaggggggatactacaatggaacaagaggagacagaaacaagctgaggcatctaatt
tcagtcaaattgggcaaaatcccaacagtagagaactccattttccacatggcagcatg
gagcgggtccgcgtgccatgatggtaaggaatggacatatatcggagttgatggccct
gacaataatgcattgctcaaagtaaaatatggagaagcatatactgacacataccattcc
tatgcaaacaacatcctaagaacacaagaaagtgcctgcaattgcatcggggggaaatt
gttatctaatgataactgatggctcagcttcaggtgttagtgaatgcagatttcttaagattc
gagagggccgaataataaaagaaatatttccaacaggaagagtaaaacacactgagg
aatgcacatgcggatttgccagcaataaaaccatagaatgtgcctgtagagacaacag
gtacacagcaaaaagacctttgtcaaattaaacgtggagactgatacagcagaataa
ggttgatgtgcacagataacctatttggacaccccccagaccaaatgatggaagcataaca
ggcccttgtgaatctgatggggacaaagggagtggaggcatcaagggaggatttgttc
atcaaagaatgaaatccaagattggaaggtggtactctcgaacgatgtctcaaactgaa
aggatggggatgggactgtatgtcaagtatggtggagacccatgggctgacagtgatg
ccctagcttttagtggagtaatggtttcaatgaaagaacctggttggtattcctttggcttcg
aaataaaagataagaaatgcgatgtcccctgtattgggatagagatggtacatgatggt
ggaaaagagacttggcactcagcagcaacagccatttactgtttaatgggctcaggaca
gctgctgtgggacactgtcacaggtgttgacatggctctgtaa -continued

| SEQ ID NO: | Construct | Sequence |
|---|---|---|
| 62 | B-MPP | *MLLVNQSHQGFNKEHTSKMVSAIVLYVLLAAAAHSAFAAD* *PHHHHHH*GDHYDDELFSDVQDIKTALAKIHEDNQKIIS <u>KLESLLLLKGEVESIKKQINRQNISISTLEGHLSSIMIAIP</u> <u>GLSLVPRGSPSR</u>LLLPEPEWTYPRLSCPGSTFQKALLI SPHRFGETKGNSAPLIIREPFVACGPNECKHFALTHY AAQPGGYYNGTRGDRNKLRHLISVKLGKIPTVENSI FHMAAWSGSACHDGKEWTYIGVDGPDNNALLKVK YGEAYTDTYHSYANNILRTQESACNCIGGNCYLMIT DGSASGVSECRFLKIREGRIIKEIFPTGRVKHTEECT CGFASNKTIECACRDNRYTAKRPFVKLNVETDTAEI RLMCTDTYLDTPRPNDGSITGPCESDGDKGSGGIKG GFVHQRMKSKIGRWYSRTMSQTERMGMGLYVKY GGDPWADSDALAFSGVMVSMKEPGWYSFGFEIKDK KCDVPCIGIEMVHDGGKETWHSAATAIYCLMGSGQ LLWDTVTGVDMAL* (signal peptide and his tag are italicized; MPP tetramerization domain is underlined; thrombin cleavage site plus two amino acid residues is double underline; NA globular domain of influenza virus B/Colorado/06/2017 is bold) |

Mouse vaccination and challenge studies. The protective efficacy of recombinant neuraminidase proteins was tested in 6-8 week old female BALB/c mice or DBA2 mice (n=5 per group). The BALB/c mice were used for H1N1 and influenza B virus experiments and the DBA2 mice were used for the H3N2 experiments. The mice were vaccinated intramuscular with 3 µg of the specified recombinant NA protein (in 50 µl PBS). For mice vaccinated with a recombinant NA protein adjuvanted with AddaVax (InvivoGen), a 1:1 ratio of recombinant NA protein and AddaVax was used. An irrelevant protein was administered to one of the groups as negative control and an NA protein, containing a VASP tetramerization domain and the globular head of NA matching the specified recombinant NA protein was included as a positive control, whenever a positive control was used. The mice were vaccinated twice in an interval of 3 weeks. Three or four weeks after the second vaccination, the mice were challenged with indicated dose of the specified virus. Survival as well as the weight loss were monitored over a number of days. Mice that lost more than 25% of their initial body weight were humanely euthanized.

SDS-PAGE. The SDS-PAGE was generally performed as described in Example 1.

ELISA. The ELISAs were generally performed as described in Example 1 using the specified recombinant protein.

NA-Star assay. The NA-Star assay was generally performed as described in Example 1.

NA inhibition assay. For NI assays, microtiter 96-well plates (Immulon 4 HBX; Thermo Fisher Scientific) were coated using a method similar to that employed for the NA assay. The next day, RDE-treated human serum samples were serially diluted 1:2 in separate 96-well plates, with a starting concentration of 1:10. The final volume of diluted serum samples in all wells was 75 µl. Virus stocks were diluted in PBS to the determined EC90 concentration. After virus (75 µl/well) was added to the serum plates, the plates were incubated at room temperature for 1.5 h. The fetuin-coated plates were blocked and then washed under conditions similar to those used for the NA assay. A 100-µl volume of the virus/serum mixture was transferred to the washed fetuin-coated plates, which were then incubated for 2 h at 37° C. The plates were washed four times with PBS-T, and PNA-HRP (Sigma) diluted to 5 µg/ml in PBS (100

µl/well) was added. The NA assay protocol was followed for the remaining NI assay steps. The human serum sample reactivity was determined by subtracting the background absorbance value from the raw absorbance value of human serum samples. The obtained value was divided by the average value from virus-only control wells and then multiplied by a factor of 100 to calculate the NA activity. Percent NI was determined by subtracting NA activity from 100%. Using GraphPad Prism 7, the percent NI was fitted to a nonlinear regression to determine the 50% inhibitory concentration (IC50) of the serum samples. See the website mbio.asm.org/content/8/2/e02281-16.long.

FIG. 11A depicts the results from an ELISA measuring the binding of sera from mice immunized in accordance with the protocol provided in FIG. 10 and the legend for FIG. 10 for groups 1 to 6 to recombinant N1-VASP. The recombinant NT-MPP protein induced good immune responses against NA both when given without adjuvant, with adjuvant or with QIV but in different legs. If given in the same leg with QIV, the anti-NA immune response seems to be dampened. This is not the case with the response to the H1 in the QIV. FIG. 11B depicts the results from an ELISA measuring the binding of sera from mice immunized in accordance with the protocol provided in FIG. 10 and the legend for FIG. 10 for groups 1 to 6 to recombinant H1 to. Sera from mice vaccinated with N1-MPP did not bind to the recombinant H1. FIG. 11C shows the ability of sera from mice immunized in accordance with the protocol provided in FIG. 10 and the legend for FIG. 10 for groups 1 to 6 to inhibit the neuraminidase function of an H7N1 re-assortant virus that contains a matched N1 NA was assessed. The recombinant N1-MPP induced antibodies capable of inhibiting neuraminidase activity.

Figures 1A, 1B, 1C:
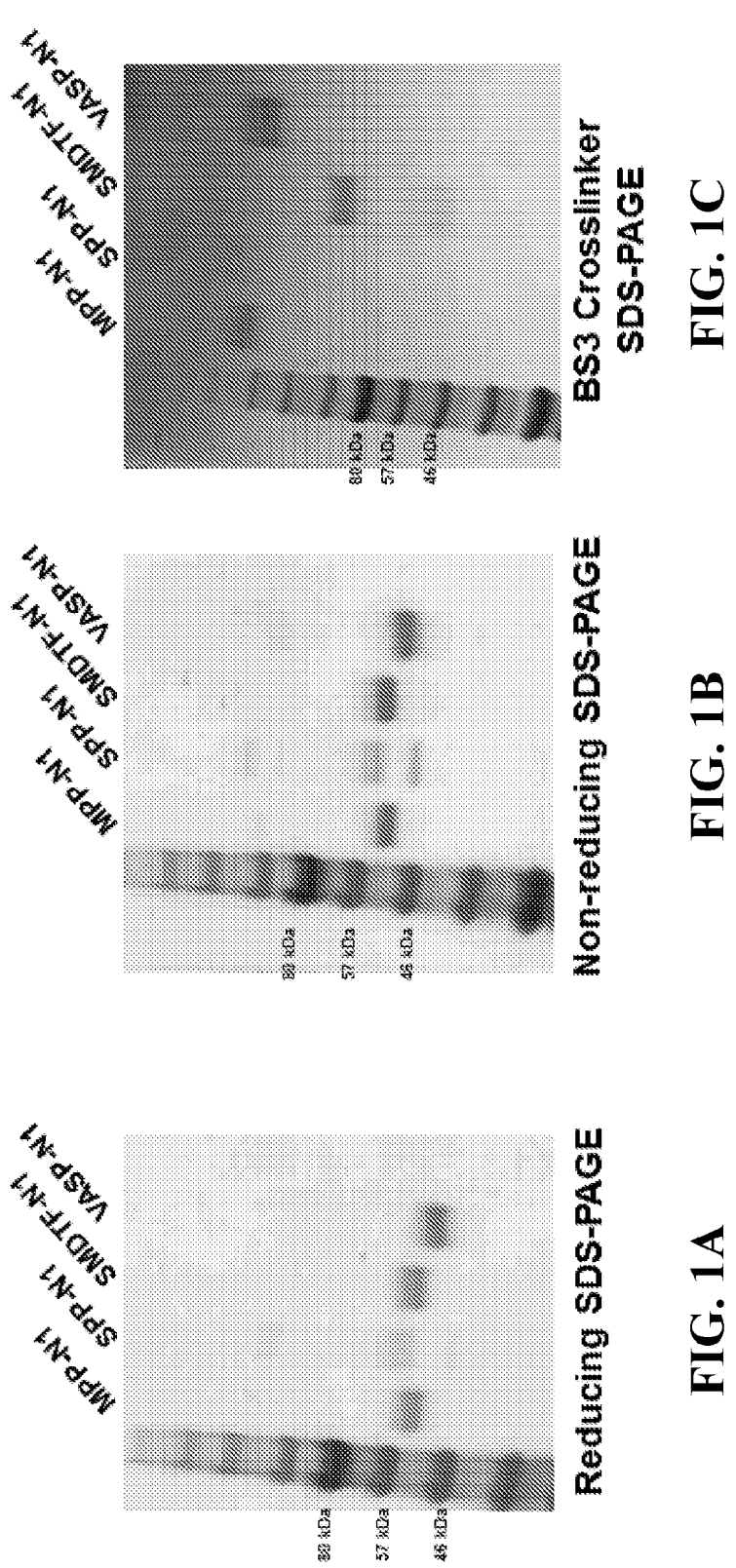
Figure 2:
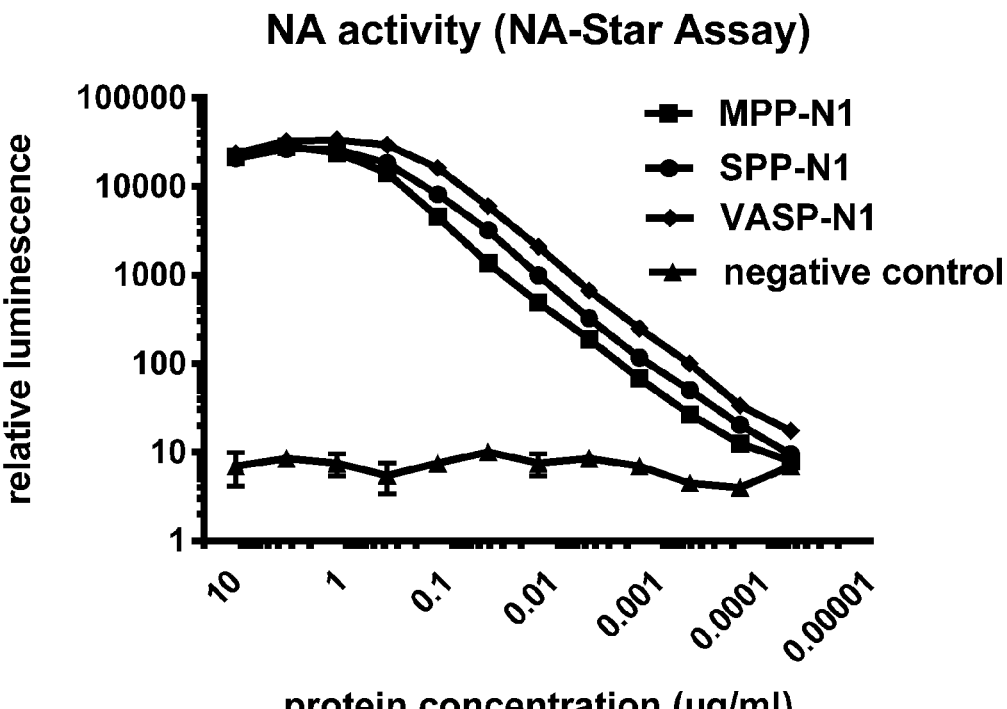
Figure 3:
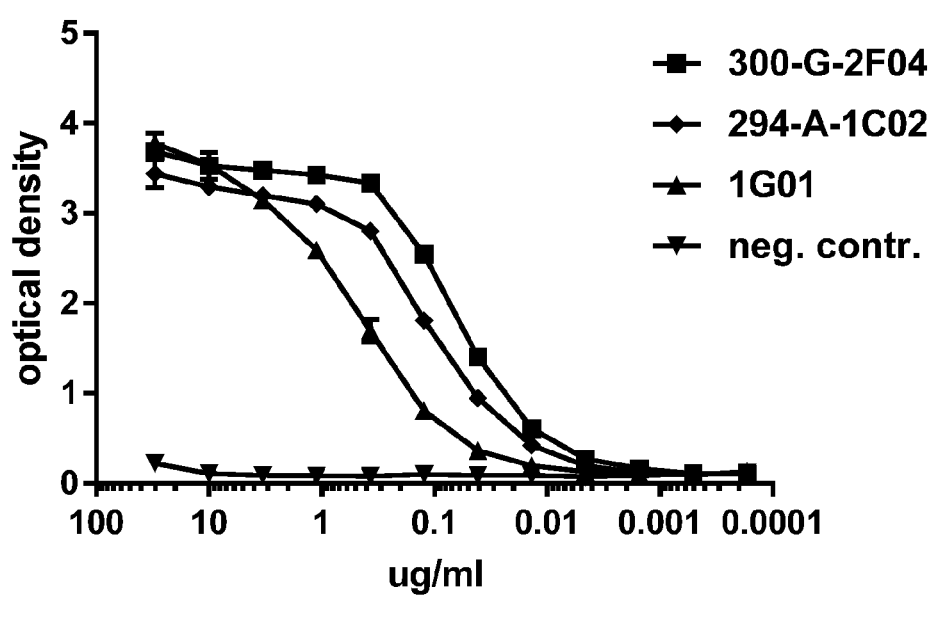
Figure 4:
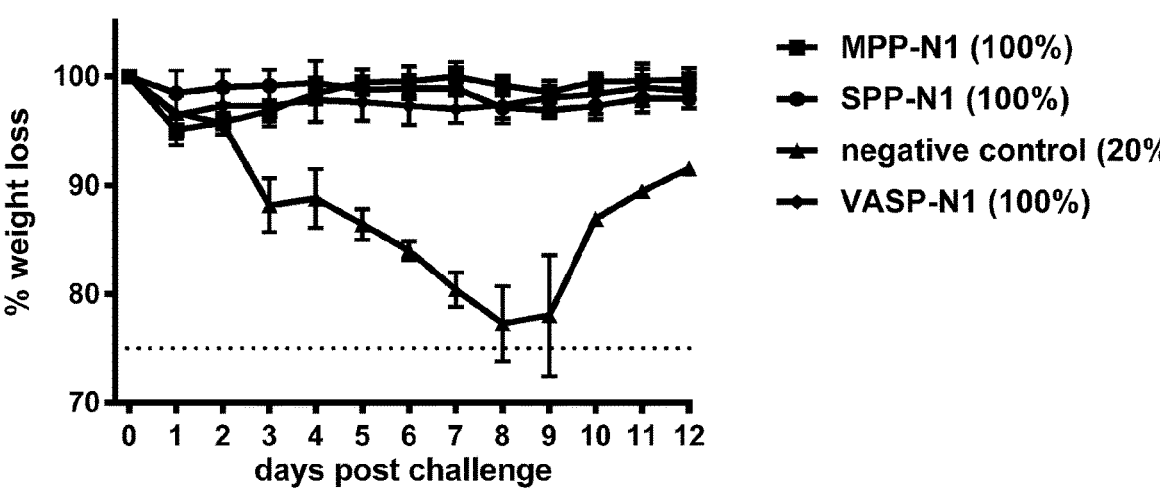
Figure 5:
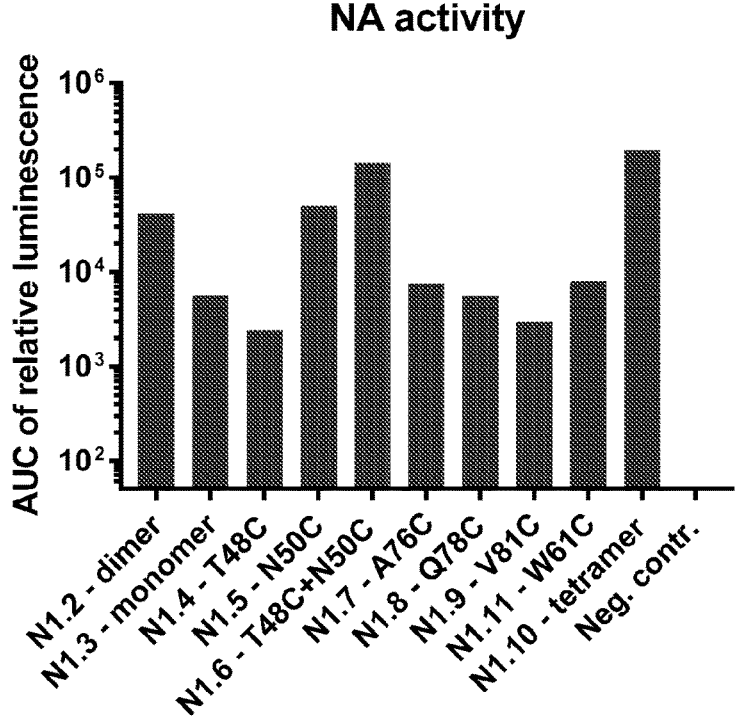
Figures 6A, 6B:
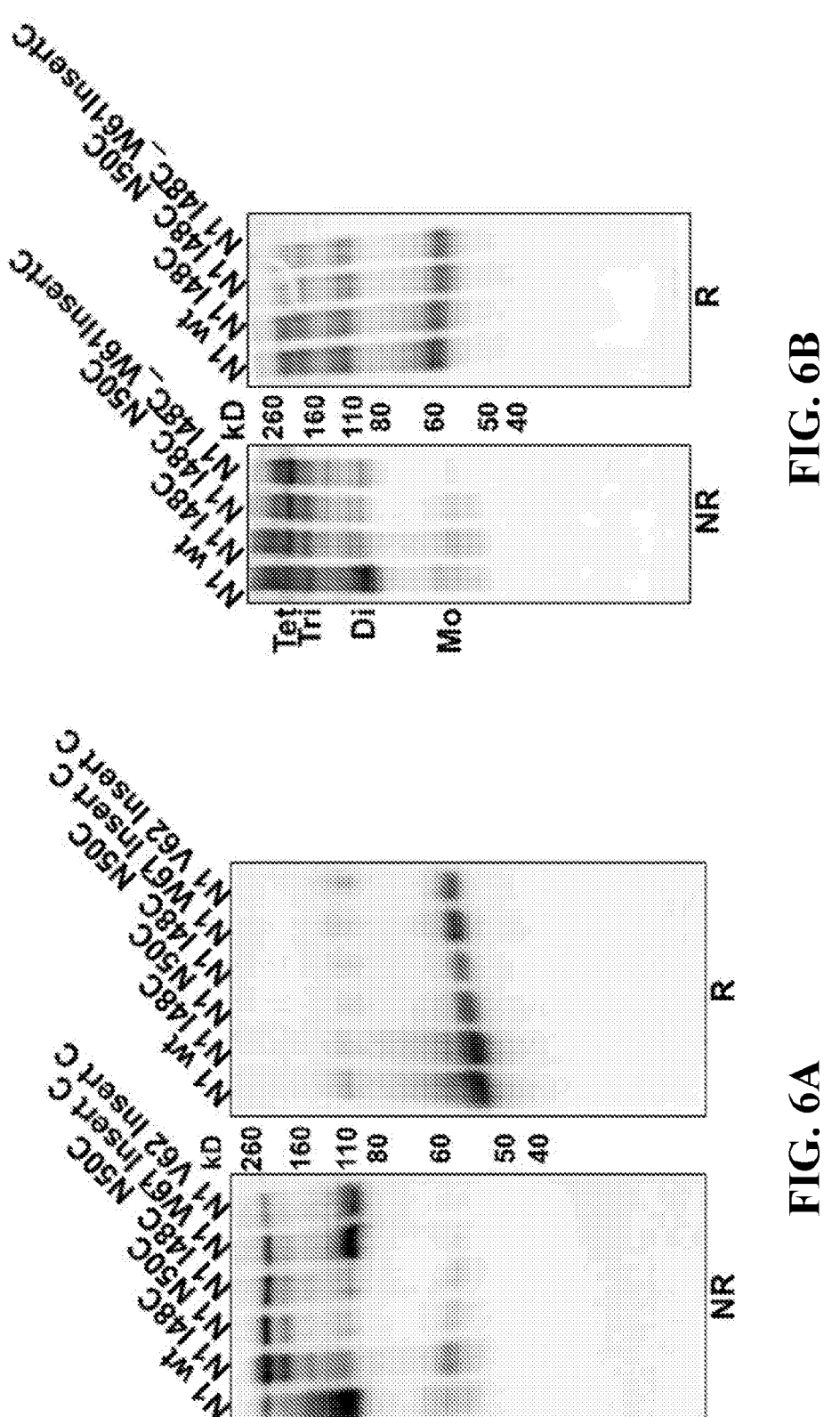
Figure 7:
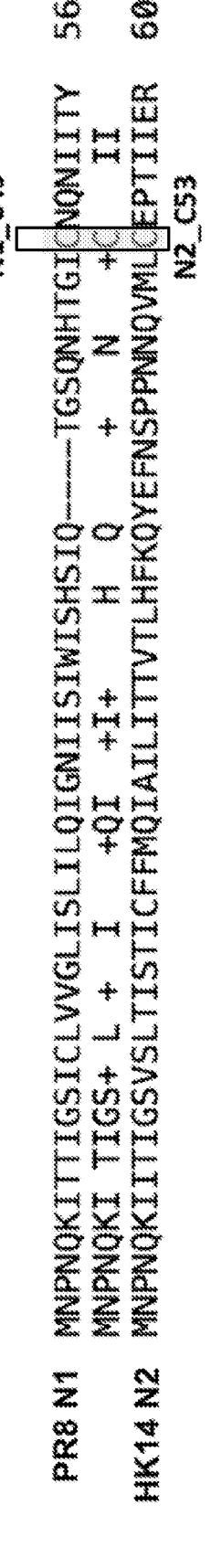
Figure 8B:
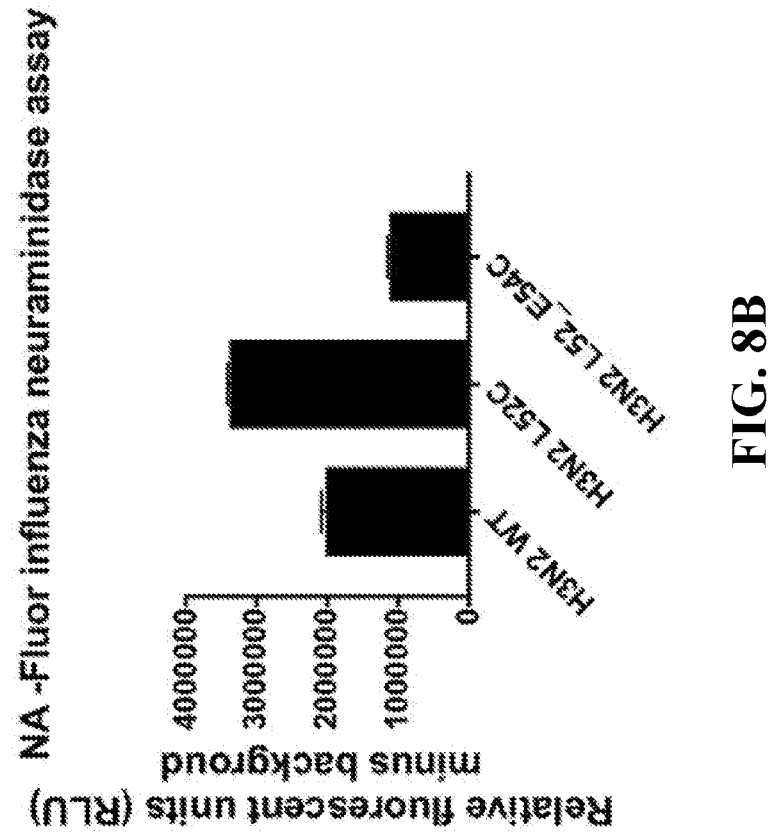
Figure 8A:
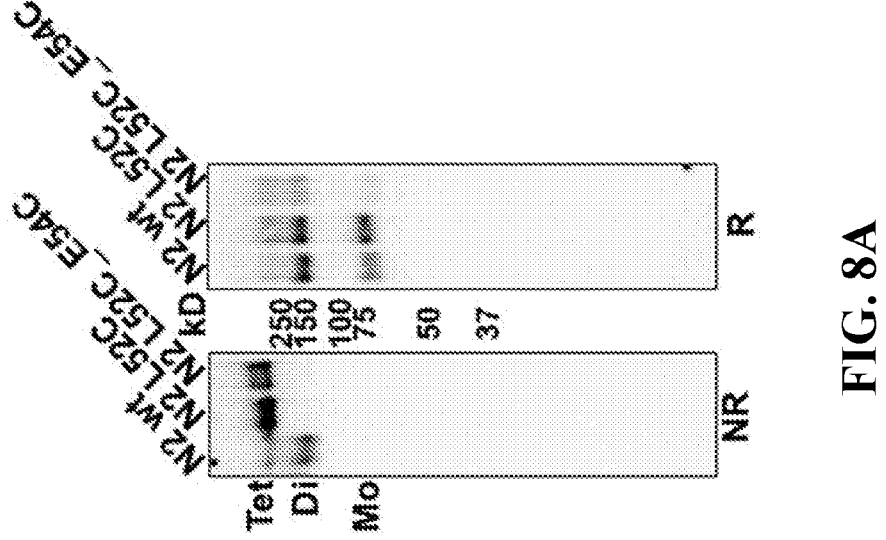
Figure 10:
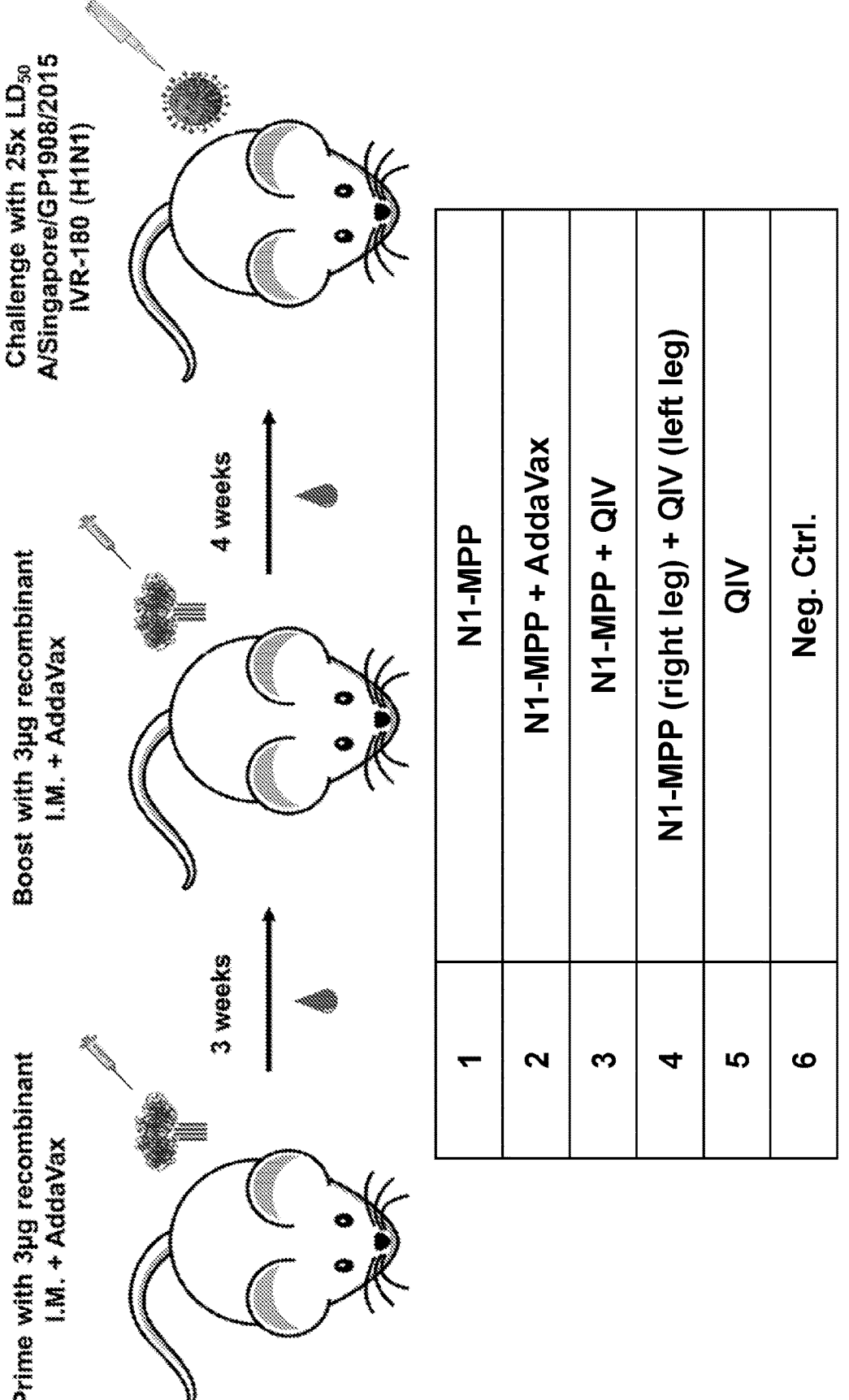
Figure 11A:
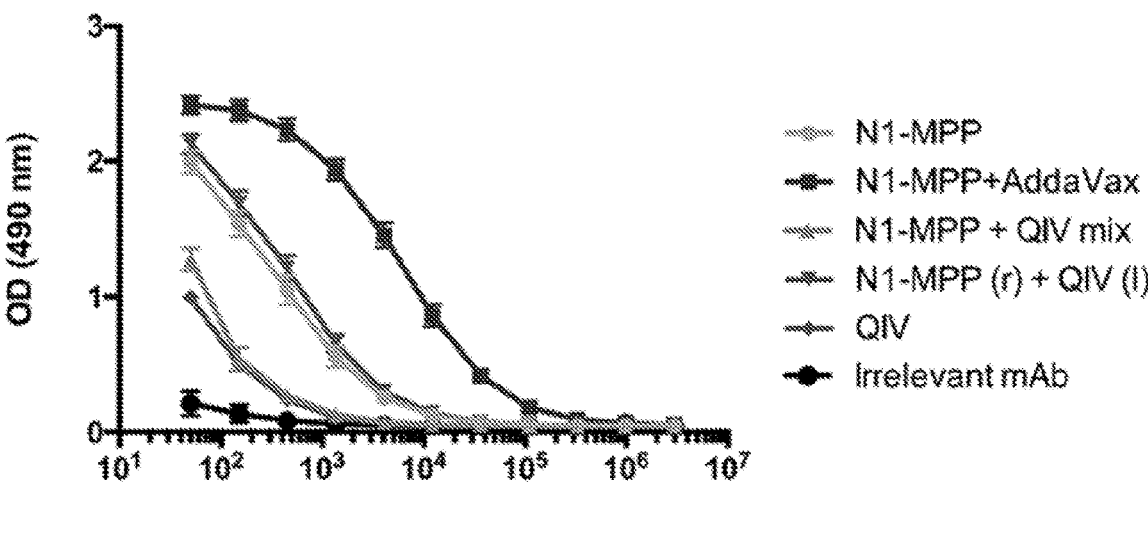
Figure 11B:
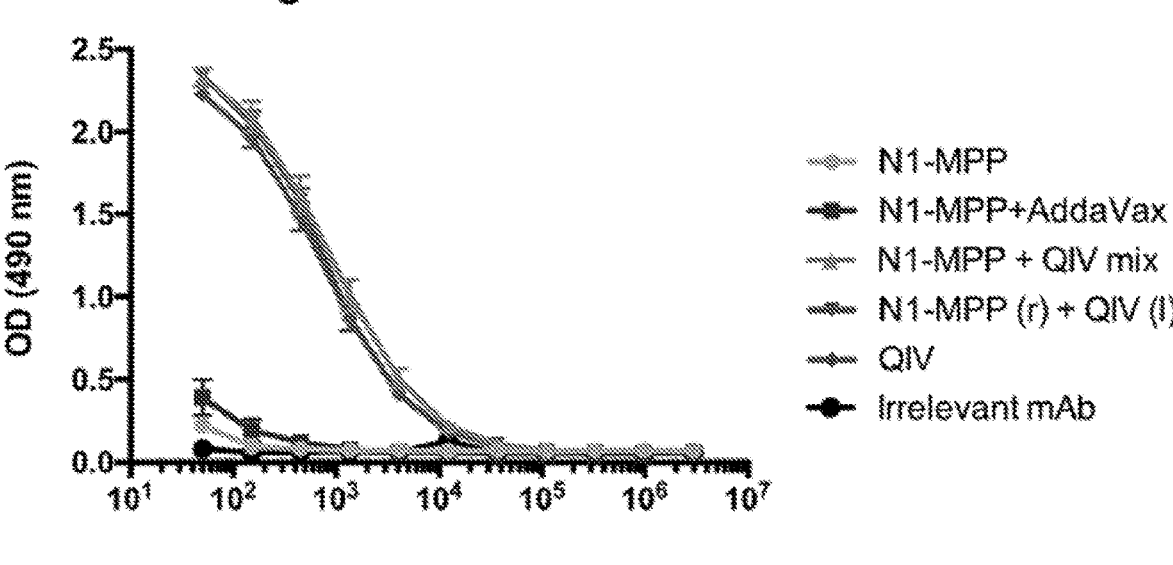
Figure 11C:
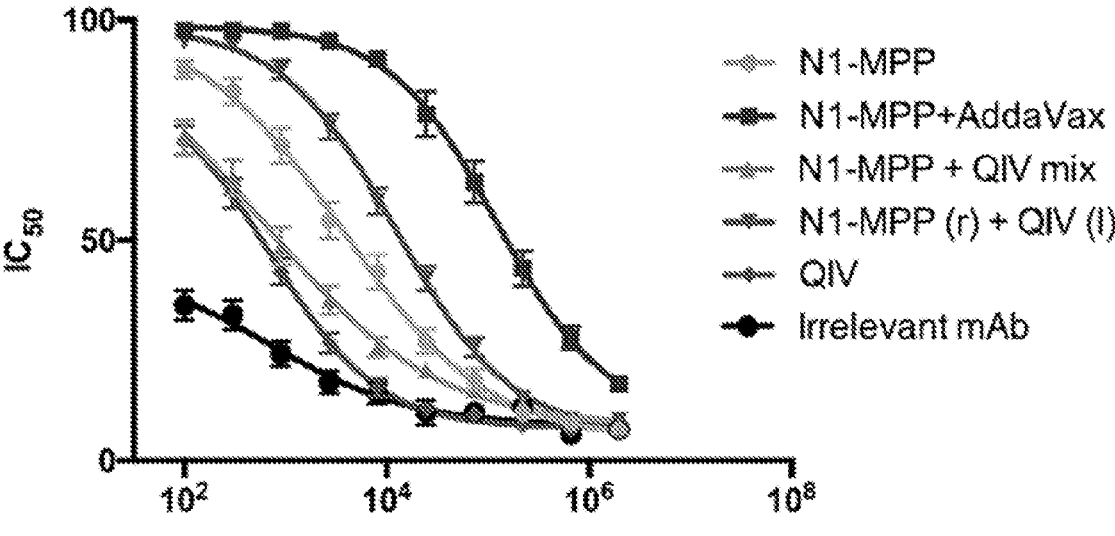
Figure 12A:
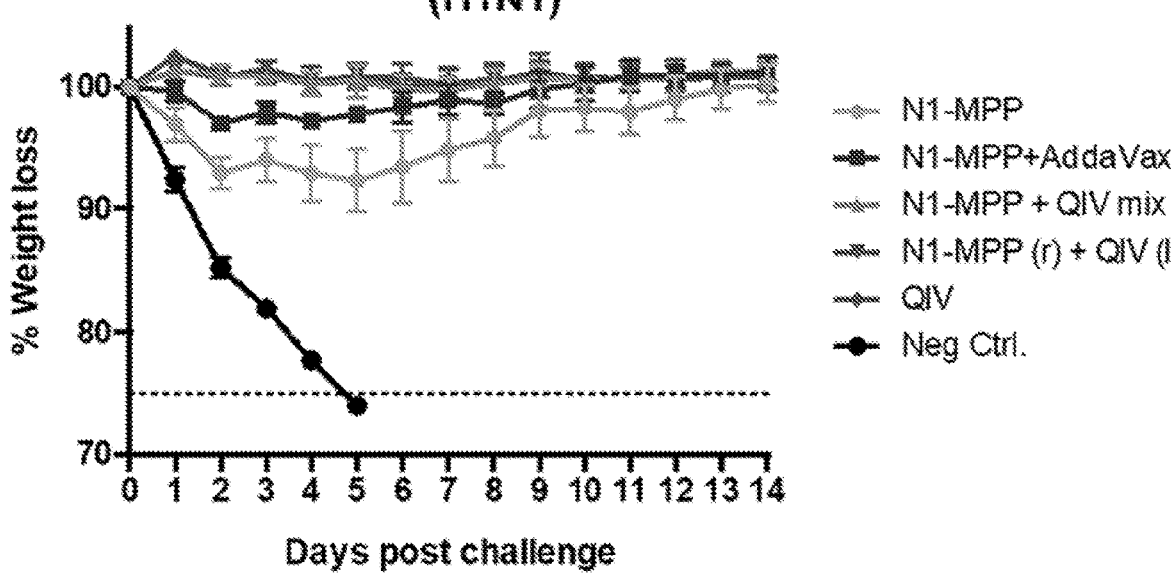
FIG. 12A and FIG. 12B shows that all mice immunized with N1-MPP were protected from weight loss had increased survival following challenge with $25 \times LD_{50}$ of A/Singapore/GP1908/2015 IVR-180 (HINT), respectively.
Figure 12B:
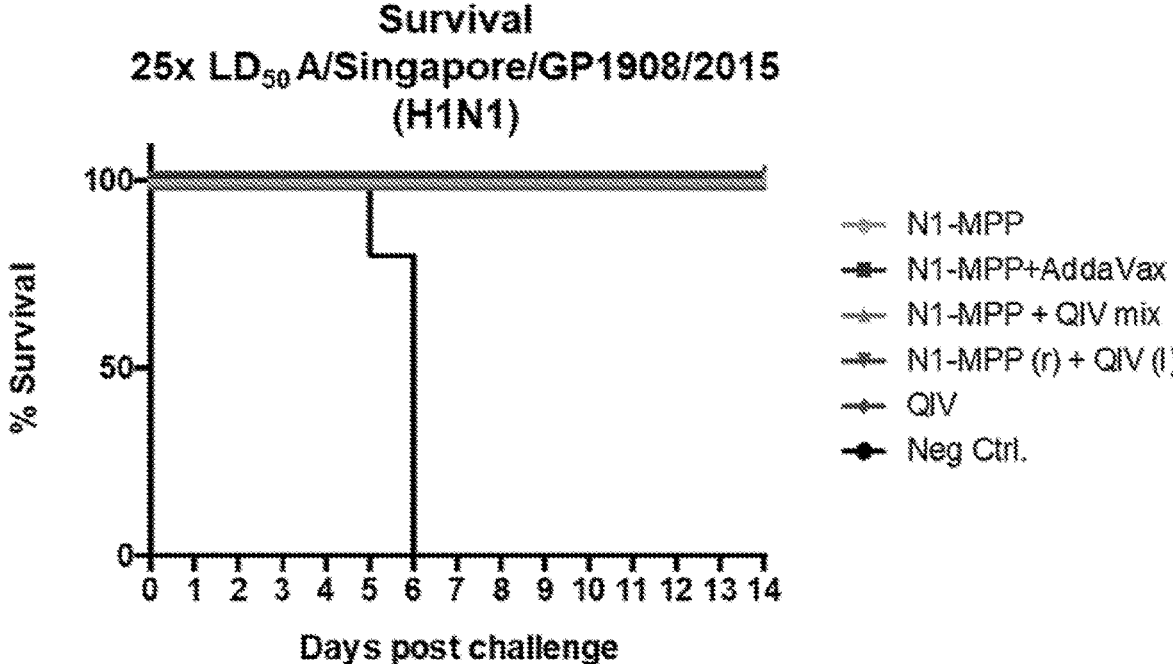
Figure 13A:
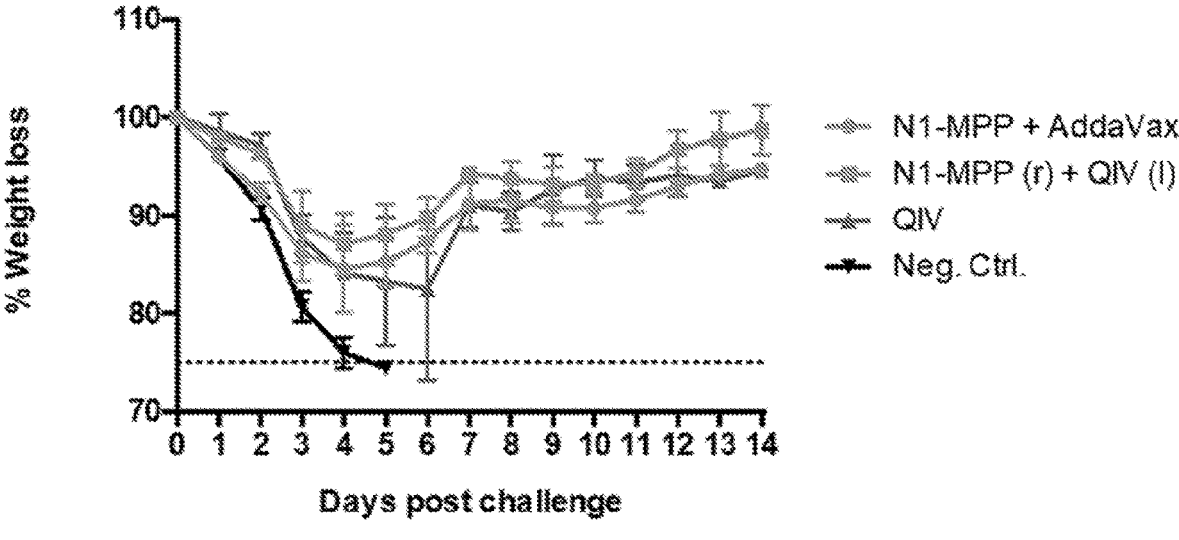
FIG. 13A and FIG. 13B show that all mice immunized with N1-MPP were protected from severe weight loss and had increased survival following challenge with $400 \times LD_{50}$ of A/Singapore/GP1908/2015 IVR-180 (H1N1), respectively.
Figure 13B:
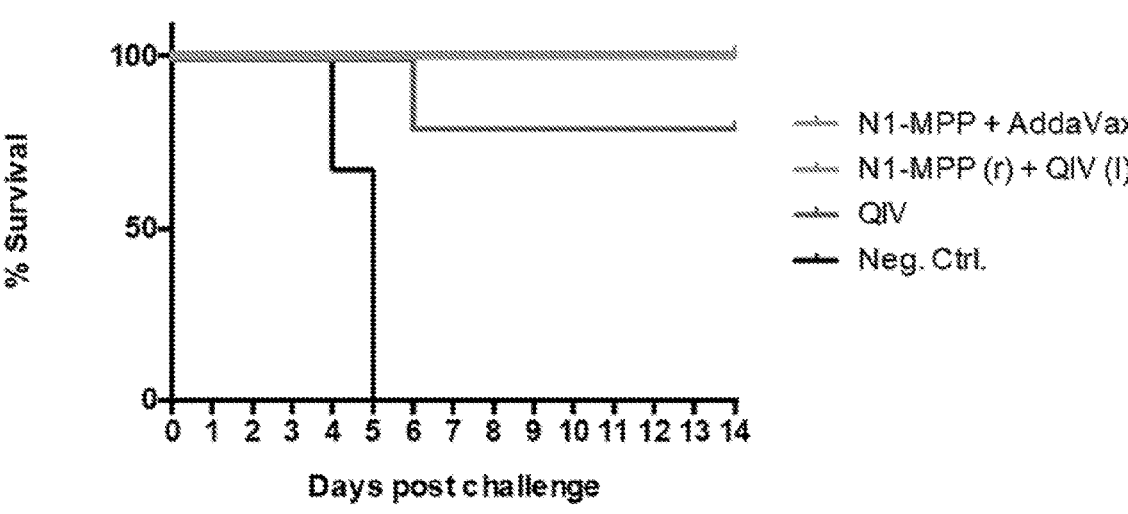
Figure 14A:
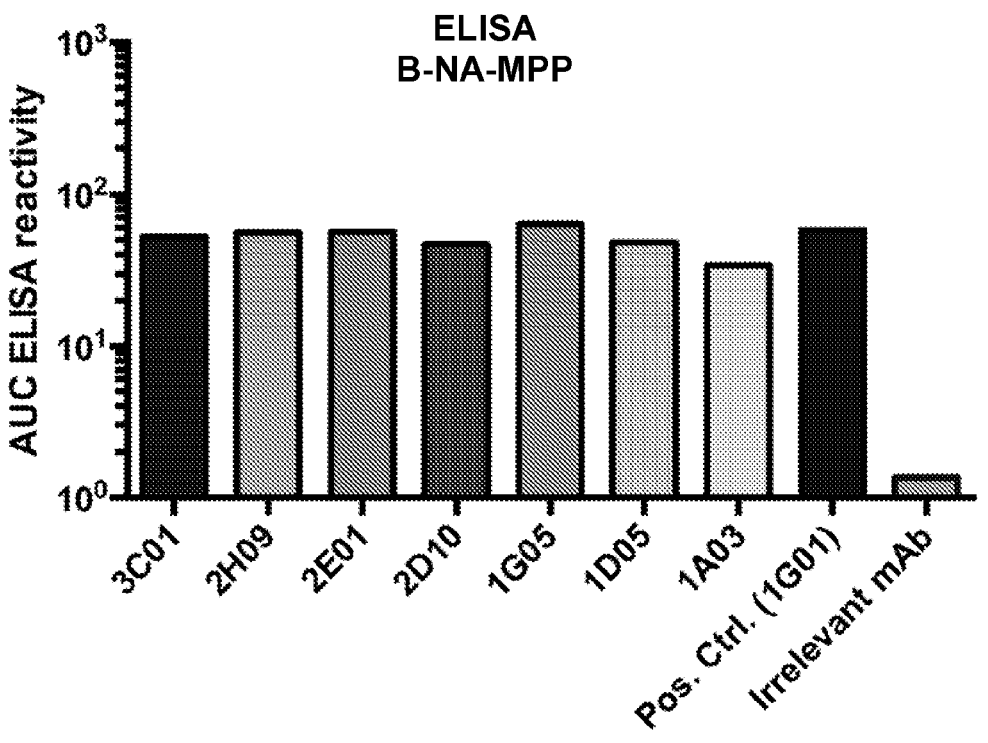
Figure 14B:
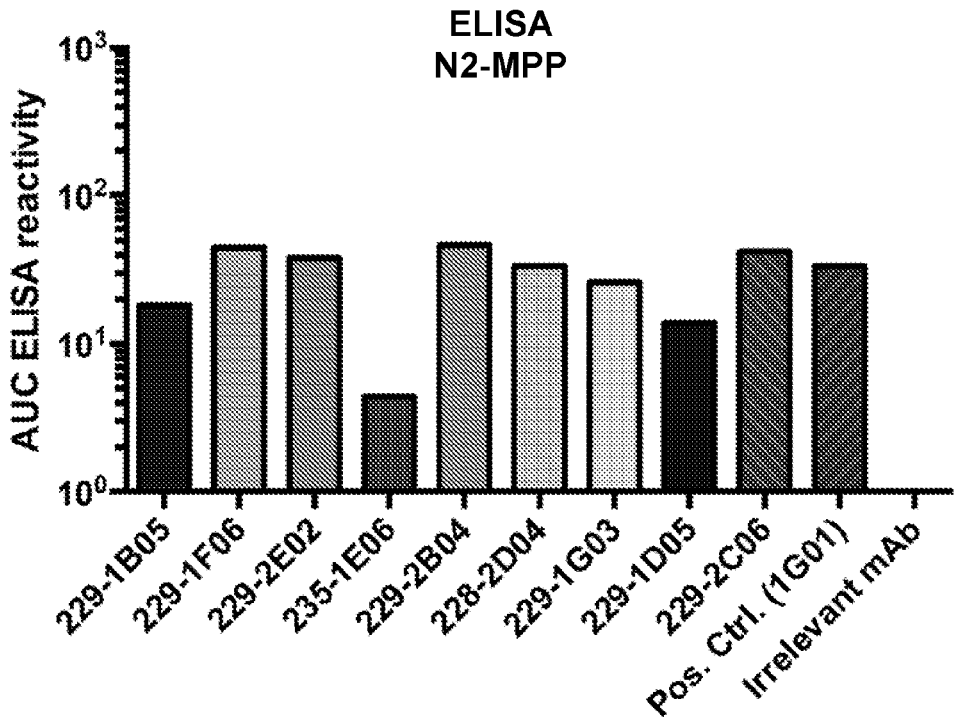
Figure 14C:
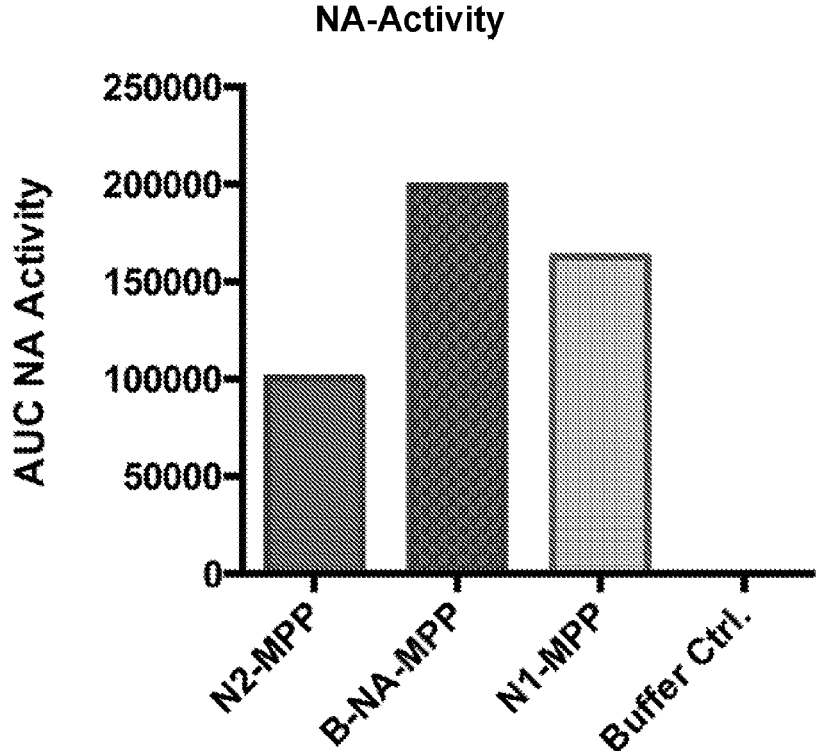
Figure 14E:
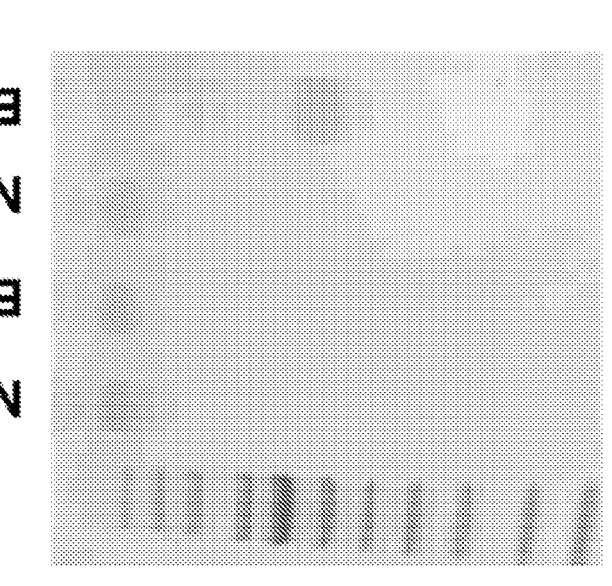
Figure 14D:
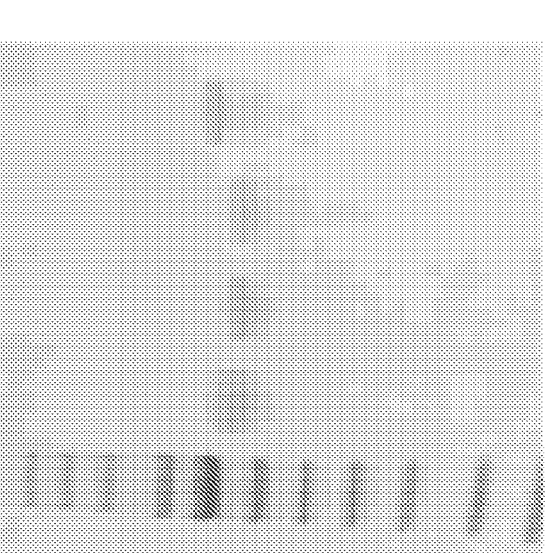

FIG. 14A shows the reactivity of broadly reactive anti-influenza B virus NA monoclonal antibodies to recombinant B-MPP. FIG. 14B shows the reactivity of broadly reactive anti-influenza A virus N2 NA monoclonal antibodies to recombinant N2-MPP. FIG. 14C shows the NA activity of recombinant N1-MPP (SEQ ID NO: 27), recombinant N2-MPP (SEQ ID NO:60), and recombinant B-MPP (SEQ ID NO:62) in an NA-star assay. The NA activity of the recombinant NA proteins indicates that the proteins are correctly folded. FIG. 14D shows recombinant N1-MPP (SEQ ID NO: 27), recombinant N2-MPP (SEQ ID NO:60), and recombinant B-MPP (SEQ ID NO:62) in a reducing SDS-PAGE. FIG. 14E shows recombinant N1-MPP (SEQ ID NO: 27), recombinant N2-MPP (SEQ ID NO:60), and recombinant B-MPP (SEQ ID NO:62) in a cross-linking SDS-PAGE, which indicates tetramer formation.

Figure 16A:
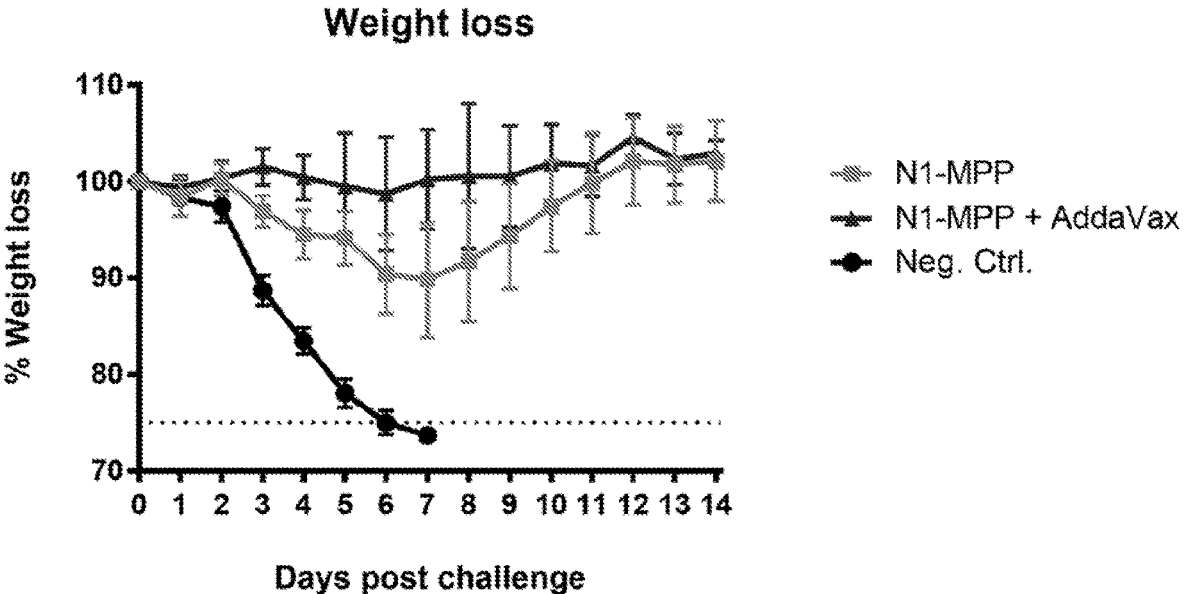
Figure 16B:
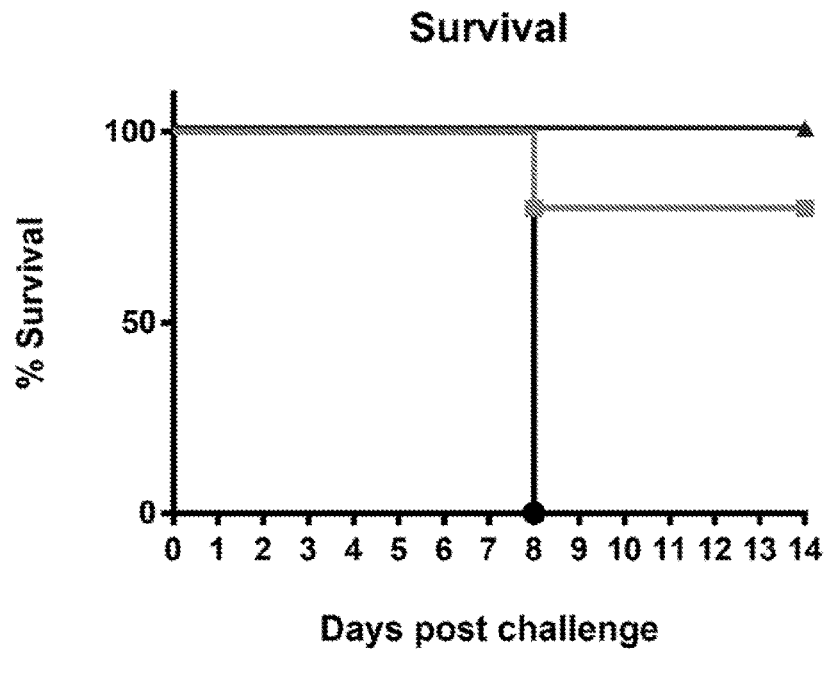

FIG. 16A and FIG. 16B show that all mice immunized with N1-MPP protective mice from weight loss of mice and increased survival following challenge with $25 \times LD_{50}$ of A/Singapore/GP1908/2015 IVR-180 (H1N1), respectively.

Figure 16C:
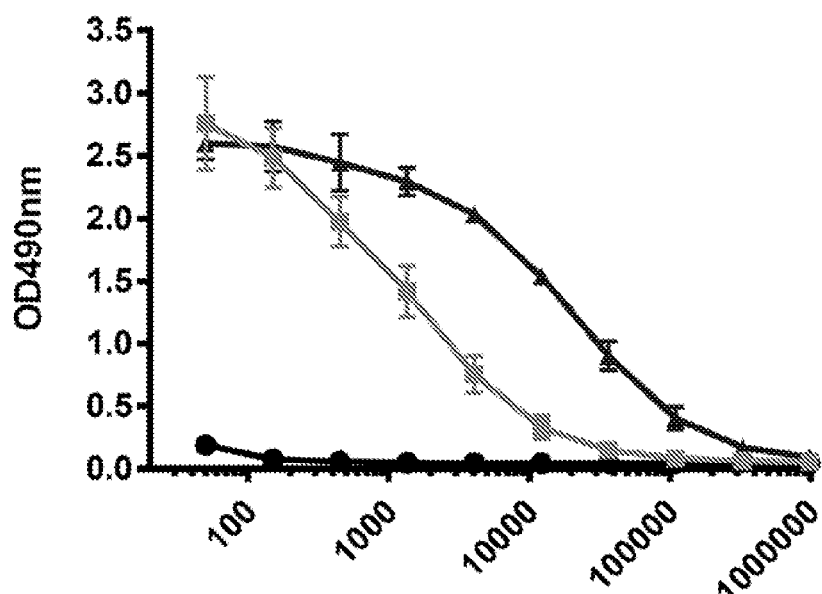

FIG. 16C depicts the results from an ELISA measuring the binding of sera from mice immunized in accordance with the protocol provided in FIG. 15 and the legend for FIG. 15 for groups 1 to 3 to recombinant N1-VASP (which comprises the globular head domain of influenza virus A/Michigan/45/15 NA and the human VASP tetramerization domain). The sera from N1-MPP vaccinated mice is able to bind to N1-VASP.

Figure 16D:
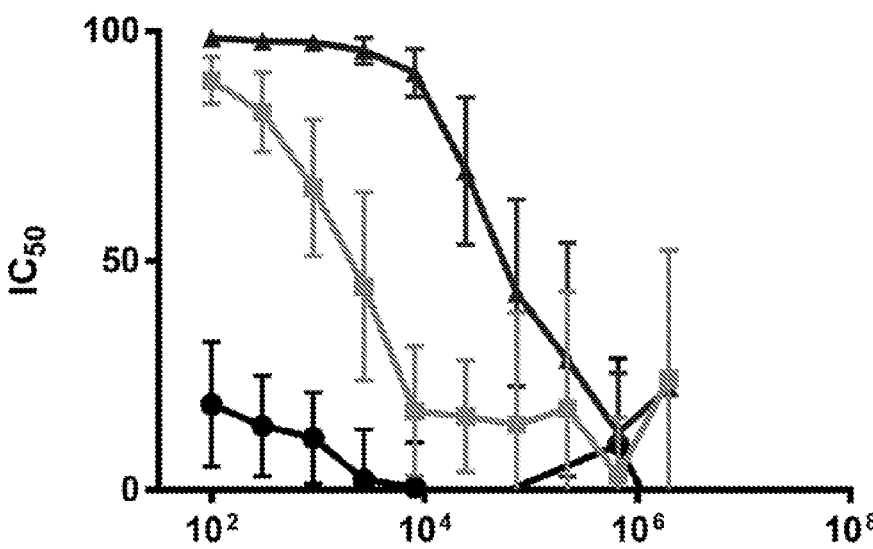

FIG. 16D depicts the results from functional neuraminidase inhibition assays. Sera from mice vaccinated with N1-MPP as described in FIG. 15 and the legend for FIG. 15 is able to inhibit the neuraminidase function of an H7N1 re-assortant virus that contains a matched N1 NA was assessed.

Figure 17A:
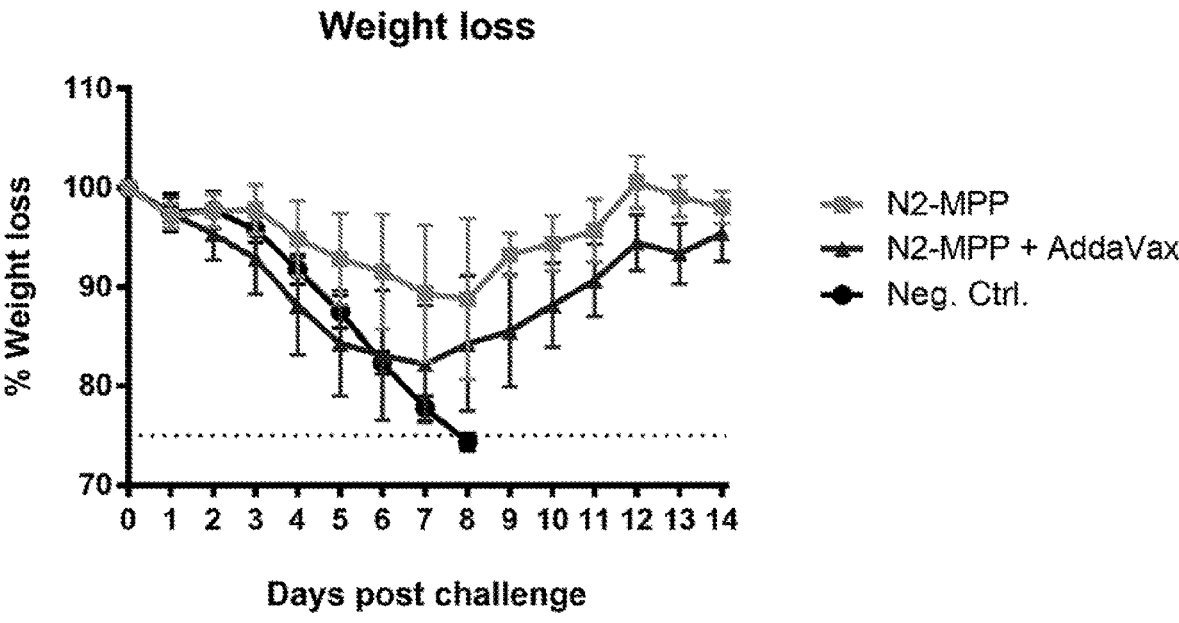
Figure 17B:
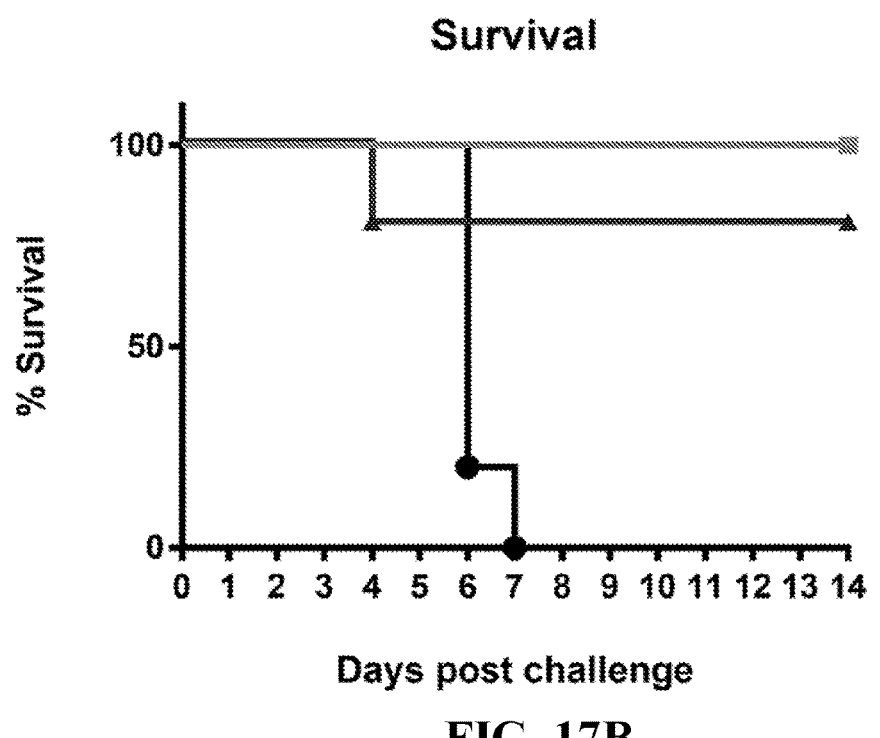

FIG. 17A and FIG. 17B show that all mice immunized with N2-MPP are protected from weight loss and show increased survival following challenge with $25 \times LD_{50}$ of A/Switzerland/9715293/2013 (H3N2, mouse adapted), respectively.

Figure 17C:
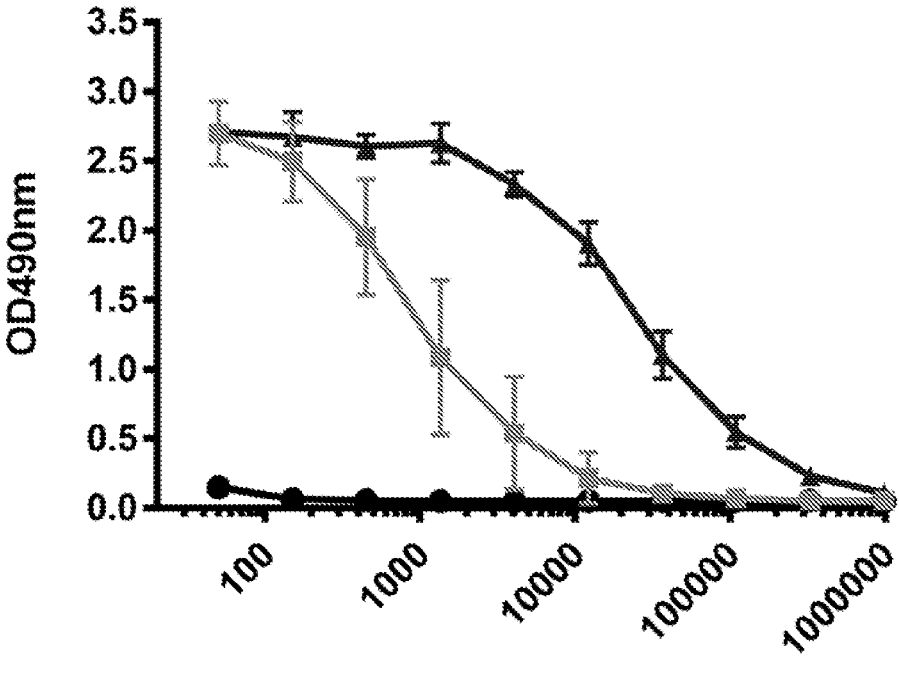

FIG. 17C depicts the results from an ELISA measuring the binding of sera from mice immunized in accordance with the protocol provided in FIG. 15 and the legend for FIG. 15 for groups 1 to 3 to recombinant N2-VASP (which comprises the globular head domain of influenza virus A/Kansas/14/2017 NA and the human VASP tetramerization domain).

Figure 18A:
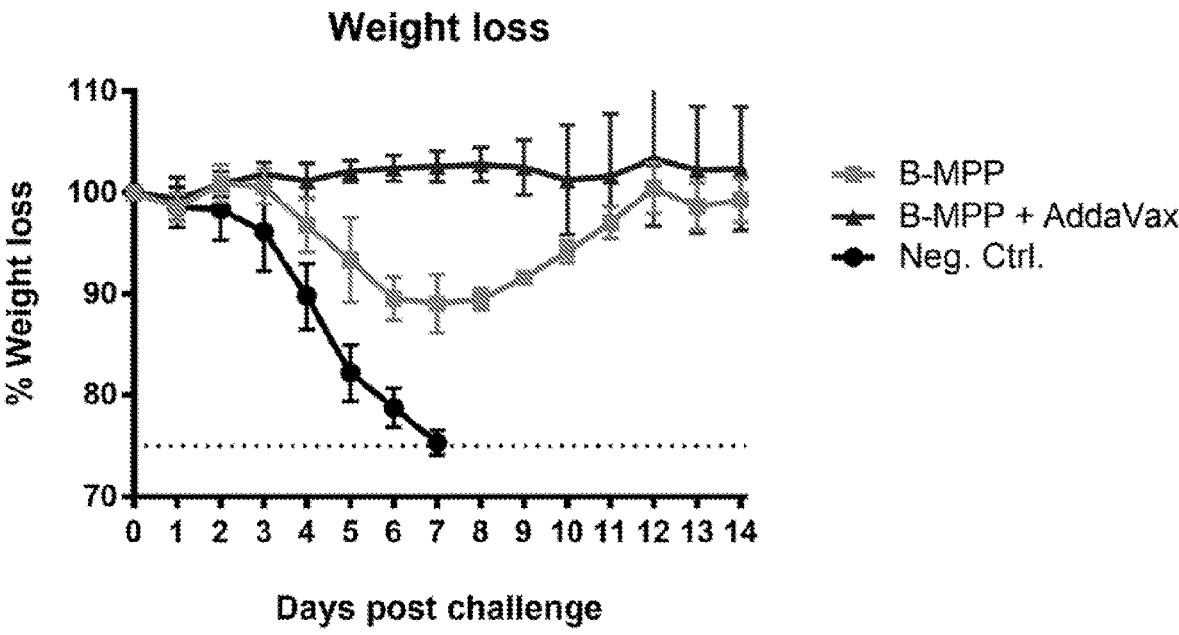
Figure 18B:
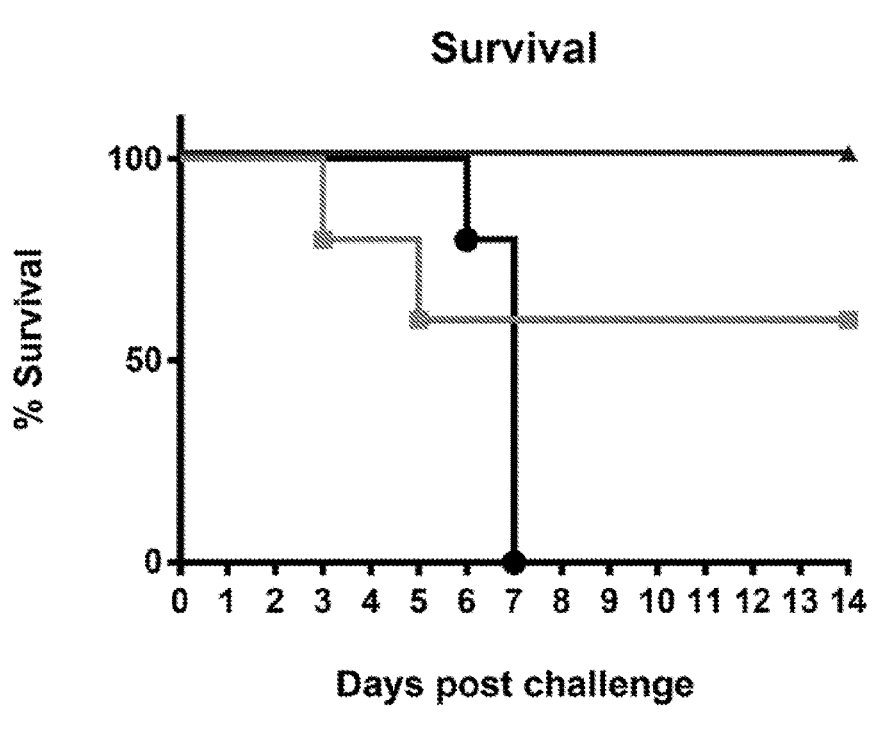

FIG. 18A and FIG. 18B show that all mice immunized with B-MPP are protected from weight loss and show increased survival following challenge with $25 \times LD_{50}$ of B/New York/PV01181/2018, respectively.

Figure 18C:
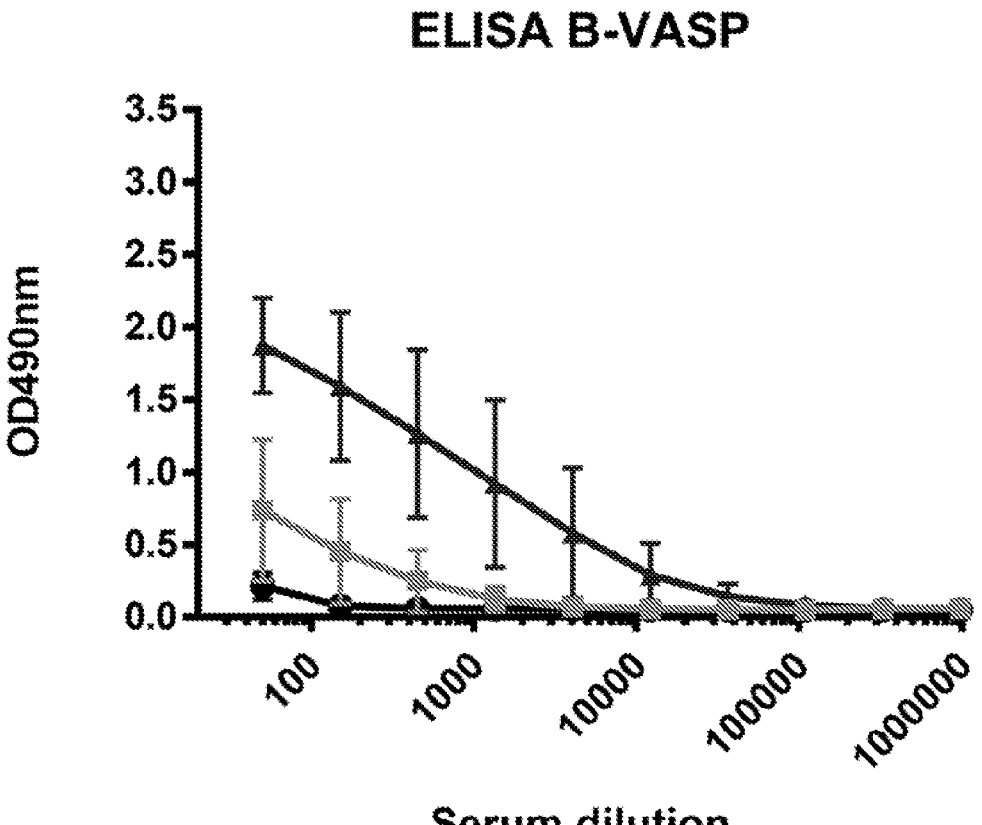

FIG. 18C depicts the results from an ELISA measuring the binding of sera from mice immunized in accordance with the protocol provided in the legend for FIG. 15 and FIG. 15 for groups 1 to 3 to recombinant B-VASP (which comprises the globular head domain of influenza virus B/Colorado/06/2017 NA and the human VASP tetramerization domain).

The results described in this example demonstrate that the recombinant N1-MPP protein, recombinant N2-MPP, and recombinant B-MPP are conformationally correct and induce an immune response that is protective in the mouse model against challenge with a virus of the same subtype.

7. EMBODIMENTS

1. A recombinant neuraminidase comprising a mutated influenza virus neuraminidase ectodomain, wherein the mutated ectodomain comprises an influenza virus neuraminidase ectodomain comprising amino acid substitutions to cysteine at amino acid residues 48 and 50 of an N1 subtype or at amino acid residues corresponding to amino acid residues 48 and 50 of influenza virus A/Puerto Rico/08/1934.

2. A recombinant neuraminidase comprising a mutated influenza virus neuraminidase ectodomain, wherein the mutated ectodomain comprises an influenza virus neuraminidase ectodomain comprising an amino acid substitution to cysteine at amino acid residue 61 of an N1 subtype or at an amino acid residue corresponding to amino acid residue 61 of influenza virus A/Puerto Rico/08/1934.

3. The recombinant neuraminidase of embodiment 2, wherein the mutated influenza virus neuraminidase ectodomain further comprises an amino acid substitution to a cysteine at amino acid residue 48 of an N1 subtype or at an amino acid residue corresponding to amino acid residue 48 of influenza virus A/Puerto Rico/08/1934.

4. The recombinant neuraminidase of any one of embodiments 1 to 3, wherein the influenza virus neuraminidase ectodomain is of subtype N1 or N2.

5. The recombinant neuraminidase of any one of embodiments 1 to 3, wherein the influenza virus neuraminidase ectodomain is of subtype N3, N4, N5, N6, N7, N8 or N9 subtype.

6. The recombinant neuraminidase of any one of embodiments 1 to 5, wherein the recombinant neuraminidase further comprises the influenza virus neuraminidase transmembrane and cytoplasmic domains.

7. The recombinant neuraminidase of any one of embodiments 1 to 5, wherein the recombinant neuraminidase further comprises a tetramerization domain.

8. The recombinant neuraminidase of embodiment 7, wherein the tetramerization domain comprises a measles virus phosphoprotein tetramerization domain or a Sendai virus phosphoprotein tetramerization domain.

9. A recombinant neuraminidase comprising a mutated influenza virus neuraminidase ectodomain and a tetramerization domain, wherein the mutated ectodomain comprises an influenza virus neuraminidase ectodomain comprising an amino acid substitution to a cysteine at amino acid residue 48 of an N1 subtype or at an amino acid residue corresponding to amino acid residue 48 of influenza virus A/Puerto Rico/08/1934.

10. The recombinant neuraminidase of embodiment 9, wherein the tetramerization domain comprises a measles virus phosphoprotein tetramerization domain or a Sendai virus phosphoprotein tetramerization domain.

11. A recombinant neuraminidase comprising an influenza virus neuraminidase globular head domain and a tetramerization domain of a paramyxovirus protein, wherein the recombinant neuraminidase lacks of influenza virus neuraminidase stalk domain, transmembrane domain and cytoplasmic domain.

12. The recombinant neuraminidase of embodiment 11, wherein the tetramizeration domain is a tetramerization domain of a paramyxovirus phosphoprotein.

13. The recombinant neuraminidase of embodiment 12, wherein the paramyxovirus phosphoprotein is a Nipah virus phosphoprotein, a Hendra virus phosphoprotein, a respiratory syncytial virus phosphoprotein, human parainfluenza virus (hPIV) phosphoprotein, bovine parainfluenza virus phosphoprotein, a mumps virus phosphoprotein, a Cedar virus phosphoprotein, a Ghana virus phosphoprotein, a Newcastle disease virus phosphoprotein, a canine distemper virus phosphoprotein, or a Peste des petits ruminants virus (PPRV) phosphoprotein.

14. The recombinant neuraminidase of embodiment 12, wherein the tetramerization domain is a measles virus phosphoprotein tetramerization domain or a Sendai virus phosphoprotein tetramerization domain.

15. A recombinant neuraminidase comprising a mutated influenza virus neuraminidase ectodomain, wherein the mutated ectodomain comprises an influenza virus neuraminidase ectodomain comprising an amino acid substitution to cysteine at amino acid residue 52 of an N2 subtype or at an amino acid residue corresponding to amino acid residue 52 of influenza virus A/Hong Kong/4801/2014, wherein the ectodomain is from an influenza A virus N2, N3, N4, N5, N6, N7, N8 or N9 subtype.

16. A recombinant neuraminidase comprising a mutated influenza virus neuraminidase ectodomain, wherein the mutated ectodomain comprises an influenza virus neuraminidase ectodomain comprising an amino acid substitution to cysteine at amino acid residue 54 of an N2 subtype or at an amino acid residue corresponding to amino acid residue 54 of A/Hong Kong/4801/2014, wherein the ectodomain is from an influenza A virus N2, N3, N4, N5, N6, N7, N8 or N9 subtype.

17. The recombinant neuraminidase of embodiment 15, wherein the mutated ectodomain further comprises an amino acid substitution to cysteine at amino acid residue 54 of an N2 subtype or at amino acid residue corresponding to amino acid residue 54 of A/Hong Kong/4801/2014.

18. The recombinant neuraminidase of any one of embodiments 15 to 17, wherein the neuraminidase further comprises the influenza virus neuraminidase transmembrane domain and cytoplasmic domain.

19. The recombinant neuraminidase of any one of embodiments 15 to 17, wherein the neuraminidase further comprises a tetramerization domain.

20. The recombinant neuraminidase of embodiment 19, wherein the tetramerization domain comprises a measles virus phosphoprotein tetramerization domain or a Sendai virus phosphoprotein tetramerization domain.

21. The recombinant neuraminidase of any one of embodiments 1 to 20, wherein the recombinant neuraminidase comprises a signal peptide.

22. The recombinant neuraminidase of any one of embodiments 1 to 21, wherein the recombinant neuraminidase further comprises a histidine tag, a Flag tag, or other purification tag.

23. A recombinant neuraminidase comprising the amino acid sequence set forth in SEQ ID NO: 27, 56, 58, 60 or 62.

24. A nucleic acid sequence comprising a nucleotide sequence encoding a recombinant neuraminidase of any one of embodiments 1 to 23.

25. A nucleic acid sequence comprising the nucleotide sequence of SEQ ID NO: 55, 57, 59 or 61.

26. An expression vector comprising the nucleic acid sequence of embodiment 24 or 25.

27. A host cell capable of expressing the nucleic acid sequence of embodiment 24 or 25.

28. A recombinant influenza virus comprising the neuraminidase of any one of embodiments 1 to 8 or 15 to 20.

29. A recombinant influenza virus comprising a genome, wherein the genome comprises a gene segment comprising a nucleic acid sequence encoding the recombinant neuraminidase of any one of embodiments 1 to 8 or 15 to 20 such that the recombinant neuraminidase is expressed by a cell infected with the recombinant influenza virus.

30. A recombinant influenza virus comprising a neuraminidase, wherein the neuraminidase comprises a mutated influenza virus neuraminidase ectodomain, wherein the mutated ectodomain comprises an influenza virus neuraminidase ectodomain comprising an amino acid substitution to cysteine at amino acid residue 48 of an N1 subtype or at an amino acid residue corresponding to amino acid residue 48 of influenza virus A/Puerto Rico/8/1934.

31. A recombinant influenza virus comprising a genome, wherein the genome comprises a gene segment comprising a nucleotide sequence encoding a neuraminidase such that the neuraminidase is expressed by an infected cell, wherein the neuraminidase comprises a mutated influenza virus neuraminidase ectodomain, wherein the mutated ectodomain comprises an influenza virus neuraminidase ectodomain comprising an amino acid substitution to cysteine at amino acid residue 48 of an N1 subtype or at amino acid residue corresponding to amino acid residue 48 of influenza virus A/Puerto Rico/8/1934.

32. A recombinant influenza virus comprising the recombinant neuraminidase of any one of embodiments 9 to 14.

33. A recombinant influenza virus comprising a genome, wherein the genome comprises a gene segment comprising a nucleic acid sequence encoding the recombinant neuraminidase of any one of embodiments 9 to 14 such that the recombinant neuraminidase is expressed by a cell infected by the recombinant influenza virus.

34. The recombinant influenza virus of embodiment 28, 30 or 32, wherein the recombinant influenza virus is inactivated.

35. The recombinant influenza virus of embodiment 28, 30 or 32, wherein the recombinant influenza virus is split.

36. The recombinant influenza virus of any one of embodiments 28 to 35, wherein the recombinant influenza virus is a recombinant influenza A virus.

37. The recombinant influenza virus of any one of embodiments 28 to 33, wherein the recombinant influenza virus is a live attenuated influenza virus.

38. The recombinant influenza virus of embodiment 37, wherein the recombinant influenza A virus is an H1 or H3 subtype.

39. An immunogenic composition comprising the recombinant neuraminidase of any one of embodiments 1 to 23.

40. The immunogenic composition of embodiment 39, wherein the composition further comprises a trivalent inactivated influenza vaccine (TIV), quadrivalent inactivated influenza virus vaccine (QIV), or recombinant influenza virus vaccine.

41. An immunogenic composition comprising the recombinant influenza virus of any one of embodiments 28 to 38.

42. The immunogenic composition of any one of embodiments 39 to 41, wherein the composition further comprises an adjuvant.

43. A method of immunizing against influenza virus, comprising administering a subject a dose of the immunogenic composition of any one of embodiments 39 to 42.

44. A method of inducing an immune response against influenza virus, comprising administering a subject a dose of the immunogenic composition of any one of embodiments 39 to 42.

45. A method of preventing an influenza virus disease, comprising administrant to a subject a dose of the immunogenic composition of any one of embodiments 39 to 42.

46. The method of any one of embodiments 43 to 45, wherein the subject is administered a further dose of the immunogenic composition as a boost.

47. The method of any one of embodiments 43 to 46, wherein the subject is human

48. The method of any one of embodiments 43 to 47, wherein the immunogenic composition is administered intramuscularly to the subject.

The foregoing is not to be limited in scope by the specific embodiments described herein. Indeed, various modifications of the antibodies and methods provided herein and their equivalents, in addition to those described herein will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

We claim:

1. A recombinant neuraminidase comprising the amino acid sequence of SEQ ID NO: 56, 58, 27, 60, or 62.

2. A recombinant neuraminidase comprising:
(a) an influenza virus neuraminidase globular head domain and a tetramerization domain, wherein the recombinant neuraminidase lacks an influenza virus neuraminidase stalk domain, transmembrane domain and cytoplasmic domain, wherein the tetramerization domain comprises a paramyxovirus phosphoprotein tetramerization domain, and wherein the paramyxovirus phosphoprotein tetramerization domain is a Sendai virus phosphoprotein tetramerization domain that comprises the amino acid sequence of SEQ ID NO: 2; or
(b) the amino acid sequence of SEQ ID NO: 25.

3. The recombinant neuraminidase of claim 1, wherein the recombinant neuraminidase comprises the amino acid sequence of SEQ ID NO: 27.

4. The recombinant neuraminidase of claim 1, wherein the recombinant neuraminidase comprises the amino acid sequence of SEQ ID NO: 56.

5. The recombinant neuraminidase of claim 1, wherein the recombinant neuraminidase comprises the amino acid sequence of SEQ ID NO: 58.

6. The recombinant neuraminidase of claim 1, wherein the recombinant neuraminidase comprises the amino acid sequence of SEQ ID NO: 60.

7. A recombinant influenza virus comprising: (a) the recombinant neuraminidase of claim 1; and (b) a genome, wherein the genome comprises a gene segment comprising a nucleic acid sequence encoding the recombinant neuraminidase of claim 1, such that the recombinant neuraminidase is expressed by a cell infected by the recombinant influenza virus.

8. An immunogenic composition comprising the recombinant neuraminidase of claim 1.

9. The immunogenic composition of claim 8, wherein the composition further comprises a trivalent inactivated influenza vaccine (TIV), quadrivalent inactivated influenza virus vaccine (QIV), or recombinant influenza virus vaccine.

10. An immunogenic composition comprising the recombinant influenza virus of claim 7.

11. The recombinant neuraminidase of claim 1, wherein the recombinant neuraminidase comprises the amino acid sequence of SEQ ID NO: 62.

12. The recombinant neuraminidase of claim 1, wherein the amino acid sequence of the recombinant neuraminidase consists of the amino acid sequence of SEQ ID NO: 56, 58, or 27.

13. The recombinant neuraminidase of claim 1, wherein the amino acid sequence of the recombinant neuraminidase consists of the amino acid sequence of SEQ ID NO: 60.

14. The recombinant neuraminidase of claim 1, wherein the amino acid sequence of the recombinant neuraminidase consists of the amino acid sequence of SEQ ID NO: 62.

15. An immunogenic composition comprising the recombinant neuraminidase of claim 11.

16. An immunogenic composition comprising the recombinant neuraminidase of claim 12.

17. An immunogenic composition comprising the recombinant neuraminidase of claim 13.

18. An immunogenic composition comprising the recombinant neuraminidase of claim 14.

* * * * *